United States Patent
Kozono et al.

(10) Patent No.: US 11,859,256 B2
(45) Date of Patent: Jan. 2, 2024

(54) STOMACH CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Satoko Kozono, Kamakura (JP); Hitoshi Nobumasa, Kamakura (JP); Satoshi Kondou, Kamakura (JP); Hiroko Sudo, Kamakura (JP); Junpei Kawauchi, Kamakura (JP); Atsushi Ochiai, Kashiwa (JP); Motohiro Kojima, Kashiwa (JP)

(73) Assignees: TORAY INDUSTRIES, LTD., Tokyo (JP); NATIONAL CANCER CENTER, Tokyo (JP)

( * ) Notice: Subject to any disclaimer, the term of this patent is extended or adjusted under 35 U.S.C. 154(b) by 0 days.

(21) Appl. No.: 17/948,560

(22) Filed: Sep. 20, 2022

(65) Prior Publication Data
US 2023/0002836 A1    Jan. 5, 2023

Related U.S. Application Data

(62) Division of application No. 16/789,943, filed on Feb. 13, 2020, now Pat. No. 11,486,009, which is a division of application No. 15/319,203, filed as application No. PCT/JP2015/067267 on Jun. 16, 2015, now Pat. No. 10,597,727.

(30) Foreign Application Priority Data

Jun. 16, 2014  (JP) ................... 2014-123224
Mar. 31, 2015  (JP) ................... 2015-071485

(51) Int. Cl.
| | |
|---|---|
| *C12Q 1/68* | (2018.01) |
| *C12P 19/34* | (2006.01) |
| *C12Q 1/6886* | (2018.01) |
| *G01N 33/53* | (2006.01) |
| *C12Q 1/06* | (2006.01) |
| *G01N 37/00* | (2006.01) |

(52) U.S. Cl.
CPC ............. *C12Q 1/6886* (2013.01); *C12Q 1/06* (2013.01); *G01N 33/53* (2013.01); *G01N 37/00* (2013.01); *C12Q 2600/158* (2013.01); *C12Q 2600/178* (2013.01)

(58) Field of Classification Search
CPC .. C12Q 1/6886; C12Q 1/68; C12Q 2600/158; C12Q 2600/178
See application file for complete search history.

(56) References Cited

U.S. PATENT DOCUMENTS

| | | |
|---|---|---|
| 2001/0053519 A1 | 12/2001 | Fodor et al. |
| 2011/0263680 A1 | 10/2011 | Khvorova et al. |
| 2013/0142728 A1 | 6/2013 | Beaudenon-Huibregtse et al. |

FOREIGN PATENT DOCUMENTS

| | | |
|---|---|---|
| CN | 103476947 A | 12/2013 |
| JP | 2012-507300 A | 3/2012 |
| JP | 2013-85542 A | 5/2013 |
| JP | 2014-60993 A | 4/2014 |
| WO | WO 2007/081740 A2 | 7/2007 |
| WO | WO 2009/108853 A1 | 9/2009 |
| WO | WO 2010/062706 A2 | 6/2010 |
| WO | WO 2012/119051 A2 | 9/2012 |

OTHER PUBLICATIONS

Michael G Schrauder, et al. "Circulating micro-RNAs as potential blood-based markers for early stage breast cancer detection" PLoS One . 2012;7(1):e29770. doi: 10.1371/journal.pone.0029770. Epub Jan. 5, 2012. (Year: 2012).*
Sirjana Shrestha, et al. "A systematic review of microRNA expression profiling studies in human gastric cancer" Cancer Medicine, vol. 3, Issue 4, Aug. 2014 pp. 878-888. (Year: 2014).*
American Cancer Society, "Stomach Cancer", 2013, p. 3, 6, and 18-20.
Berillo et al., "Binding of intronic miRNAs to the mRNAs of host genes encoding intronic miRNAs and proteins that participate in tumourigenesis," Computers in Biology and Medicine (2013), vol. 43, pp. 1374-1381.
Cheung et al., "Natural variation in human gene expression assessed in lymphoblastoid cells." Nature Genetics, vol. 33, Mar. 2003, pp. 422-425.
Chuma et al., "Circulating microRNA-1246 as a possible biomarker for early tumor recurrence of hepatocellular carcinoma," Hepatology Research (2019), vol. 49, pp. 810-822.
Cobb et al., "Sepsis gene expression profiling: murine splenic compared with hepatic responses determined by using complementary DNA microarrays." Critical Care Medicine, vol. 30, No. 12, 2002, pp. 2711-2721.
Communication Pursuant to Rule 164(1) EPC dated Dec. 15, 2017, in European Patent Application No. 15809520.8.
Eto et al., "Prospect of microRNA toward laboratory medicine Gastrointestinal Cancer and microRNA", Clinical Chemistry, vol. 43, No. 2, 2014, p. 99-105.
Genechip: "Data Sheet GeneChip TM miRNA 3.0 Array," Mar. 29, 2012, XP055222758, Retrieved from the Internet: URL:http://www.carreraresearch.org/genech ip-mirna-3-0-array-38713.pdf.

(Continued)

*Primary Examiner* — Stephen T Kapushoc
(74) *Attorney, Agent, or Firm* — Birch, Stewart, Kolasch & Birch, LLP

(57) ABSTRACT

Disclosed is a kit or a device for the detection of stomach cancer and a method for detecting stomach cancer, and provides a kit or a device for the detection of stomach cancer, including a nucleic acid(s) capable of specifically binding to a miRNA(s) in a sample from a subject, and a method for detecting stomach cancer, including measuring the miRNA(s) in vitro.

6 Claims, 4 Drawing Sheets

Specification includes a Sequence Listing.

(56) References Cited

OTHER PUBLICATIONS

He, M. and Z.-W. Wang, "Current status and development of miRNA and siRNA research on gastric cancer," Hereditas (Beijing) (2011), vol. 33, No. 9, pp. 925-930 (with English abstract).
Hoshikawa et al., "Hypoxia induces different genes in the lungs of rats compared with mice." Physiological Genomics, vol. 12, 2003, pp. 209-219.
International Search Report, issued in PCT/JP2015/067267, PCT/ISA/210, dated Sep. 15, 2015.
Kim et al., "Chemotherapy-induced transient CEA and CA19-9 surges in patients with metastatic or recurrent gastric cancer", Acta Oncologica, 2009, vol. 48, p. 385-390.
Li et al., "Plasma microRNAs, miR-223, miR-21 and miR-218, as Novel Potential Biomarkers for Gastric Cancer Detection," PLoS ONE (Jul. 2012), vol. 7, No. 7, e41629, pp. 1-8.
Liu et al,. "A five-microRNA signature identified from genome-wide serum microRNA expression profiling serves as a fingerprint for gastric cancer diagnosis," European Journal of Cancer (2011), vol. 47, pp. 784-791.
Liu et al., "MicroRNA expression profile of gastric cancer stem cells in the MKN-45 cancer cell line," Acta Biochim. Biophys. Sin. (2014), vol. 46, pp. 92-99.
Lu et al., "Predictive value of miR-9 as a potential biomarker for nasopharyngeal carcinoma metastasis." British Journal of Cancer, vol. 110, 2014, pp. 392-398.
Office Action dated Dec. 1, 2020, in Japanese Patent Application No. 2016-529360.
Office Action dated Feb. 26, 2019, in Chinese Patent Application No. 201580031876.5.
Office Action dated Sep. 17, 2020, in Indian Patent Application No. 201737001441.
Office Action dated Sep. 24, 2021, in Republic of Korea Patent Application No. 10-2017-7000937.

Olsen et al., "p63 Attenuates Epithelial to Mesenchymal Potential in an Experimental Prostate Cell Model," PLoS ONE (2013), vol. 8, No. 5, e62547, 12 pages.
Phua et al., "Global fecal microRNA profiling in the identification of biomarkers for colorectal cancer screening among Asians." Oncology Reports, vol. 32, 2014, pp. 97-104.
Qu et al., "MiR-182 and miR-203 induce mesenchymal to epithelial transition and self-sufficiency of growth signals via repressing SNAI2 in prostate cells," Int. J. Cancer (2013) vol. 133, pp. 544-556.
Quiagen Product Description of "miScript™ miRNA PCR Array 384-well, 384HC) Human miR Base Profiler HC Plate 4", document 1073798, Aug. 2012, from htttps://b2b.qiagen.com/~/mediagenetable/mihs-3404z (2012).
Schrauder et al., "Circulating micro-RNAs as potential blood-based markers for early stage breast cancer detection."PloS one, vol. 7, Issue 1, e29770, Jan. 2012, pp. 1-9.
Sobin et al., "TNM Classification of Malignant Tumours, the 7th edition, Japanese version", 2010, p. 69-73.
Takizawa et al., "miRNA Profiling in Serum Samples Using DNA Chip 3D-Gene®", BIO Clinica, Jun. 10, 2014, vol. 29, No. 6, pp. 588-589.
Takizawa et al., "Simultaneous Profiling of Multiple miRNAs in FFPE or Serum Samples Using DNA Chip 3D-Gene®", BIO Clinica, 2013, vol. 28, No. 9, pp. 872-873.
Tsujiura et al., "Circulating microRNAs in plasma of patients with gastric cancers," British Journal of Cancer (2010), vol. 102, pp. 1174-1179.
Written Opinion of the International Searching Authority, issued in PCT/JP2015/067267, PCT/ISA/237, dated Sep. 15, 2015.
Zhu et al., "Identification of Circulating MicroRNAs as Novel Potential Biomarkers for Gastric Cancer Detection: A Systematic Review and Meta-Analysis," Dig. Dis. Sci. (2014); vol. 59, pp. 911-919.

* cited by examiner

Fig. 1

```
         ua    c    u    --- gg  -ag  aca   cgcccuggggcu
   uggg    cggc cag  ggg  gg   ag   gg          ||||||||| c
   ||||    |||| ||| |||  ||   ||   ||          gugggacccgu
   accc    gccg guc  ccc  uc   uc   cc
     g --- cc    u    --- ag   agg  gac
                        gag i
``` hsa-miR-1225-5p (SEQ ID NO: 52)
hsa-miR-1225-3p (SEQ ID NO: 7)
hsa-mir-1225 (SEQ ID NO: 206)

STOMACH CANCER DETECTION KIT OR DEVICE, AND DETECTION METHOD

CROSS-REFERENCE TO RELATED APPLICATIONS

This application is a Divisional of U.S. application Ser. No. 16/789,943 filed on Feb. 13, 2020, which is a Divisional of U.S. application Ser. No. 15/319,203 filed on Dec. 15, 2016 (now U.S. Pat. No. 10,597,727), which is a National Phase of PCT International Application No. PCT/JP2015/067267 filed on Jun. 16, 2015, which claims the benefit under 35 U.S.C. § 119(a) to Patent Application Nos. 2015-071485 and 2014-123224, filed in Japan on Mar. 31, 2015 and Jun. 16, 2014, respectively. All of the above applications are hereby expressly incorporated by reference into the present application.

REFERENCE TO ELECTRONIC SEQUENCE LISTING

The application contains a Sequence Listing which has been submitted electronically in .XML format and is hereby incorporated by reference in its entirety. Said .XML copy, created on Sep. 14, 2022, is named "PH-6236-PCT-US-DIV1-DIV1.xml" and is 591,826 bytes in size. The sequence listing contained in this .XML file is part of the specification and is hereby incorporated by reference herein in its entirety.

TECHNICAL FIELD

The present invention relates to a kit or a device for the detection of stomach cancer, comprising a nucleic acid(s) capable of specifically binding to a particular miRNA(s), which is used for examining the presence or absence of stomach cancer in a subject, and a method for detecting stomach cancer, comprising measuring an expression level(s) of the miRNA(s) using the nucleic acid.

BACKGROUND ART

The stomach is a sac-like digestive organ connected to the esophagus. The stomach temporarily stores food from the esophagus and plays a role in the first step of digestion by secreting gastric juice. The stomach is divided into the cardial end located around the inlet leading to the esophagus, the pyloric end located around the outlet leading to the duodenum, and the other site called the gastric corpus (Non-Patent Literature 1). According to the statistics of the number of cancer type-specific incidences and deaths in Japan disclosed by the Center for Cancer Control and Information Services, National Cancer Center, estimated 125,730 individuals in total involving 86,728 males and 39,002 females were affected by stomach cancer in 2010. The number of stomach cancer deaths was a total of 49,129 people involving 32,206 males and 16,923 females in 2012. Thus, stomach cancer was the second leading cause of cancer death in Japan. Also, 22,220 Americans were affected by stomach cancer in 2014, among which 10,990 people would die of stomach cancer (Non-Patent Literature 1).

The stages of stomach cancer progression are defined in Non-Patent Literature 2 and classified into stages 0, IA, IB, IIA, IIB, IIIA, IIIB, IIIC, and IV according to tumor size, infiltration, lymph node metastasis, distant metastasis, etc. The 5-year relative survival rate of stomach cancer largely depends on the stages of cancer progression and is reportedly 57 to 71% for stage I, 33 to 46% for stage II, 9 to 20% for stage III, and 4% for stage IV (Non-Patent Literature 1). Thus, the early detection of stomach cancer leads to improvement in the survival rate. Therefore, an approach that enables early detection is strongly desired.

The treatment of stomach cancer is performed by the combined use of surgical therapy, drug therapy, and radiotherapy. Particularly, in very early stomach cancer under no suspicion of lymph node metastasis, endoscopic mucosal resection (EMR) or endoscopic submucosal dissection (ESD) is often applicable and the cancer can thus be treated without any burden on patients.

With the aim of detecting stomach cancer early, Japanese men and women aged 40 or older are recommended to take stomach cancer screening once a year. The efficacy of "gastric X-ray examination" as a method for stomach cancer screening has been shown. When detailed examination is required as a result of X-ray examination, gastroscopy is carried out. Alternatively, diagnostic imaging such as CT, PET, or MRI is also utilized for detecting stomach cancer (Non-Patent Literature 1).

On the other hand, no blood marker has been established for the screening of stomach cancer. Although the association of protein tumor markers such as CEA and CA19-9 in serum with stomach cancer has been suggested (Non-Patent Literature 3), there is no enough evidence to recommend using these markers for the purpose of screening. Meanwhile, as shown in Patent Literatures 1 to 3, there are reports, albeit at a research stage, on the detection of stomach cancer using the expression levels of microRNAs (miRNAs) or combinations of the expression levels of miRNAs and the expression levels of additional protein markers in biological samples including blood.

Patent Literature 1 discloses a method for detecting cancers including stomach cancer using hsa-miR-125a-3p in blood.

Patent Literature 2 discloses a method for detecting stomach cancer using hsa-miR-23a-3p, miR-92-1, and miR-92-2 (miR-92a-1-3p and miR-92a-2-3p) and also using miR-128b (miR-128-2-3p), miR-30c (miR-30c-5p), miR-135-1, miR-135-2 (miR-135a-5p), and miR-149 (miR-149-5p), and other miRNAs in blood or tissues.

Patent Literature 3 discloses a method for detecting stomach cancer using hsa-miR-451 and 468 (hsa-miR-468-5p) in blood.

CITATION LIST

Patent Literature

Patent Literature 1: International Publication No. WO 2010/062706
Patent Literature 2: JP Patent Publication (Kokai) No. 2014-060993 A (2014)
Patent Literature 3: JP Patent Publication (Kokai) No. 2013-085542 A (2013).

Non-Patent Literature

Non-Patent Literature 1: American Cancer Society, "Stomach Cancer", 2013, p. 3, 6, and 18 to 20, http://www.cancer.org/acs/groups/cid/documents/webcontent/003141-pdf.pdf
Non-Patent Literature 2: Sobin, L. et al, "TNM Classification of Malignant Tumours, the 7th edition, Japanese version", 2010, p. 69 to 73

Non-Patent Literature 3: Kim, H. J. et al., Acta Oncologica, 2009, Vol. 48, p. 385 to 390

SUMMARY OF INVENTION

Technical Problem

An object of the present invention is to find a novel tumor marker(s) for stomach cancer and to provide a method that can effectively detect stomach cancer using a nucleic acid(s) capable of specifically binding to the marker(s). Primary tests of stomach cancer include imaging tests such as gastric X-ray examination, which is routinely used in Japan, as well as CT, PET, and MRI (Non-Patent Literature 1). In Japan, however, stomach cancer is still the second leading cause of cancer death. Thus, the imaging tests cannot always work as a deterrent against stomach cancer death.

For example, CEA and CA19-9 are known as tumor markers for the detection of stomach cancer. In general, as shown in Non-Patent Literature 3, 5 ng/mL for CEA and 37 U/mL for CA19-9 are used as reference values. Although these tumor markers may be helpful in confirming the recurrence of or therapeutic effects on stomach cancer, their expression very rarely elevates in early stomach cancer. Therefore, these markers may not be useful for the purpose of stomach cancer screening. The tumor markers such as CEA and CA19-9 may also elevate for reasons other than those due to stomach cancer. Therefore, these markers alone allegedly fail to determine the presence or absence of stomach cancer. The false diagnosis of other cancers as stomach cancer wastes appropriate therapeutic opportunity or places unnecessary economical and physical burdens on patients due to the application of wrong medicine.

As described below, there are reports, albeit at a research stage, on the determination of stomach cancer using the expression levels of microRNAs (miRNAs) in biological samples including blood, none of which, however, have yet been brought into practical use.

Patent Literature 1 discloses a method for detecting cancers including stomach cancer using hsa-miR-125a-3p and other miRNAs in blood. This detection method, however, does not describe specific detection performance such as accuracy, sensitivity, or specificity for determining stomach cancer and is thus industrially less practical.

Patent Literature 2 discloses a method for detecting stomach cancer using hsa-miR-23a-3p, miR-92-1, and miR-92-2 (miR-92a-1-3p and miR-92a-2-3p) and further using miR-128 (miR-128-2-5p), miR-30c (miR-30c-5p), miR-135-1, miR-135-2 (miR-135a-5p), miR-149 (miR-149-5p), and other miRNAs in blood or tissues.

Among them, hsa-miR-23a-3p, miR-92-1, and miR-92-2 (miR-92a-1-3p and miR-92a-2-3p) are particularly described as miRNAs for detecting stomach cancer. According to the description therein, these markers in blood, however, were not validated, and specific detection examples were given for miRNAs in tissues. This is not an easy screening test. Therefore, this detection method is industrially less practical.

As mentioned above, the existing tumor markers exhibit low performance in the detection of stomach cancer, or neither detection methods nor performance is specifically shown as to the markers at a research stage. Therefore, use of these markers might lead to carrying out needless extra examination due to the false detection of healthy subjects as being stomach cancer patients, or might waste therapeutic opportunity because of overlooking stomach cancer patients. In addition, the measurement of dozens to several hundreds of miRNAs increases examination cost and is therefore difficult to use in large-scale screening for medical checkup, etc. Furthermore, the collection of gastric tissues for measuring the tumor markers is highly invasive to patients and is not favorable. Hence, there is a demand for a highly accurate stomach cancer marker that is detectable from blood, which can be collected with limited invasiveness, and is capable of correctly discriminating a stomach cancer patient from a healthy subject. Particularly, screening based on an imaging test, such as gastric X-ray examination, which is currently carried out for the early detection of stomach cancer, presents problems associated with radiation exposure, high cost, etc. Therefore, the provision of a more convenient primary screening test of stomach cancer probably leads to benefits to subjects and the health service.

Solution to Problem

The present inventors have conducted diligent studies to attain the object and consequently completed the present invention by finding multiple genes usable as markers for the detection of stomach cancer from blood, which can be collected with limited invasiveness, and finding that stomach cancer can be significantly detected by using a nucleic acid(s) capable of specifically binding to any of these markers.

SUMMARY OF INVENTION

Specifically, the present invention has the following features:

(1) A kit for the detection of stomach cancer, comprising a nucleic acid(s) capable of specifically binding to at least one or more polynucleotides selected from the group consisting of the following stomach cancer markers: miR-4257, miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR-4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-1915-3p, miR-6716-5p, miR-718, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-6848-5p, miR-762, miR-2861, miR-1203, miR-1260b, miR-4476, miR-6885-5p, miR-6769b-5p, miR-23b-3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p.

(2) The kit according to (1), wherein miR-4257 is hsa-miR-4257, miR-6726-5p is hsa-miR-6726-5p, miR-1343-3p is hsa-miR-1343-3p, miR-1247-3p is hsa-miR-1247-3p, miR-6787-5p is hsa-miR-6787-5p, miR-6875-5p is hsa-miR-6875-5p, miR-1225-3p is hsa-miR-1225-3p, miR-8063 is hsa-miR-8063, miR-6781-5p is hsa-miR-6781-5p, miR-4746-3p is hsa-miR-4746-3p, miR-1908-5p is hsa-miR-1908-5p, miR-6756-5p is hsa-miR-6756-5p, miR-204-3p is hsa-miR-204-3p, miR-4651 is hsa-miR-4651, miR-6757-5p is hsa-miR-6757-5p, miR-6825-5p is hsa-miR-6825-5p, miR-7108-5p is hsa-miR-7108-5p, miR-4792 is hsa-miR-4792, miR-7641 is hsa-miR-7641, miR-3188 is hsa-miR-3188, miR-3131 is hsa-miR-3131, miR-6780b-5p is hsa-miR-6780b-5p, miR-8069 is hsa-miR-8069, miR-6840-3p is hsa-miR-6840-3p, miR-8072 is hsa-miR-8072, miR-1233-5p is hsa-miR-1233-5p, miR-6887-5p is hsa-miR-6887-5p, miR-1231 is hsa-miR-1231, miR-5572 is hsa-miR-5572, miR-6738-5p is hsa-miR-6738-5p, miR-6784-5p is hsa-miR-6784-5p, miR-6791-5p is hsa-miR-6791-5p, miR-6749-5p is hsa-miR-6749-5p, miR-6741-5p is hsa-miR-6741-5p, miR-128-1-5p is hsa-miR-128-1-5p, miR-4419b is hsa-miR-4419b, miR-6746-5p is hsa-miR-6746-5p, miR-3184-5p is hsa-miR-3184-5p, miR-3679-5p is hsa-miR-3679-5p, miR-7110-5p is hsa-miR-7110-5p, miR-4516 is hsa-miR-4516, miR-6717-5p is hsa-miR-6717-5p, miR-6826-5p is hsa-miR-6826-5p, miR-4433b-3p is hsa-miR-4433b-3p, miR-3679-3p is hsa-miR-3679-3p, miR-3135b is hsa-miR-3135b, miR-3622a-5p is hsa-miR-3622a-5p, miR-711 is hsa-miR-711, miR-4467 is hsa-miR-4467, miR-6857-5p is hsa-miR-6857-5p, miR-6515-3p is hsa-miR-6515-3p, miR-1225-5p is hsa-miR-1225-5p, miR-187-5p is hsa-miR-187-5p, miR-3185 is hsa-miR-3185, miR-642b-3p is hsa-miR-642b-3p, miR-1249 is hsa-miR-1249, miR-744-5p is hsa-miR-744-5p, miR-4442 is hsa-miR-4442, miR-1228-3p is hsa-miR-1228-3p, miR-939-5p is hsa-miR-939-5p, miR-6845-5p is hsa-miR-6845-5p, miR-887-3p is hsa-miR-887-3p, miR-7845-5p is hsa-miR-7845-5p, miR-6729-5p is hsa-miR-6729-5p, miR-4632-5p is hsa-miR-4632-5p, miR-615-5p is hsa-miR-615-5p, miR-6724-5p is hsa-miR-6724-5p, miR-4728-5p is hsa-miR-4728-5p, miR-6732-5p is hsa-miR-6732-5p, miR-6816-5p is hsa-miR-6816-5p, miR-4695-5p is hsa-miR-4695-5p, miR-6088 is hsa-miR-6088, miR-7975 is hsa-miR-7975, miR-3197 is hsa-miR-3197, miR-6125 is hsa-miR-6125, miR-4433-3p is hsa-miR-4433-3p, miR-6727-5p is hsa-miR-6727-5p, miR-4706 is hsa-miR-4706, miR-7847-3p is hsa-miR-7847-3p, miR-6805-3p is hsa-miR-6805-3p, miR-6766-3p is hsa-miR-6766-3p, miR-1913 is hsa-miR-1913, miR-4649-5p is hsa-miR-4649-5p, miR-602 is hsa-miR-602, miR-3663-3p is hsa-miR-3663-3p, miR-6893-5p is hsa-miR-6893-5p, miR-6861-5p is hsa-miR-6861-5p, miR-4449 is hsa-miR-4449, miR-6842-5p is hsa-miR-6842-5p, miR-4454 is hsa-miR-4454, miR-5195-3p is hsa-miR-5195-3p, miR-663b is hsa-miR-663b, miR-6765-5p is hsa-miR-6765-5p, miR-4513 is hsa-miR-4513, miR-614 is hsa-miR-614, miR-6785-5p is hsa-miR-6785-5p, miR-6777-5p is hsa-miR-6777-5p, miR-940 is hsa-miR-940, miR-4741 is hsa-miR-4741, miR-6870-5p is hsa-miR-6870-5p, miR-6131 is hsa-miR-6131, miR-150-3p is hsa-miR-150-3p, miR-4707-5p is hsa-miR-4707-5p, miR-1915-3p is hsa-miR-1915-3p, miR-3937 is hsa-miR-3937, miR-937-5p is hsa-miR-937-5p, miR-4443 is hsa-miR-4443, miR-1914-3p is hsa-miR-1914-3p, miR-3620-5p is hsa-miR-3620-5p, miR-1268b is hsa-miR-1268b, miR-1227-5p is hsa-miR-1227-5p, miR-6880-5p is hsa-miR-6880-5p, miR-4417 is hsa-miR-4417, miR-6802-5p is hsa-miR-6802-5p, miR-6769a-5p is hsa-miR-6769a-5p, miR-663a is hsa-miR-663a, miR-6721-5p is hsa-miR-6721-5p, miR-4532 is hsa-miR-4532, miR-7977 is hsa-miR-7977, miR-92b-5p is hsa-miR-92b-5p, miR-371a-5p is hsa-miR-371a-5p, miR-6126 is hsa-miR-6126, miR-4734 is hsa-miR-4734, miR-4665-3p is hsa-miR-4665-3p, miR-423-5p is hsa-miR-423-5p, miR-1469 is hsa-miR-1469, miR-4675 is hsa-miR-4675, miR-1915-5p is hsa-miR-1915-5p, miR-6716-5p is hsa-miR-6716-5p, miR-718 is hsa-miR-718, miR-4281 is hsa-miR-4281, miR-6820-5p is hsa-miR-6820-5p, miR-6795-5p is hsa-miR-6795-5p, miR-6779-5p is hsa-miR-6779-5p, miR-7109-5p is hsa-miR-7109-5p, miR-6798-5p is hsa-miR-6798-5p, miR-4648 is hsa-miR-4648, miR-8059 is hsa-miR-8059, miR-6765-3p is hsa-miR-6765-3p, miR-6132 is hsa-miR-6132, miR-4492 is hsa-miR-4492, miR-7107-5p is hsa-miR-7107-5p, miR-3195 is hsa-miR-3195, miR-3180 is hsa-miR-3180, miR-296-3p is hsa-miR-296-3p, miR-564 is hsa-miR-564, miR-1268a is hsa-miR-1268a, miR-6848-5p is hsa-miR-6848-5p, miR-762 is hsa-miR-762, miR-2861 is hsa-miR-2861, miR-1203 is hsa-miR-1203, miR-1260b is hsa-miR-1260b, miR-4476 is hsa-miR-4476, miR-6885-5p is hsa-miR-6885-5p, miR-6769b-5p is hsa-miR-6769b-5p, miR-23b-3p is hsa-miR-23b-3p, miR-1343-5p is hsa-miR-1343-5p, miR-3621 is hsa-miR-3621, miR-4688 is hsa-miR-4688, miR-4286 is hsa-miR-4286, miR-4640-5p is hsa-miR-4640-5p, miR-4739 is hsa-miR-4739, miR-1260a is hsa-miR-1260a, miR-4276 is hsa-miR-4276, miR-7106-5p is hsa-miR-7106-5p, miR-6794-5p is hsa-miR-6794-5p, miR-6774-5p is hsa-miR-6774-5p, miR-4707-3p is hsa-miR-4707-3p, miR-4534 is hsa-miR-4534, miR-4294 is hsa-miR-4294, miR-6850-5p is hsa-miR-6850-5p, miR-6089 is hsa-miR-6089, and miR-671-5p is hsa-miR-671-5p.

(3) The kit according to (1) or (2), wherein the nucleic acid is a polynucleotide selected from the group consisting of the following polynucleotides (a) to (e):
  (a) a polynucleotide consisting of a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides,
  (b) a polynucleotide comprising a nucleotide sequence represented by any of SEQ ID NOs: 1 to 165 and 635 to 642,
  (c) a polynucleotide consisting of a nucleotide sequence complementary to a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides,
  (d) a polynucleotide comprising a nucleotide sequence complementary to a nucleotide sequence represented by any of SEQ ID NOs: 1 to 165 and 635 to 642 or a nucleotide sequence derived from the nucleotide sequence by the replacement of u with t, and
  (e) a polynucleotide hybridizing under stringent conditions to any of the polynucleotides (a) to (d).

(4) The kit according to any of (1) to (3), wherein the kit further comprises a nucleic acid(s) capable of specifically binding to at least one or more polynucleotides selected from the group consisting of the following other stomach cancer markers: miR-128-2-5p, miR-125a-3p, miR-92a-2-5p, and miR-486-3p.

(5) The kit according to (4), wherein miR-128-2-5p is hsa-miR-128-2-5p, miR-125a-3p is hsa-miR-125a-3p, miR-92a-2-5p is hsa-miR-92a-2-5p, and miR-486-3p is hsa-miR-486-3p.

(6) The kit according to (4) or (5), wherein the nucleic acid is a polynucleotide selected from the group consisting of the following polynucleotides (f) to (j):

(f) a polynucleotide consisting of a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 166 to 169, (h) a polynucleotide consisting of a nucleotide sequence complementary to a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 166 to 169 or a nucleotide sequence derived from the nucleotide sequence by the replacement of u with t, and (j) a polynucleotide hybridizing under stringent conditions to any of the polynucleotides (f) to (i).

(7) The kit according to any of (1) to (6), wherein the kit further comprises a nucleic acid(s) capable of specifically binding to at least one or more polynucleotides selected from the group consisting of the following other stomach cancer markers: miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141 and miR-1199-5p.

(8) The kit according to (7), wherein miR-3196 is hsa-miR-3196, miR-211-3p is hsa-miR-211-3p, miR-4271 is hsa-miR-4271, miR-6851-5p is hsa-miR-6851-5p, miR-149-3p is hsa-miR-149-3p, miR-4667-5p is hsa-miR-4667-5p, miR-135a-3p is hsa-miR-135a-3p, miR-4486 is hsa-miR-4486, miR-4697-5p is hsa-miR-4697-5p, miR-4725-3p is hsa-miR-4725-3p, miR-6510-5p is hsa-miR-6510-5p, miR-5001-5p is hsa-miR-5001-5p, miR-4673 is hsa-miR-4673, miR-4466 is hsa-miR-4466, miR-23a-3p is hsa-miR-23a-3p, miR-3656 is hsa-miR-3656, miR-6782-5p is hsa-miR-6782-5p, miR-4689 is hsa-miR-4689, miR-451a is hsa-miR-451a, miR-4446-3p is hsa-miR-4446-3p, miR-3180-3p is hsa-miR-3180-3p, miR-642a-3p is hsa-miR-642a-3p, miR-6889-5p is hsa-miR-6889-5p, miR-3178 is hsa-miR-3178, miR-4665-5p is hsa-miR-4665-5p, miR-6722-3p is hsa-miR-6722-3p, miR-30c-1-3p is hsa-miR-30c-1-3p, miR-4507 is hsa-miR-4507, miR-3141 is hsa-miR-3141, and miR-1199-5p is hsa-miR-1199-5p.

(9) The kit according to (7) or (8), wherein the nucleic acid is a polynucleotide selected from the group consisting of the following polynucleotides (k) to (o):

(k) a polynucleotide consisting of a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 170 to 199, (m) a polynucleotide consisting of a nucleotide sequence complementary to a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 170 to 199 or a nucleotide sequence derived from the nucleotide sequence by the replacement of u with t, and (o) a polynucleotide hybridizing under stringent conditions to any of the polynucleotides (k) to (n).

(10) The kit according to any one of (1) to (9), wherein the kit comprises at least two or more nucleic acids capable of specifically binding to at least two or more polynucleotides, respectively, selected from all of the stomach cancer markers according to (1) or (2).

(11) A device for the detection of stomach cancer, comprising a nucleic acid(s) capable of specifically binding to at least one or more polynucleotides selected from the group consisting of the following stomach cancer markers: miR-4257, miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR-4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-1915-5p, miR-6716-5p, miR-718, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-6848-5p, miR-762, miR-2861, miR-1203, miR-1260b, miR-4476, miR-6885-5p, miR-6769b-5p, miR-23b-

3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p.

(12) The device according to (11), wherein miR-4257 is hsa-miR-4257, miR-6726-5p is hsa-miR-6726-5p, miR-1343-3p is hsa-miR-1343-3p, miR-1247-3p is hsa-miR-1247-3p, miR-6787-5p is hsa-miR-6787-5p, miR-6875-5p is hsa-miR-6875-5p, miR-1225-3p is hsa-miR-1225-3p, miR-8063 is hsa-miR-8063, miR-6781-5p is hsa-miR-6781-5p, miR-4746-3p is hsa-miR-4746-3p, miR-1908-5p is hsa-miR-1908-5p, miR-6756-5p is hsa-miR-6756-5p, miR-204-3p is hsa-miR-204-3p, miR-4651 is hsa-miR-4651, miR-6757-5p is hsa-miR-6757-5p, miR-6825-5p is hsa-miR-6825-5p, miR-7108-5p is hsa-miR-7108-5p, miR-4792 is hsa-miR-4792, miR-7641 is hsa-miR-7641, miR-3188 is hsa-miR-3188, miR-3131 is hsa-miR-3131, miR-6780b-5p is hsa-miR-6780b-5p, miR-8069 is hsa-miR-8069, miR-6840-3p is hsa-miR-6840-3p, miR-8072 is hsa-miR-8072, miR-1233-5p is hsa-miR-1233-5p, miR-6887-5p is hsa-miR-6887-5p, miR-1231 is hsa-miR-1231, miR-5572 is hsa-miR-5572, miR-6738-5p is hsa-miR-6738-5p, miR-6784-5p is hsa-miR-6784-5p, miR-6791-5p is hsa-miR-6791-5p, miR-6749-5p is hsa-miR-6749-5p, miR-6741-5p is hsa-miR-6741-5p, miR-128-1-5p is hsa-miR-128-1-5p, miR-4419b is hsa-miR-4419b, miR-6746-5p is hsa-miR-6746-5p, miR-3184-5p is hsa-miR-3184-5p, miR-3679-5p is hsa-miR-3679-5p, miR-7110-5p is hsa-miR-7110-5p, miR-4516 is hsa-miR-4516, miR-6717-5p is hsa-miR-6717-5p, miR-6826-5p is hsa-miR-6826-5p, miR-4433b-3p is hsa-miR-4433b-3p, miR-3679-3p is hsa-miR-3679-3p, miR-3135b is hsa-miR-3135b, miR-3622a-5p is hsa-miR-3622a-5p, miR-711 is hsa-miR-711, miR-4467 is hsa-miR-4467, miR-6857-5p is hsa-miR-6857-5p, miR-6515-3p is hsa-miR-6515-3p, miR-1225-5p is hsa-miR-1225-5p, miR-187-5p is hsa-miR-187-5p, miR-3185 is hsa-miR-3185, miR-642b-3p is hsa-miR-642b-3p, miR-1249 is hsa-miR-1249, miR-744-5p is hsa-miR-744-5p, miR-4442 is hsa-miR-4442, miR-1228-3p is hsa-miR-1228-3p, miR-939-5p is hsa-miR-939-5p, miR-6845-5p is hsa-miR-6845-5p, miR-887-3p is hsa-miR-887-3p, miR-7845-5p is hsa-miR-7845-5p, miR-6729-5p is hsa-miR-6729-5p, miR-4632-5p is hsa-miR-4632-5p, miR-615-5p is hsa-miR-615-5p, miR-6724-5p is hsa-miR-6724-5p, miR-4728-5p is hsa-miR-4728-5p, miR-6732-5p is hsa-miR-6732-5p, miR-6816-5p is hsa-miR-6816-5p, miR-4695-5p is hsa-miR-4695-5p, miR-6088 is hsa-miR-6088, miR-7975 is hsa-miR-7975, miR-3197 is hsa-miR-3197, miR-6125 is hsa-miR-6125, miR-4433-3p is hsa-miR-4433-3p, miR-6727-5p is hsa-miR-6727-5p, miR-4706 is hsa-miR-4706, miR-7847-3p is hsa-miR-7847-3p, miR-6805-3p is hsa-miR-6805-3p, miR-6766-3p is hsa-miR-6766-3p, miR-1913 is hsa-miR-1913, miR-4649-5p is hsa-miR-4649-5p, miR-602 is hsa-miR-602, miR-3663-3p is hsa-miR-3663-3p, miR-6893-5p is hsa-miR-6893-5p, miR-6861-5p is hsa-miR-6861-5p, miR-4449 is hsa-miR-4449, miR-6842-5p is hsa-miR-6842-5p, miR-4454 is hsa-miR-4454, miR-5195-3p is hsa-miR-5195-3p, miR-663b is hsa-miR-663b, miR-6765-5p is hsa-miR-6765-5p, miR-4513 is hsa-miR-4513, miR-614 is hsa-miR-614, miR-6785-5p is hsa-miR-6785-5p, miR-6777-5p is hsa-miR-6777-5p, miR-940 is hsa-miR-940, miR-4741 is hsa-miR-4741, miR-6870-5p is hsa-miR-6870-5p, miR-6131 is hsa-miR-6131, miR-150-3p is hsa-miR-150-3p, miR-4707-5p is hsa-miR-4707-5p, miR-1915-3p is hsa-miR-1915-3p, miR-3937 is hsa-miR-3937, miR-937-5p is hsa-miR-937-5p, miR-4443 is hsa-miR-4443, miR-1914-3p is hsa-miR-1914-3p, miR-3620-5p is hsa-miR-3620-5p, miR-1268b is hsa-miR-1268b, miR-1227-5p is hsa-miR-1227-5p, miR-6880-5p is hsa-miR-6880-5p, miR-4417 is hsa-miR-4417, miR-6802-5p is hsa-miR-6802-5p, miR-6769a-5p is hsa-miR-6769a-5p, miR-663a is hsa-miR-663a, miR-6721-5p is hsa-miR-6721-5p, miR-4532 is hsa-miR-4532, miR-7977 is hsa-miR-7977, miR-92b-5p is hsa-miR-92b-5p, miR-371a-5p is hsa-miR-371a-5p, miR-6126 is hsa-miR-6126, miR-4734 is hsa-miR-4734, miR-4665-3p is hsa-miR-4665-3p, miR-423-5p is hsa-miR-423-5p, miR-1469 is hsa-miR-1469, miR-4675 is hsa-miR-4675, miR-1915-5p is hsa-miR-1915-5p, miR-6716-5p is hsa-miR-6716-5p, miR-718 is hsa-miR-718, miR-4281 is hsa-miR-4281, miR-6820-5p is hsa-miR-6820-5p, miR-6795-5p is hsa-miR-6795-5p, miR-6779-5p is hsa-miR-6779-5p, miR-7109-5p is hsa-miR-7109-5p, miR-6798-5p is hsa-miR-6798-5p, miR-4648 is hsa-miR-4648, miR-8059 is hsa-miR-8059, miR-6765-3p is hsa-miR-6765-3p, miR-6132 is hsa-miR-6132, miR-4492 is hsa-miR-4492, miR-7107-5p is hsa-miR-7107-5p, miR-3195 is hsa-miR-3195, miR-3180 is hsa-miR-3180, miR-296-3p is hsa-miR-296-3p, miR-564 is hsa-miR-564, miR-1268a is hsa-miR-1268a, miR-6848-5p is hsa-miR-6848-5p, miR-762 is hsa-miR-762, miR-2861 is hsa-miR-2861, miR-1203 is hsa-miR-1203, miR-1260b is hsa-miR-1260b, miR-4476 is hsa-miR-4476, miR-6885-5p is hsa-miR-6885-5p, miR-6769b-5p is hsa-miR-6769b-5p, miR-23b-3p is hsa-miR-23b-3p, miR-1343-5p is hsa-miR-1343-5p, miR-3621 is hsa-miR-3621, miR-4688 is hsa-miR-4688, miR-4286 is hsa-miR-4286, miR-4640-5p is hsa-miR-4640-5p, miR-4739 is hsa-miR-4739, miR-1260a is hsa-miR-1260a, miR-4276 is hsa-miR-4276, miR-7106-5p is hsa-miR-7106-5p, miR-6794-5p is hsa-miR-6794-5p, miR-6774-5p is hsa-miR-6774-5p, miR-4707-3p is hsa-miR-4707-3p, miR-4534 is hsa-miR-4534, miR-4294 is hsa-miR-4294, miR-6850-5p is hsa-miR-6850-5p, miR-6089 is hsa-miR-6089, and miR-671-5p is hsa-miR-671-5p.

(13) The device according to (11) or (12), wherein the nucleic acid is a polynucleotide selected from the group consisting of the following polynucleotides (a) to (e):
  (a) a polynucleotide consisting of a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides,
  (b) a polynucleotide comprising a nucleotide sequence represented by any of SEQ ID NOs: 1 to 165 and 635 to 642,
  (c) a polynucleotide consisting of a nucleotide sequence complementary to a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides,
  (d) a polynucleotide comprising a nucleotide sequence complementary to a nucleotide sequence represented by any of SEQ ID NOs: 1 to 165 and 635 to 642 or a nucleotide sequence derived from the nucleotide sequence by the replacement of u with t, and
  (e) a polynucleotide hybridizing under stringent conditions to any of the polynucleotides (a) to (d).

(14) The device according to any of (11) to (13), wherein the device further comprises a nucleic acid(s) capable of specifically binding to at least one or more polynucleotides selected from the group consisting of the following other stomach cancer markers: miR-128-2-5p, miR-125a-3p, miR-92a-2-5p, and miR-486-3p.

(15) The device according to (14), wherein miR-128-2-5p is hsa-miR-128-2-5p, miR-125a-3p is hsa-miR-125a-3p, miR-92a-2-5p is hsa-miR-92a-2-5p, and miR-486-3p is hsa-miR-486-3p.

(16) The device according to (14) or (15), wherein the nucleic acid is a polynucleotide selected from the group consisting of the following polynucleotides (f) to (j):

(f) a polynucleotide consisting of a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 166 to 169, (h) a polynucleotide consisting of a nucleotide sequence complementary to a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 166 to 169 or a nucleotide sequence derived from the nucleotide sequence by the replacement of u with t, and (j) a polynucleotide hybridizing under stringent conditions to any of the polynucleotides (f) to (i).

(17) The device according to any of (11) to (16), wherein the device further comprises a nucleic acid(s) capable of specifically binding to at least one or more polynucleotides selected from the group consisting of the following other stomach cancer markers: miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141 and miR-1199-5p.

(18) The device according to (17), wherein miR-3196 is hsa-miR-3196, miR-211-3p is hsa-miR-211-3p, miR-4271 is hsa-miR-4271, miR-6851-5p is hsa-miR-6851-5p, miR-149-3p is hsa-miR-149-3p, miR-4667-5p is hsa-miR-4667-5p, miR-135a-3p is hsa-miR-135a-3p, miR-4486 is hsa-miR-4486, miR-4697-5p is hsa-miR-4697-5p, miR-4725-3p is hsa-miR-4725-3p, miR-6510-5p is hsa-miR-6510-5p, miR-5001-5p is hsa-miR-5001-5p, miR-4673 is hsa-miR-4673, miR-4466 is hsa-miR-4466, miR-23a-3p is hsa-miR-23a-3p, miR-3656 is hsa-miR-3656, miR-6782-5p is hsa-miR-6782-5p, miR-4689 is hsa-miR-4689, miR-451a is hsa-miR-451a, miR-4446-3p is hsa-miR-4446-3p, miR-3180-3p is hsa-miR-3180-3p, miR-642a-3p is hsa-miR-642a-3p, miR-6889-5p is hsa-miR-6889-5p, miR-3178 is hsa-miR-3178, miR-4665-5p is hsa-miR-4665-5p, miR-6722-3p is hsa-miR-6722-3p, miR-30c-1-3p is hsa-miR-30c-1-3p, miR-4507 is hsa-miR-4507, miR-3141 is hsa-miR-3141, and miR-1199-5p is hsa-miR-1199-5p.

(19) The device according to (17) or (18), wherein the nucleic acid is a polynucleotide selected from the group consisting of the following polynucleotides (k) to (o):

(k) a polynucleotide consisting of a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 170 to 199, (m) a polynucleotide consisting of a nucleotide sequence complementary to a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 170 to 199 or a nucleotide sequence derived from the nucleotide sequence by the replacement of u with t, and (o) a polynucleotide hybridizing under stringent conditions to any of the polynucleotides (k) to (n).

(20) The device according to any one of (11) to (19), wherein the device is for measurement based on a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the stomach cancer markers according to (11) or (12).

(23) A method for detecting stomach cancer, comprising measuring an expression level(s) of a target nucleic acid(s) in a sample from a subject using the kit according to any one of (1) to (10) or the device according to any one of (11) to (22), and evaluating in vitro whether or not the subject has stomach cancer using both of the measured expression level(s) and a control expression level(s) in a sample from a healthy subject measured in the same way.

(24) The method according to (23), wherein the subject is a human.

(25) The method according to (23) or (24), wherein the sample is blood, serum, or plasma.

Definition of Terms

The terms used herein are defined as follows.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid including all of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Herein, the "synthetic DNA" and the "synthetic RNA" refer to DNA and RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence containing substitution, deletion, insertion, and/or addition of one or more nucleotides (i.e., a variant sequence) and a sequence containing one or more modified nucleotides (i.e., a modified sequence), which are different from the natural sequence. Herein, the polynucleotide is used interchangeably with a nucleic acid.

The term "fragment" used herein is a polynucleotide having a nucleotide sequence having a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus strand (or a sense strand) or a complementary strand (or an antisense strand) that constitutes a duplex. The gene is not particularly limited by its length.

Thus, herein, the "gene" includes any of double-stranded DNA including human genomic DNA, single-stranded DNA (plus strand), single-stranded DNA having a sequence complementary to the plus strand (complementary strand) including cDNA, microRNA (miRNA), and their fragments, and their transcripts, unless otherwise specified. The "gene" includes not only a "gene" represented by a particular nucleotide sequence (or SEQ ID NO) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 657 or a nucleotide sequence derived from the nucleotide sequence by the replacement of u with t. The "gene" is not particularly limited by its functional region and can contain, for example, an expression regulatory region(s), a coding region(s), an exon(s), or an intron(s). The "gene" may be contained in a cell or may exist alone after being released from a cell. Alternatively, the "gene" may be enclosed in a vesicle called exosome.

The term "exosome" used herein is a vesicle that is delimited by a lipid bilayer and secreted from a cell. The exosome is derived from a multivesicular endosome and may incorporate biomaterials such as a "gene" (e.g., RNA or DNA) or a protein when released into an extracellular environment. The exosome is known to be contained in a body fluid such as blood, serum, plasma, or lymph.

The term "transcript" used herein refers to an RNA synthesized from the DNA sequence of a gene as a template. RNA polymerase binds to a site called a promoter located upstream of the gene and adds ribonucleotides complementary to the nucleotide sequence of the DNA to the 3' end to synthesize RNA. This RNA contains not only the gene itself but also the whole sequence from a transcription initiation site to the end of a polyA sequence, including an expression regulatory region, a coding region, an exon, or an intron.

Unless otherwise specified, the term "microRNA (miRNA)" used herein is intended to mean a 15- to 25-nucleotide non-coding RNA that is involved in the suppression of translation of mRNA, and that transcribed as an RNA precursor having a hairpin-like structure, cleaved by a dsRNA-cleaving enzyme which has RNase III cleavage activity, and integrated into a protein complex called RISC. The term "miRNA" used herein includes not only a "miRNA" represented by a particular nucleotide sequence (or SEQ ID NO) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 657. The term "miRNA" used herein may be a gene product of a miR gene. Such a gene product includes a mature miRNA (e.g., a 15- to 25-nucleotide or 19-to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting RNA resulting from the expression of a gene or a polynucleotide derived from the RNA, and/or a polynucleotide complementary thereto.

The term "primer" used herein includes a polynucleotide that specifically recognizes and amplifies RNA resulting from the expression of a gene or a polynucleotide derived from the RNA, and/or a polynucleotide complementary thereto.

In this context, the complementary polynucleotide (complementary strand or reverse strand) means a polynucleotide in a complementary relationship of A:T (U) and G:C base pairs with the full-length sequence of a polynucleotide consisting of a nucleotide sequence defined by any of SEQ ID NOs: 1 to 657 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence that is 100% complementary to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more nucleotides in a nucleotide sequence represented by any of SEQ ID NOs: 1 to 657 or a nucleotide sequence derived from the nucleotide sequence by the replacement of u with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant used herein can be prepared by use of a well-known technique such as site-directed mutagenesis or PCR-based mutagenesis.

The term "percent (%) identity" used herein can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A, Vol. 85, p. 2444-2448).

The term "derivative" used herein is meant to include a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

The "nucleic acid" used herein capable of specifically binding to a polynucleotide selected from the stomach cancer marker miRNAs described above is a synthesized or prepared nucleic acid and specifically includes a "nucleic acid probe" or a "primer". The "nucleic acid" is utilized directly or indirectly for detecting the presence or absence of stomach cancer in a subject, for diagnosing the presence or absence of stomach cancer, the severity of stomach cancer, the presence or absence of amelioration or the degree of amelioration of stomach cancer, or the therapeutic sensitivity of stomach cancer, or for screening for a candidate substance useful in the prevention, amelioration, or treatment of stomach cancer. The "nucleic acid" includes a nucleotide, an oligonucleotide, and a polynucleotide capable of specifically recognizing and binding to a transcript represented by any of SEQ ID NOs: 1 to 657 or a synthetic cDNA nucleic acid thereof in vivo, particularly, in a sample such as a body fluid (e.g., blood or urine), in relation to the development of stomach cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". The term "evaluation" used herein is meant to include diagnosis or evaluation support on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used herein refers to a probability at which a more extreme statistic than that actually calculated from data under null hypothesis is observed in a statistical test. Thus, smaller "P" or "P value" is regarded as being a more significant difference between subjects to be compared.

The term "sensitivity" used herein means a value of (the number of true positives)/(the number of true positives+the number of false negatives). High sensitivity allows stomach cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being stomach cancer patients, leading to reduction in burden on patients and reduction in medical expense.

The term "accuracy" used herein means a value of (the number of true positives+the number of true negatives)/(the total number of cases). The accuracy indicates the ratio of samples that identified correctly in the discriminant results to all samples, and serves as a primary index for evaluating detection performance.

The "sample" used herein that is subject to determination, detection, or diagnosis refers to a tissue and a biological material in which the expression of the gene of the present invention varies as stomach cancer develops, as stomach cancer progresses, or as therapeutic effects on stomach cancer are exerted. Specifically, the "sample" refers to a gastric tissue, a perigastric vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-4257 gene" or "hsa-miR-4257" used herein includes the hsa-miR-4257 gene (miRBase Accession No. MIMAT0016878) described in SEQ ID NO: 1, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. MI0015856, SEQ ID NO: 200) having a hairpin-like structure is known as a precursor of "hsa-miR-4257".

The term "hsa-miR-6726-5p gene" or "hsa-miR-6726-5p" used herein includes the hsa-miR-6726-5p gene (miRBase Accession No. MIMAT0027353) described in SEQ ID NO: 2, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 201) having a hairpin-like structure is known as a precursor of "hsa-miR-6726-5p".

The term "hsa-miR-1343-3p gene" or "hsa-miR-1343-3p" used herein includes the hsa-miR-1343-3p gene (miRBase Accession No. MIMAT0019776) described in SEQ ID NO: 3, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 202) having a hairpin-like structure is known as a precursor of "hsa-miR-1343-3p".

The term "hsa-miR-1247-3p gene" or "hsa-miR-1247-3p" used herein includes the hsa-miR-1247-3p gene (miRBase Accession No. MIMAT0022721) described in SEQ ID NO: 4, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 203) having a hairpin-like structure is known as a precursor of "hsa-miR-1247-3p".

The term "hsa-miR-6787-5p gene" or "hsa-miR-6787-5p" used herein includes the hsa-miR-6787-5p gene (miRBase Accession No. MIMAT0027474) described in SEQ ID NO: 5, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 204) having a hairpin-like structure is known as a precursor of "hsa-miR-6787-5p".

The term "hsa-miR-6875-5p gene" or "hsa-miR-6875-5p" used herein includes the hsa-miR-6875-5p gene (miRBase Accession No. MIMAT0027650) described in SEQ ID NO: 6, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 205) having a hairpin-like structure is known as a precursor of "hsa-miR-6875-5p".

The term "hsa-miR-1225-3p gene" or "hsa-miR-1225-3p" used herein includes the hsa-miR-1225-3p gene (miRBase Accession No. MIMAT0005573) described in SEQ ID NO: 7, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 206) having a hairpin-like structure is known as a precursor of "hsa-miR-1225-3p".

The term "hsa-miR-8063 gene" or "hsa-miR-8063" used herein includes the hsa-miR-8063 gene (miRBase Accession No. MIMAT0030990) described in SEQ ID NO: 8, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 207) having a hairpin-like structure is known as a precursor of "hsa-miR-8063".

The term "hsa-miR-6781-5p gene" or "hsa-miR-6781-5p" used herein includes the hsa-miR-6781-5p gene (miRBase Accession No. MIMAT0027462) described in SEQ ID NO: 9, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 208) having a hairpin-like structure is known as a precursor of "hsa-miR-6781-5p".

The term "hsa-miR-4746-3p gene" or "hsa-miR-4746-3p" used herein includes the hsa-miR-4746-3p gene (miRBase Accession No. MIMAT0019881) described in SEQ ID NO: 10, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 209) having a hairpin-like structure is known as a precursor of "hsa-miR-4746-3p".

The term "hsa-miR-1908-5p gene" or "hsa-miR-1908-5p" used herein includes the hsa-miR-1908-5p gene (miRBase Accession No. MIMAT0007881) described in SEQ ID NO: 11, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 210) having a hairpin-like structure is known as a precursor of "hsa-miR-1908-5p".

The term "hsa-miR-6756-5p gene" or "hsa-miR-6756-5p" used herein includes the hsa-miR-6756-5p gene (miRBase Accession No. MIMAT0027412) described in SEQ ID NO: 12, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 211) having a hairpin-like structure is known as a precursor of "hsa-miR-6756-5p".

The term "hsa-miR-204-3p gene" or "hsa-miR-204-3p" used herein includes the hsa-miR-204-3p gene (miRBase Accession No. MIMAT0022693) described in SEQ ID NO: 13, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 212) having a hairpin-like structure is known as a precursor of "hsa-miR-204-3p".

The term "hsa-miR-4651 gene" or "hsa-miR-4651" used herein includes the hsa-miR-4651 gene (miRBase Accession No. MIMAT0019715) described in SEQ ID NO: 14, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 213) having a hairpin-like structure is known as a precursor of "hsa-miR-4651".

The term "hsa-miR-6757-5p gene" or "hsa-miR-6757-5p" used herein includes the hsa-miR-6757-5p gene (miRBase Accession No. MIMAT0027414) described in SEQ ID NO: 15, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 214) having a hairpin-like structure is known as a precursor of "hsa-miR-6757-5p".

The term "hsa-miR-6825-5p gene" or "hsa-miR-6825-5p" used herein includes the hsa-miR-6825-5p gene (miRBase Accession No. MIMAT0027550) described in SEQ ID NO: 16, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 215) having a hairpin-like structure is known as a precursor of "hsa-miR-6825-5p".

The term "hsa-miR-7108-5p gene" or "hsa-miR-7108-5p" used herein includes the hsa-miR-7108-5p gene (miRBase Accession No. MIMAT0028113) described in SEQ ID NO: 17, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 216) having a hairpin-like structure is known as a precursor of "hsa-miR-7108-5p".

The term "hsa-miR-4792 gene" or "hsa-miR-4792" used herein includes the hsa-miR-4792 gene (miRBase Accession No. MIMAT0019964) described in SEQ ID NO: 18, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 217) having a hairpin-like structure is known as a precursor of "hsa-miR-4792".

The term "hsa-miR-7641 gene" or "hsa-miR-7641" used herein includes the hsa-miR-7641 gene (miRBase Accession No. MIMAT0029782) described in SEQ ID NO: 19, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NO: 218 and 219) having a hairpin-like structure are known as precursors of "hsa-miR-7641".

The term "hsa-miR-3188 gene" or "hsa-miR-3188" used herein includes the hsa-miR-3188 gene (miRBase Accession No. MIMAT0015070) described in SEQ ID NO: 20, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 220) having a hairpin-like structure is known as a precursor of "hsa-miR-3188".

The term "hsa-miR-3131 gene" or "hsa-miR-3131" used herein includes the hsa-miR-3131 gene (miRBase Accession No. MIMAT0014996) described in SEQ ID NO: 21, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 221) having a hairpin-like structure is known as a precursor of "hsa-miR-3131".

The term "hsa-miR-6780b-5p gene" or "hsa-miR-6780b-5p" used herein includes the hsa-miR-6780b-5p gene (miRBase Accession No. MIMAT0027572) described in SEQ ID NO: 22, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 222) having a hairpin-like structure is known as a precursor of "hsa-miR-6780b-5p".

The term "hsa-miR-8069 gene" or "hsa-miR-8069" used herein includes the hsa-miR-8069 gene (miRBase Accession No. MIMAT0030996) described in SEQ ID NO: 23, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 223) having a hairpin-like structure is known as a precursor of "hsa-miR-8069".

The term "hsa-miR-6840-3p gene" or "hsa-miR-6840-3p" used herein includes the hsa-miR-6840-3p gene (miRBase Accession No. MIMAT0027583) described in SEQ ID NO: 24, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 224) having a hairpin-like structure is known as a precursor of "hsa-miR-6840-3p".

The term "hsa-miR-8072 gene" or "hsa-miR-8072" used herein includes the hsa-miR-8072 gene (miRBase Accession No. MIMAT0030999) described in SEQ ID NO: 25, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 225) having a hairpin-like structure is known as a precursor of "hsa-miR-8072".

The term "hsa-miR-1233-5p gene" or "hsa-miR-1233-5p" used herein includes the hsa-miR-1233-5p gene (miRBase Accession No. MIMAT0022943) described in SEQ ID NO: 26, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 226 and 227) having a hairpin-like structure are known as precursors of "hsa-miR-1233-5p".

The term "hsa-miR-6887-5p gene" or "hsa-miR-6887-5p" used herein includes the hsa-miR-6887-5p gene (miRBase Accession No. MIMAT0027674) described in SEQ ID NO: 27, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 228) having a hairpin-like structure is known as a precursor of "hsa-miR-6887-5p".

The term "hsa-miR-1231 gene" or "hsa-miR-1231" used herein includes the hsa-miR-1231 gene (miRBase Accession No. MIMAT0005586) described in SEQ ID NO: 28, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 229) having a hairpin-like structure is known as a precursor of "hsa-miR-1231".

The term "hsa-miR-5572 gene" or "hsa-miR-5572" used herein includes the hsa-miR-5572 gene (miRBase Accession No. MIMAT0022260) described in SEQ ID NO: 29, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 230) having a hairpin-like structure is known as a precursor of "hsa-miR-5572".

The term "hsa-miR-6738-5p gene" or "hsa-miR-6738-5p" used herein includes the hsa-miR-6738-5p gene (miRBase Accession No. MIMAT0027377) described in SEQ ID NO: 30, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 231) having a hairpin-like structure is known as a precursor of "hsa-miR-6738-5p".

The term "hsa-miR-6784-5p gene" or "hsa-miR-6784-5p" used herein includes the hsa-miR-6784-5p gene (miRBase Accession No. MIMAT0027468) described in SEQ ID NO: 31, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 232) having a hairpin-like structure is known as a precursor of "hsa-miR-6784-5p".

The term "hsa-miR-6791-5p gene" or "hsa-miR-6791-5p" used herein includes the hsa-miR-6791-5p gene (miRBase Accession No. MIMAT0027482) described in SEQ ID NO: 32, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 233) having a hairpin-like structure is known as a precursor of "hsa-miR-6791-5p".

The term "hsa-miR-6749-5p gene" or "hsa-miR-6749-5p" used herein includes the hsa-miR-6749-5p gene (miRBase Accession No. MIMAT0027398) described in SEQ ID NO: 33, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 234) having a hairpin-like structure is known as a precursor of "hsa-miR-6749-5p".

The term "hsa-miR-6741-5p gene" or "hsa-miR-6741-5p" used herein includes the hsa-miR-6741-5p gene (miRBase Accession No. MIMAT0027383) described in SEQ ID NO: 34, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 235) having a hairpin-like structure is known as a precursor of "hsa-miR-6741-5p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 35, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 236) having a hairpin-like structure is known as a precursor of "hsa-miR-128-1-5p".

The term "hsa-miR-4419b gene" or "hsa-miR-4419b" used herein includes the hsa-miR-4419b gene (miRBase Accession No. MIMAT0019034) described in SEQ ID NO: 36, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 237) having a hairpin-like structure is known as a precursor of "hsa-miR-4419b".

The term "hsa-miR-6746-5p gene" or "hsa-miR-6746-5p" used herein includes the hsa-miR-6746-5p gene (miRBase Accession No. MIMAT0027392) described in SEQ ID NO: 37, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 238) having a hairpin-like structure is known as a precursor of "hsa-miR-6746-5p".

The term "hsa-miR-3184-5p gene" or "hsa-miR-3184-5p" used herein includes the hsa-miR-3184-5p gene (miRBase Accession No. MIMAT0015064) described in SEQ ID NO: 38, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 239) having a hairpin-like structure is known as a precursor of "hsa-miR-3184-5p".

The term "hsa-miR-3679-5p gene" or "hsa-miR-3679-5p" used herein includes the hsa-miR-3679-5p gene (miRBase Accession No. MIMAT0018104) described in SEQ ID NO: 39, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 240) having a hairpin-like structure is known as a precursor of "hsa-miR-3679-5p".

The term "hsa-miR-7110-5p gene" or "hsa-miR-7110-5p" used herein includes the hsa-miR-7110-5p gene (miRBase Accession No. MIMAT0028117) described in SEQ ID NO: 40, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 241) having a hairpin-like structure is known as a precursor of "hsa-miR-7110-5p".

The term "hsa-miR-4516 gene" or "hsa-miR-4516" used herein includes the hsa-miR-4516 gene (miRBase Accession No. MIMAT0019053) described in SEQ ID NO: 41, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 242) having a hairpin-like structure is known as a precursor of "hsa-miR-4516".

The term "hsa-miR-6717-5p gene" or "hsa-miR-6717-5p" used herein includes the hsa-miR-6717-5p gene (miRBase Accession No. MIMAT0025846) described in SEQ ID NO: 42, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 243) having a hairpin-like structure is known as a precursor of "hsa-miR-6717-5p".

The term "hsa-miR-6826-5p gene" or "hsa-miR-6826-5p" used herein includes the hsa-miR-6826-5p gene (miRBase Accession No. MIMAT0027552) described in SEQ ID NO: 43, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 244) having a hairpin-like structure is known as a precursor of "hsa-miR-6826-5p".

The term "hsa-miR-4433b-3p gene" or "hsa-miR-4433b-3p" used herein includes the hsa-miR-4433b-3p gene (miRBase Accession No. MIMAT0030414) described in SEQ ID NO: 44, a homolog or an ortholog of a different organism species, and the like. The hsa-miR-4433b-3p gene can be obtained by a method described in Ple H et al., 2012, PLoS One, Vol. 7, e50746. Also, "hsa-mir-4433b" (miRBase Accession No. MI0025511, SEQ ID NO: 245) having a hairpin-like structure is known as a precursor of "hsa-miR-4433b-3p".

The term "hsa-miR-3679-3p gene" or "hsa-miR-3679-3p" used herein includes the hsa-miR-3679-3p gene (miRBase Accession No. MIMAT0018105) described in SEQ ID NO: 45, a homolog or an ortholog of a different organism species, and the like. The hsa-miR-3679-3p gene can be obtained by a method described in Creighton C J et al., 2010, PLoS One, Vol. 5, e9637. Also, "hsa-mir-3679" (miRBase Accession No. MI0016080, SEQ ID NO: 240) having a hairpin-like structure is known as a precursor of "hsa-miR-3679-3p".

The term "hsa-miR-3135b gene" or "hsa-miR-3135b" used herein includes the hsa-miR-3135b gene (miRBase Accession No. MIMAT0018985) described in SEQ ID NO: 46, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 246) having a hairpin-like structure is known as a precursor of "hsa-miR-3135b".

The term "hsa-miR-3622a-5p gene" or "hsa-miR-3622a-5p" used herein includes the hsa-miR-3622a-5p gene (miRBase Accession No. MIMAT0018003) described in SEQ ID NO: 47, a homolog or an ortholog of a different organism species, and the like. The hsa-miR-3622a-5p gene can be obtained by a method described in Witten D et al., 2010, BMC Biol, Vol. 8, p. 58. Also, "hsa-mir-3622a" (miRBase Accession No. MI0016013, SEQ ID NO: 247) having a hairpin-like structure is known as a precursor of "hsa-miR-3622a-5p".

The term "hsa-miR-711 gene" or "hsa-miR-711" used herein includes the hsa-miR-711 gene (miRBase Accession No. MIMAT0012734) described in SEQ ID NO: 48, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 248) having a hairpin-like structure is known as a precursor of "hsa-miR-711".

The term "hsa-miR-4467 gene" or "hsa-miR-4467" used herein includes the hsa-miR-4467 gene (miRBase Accession No. MIMAT0018994) described in SEQ ID NO: 49, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 249) having a hairpin-like structure is known as a precursor of "hsa-miR-4467".

The term "hsa-miR-6857-5p gene" or "hsa-miR-6857-5p" used herein includes the hsa-miR-6857-5p gene (miRBase Accession No. MIMAT0027614) described in SEQ ID NO: 50, a homolog or an ortholog of a different organism species, and the like. The hsa-miR-6857-5p gene can be obtained by a method described in Ladewig E et al., 2012, Genome Res, Vol. 22, p. 1634-1645. Also, "hsa-mir-6857" (miRBase Accession No. MI0022703, SEQ ID NO: 250) having a hairpin-like structure is known as a precursor of "hsa-miR-6857-5p".

The term "hsa-miR-6515-3p gene" or "hsa-miR-6515-3p" used herein includes the hsa-miR-6515-3p gene (miRBase Accession No. MIMAT0025487) described in SEQ ID NO: 51, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 251) having a hairpin-like structure is known as a precursor of "hsa-miR-6515-3p".

The term "hsa-miR-1225-5p gene" or "hsa-miR-1225-5p" used herein includes the hsa-miR-1225-5p gene (miRBase Accession No. MIMAT0005572) described in SEQ ID NO: 52, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 206) having a hairpin-like structure is known as a precursor of "hsa-miR-1225-5p".

The term "hsa-miR-187-5p gene" or "hsa-miR-187-5p" used herein includes the hsa-miR-187-5p gene (miRBase Accession No. MIMAT0004561) described in SEQ ID NO: 53, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 252) having a hairpin-like structure is known as a precursor of "hsa-miR-187-5p".

The term "hsa-miR-3185 gene" or "hsa-miR-3185" used herein includes the hsa-miR-3185 gene (miRBase Accession No. MIMAT0015065) described in SEQ ID NO: 54, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 253) having a hairpin-like structure is known as a precursor of "hsa-miR-3185".

The term "hsa-miR-642b-3p gene" or "hsa-miR-642b-3p" used herein includes the hsa-miR-642b-3p gene (miRBase Accession No. MIMAT0018444) described in SEQ ID NO: 55, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 254) having a hairpin-like structure is known as a precursor of "hsa-miR-642b-3p".

The term "hsa-miR-1249 gene" or "hsa-miR-1249" used herein includes the hsa-miR-1249 gene (miRBase Accession No. MIMAT0005901) described in SEQ ID NO: 56, a homolog or an ortholog of a different organism species, and the like. The hsa-miR-1249 gene can be obtained by a method described in Morin R D et al., 2008, Genome Res, Vol. 18, p. 610-621. Also, "hsa-mir-1249" (miRBase Accession No. MI0006384, SEQ ID NO: 255) having a hairpin-like structure is known as a precursor of "hsa-miR-1249".

The term "hsa-miR-744-5p gene" or "hsa-miR-744-5p" used herein includes the hsa-miR-744-5p gene (miRBase Accession No. MIMAT0004945) described in SEQ ID NO: 57, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 256) having a hairpin-like structure is known as a precursor of "hsa-miR-744-5p".

The term "hsa-miR-4442 gene" or "hsa-miR-4442" used herein includes the hsa-miR-4442 gene (miRBase Accession No. MIMAT0018960) described in SEQ ID NO: 58, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 257) having a hairpin-like structure is known as a precursor of "hsa-miR-4442".

The term "hsa-miR-1228-3p gene" or "hsa-miR-1228-3p" used herein includes the hsa-miR-1228-3p gene (miRBase Accession No. MIMAT0005583) described in SEQ ID NO: 59, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 258) having a hairpin-like structure is known as a precursor of "hsa-miR-1228-3p".

The term "hsa-miR-939-5p gene" or "hsa-miR-939-5p" used herein includes the hsa-miR-939-5p gene (miRBase Accession No. MIMAT0004982) described in SEQ ID NO: 60, a homolog or an ortholog of a different organism species, and the like. The hsa-miR-939-5p gene can be obtained by a method described in Lui W O et al., 2007, Cancer Res, Vol.

67, p. 6031-6043. Also, "hsa-mir-939" (miRBase Accession No. MI0005761, SEQ ID NO: 259) having a hairpin-like structure is known as a precursor of "hsa-miR-939-5p".

The term "hsa-miR-6845-5p gene" or "hsa-miR-6845-5p" used herein includes the hsa-miR-6845-5p gene (miRBase Accession No. MIMAT0027590) described in SEQ ID NO: 61, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 260) having a hairpin-like structure is known as a precursor of "hsa-miR-6845-5p".

The term "hsa-miR-887-3p gene" or "hsa-miR-887-3p" used herein includes the hsa-miR-887-3p gene (miRBase Accession No. MIMAT0004951) described in SEQ ID NO: 62, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 261) having a hairpin-like structure is known as a precursor of "hsa-miR-887-3p".

The term "hsa-miR-7845-5p gene" or "hsa-miR-7845-5p" used herein includes the hsa-miR-7845-5p gene (miRBase Accession No. MIMAT0030420) described in SEQ ID NO: 63, a homolog or an ortholog of a different organism species, and the like. The hsa-miR-7845-5p gene can be obtained by a method described in Ple H et al., 2012, PLoS One, Vol. 7, e50746. Also, "hsa-mir-7845" (miRBase Accession No. MI0025515, SEQ ID NO: 262) having a hairpin-like structure is known as a precursor of "hsa-miR-7845-5p".

The term "hsa-miR-6729-5p gene" or "hsa-miR-6729-5p" used herein includes the hsa-miR-6729-5p gene (miRBase Accession No. MIMAT0027359) described in SEQ ID NO: 64, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 263) having a hairpin-like structure is known as a precursor of "hsa-miR-6729-5p".

The term "hsa-miR-4632-5p gene" or "hsa-miR-4632-5p" used herein includes the hsa-miR-4632-5p gene (miRBase Accession No. MIMAT0022977) described in SEQ ID NO: 65, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 264) having a hairpin-like structure is known as a precursor of "hsa-miR-4632-5p".

The term "hsa-miR-615-5p gene" or "hsa-miR-615-5p" used herein includes the hsa-miR-615-5p gene (miRBase Accession No. MIMAT0004804) described in SEQ ID NO: 66, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 265) having a hairpin-like structure is known as a precursor of "hsa-miR-615-5p".

The term "hsa-miR-6724-5p gene" or "hsa-miR-6724-5p" used herein includes the hsa-miR-6724-5p gene (miRBase Accession No. MIMAT0025856) described in SEQ ID NO: 67, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 266) having a hairpin-like structure is known as a precursor of "hsa-miR-6724-5p".

The term "hsa-miR-4728-5p gene" or "hsa-miR-4728-5p" used herein includes the hsa-miR-4728-5p gene (miRBase Accession No. MIMAT0019849) described in SEQ ID NO: 68, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 267) having a hairpin-like structure is known as a precursor of "hsa-miR-4728-5p".

The term "hsa-miR-6732-5p gene" or "hsa-miR-6732-5p" used herein includes the hsa-miR-6732-5p gene (miRBase Accession No. MIMAT0027365) described in SEQ ID NO: 69, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 268) having a hairpin-like structure is known as a precursor of "hsa-miR-6732-5p".

The term "hsa-miR-6816-5p gene" or "hsa-miR-6816-5p" used herein includes the hsa-miR-6816-5p gene (miRBase Accession No. MIMAT0027532) described in SEQ ID NO: 70, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 269) having a hairpin-like structure is known as a precursor of "hsa-miR-6816-5p".

The term "hsa-miR-4695-5p gene" or "hsa-miR-4695-5p" used herein includes the hsa-miR-4695-5p gene (miRBase Accession No. MIMAT0019788) described in SEQ ID NO: 71, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 270) having a hairpin-like structure is known as a precursor of "hsa-miR-4695-5p".

The term "hsa-miR-6088 gene" or "hsa-miR-6088" used herein includes the hsa-miR-6088 gene (miRBase Accession No. MIMAT0023713) described in SEQ ID NO: 72, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 271) having a hairpin-like structure is known as a precursor of "hsa-miR-6088".

The term "hsa-miR-7975 gene" or "hsa-miR-7975" used herein includes the hsa-miR-7975 gene (miRBase Accession No. MIMAT0031178) described in SEQ ID NO: 73, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 272) having a hairpin-like structure is known as a precursor of "hsa-miR-7975".

The term "hsa-miR-3197 gene" or "hsa-miR-3197" used herein includes the hsa-miR-3197 gene (miRBase Accession No. MIMAT0015082) described in SEQ ID NO: 74, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No.

MI0014245, SEQ ID NO: 273) having a hairpin-like structure is known as a precursor of "hsa-miR-3197".

The term "hsa-miR-6125 gene" or "hsa-miR-6125" used herein includes the hsa-miR-6125 gene (miRBase Accession No. MIMAT0024598) described in SEQ ID NO: 75, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 274) having a hairpin-like structure is known as a precursor of "hsa-miR-6125".

The term "hsa-miR-4433-3p gene" or "hsa-miR-4433-3p" used herein includes the hsa-miR-4433-3p gene (miRBase Accession No. MIMAT0018949) described in SEQ ID NO: 76, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 275) having a hairpin-like structure is known as a precursor of "hsa-miR-4433-3p".

The term "hsa-miR-6727-5p gene" or "hsa-miR-6727-5p" used herein includes the hsa-miR-6727-5p gene (miRBase Accession No. MIMAT0027355) described in SEQ ID NO: 77, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 276) having a hairpin-like structure is known as a precursor of "hsa-miR-6727-5p".

The term "hsa-miR-4706 gene" or "hsa-miR-4706" used herein includes the hsa-miR-4706 gene (miRBase Accession No. MIMAT0019806) described in SEQ ID NO: 78, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 277) having a hairpin-like structure is known as a precursor of "hsa-miR-4706".

The term "hsa-miR-7847-3p gene" or "hsa-miR-7847-3p" used herein includes the hsa-miR-7847-3p gene (miRBase Accession No. MIMAT0030422) described in SEQ ID NO: 79, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 278) having a hairpin-like structure is known as a precursor of "hsa-miR-7847-3p".

The term "hsa-miR-6805-3p gene" or "hsa-miR-6805-3p" used herein includes the hsa-miR-6805-3p gene (miRBase Accession No. MIMAT0027511) described in SEQ ID NO: 80, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 279) having a hairpin-like structure is known as a precursor of "hsa-miR-6805-3p".

The term "hsa-miR-6766-3p gene" or "hsa-miR-6766-3p" used herein includes the hsa-miR-6766-3p gene (miRBase Accession No. MIMAT0027433) described in SEQ ID NO: 81, a homolog or an ortholog of a different organism species, and the like. The hsa-miR-6766-3p gene can be obtained by a method described in Ladewig E et al., 2012, Genome Res, Vol. 22, p. 1634-1645. Also, "hsa-mir-6766" (miRBase Accession No. MI0022611, SEQ ID NO: 280) having a hairpin-like structure is known as a precursor of "hsa-miR-6766-3p".

The term "hsa-miR-1913 gene" or "hsa-miR-1913" used herein includes the hsa-miR-1913 gene (miRBase Accession No. MIMAT0007888) described in SEQ ID NO: 82, a homolog or an ortholog of a different organism species, and the like. The hsa-miR-1913 gene can be obtained by a method described in Bar M et al., 2008, Stem Cells, Vol. 26, p. 2496-2505. Also, "hsa-mir-1913" (miRBase Accession No. MI0008334, SEQ ID NO: 281) having a hairpin-like structure is known as a precursor of "hsa-miR-1913".

The term "hsa-miR-4649-5p gene" or "hsa-miR-4649-5p" used herein includes the hsa-miR-4649-5p gene (miRBase Accession No. MIMAT0019711) described in SEQ ID NO: 83, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 282) having a hairpin-like structure is known as a precursor of "hsa-miR-4649-5p".

The term "hsa-miR-602 gene" or "hsa-miR-602" used herein includes the hsa-miR-602 gene (miRBase Accession No. MIMAT0003270) described in SEQ ID NO: 84, a homolog or an ortholog of a different organism species, and the like. The hsa-miR-602 gene can be obtained by a method described in Cummins J M et al., 2006, Proc Natl Acad Sci USA, Vol. 103, p. 3687-3692. Also, "hsa-mir-602" (miRBase Accession No. MI0003615, SEQ ID NO: 283) having a hairpin-like structure is known as a precursor of "hsa-miR-602".

The term "hsa-miR-3663-3p gene" or "hsa-miR-3663-3p" used herein includes the hsa-miR-3663-3p gene (miRBase Accession No. MIMAT0018085) described in SEQ ID NO: 85, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 284) having a hairpin-like structure is known as a precursor of "hsa-miR-3663-3p".

The term "hsa-miR-6893-5p gene" or "hsa-miR-6893-5p" used herein includes the hsa-miR-6893-5p gene (miRBase Accession No. MIMAT0027686) described in SEQ ID NO: 86, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 285) having a hairpin-like structure is known as a precursor of "hsa-miR-6893-5p".

The term "hsa-miR-6861-5p gene" or "hsa-miR-6861-5p" used herein includes the hsa-miR-6861-5p gene (miRBase Accession No. MIMAT0027623) described in SEQ ID NO: 87, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 286) having a hairpin-like structure is known as a precursor of "hsa-miR-6861-5p".

The term "hsa-miR-4449 gene" or "hsa-miR-4449" used herein includes the hsa-miR-4449 gene (miRBase Accession No. MIMAT0018968) described in SEQ ID NO: 88, a homolog or an ortholog of a different organism species, and the like. The hsa-miR-4449 gene can be obtained by a method described in Jima D D et al., 2010, Blood, Vol. 116, e118-e127. Also, "hsa-mir-4449" (miRBase Accession No.

MI0016792, SEQ ID NO: 287) having a hairpin-like structure is known as a precursor of "hsa-miR-4449".

The term "hsa-miR-6842-5p gene" or "hsa-miR-6842-5p" used herein includes the hsa-miR-6842-5p gene (miRBase Accession No. MIMAT0027586) described in SEQ ID NO: 89, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 288) having a hairpin-like structure is known as a precursor of "hsa-miR-6842-5p".

The term "hsa-miR-4454 gene" or "hsa-miR-4454" used herein includes the hsa-miR-4454 gene (miRBase Accession No. MIMAT0018976) described in SEQ ID NO: 90, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 289) having a hairpin-like structure is known as a precursor of "hsa-miR-4454".

The term "hsa-miR-5195-3p gene" or "hsa-miR-5195-3p" used herein includes the hsa-miR-5195-3p gene (miRBase Accession No. MIMAT0021127) described in SEQ ID NO: 91, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 290) having a hairpin-like structure is known as a precursor of "hsa-miR-5195-3p".

The term "hsa-miR-663b gene" or "hsa-miR-663b" used herein includes the hsa-miR-663b gene (miRBase Accession No. MIMAT0005867) described in SEQ ID NO: 92, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 291) having a hairpin-like structure is known as a precursor of "hsa-miR-663b".

The term "hsa-miR-6765-5p gene" or "hsa-miR-6765-5p" used herein includes the hsa-miR-6765-5p gene (miRBase Accession No. MIMAT0027430) described in SEQ ID NO: 93, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 292) having a hairpin-like structure is known as a precursor of "hsa-miR-6765-5p".

The term "hsa-miR-4513 gene" or "hsa-miR-4513" used herein includes the hsa-miR-4513 gene (miRBase Accession No. MIMAT0019050) described in SEQ ID NO: 94, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 293) having a hairpin-like structure is known as a precursor of "hsa-miR-4513".

The term "hsa-miR-614 gene" or "hsa-miR-614" used herein includes the hsa-miR-614 gene (miRBase Accession No. MIMAT0003282) described in SEQ ID NO: 95, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 294) having a hairpin-like structure is known as a precursor of "hsa-miR-614".

The term "hsa-miR-6785-5p gene" or "hsa-miR-6785-5p" used herein includes the hsa-miR-6785-5p gene (miRBase Accession No. MIMAT0027470) described in SEQ ID NO: 96, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. MI0022630, SEQ ID NO: 295) having a hairpin-like structure is known as a precursor of "hsa-miR-6785-5p".

The term "hsa-miR-6777-5p gene" or "hsa-miR-6777-5p" used herein includes the hsa-miR-6777-5p gene (miRBase Accession No. MIMAT0027454) described in SEQ ID NO: 97, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. MI0022622, SEQ ID NO: 296) having a hairpin-like structure is known as a precursor of "hsa-miR-6777-5p".

The term "hsa-miR-940 gene" or "hsa-miR-940" used herein includes the hsa-miR-940 gene (miRBase Accession No. MIMAT0004983) described in SEQ ID NO: 98, a homolog or an ortholog of a different organism species, and the like. The hsa-miR-940 gene can be obtained by a method described in Lui W O et al., 2007, Cancer Res, Vol. 67, p. 6031-6043. Also, "hsa-mir-940" (miRBase Accession No. MI0005762, SEQ ID NO: 297) having a hairpin-like structure is known as a precursor of "hsa-miR-940".

The term "hsa-miR-4741 gene" or "hsa-miR-4741" used herein includes the hsa-miR-4741 gene (miRBase Accession No. MIMAT0019871) described in SEQ ID NO: 99, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 298) having a hairpin-like structure is known as a precursor of "hsa-miR-4741".

The term "hsa-miR-6870-5p gene" or "hsa-miR-6870-5p" used herein includes the hsa-miR-6870-5p gene (miRBase Accession No. MIMAT0027640) described in SEQ ID NO: 100, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 299) having a hairpin-like structure is known as a precursor of "hsa-miR-6870-5p".

The term "hsa-miR-6131 gene" or "hsa-miR-6131" used herein includes the hsa-miR-6131 gene (miRBase Accession No. MIMAT0024615) described in SEQ ID NO: 101, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 300) having a hairpin-like structure is known as a precursor of "hsa-miR-6131".

The term "hsa-miR-150-3p gene" or "hsa-miR-150-3p" used herein includes the hsa-miR-150-3p gene (miRBase Accession No. MIMAT0004610) described in SEQ ID NO: 102, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI0000479, SEQ ID NO: 301) having a hairpin-like structure is known as a precursor of "hsa-miR-150-3p".

The term "hsa-miR-4707-5p gene" or "hsa-miR-4707-5p" used herein includes the hsa-miR-4707-5p gene (miRBase Accession No. MIMAT0019807) described in SEQ ID NO: 103, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 302) having a hairpin-like structure is known as a precursor of "hsa-miR-4707-5p".

The term "hsa-miR-1915-3p gene" or "hsa-miR-1915-3p" used herein includes the hsa-miR-1915-3p gene (miRBase Accession No. MIMAT0007892) described in SEQ ID NO: 104, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 303) having a hairpin-like structure is known as a precursor of "hsa-miR-1915-3p".

The term "hsa-miR-3937 gene" or "hsa-miR-3937" used herein includes the hsa-miR-3937 gene (miRBase Accession No. MIMAT0018352) described in SEQ ID NO: 105, a homolog or an ortholog of a different organism species, and the like. The hsa-miR-3937 gene can be obtained by a method described in Liao J Y et al., 2010, PLoS One, Vol. 5, e10563. Also, "hsa-mir-3937" (miRBase Accession No. MI0016593, SEQ ID NO: 304) having a hairpin-like structure is known as a precursor of "hsa-miR-3937".

The term "hsa-miR-937-5p gene" or "hsa-miR-937-5p" used herein includes the hsa-miR-937-5p gene (miRBase Accession No. MIMAT0022938) described in SEQ ID NO: 106, a homolog or an ortholog of a different organism species, and the like. The hsa-miR-937-5p gene can be obtained by a method described in Lui W O et al., 2007, Cancer Res, Vol. 67, p. 6031-6043. Also, "hsa-mir-937" (miRBase Accession No. MI0005759, SEQ ID NO: 305) having a hairpin-like structure is known as a precursor of "hsa-miR-937-5p".

The term "hsa-miR-4443 gene" or "hsa-miR-4443" used herein includes the hsa-miR-4443 gene (miRBase Accession No. MIMAT0018961) described in SEQ ID NO: 107, a homolog or an ortholog of a different organism species, and the like. The hsa-miR-4443 gene can be obtained by a method described in Jima D D et al., 2010, Blood, Vol. 116, e118-e127. Also, "hsa-mir-4443" (miRBase Accession No. MI0016786, SEQ ID NO: 306) having a hairpin-like structure is known as a precursor of "hsa-miR-4443".

The term "hsa-miR-1914-3p gene" or "hsa-miR-1914-3p" used herein includes the hsa-miR-1914-3p gene (miRBase Accession No. MIMAT0007890) described in SEQ ID NO: 108, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 307) having a hairpin-like structure is known as a precursor of "hsa-miR-1914-3p".

The term "hsa-miR-3620-5p gene" or "hsa-miR-3620-5p" used herein includes the hsa-miR-3620-5p gene (miRBase Accession No. MIMAT0022967) described in SEQ ID NO: 109, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 308) having a hairpin-like structure is known as a precursor of "hsa-miR-3620-5p".

The term "hsa-miR-1268b gene" or "hsa-miR-1268b" used herein includes the hsa-miR-1268b gene (miRBase Accession No. MIMAT0018925) described in SEQ ID NO: 110, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 309) having a hairpin-like structure is known as a precursor of "hsa-miR-1268b".

The term "hsa-miR-1227-5p gene" or "hsa-miR-1227-5p" used herein includes the hsa-miR-1227-5p gene (miRBase Accession No. MIMAT0022941) described in SEQ ID NO: 111, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 310) having a hairpin-like structure is known as a precursor of "hsa-miR-1227-5p".

The term "hsa-miR-6880-5p gene" or "hsa-miR-6880-5p" used herein includes the hsa-miR-6880-5p gene (miRBase Accession No. MIMAT0027660) described in SEQ ID NO: 112, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 311) having a hairpin-like structure is known as a precursor of "hsa-miR-6880-5p".

The term "hsa-miR-4417 gene" or "hsa-miR-4417" used herein includes the hsa-miR-4417 gene (miRBase Accession No. MIMAT0018929) described in SEQ ID NO: 113, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 312) having a hairpin-like structure is known as a precursor of "hsa-miR-4417".

The term "hsa-miR-6802-5p gene" or "hsa-miR-6802-5p" used herein includes the hsa-miR-6802-5p gene (miRBase Accession No. MIMAT0027504) described in SEQ ID NO: 114, a homolog or an ortholog of a different organism species, and the like. The hsa-miR-6802-5p gene can be obtained by a method described in Ladewig E et al., 2012, Genome Res, Vol. 22, p. 1634-1645. Also, "hsa-mir-6802" (miRBase Accession No. MI0022647, SEQ ID NO: 313) having a hairpin-like structure is known as a precursor of "hsa-miR-6802-5p".

The term "hsa-miR-6769a-5p gene" or "hsa-miR-6769a-5p" used herein includes the hsa-miR-6769a-5p gene (miRBase Accession No. MIMAT0027438) described in SEQ ID NO: 115, a homolog or an ortholog of a different organism species, and the like. The hsa-miR-6769a-5p gene can be obtained by a method described in Ladewig E et al., 2012, Genome Res, Vol. 22, p. 1634-1645. Also, "hsa-mir-6769a" (miRBase Accession No. MI0022614, SEQ ID NO: 314) having a hairpin-like structure is known as a precursor of "hsa-miR-6769a-5p".

The term "hsa-miR-663a gene" or "hsa-miR-663a" used herein includes the hsa-miR-663a gene (miRBase Accession No. MIMAT0003326) described in SEQ ID NO: 116, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 315) having a hairpin-like structure is known as a precursor of "hsa-miR-663a".

The term "hsa-miR-6721-5p gene" or "hsa-miR-6721-5p" used herein includes the hsa-miR-6721-5p gene (miRBase Accession No. MIMAT0025852) described in SEQ ID NO: 117, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 316) having a hairpin-like structure is known as a precursor of "hsa-miR-6721-5p".

The term "hsa-miR-4532 gene" or "hsa-miR-4532" used herein includes the hsa-miR-4532 gene (miRBase Accession No. MIMAT0019071) described in SEQ ID NO: 118, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 317) having a hairpin-like structure is known as a precursor of "hsa-miR-4532".

The term "hsa-miR-7977 gene" or "hsa-miR-7977" used herein includes the hsa-miR-7977 gene (miRBase Accession No. MIMAT0031180) described in SEQ ID NO: 119, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 318) having a hairpin-like structure is known as a precursor of "hsa-miR-7977".

The term "hsa-miR-92b-5p gene" or "hsa-miR-92b-5p" used herein includes the hsa-miR-92b-5p gene (miRBase Accession No. MIMAT0004792) described in SEQ ID NO: 120, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 319) having a hairpin-like structure is known as a precursor of "hsa-miR-92b-5p".

The term "hsa-miR-371a-5p gene" or "hsa-miR-371a-5p" used herein includes the hsa-miR-371a-5p gene (miRBase Accession No. MIMAT0004687) described in SEQ ID NO: 121, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 320) having a hairpin-like structure is known as a precursor of "hsa-miR-371a-5p".

The term "hsa-miR-6126 gene" or "hsa-miR-6126" used herein includes the hsa-miR-6126 gene (miRBase Accession No. MIMAT0024599) described in SEQ ID NO: 122, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 321) having a hairpin-like structure is known as a precursor of "hsa-miR-6126".

The term "hsa-miR-4734 gene" or "hsa-miR-4734" used herein includes the hsa-miR-4734 gene (miRBase Accession No. MIMAT0019859) described in SEQ ID NO: 123, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 322) having a hairpin-like structure is known as a precursor of "hsa-miR-4734".

The term "hsa-miR-4665-3p gene" or "hsa-miR-4665-3p" used herein includes the hsa-miR-4665-3p gene (miRBase Accession No. MIMAT0019740) described in SEQ ID NO: 124, a homolog or an ortholog of a different organism species, and the like. The hsa-miR-4665-3p gene can be obtained by a method described in Persson H et al., 2011, Cancer Res, Vol. 71, p. 78-86. Also, "hsa-mir-4665" (miRBase Accession No. MI0017295, SEQ ID NO: 323) having a hairpin-like structure is known as a precursor of "hsa-miR-4665-3p".

The term "hsa-miR-423-5p gene" or "hsa-miR-423-5p" used herein includes the hsa-miR-423-5p gene (miRBase Accession No. MIMAT0004748) described in SEQ ID NO: 125, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 324) having a hairpin-like structure is known as a precursor of "hsa-miR-423-5p".

The term "hsa-miR-1469 gene" or "hsa-miR-1469" used herein includes the hsa-miR-1469 gene (miRBase Accession No. MIMAT0007347) described in SEQ ID NO: 126, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 325) having a hairpin-like structure is known as a precursor of "hsa-miR-1469".

The term "hsa-miR-4675 gene" or "hsa-miR-4675" used herein includes the hsa-miR-4675 gene (miRBase Accession No. MIMAT0019757) described in SEQ ID NO: 127, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 326) having a hairpin-like structure is known as a precursor of "hsa-miR-4675".

The term "hsa-miR-1915-5p gene" or "hsa-miR-1915-5p" used herein includes the hsa-miR-1915-5p gene (miRBase Accession No. MIMAT0007891) described in SEQ ID NO: 128, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 303) having a hairpin-like structure is known as a precursor of "hsa-miR-1915-5p".

The term "hsa-miR-6716-5p gene" or "hsa-miR-6716-5p" used herein includes the hsa-miR-6716-5p gene (miRBase Accession No. MIMAT0025844) described in SEQ ID NO: 129, a homolog or an ortholog of a different organism species, and the like. The hsa-miR-6716-5p gene can be obtained by a method described in Li Y et al., 2012, Gene, Vol. 497, p. 330-335. Also, "hsa-mir-6716" (miRBase Accession No. MI0022550, SEQ ID NO: 327) having a hairpin-like structure is known as a precursor of "hsa-miR-6716-5p".

The term "hsa-miR-718 gene" or "hsa-miR-718" used herein includes the hsa-miR-718 gene (miRBase Accession No. MIMAT0012735) described in SEQ ID NO: 130, a homolog or an ortholog of a different organism species, and the like. The hsa-miR-718 gene can be obtained by a method described in Artzi S et al., 2008, BMC Bioinformatics, Vol. 9, p. 39. Also, "hsa-mir-718" (miRBase Accession No. MI0012489, SEQ ID NO: 328) having a hairpin-like structure is known as a precursor of "hsa-miR-718".

The term "hsa-miR-4281 gene" or "hsa-miR-4281" used herein includes the hsa-miR-4281 gene (miRBase Accession No. MIMAT0016907) described in SEQ ID NO: 131, a homolog or an ortholog of a different organism species, and the like. The hsa-miR-4281 gene can be obtained by a method described in Goff L A et al., 2009, PLoS One, Vol. 4, e7192. Also, "hsa-mir-4281" (miRBase Accession No. MI0015885, SEQ ID NO: 329) having a hairpin-like structure is known as a precursor of "hsa-miR-4281".

The term "hsa-miR-6820-5p gene" or "hsa-miR-6820-5p" used herein includes the hsa-miR-6820-5p gene (miRBase Accession No. MIMAT0027540) described in SEQ ID NO: 132, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 330) having a hairpin-like structure is known as a precursor of "hsa-miR-6820-5p".

The term "hsa-miR-6795-5p gene" or "hsa-miR-6795-5p" used herein includes the hsa-miR-6795-5p gene (miRBase Accession No. MIMAT0027490) described in SEQ ID NO: 133, a homolog or an ortholog of a different organism species, and the like. The hsa-miR-6795-5p gene can be obtained by a method described in Ladewig E et al., 2012, Genome Res, Vol. 22, p. 1634-1645. Also, "hsa-mir-6795" (miRBase Accession No. MI0022640, SEQ ID NO: 331) having a hairpin-like structure is known as a precursor of "hsa-miR-6795-5p".

The term "hsa-miR-6779-5p gene" or "hsa-miR-6779-5p" used herein includes the hsa-miR-6779-5p gene (miRBase Accession No. MIMAT0027458) described in SEQ ID NO: 134, a homolog or an ortholog of a different organism species, and the like. The hsa-miR-6779-5p gene can be obtained by a method described in Ladewig E et al., 2012, Genome Res, Vol. 22, p. 1634-1645. Also, "hsa-mir-6779" (miRBase Accession No. MI0022624, SEQ ID NO: 332) having a hairpin-like structure is known as a precursor of "hsa-miR-6779-5p".

The term "hsa-miR-7109-5p gene" or "hsa-miR-7109-5p" used herein includes the hsa-miR-7109-5p gene (miRBase Accession No. MIMAT0028115) described in SEQ ID NO: 135, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 333) having a hairpin-like structure is known as a precursor of "hsa-miR-7109-5p".

The term "hsa-miR-6798-5p gene" or "hsa-miR-6798-5p" used herein includes the hsa-miR-6798-5p gene (miRBase Accession No. MIMAT0027496) described in SEQ ID NO: 136, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 334) having a hairpin-like structure is known as a precursor of "hsa-miR-6798-5p".

The term "hsa-miR-4648 gene" or "hsa-miR-4648" used herein includes the hsa-miR-4648 gene (miRBase Accession No. MIMAT0019710) described in SEQ ID NO: 137, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 335) having a hairpin-like structure is known as a precursor of "hsa-miR-4648".

The term "hsa-miR-8059 gene" or "hsa-miR-8059" used herein includes the hsa-miR-8059 gene (miRBase Accession No. MIMAT0030986) described in SEQ ID NO: 138, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 336) having a hairpin-like structure is known as a precursor of "hsa-miR-8059".

The term "hsa-miR-6765-3p gene" or "hsa-miR-6765-3p" used herein includes the hsa-miR-6765-3p gene (miRBase Accession No. MIMAT0027431) described in SEQ ID NO: 139, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 292) having a hairpin-like structure is known as a precursor of "hsa-miR-6765-3p".

The term "hsa-miR-6132 gene" or "hsa-miR-6132" used herein includes the hsa-miR-6132 gene (miRBase Accession No. MIMAT0024616) described in SEQ ID NO: 140, a homolog or an ortholog of a different organism species, and the like. The hsa-miR-6132 gene can be obtained by a method described in Dannemann M et al., 2012, Genome Biol Evol, Vol. 4, p. 552-564. Also, "hsa-mir-6132" (miRBase Accession No. MI0021277, SEQ ID NO: 337) having a hairpin-like structure is known as a precursor of "hsa-miR-6132".

The term "hsa-miR-4492 gene" or "hsa-miR-4492" used herein includes the hsa-miR-4492 gene (miRBase Accession No. MIMAT0019027) described in SEQ ID NO: 141, a homolog or an ortholog of a different organism species, and the like. The hsa-miR-4492 gene can be obtained by a method described in Jima D D et al., 2010, Blood, Vol. 116, e118-e127. Also, "hsa-mir-4492" (miRBase Accession No. MI0016854, SEQ ID NO: 338) having a hairpin-like structure is known as a precursor of "hsa-miR-4492".

The term "hsa-miR-7107-5p gene" or "hsa-miR-7107-5p" used herein includes the hsa-miR-7107-5p gene (miRBase Accession No. MIMAT0028111) described in SEQ ID NO: 142, a homolog or an ortholog of a different organism species, and the like. The hsa-miR-7107-5p gene can be obtained by a method described in Ladewig E et al., 2012, Genome Res, Vol. 22, p. 1634-1645. Also, "hsa-mir-7107" (miRBase Accession No. MI0022958, SEQ ID NO: 339) having a hairpin-like structure is known as a precursor of "hsa-miR-7107-5p".

The term "hsa-miR-3195 gene" or "hsa-miR-3195" used herein includes the hsa-miR-3195 gene (miRBase Accession No. MIMAT0015079) described in SEQ ID NO: 143, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 340) having a hairpin-like structure is known as a precursor of "hsa-miR-3195".

The term "hsa-miR-3180 gene" or "hsa-miR-3180" used herein includes the hsa-miR-3180 gene (miRBase Accession No. MIMAT0018178) described in SEQ ID NO: 144, a homolog or an ortholog of a different organism species, and the like. The hsa-miR-3180 gene can be obtained by a method described in Creighton C J et al., 2010, PLoS One, Vol. 5, e9637. Also, "hsa-mir-3180-4 and hsa-mir-3180-5" (miRBase Accession Nos. MI0016408 and MI0016409, SEQ ID NOs: 341 and 342) having a hairpin-like structure are known as precursors of "hsa-miR-3180".

The term "hsa-miR-296-3p gene" or "hsa-miR-296-3p" used herein includes the hsa-miR-296-3p gene (miRBase Accession No. MIMAT0004679) described in SEQ ID NO: 145, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 343) having a hairpin-like structure is known as a precursor of "hsa-miR-296-3p".

The term "hsa-miR-564 gene" or "hsa-miR-564" used herein includes the hsa-miR-564 gene (miRBase Accession No. MIMAT0003228) described in SEQ ID NO: 146, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 344) having a hairpin-like structure is known as a precursor of "hsa-miR-564".

The term "hsa-miR-1268a gene" or "hsa-miR-1268a" used herein includes the hsa-miR-1268a gene (miRBase Accession No. MIMAT0005922) described in SEQ ID NO: 147, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 345) having a hairpin-like structure is known as a precursor of "hsa-miR-1268a".

The term "hsa-miR-6848-5p gene" or "hsa-miR-6848-5p" used herein includes the hsa-miR-6848-5p gene (miRBase Accession No. MIMAT0027596) described in SEQ ID NO: 148, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 346) having a hairpin-like structure is known as a precursor of "hsa-miR-6848-5p".

The term "hsa-miR-762 gene" or "hsa-miR-762" used herein includes the hsa-miR-762 gene (miRBase Accession No. MIMAT0010313) described in SEQ ID NO: 149, a homolog or an ortholog of a different organism species, and the like. The hsa-miR-762 gene can be obtained by a method described in Berezikov E et al., 2006, Genome Res, Vol. 16, p. 1289-1298. Also, "hsa-mir-762" (miRBase Accession No. MI0003892, SEQ ID NO: 347) having a hairpin-like structure is known as a precursor of "hsa-miR-762".

The term "hsa-miR-2861 gene" or "hsa-miR-2861" used herein includes the hsa-miR-2861 gene (miRBase Accession No. MIMAT0013802) described in SEQ ID NO: 150, a homolog or an ortholog of a different organism species, and the like. The hsa-miR-2861 gene can be obtained by a method described in Li H et al., 2009, J Clin Invest, Vol. 119, p. 3666-3677. Also, "hsa-mir-2861" (miRBase Accession No. MI0013006, SEQ ID NO: 348) having a hairpin-like structure is known as a precursor of "hsa-miR-2861".

The term "hsa-miR-1203 gene" or "hsa-miR-1203" used herein includes the hsa-miR-1203 gene (miRBase Accession No. MIMAT0005866) described in SEQ ID NO: 151, a homolog or an ortholog of a different organism species, and the like. The hsa-miR-1203 gene can be obtained by a method described in Marton S et al., 2008, Leukemia, Vol. 22, p. 330-338. Also, "hsa-mir-1203" (miRBase Accession No. MI0006335, SEQ ID NO: 349) having a hairpin-like structure is known as a precursor of "hsa-miR-1203".

The term "hsa-miR-1260b gene" or "hsa-miR-1260b" used herein includes the hsa-miR-1260b gene (miRBase Accession No. MIMAT0015041) described in SEQ ID NO: 152, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 350) having a hairpin-like structure is known as a precursor of "hsa-miR-1260b".

The term "hsa-miR-4476 gene" or "hsa-miR-4476" used herein includes the hsa-miR-4476 gene (miRBase Accession No. MIMAT0019003) described in SEQ ID NO: 153, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 351) having a hairpin-like structure is known as a precursor of "hsa-miR-4476".

The term "hsa-miR-6885-5p gene" or "hsa-miR-6885-5p" used herein includes the hsa-miR-6885-5p gene (miRBase Accession No. MIMAT0027670) described in SEQ ID NO: 154, a homolog or an ortholog of a different organism species, and the like. The hsa-miR-6885-5p gene can be obtained by a method described in Ladewig E et al., 2012, Genome Res, Vol. 22, p. 1634-1645. Also, "hsa-mir-6885" (miRBase Accession No. MI0022732, SEQ ID NO: 352) having a hairpin-like structure is known as a precursor of "hsa-miR-6885-5p".

The term "hsa-miR-6769b-5p gene" or "hsa-miR-6769b-5p" used herein includes the hsa-miR-6769b-5p gene (miRBase Accession No. MIMAT0027620) described in SEQ ID NO: 155, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706, SEQ ID NO: 353) having a hairpin-like structure is known as a precursor of "hsa-miR-6769b-5p".

The term "hsa-miR-23b-3p gene" or "hsa-miR-23b-3p" used herein includes the hsa-miR-23b-3p gene (miRBase Accession No. MIMAT0000418) described in SEQ ID NO: 156, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 354) having a hairpin-like structure is known as a precursor of "hsa-miR-23b-3p".

The term "hsa-miR-1343-5p gene" or "hsa-miR-1343-5p" used herein includes the hsa-miR-1343-5p gene (miRBase Accession No. MIMAT0027038) described in SEQ ID NO: 157, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 202) having a hairpin-like structure is known as a precursor of "hsa-miR-1343-5p".

The term "hsa-miR-3621 gene" or "hsa-miR-3621" used herein includes the hsa-miR-3621 gene (miRBase Accession No. MIMAT0018002) described in SEQ ID NO: 158, and a homolog or an ortholog of a different organism species, and the like. The hsa-miR-3621 gene can be obtained by a method described in Witten D et al., 2010, BMC Biol, Vol. 8, p. 58. Also, "hsa-mir-3621" (miRBase Accession No. MI0016012, SEQ ID NO: 355) having a hairpin-like structure is known as a precursor of "hsa-miR-3621".

The term "hsa-miR-4688 gene" or "hsa-miR-4688" used herein includes the hsa-miR-4688 gene (miRBase Accession No. MIMAT0019777) described in SEQ ID NO: 159, a homolog or an ortholog of a different organism species, and the like. The hsa-miR-4688 gene can be obtained by a method described in Persson H et al., 2011, Cancer Res, Vol. 71, p. 78-86. Also, "hsa-mir-4688" (miRBase Accession No. MI0017321, SEQ ID NO: 356) having a hairpin-like structure is known as a precursor of "hsa-miR-4688".

The term "hsa-miR-4286 gene" or "hsa-miR-4286" used herein includes the hsa-miR-4286 gene (miRBase Accession No. MIMAT0016916) described in SEQ ID NO: 160, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 357) having a hairpin-like structure is known as a precursor of "hsa-miR-4286".

The term "hsa-miR-4640-5p gene" or "hsa-miR-4640-5p" used herein includes the hsa-miR-4640-5p gene (miRBase Accession No. MIMAT0019699) described in SEQ ID NO: 161, a homolog or an ortholog of a different organism species, and the like. The hsa-miR-4640-5p gene can be obtained by a method described in Persson H et al., 2011, Cancer Res, Vol. 71, p. 78-86. Also, "hsa-mir-4640" (miRBase Accession No. MI0017267, SEQ ID NO: 358) having a hairpin-like structure is known as a precursor of "hsa-miR-4640-5p".

The term "hsa-miR-4739 gene" or "hsa-miR-4739" used herein includes the hsa-miR-4739 gene (miRBase Accession No. MIMAT0019868) described in SEQ ID NO: 162, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. MI0017377, SEQ ID NO: 359) having a hairpin-like structure is known as a precursor of "hsa-miR-4739".

The term "hsa-miR-1260a gene" or "hsa-miR-1260a" used herein includes the hsa-miR-1260a gene (miRBase Accession No. MIMAT0005911) described in SEQ ID NO: 163, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. MI0006394, SEQ ID NO: 360) having a hairpin-like structure is known as a precursor of "hsa-miR-1260a".

The term "hsa-miR-4276 gene" or "hsa-miR-4276" used herein includes the hsa-miR-4276 gene (miRBase Accession No. MIMAT0016904) described in SEQ ID NO: 164, a homolog or an ortholog of a different organism species, and the like. The hsa-miR-4276 gene can be obtained by a method described in Goff L A et al., 2009, PLoS One, Vol. 4, e7192. Also, "hsa-mir-4276" (miRBase Accession No. MI0015882, SEQ ID NO: 361) having a hairpin-like structure is known as a precursor of "hsa-miR-4276".

The term "hsa-miR-7106-5p gene" or "hsa-miR-7106-5p" used herein includes the hsa-miR-7106-5p gene (miRBase Accession No. MIMAT0028109) described in SEQ ID NO: 165, a homolog or an ortholog of a different organism species, and the like. The hsa-miR-7106-5p gene can be obtained by a method described in Ladewig E et al., 2012, Genome Res, Vol. 22, p. 1634-1645. Also, "hsa-mir-7106" (miRBase Accession No. MI0022957, SEQ ID NO: 362) having a hairpin-like structure is known as a precursor of "hsa-miR-7106-5p".

The term "hsa-miR-128-2-5p gene" or "hsa-miR-128-2-5p" used herein includes the hsa-miR-128-2-5p gene (miRBase Accession No. MIMAT0031095) described in SEQ ID NO: 166, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 363) having a hairpin-like structure is known as a precursor of "hsa-miR-128-2-5p".

The term "hsa-miR-125a-3p gene" or "hsa-miR-125a-3p" used herein includes the hsa-miR-125a-3p gene (miRBase Accession No. MIMAT0004602) described in SEQ ID NO: 167, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 364) having a hairpin-like structure is known as a precursor of "hsa-miR-125a-3p".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 168, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 365) having a hairpin-like structure is known as a precursor of "hsa-miR-92a-2-5p".

The term "hsa-miR-486-3p gene" or "hsa-miR-486-3p" used herein includes the hsa-miR-486-3p gene (miRBase Accession No. MIMAT0004762) described in SEQ ID NO: 169, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 366 and 367) having a hairpin-like structure are known as precursors of "hsa-miR-486-3p".

The term "hsa-miR-3196 gene" or "hsa-miR-3196" used herein includes the hsa-miR-3196 gene (miRBase Accession No. MIMAT0015080) described in SEQ ID NO: 170, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 368) having a hairpin-like structure is known as a precursor of "hsa-miR-3196".

The term "hsa-miR-211-3p gene" or "hsa-miR-211-3p" used herein includes the hsa-miR-211-3p gene (miRBase Accession No. MIMAT0022694) described in SEQ ID NO: 171, a homolog or an ortholog of a different organism species, and the like. The hsa-miR-211-3p gene can be obtained by a method described in Lim L P et al., 2003, Science, Vol. 299, p. 1540. Also, "hsa-mir-211" (miRBase Accession No. MI0000287, SEQ ID NO: 369) having a hairpin-like structure is known as a precursor of "hsa-miR-211-3p".

The term "hsa-miR-4271 gene" or "hsa-miR-4271" used herein includes the hsa-miR-4271 gene (miRBase Accession No. MIMAT0016901) described in SEQ ID NO: 172, a homolog or an ortholog of a different organism species, and the like. The hsa-miR-4271 gene can be obtained by a method described in Goff L A et al., 2009, PLoS One, Vol. 4, e7192. Also, "hsa-mir-4271" (miRBase Accession No. MI0015879, SEQ ID NO: 370) having a hairpin-like structure is known as a precursor of "hsa-miR-4271".

The term "hsa-miR-6851-5p gene" or "hsa-miR-6851-5p" used herein includes the hsa-miR-6851-5p gene (miRBase Accession No. MIMAT0027602) described in SEQ ID NO: 173, a homolog or an ortholog of a different organism species, and the like. The hsa-miR-6851-5p gene can be obtained by a method described in Ladewig E et al., 2012, Genome Res, Vol. 22, p. 1634-1645. Also, "hsa-mir-6851" (miRBase Accession No. MI0022697, SEQ ID NO: 371) having a hairpin-like structure is known as a precursor of "hsa-miR-6851-5p".

The term "hsa-miR-149-3p gene" or "hsa-miR-149-3p" used herein includes the hsa-miR-149-3p gene (miRBase Accession No. MIMAT0004609) described in SEQ ID NO: 174, a homolog or an ortholog of a different organism species, and the like. The hsa-miR-149-3p gene can be obtained by a method described in Lagos-Quintana M et al., 2002, Curr Biol, Vol. 12, p. 735-739. Also, "hsa-mir-149" (miRBase Accession No. MI0000478, SEQ ID NO: 372) having a hairpin-like structure is known as a precursor of "hsa-miR-149-3p".

The term "hsa-miR-4667-5p gene" or "hsa-miR-4667-5p" used herein includes the hsa-miR-4667-5p gene (miRBase Accession No. MIMAT0019743) described in SEQ ID NO: 175, a homolog or an ortholog of a different organism species, and the like. The hsa-miR-4667-5p gene can be obtained by a method described in Persson H et al., 2011, Cancer Res, Vol. 71, p. 78-86. Also, "hsa-mir-4667" (miRBase Accession No. MI0017297, SEQ ID NO: 373) having a hairpin-like structure is known as a precursor of "hsa-miR-4667-5p".

The term "hsa-miR-135a-3p gene" or "hsa-miR-135a-3p" used herein includes the hsa-miR-135a-3p gene (miRBase Accession No. MIMAT0004595) described in SEQ ID NO: 176, a homolog or an ortholog of a different organism species, and the like. The hsa-miR-135a-3p gene can be obtained by a method described in Lagos-Quintana M et al., 2002, Curr Biol, Vol. 12, p. 735-739. Also, "hsa-mir-135a-1" (miRBase Accession No. MI0000452, SEQ ID NO: 374) having a hairpin-like structure is known as a precursor of "hsa-miR-135a-3p".

The term "hsa-miR-4486 gene" or "hsa-miR-4486" used herein includes the hsa-miR-4486 gene (miRBase Accession No. MIMAT0019020) described in SEQ ID NO: 177, a homolog or an ortholog of a different organism species, and the like. The hsa-miR-4486 gene can be obtained by a method described in Jima D D et al., 2010, Blood, Vol. 116, e118-e127. Also, "hsa-mir-4486" (miRBase Accession No. MI0016847, SEQ ID NO: 375) having a hairpin-like structure is known as a precursor of "hsa-miR-4486".

The term "hsa-miR-4697-5p gene" or "hsa-miR-4697-5p" used herein includes the hsa-miR-4697-5p gene (miRBase Accession No. MIMAT0019791) described in SEQ ID NO: 178, a homolog or an ortholog of a different organism species, and the like. The hsa-miR-4697-5p gene can be obtained by a method described in Persson H et al., 2011, Cancer Res, Vol. 71, p. 78-86. Also, "hsa-mir-4697" (miRBase Accession No. MI0017330, SEQ ID NO: 376) having a hairpin-like structure is known as a precursor of "hsa-miR-4697-5p".

The term "hsa-miR-4725-3p gene" or "hsa-miR-4725-3p" used herein includes the hsa-miR-4725-3p gene (miRBase Accession No. MIMAT0019844) described in SEQ ID NO: 179, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 377) having a hairpin-like structure is known as a precursor of "hsa-miR-4725-3p".

The term "hsa-miR-6510-5p gene" or "hsa-miR-6510-5p" used herein includes the hsa-miR-6510-5p gene (miRBase Accession No. MIMAT0025476) described in SEQ ID NO: 180, a homolog or an ortholog of a different organism species, and the like. The hsa-miR-6510-5p gene can be obtained by a method described in Joyce C E et al., 2011, Hum Mol Genet, Vol. 20, p. 4025-4040. Also, "hsa-mir-6510" (miRBase Accession No. MI0022222, SEQ ID NO: 378) having a hairpin-like structure is known as a precursor of "hsa-miR-6510-5p".

The term "hsa-miR-5001-5p gene" or "hsa-miR-5001-5p" used herein includes the hsa-miR-5001-5p gene (miRBase Accession No. MIMAT0021021) described in SEQ ID NO: 181, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 379) having a hairpin-like structure is known as a precursor of "hsa-miR-5001-5p".

The term "hsa-miR-4673 gene" or "hsa-miR-4673" used herein includes the hsa-miR-4673 gene (miRBase Accession No. MIMAT0019755) described in SEQ ID NO: 182, a homolog or an ortholog of a different organism species, and the like. The hsa-miR-4673 gene can be obtained by a method described in Persson H et al., 2011, Cancer Res, Vol. 71, p. 78-86. Also, "hsa-mir-4673" (miRBase Accession No. MI0017304, SEQ ID NO: 380) having a hairpin-like structure is known as a precursor of "hsa-miR-4673".

The term "hsa-miR-4466 gene" or "hsa-miR-4466" used herein includes the hsa-miR-4466 gene (miRBase Accession No. MIMAT0018993) described in SEQ ID NO: 183, a homolog or an ortholog of a different organism species, and the like. The hsa-miR-4466 gene can be obtained by a method described in Jima D D et al., 2010, Blood, Vol. 116, e118-e127. Also, "hsa-mir-4466" (miRBase Accession No. MI0016817, SEQ ID NO: 381) having a hairpin-like structure is known as a precursor of "hsa-miR-4466".

The term "hsa-miR-23a-3p gene" or "hsa-miR-23a-3p" used herein includes the hsa-miR-23a-3p gene (miRBase Accession No. MIMAT0000078) described in SEQ ID NO: 184, a homolog or an ortholog of a different organism species, and the like. The hsa-miR-23a-3p gene can be obtained by a method described in Lagos-Quintana M et al., 2001, Science, Vol. 294, p. 853-858. Also, "hsa-mir-23a" (miRBase Accession No. MI0000079, SEQ ID NO: 382) having a hairpin-like structure is known as a precursor of "hsa-miR-23a-3p".

The term "hsa-miR-3656 gene" or "hsa-miR-3656" used herein includes the hsa-miR-3656 gene (miRBase Accession No. MIMAT0018076) described in SEQ ID NO: 185, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 383) having a hairpin-like structure is known as a precursor of "hsa-miR-3656".

The term "hsa-miR-6782-5p gene" or "hsa-miR-6782-5p" used herein includes the hsa-miR-6782-5p gene (miRBase Accession No. MIMAT0027464) described in SEQ ID NO: 186, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 384) having a hairpin-like structure is known as a precursor of "hsa-miR-6782-5p".

The term "hsa-miR-4689 gene" or "hsa-miR-4689" used herein includes the hsa-miR-4689 gene (miRBase Accession No. MIMAT0019778) described in SEQ ID NO: 187, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 385) having a hairpin-like structure is known as a precursor of "hsa-miR-4689".

The term "hsa-miR-451a gene" or "hsa-miR-451a" used herein includes the hsa-miR-451a gene (miRBase Accession No. MIMAT0001631) described in SEQ ID NO: 188, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 386) having a hairpin-like structure is known as a precursor of "hsa-miR-451a".

The term "hsa-miR-4446-3p gene" or "hsa-miR-4446-3p" used herein includes the hsa-miR-4446-3p gene (miRBase Accession No. MIMAT0018965) described in SEQ ID NO: 189, a homolog or an ortholog of a different organism species, and the like. The hsa-miR-4446-3p gene can be obtained by a method described in Jima D D et al., 2010, Blood, Vol. 116, e118-e127. Also, "hsa-mir-4446" (miRBase Accession No. MI0016789, SEQ ID NO: 387) having a hairpin-like structure is known as a precursor of "hsa-miR-4446-3p".

The term "hsa-miR-3180-3p gene" or "hsa-miR-3180-3p" used herein includes the hsa-miR-3180-3p gene (miRBase Accession No. MIMAT0015058) described in SEQ ID NO: 190, a homolog or an ortholog of a different organism species, and the like. The hsa-miR-3180-3p gene can be obtained by a method described in Creighton C J et al., 2010, PLoS One, Vol. 5, e9637. Also, "hsa-mir-3180-1, hsa-mir-3180-2, and hsa-mir-3180-3" (miRBase Accession Nos. MI0014214, MI0014215, and MI0014217, SEQ ID NOs: 388, 389, and 390) having a hairpin-like structure are known as precursors of "hsa-miR-3180-3p".

The term "hsa-miR-642a-3p gene" or "hsa-miR-642a-3p" used herein includes the hsa-miR-642a-3p gene (miRBase Accession No. MIMAT0020924) described in SEQ ID NO: 191, a homolog or an ortholog of a different organism species, and the like. The hsa-miR-642a-3p gene can be obtained by a method described in Cummins J M et al., 2006, Proc Natl Acad Sci U S A, Vol. 103, p. 3687-3692. Also, "hsa-mir-642a" (miRBase Accession No. MI0003657, SEQ ID NO: 391) having a hairpin-like structure is known as a precursor of "hsa-miR-642a-3p".

The term "hsa-miR-6889-5p gene" or "hsa-miR-6889-5p" used herein includes the hsa-miR-6889-5p gene (miRBase Accession No. MIMAT0027678) described in SEQ ID NO: 192, a homolog or an ortholog of a different organism species, and the like. The hsa-miR-6889-5p gene can be obtained by a method described in Ladewig E et al., 2012, Genome Res, Vol. 22, p. 1634-1645. Also, "hsa-mir-6889" (miRBase Accession No. MI0022736, SEQ ID NO: 392) having a hairpin-like structure is known as a precursor of "hsa-miR-6889-5p".

The term "hsa-miR-3178 gene" or "hsa-miR-3178" used herein includes the hsa-miR-3178 gene (miRBase Accession No. MIMAT0015055) described in SEQ ID NO: 193, a homolog or an ortholog of a different organism species, and the like. The hsa-miR-3178 gene can be obtained by a method described in Stark M S et al., 2010, PLoS One, Vol. 5, e9685. Also, "hsa-mir-3178" (miRBase Accession No. MI0014212, SEQ ID NO: 393) having a hairpin-like structure is known as a precursor of "hsa-miR-3178".

The term "hsa-miR-4665-5p gene" or "hsa-miR-4665-5p" used herein includes the hsa-miR-4665-5p gene (miRBase Accession No. MIMAT0019739) described in SEQ ID NO: 194, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 323) having a hairpin-like structure is known as a precursor of "hsa-miR-4665-5p".

The term "hsa-miR-6722-3p gene" or "hsa-miR-6722-3p" used herein includes the hsa-miR-6722-3p gene (miRBase Accession No. MIMAT0025854) described in SEQ ID NO: 195, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 394) having a hairpin-like structure is known as a precursor of "hsa-miR-6722-3p".

The term "hsa-miR-30c-1-3p gene" or "hsa-miR-30c-1-3p" used herein includes the hsa-miR-30c-1-3p gene (miRBase Accession No. MIMAT0004674) described in SEQ ID NO: 196, a homolog or an ortholog of a different organism species, and the like. The hsa-miR-30c-1-3p gene can be obtained by a method described in Lagos-Quintana M et al., 2002, Curr Biol, Vol. 12, p. 735-739. Also, "hsa-miR-30c-1" (miRBase Accession No. MI0000736, SEQ ID NO: 395) having a hairpin-like structure is known as a precursor of "hsa-miR-30c-1-3p".

The term "hsa-miR-4507 gene" or "hsa-miR-4507" used herein includes the hsa-miR-4507 gene (miRBase Accession No. MIMAT0019044) described in SEQ ID NO: 197, a homolog or an ortholog of a different organism species, and the like. The hsa-miR-4507 gene can be obtained by a method described in Jima D D et al., 2010, Blood, Vol. 116, e118-e127. Also, "hsa-mir-4507" (miRBase Accession No. MI0016871, SEQ ID NO: 396) having a hairpin-like structure is known as a precursor of "hsa-miR-4507".

The term "hsa-miR-3141 gene" or "hsa-miR-3141" used herein includes the hsa-miR-3141 gene (miRBase Accession No. MIMAT0015010) described in SEQ ID NO: 198, a homolog or an ortholog of a different organism species, and the like. The hsa-miR-3141 gene can be obtained by a method described in Stark M S et al., 2010, PLoS One, Vol. 5, e9685. Also, "hsa-mir-3141" (miRBase Accession No. MI0014165, SEQ ID NO: 397) having a hairpin-like structure is known as a precursor of "hsa-miR-3141".

The term "hsa-miR-1199-5p gene" or "hsa-miR-1199-5p" used herein includes the hsa-miR-1199-5p gene (miRBase Accession No. MIMAT0031119) described in SEQ ID NO:

199, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 398) having a hairpin-like structure is known as a precursor of "hsa-miR-1199-5p".

The term "hsa-miR-6794-5p gene" or "hsa-miR-6794-5p" used herein includes the hsa-miR-6794-5p gene (miRBase Accession No. MIMAT0027488) described in SEQ ID NO: 635, a homolog or an ortholog of a different organism species, and the like. The hsa-miR-6794-5p gene can be obtained by a method described in Ladewig E et al., 2012, Genome Res, Vol. 22, p. 1634-1645. Also, "hsa-mir-6794" (miRBase Accession No. MI0022639, SEQ ID NO: 643) having a hairpin-like structure is known as a precursor of "hsa-miR-6794-5p".

The term "hsa-miR-6774-5p gene" or "hsa-miR-6774-5p" used herein includes the hsa-miR-6774-5p gene (miRBase Accession No. MIMAT0027448) described in SEQ ID NO: 636, a homolog or an ortholog of a different organism species, and the like. The hsa-miR-6774-5p gene can be obtained by a method described in Ladewig E et al., 2012, Genome Res, Vol. 22, p. 1634-1645. Also, "hsa-mir-6774" (miRBase Accession No. MI0022619, SEQ ID NO: 644) having a hairpin-like structure is known as a precursor of "hsa-miR-6774-5p".

The term "hsa-miR-4707-3p gene" or "hsa-miR-4707-3p" used herein includes the hsa-miR-4707-3p gene (miRBase Accession No. MIMAT0019808) described in SEQ ID NO: 637, a homolog or an ortholog of a different organism species, and the like. The hsa-miR-4707-3p gene can be obtained by a method described in Persson H et al., 2011, Cancer Res, Vol. 71, p. 78-86. Also, "hsa-mir-4707" (miRBase Accession No. MI0017340, SEQ ID NO: 645) having a hairpin-like structure is known as a precursor of "hsa-miR-4707-3p".

The term "hsa-miR-4534 gene" or "hsa-miR-4534" used herein includes the hsa-miR-4534 gene (miRBase Accession No. MIMAT0019073) described in SEQ ID NO: 638, a homolog or an ortholog of a different organism species, and the like. The hsa-miR-4534 gene can be obtained by a method described in Jima D D et al., 2010, Blood., Vol. 116, e118-e127. Also, "hsa-mir-4534" (miRBase Accession No. MI0016901, SEQ ID NO: 646) having a hairpin-like structure is known as a precursor of "hsa-miR-4534".

The term "hsa-miR-4294 gene" or "hsa-miR-4294" used herein includes the hsa-miR-4294 gene (miRBase Accession No. MIMAT0016849) described in SEQ ID NO: 639, a homolog or an ortholog of a different organism species, and the like. The hsa-miR-4294 gene can be obtained by a method described in Goff L A et al., 2009, PLoS One., Vol. 4, e7192. Also, "hsa-mir-4294" (miRBase Accession No. MI0015827, SEQ ID NO: 647) having a hairpin-like structure is known as a precursor of "hsa-miR-4294".

The term "hsa-miR-6850-5p gene" or "hsa-miR-6850-5p" used herein includes the hsa-miR-6850-5p gene (miRBase Accession No. MIMAT0027600) described in SEQ ID NO: 640, a homolog or an ortholog of a different organism species, and the like. The hsa-miR-6850-5p gene can be obtained by a method described in Ladewig E et al., 2012, Genome Res., Vol. 22, p. 1634-1645. Also, "hsa-mir-6850" (miRBase Accession No. MI0022696, SEQ ID NO: 648) having a hairpin-like structure is known as a precursor of "hsa-miR-6850-5p".

The term "hsa-miR-6089 gene" or "hsa-miR-6089" used herein includes the hsa-miR-6089 gene (miRBase Accession No. MIMAT0023714) described in SEQ ID NO: 641, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1 and hsa-mir-6089-2" (miRBase Accession Nos. MI0020366 and MI0023563, SEQ ID NOs: 649 and 650) having a hairpin-like structure are known as precursors of "hsa-miR-6089".

The term "hsa-miR-671-5p gene" or "hsa-miR-671-5p" used herein includes the hsa-miR-671-5p gene (miRBase Accession No. MIMAT0003880) described in SEQ ID NO: 642, a homolog or an ortholog of a different organism species, and the like. The hsa-miR-671-5p gene can be obtained by a method described in Berezikov E et al., 2006, Genome Res, Vol. 16, p. 1289-1298. Also, "hsa-mir-671" (miRBase Accession No. MI0003760, SEQ ID NO: 651) having a hairpin-like structure is known as a precursor of "hsa-miR-671-5p".

A mature miRNA may become a variant due to the sequence cleaved shorter or longer by one to several flanking nucleotides or due to substitution of nucleotides when cleaved as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 199 and 635 to 642 as well as a large number of the nucleotide sequence variants and fragments represented by SEQ ID NOs: 399 to 634 and 652 to 657, called isomiRs. These variants can also be obtained as miRNAs having a nucleotide sequence represented by any of SEQ ID NOs: 1 to 199 and 635 to 642.

Specifically, among the variants of polynucleotides consisting of the nucleotide sequence represented by any of SEQ ID NOs: 3, 4, 11, 13, 14, 18, 20, 21, 26, 29, 35, 36, 39, 41, 42, 45, 46, 47, 48, 49, 51, 53, 54, 55, 56, 57, 58, 59, 60, 62, 65, 66, 67, 68, 71, 72, 73, 74, 75, 76, 78, 82, 83, 88, 90, 91, 92, 94, 95, 98, 99, 101, 102, 103, 104, 106, 107, 108, 109, 110, 113, 116, 117, 118, 120, 121, 122, 123, 125, 128, 129, 130, 131, 137, 140, 141, 143, 144, 145, 146, 147, 150, 152, 153, 156, 159, 160, 161, 162, 163, 166, 167, 168, 169, 170, 171, 172, 174, 175, 176, 177, 179, 180, 181, 182, 183, 184, 185, 187, 188, 189, 190, 191, 193, 194, 196, 197, 198, 637, 641 and 642 or a nucleotide sequence derived from the nucleotide sequence by the replacement of u with t according to the present invention, examples of the longest variants registered in the miRBase Release 20 include polynucleotides represented by SEQ ID NOs: 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 652, 654 and 656, respectively.

Also, among the variants of polynucleotides consisting of a nucleotide sequence represented by any of SEQ ID NOs: 3, 4, 11, 13, 14, 18, 20, 21, 26, 29, 35, 36, 39, 41, 42, 45, 46, 47, 48, 49, 51, 53, 54, 55, 56, 57, 58, 59, 60, 62, 65, 66, 67, 68, 71, 72, 73, 74, 75, 76, 78, 82, 83, 88, 90, 91, 92, 94, 95, 98, 99, 101, 102, 103, 104, 106, 107, 108, 109, 110, 113, 116, 117, 118, 120, 121, 122, 123, 125, 128, 129, 130, 131, 137, 140, 141, 143, 144, 145, 146, 147, 150, 152, 153, 156, 159, 160, 161, 162, 163, 166, 167, 168, 169, 170, 171, 172, 174, 175, 176, 177, 179, 180, 181, 182, 183, 184, 185, 187, 188, 189, 190, 191, 193, 194, 196, 197, 198, 637, 641 and 642 or a nucleotide sequence derived from the nucleotide sequence by the replacement of u with t according to the present invention, examples of the shortest variants registered in the miRBase Release 20 include polynucleotides having sequences represented by SEQ ID NOs: 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 653, 655 and 657, respectively. In addition to these variants and fragments, examples thereof include a large number of isomiR polynucleotides of SEQ ID NOs: 1 to 199 and 635 to 642 registered in the miRBase. Examples of the polynucleotide comprising a nucleotide sequence represented by any of SEQ ID NOs: 1 to 199 and 635 to 642 include a polynucleotide represented by any of SEQ ID NOs: 200 to 398 and 643 to 651, which are their respective precursors.

The terms and miRBase Accession Nos. (registration numbers) of the genes represented by SEQ ID NOs: 1 to 657 are shown in Table 1.

The term "capable of specifically binding" used herein means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-4257 | MIMAT0016878 |
| 2 | hsa-miR-6726-5p | MIMAT0027353 |
| 3 | hsa-miR-1343-3p | MIMAT0019776 |
| 4 | hsa-miR-1247-3p | MIMAT0022721 |
| 5 | hsa-miR-6787-5p | MIMAT0027474 |
| 6 | hsa-miR-6875-5p | MIMAT0027650 |
| 7 | hsa-miR-1225-3p | MIMAT0005573 |
| 8 | hsa-miR-8063 | MIMAT0030990 |
| 9 | hsa-miR-6781-5p | MIMAT0027462 |
| 10 | hsa-miR-4746-3p | MIMAT0019881 |
| 11 | hsa-miR-1908-5p | MIMAT0007881 |
| 12 | hsa-miR-6756-5p | MIMAT0027412 |
| 13 | hsa-miR-204-3p | MIMAT0022693 |
| 14 | hsa-miR-4651 | MIMAT0019715 |
| 15 | hsa-miR-6757-5p | MIMAT0027414 |
| 16 | hsa-miR-6825-5p | MIMAT0027550 |
| 17 | hsa-miR-7108-5p | MIMAT0028113 |
| 18 | hsa-miR-4792 | MIMAT0019964 |
| 19 | hsa-miR-7641 | MIMAT0029782 |
| 20 | hsa-miR-3188 | MIMAT0015070 |
| 21 | hsa-miR-3131 | MIMAT0014996 |
| 22 | hsa-miR-6780b-5p | MIMAT0027572 |
| 23 | hsa-miR-8069 | MIMAT0030996 |
| 24 | hsa-miR-6840-3p | MTMAT0027583 |
| 25 | hsa-miR-8072 | MIMAT0030999 |
| 26 | hsa-niiR-1233-5p | MIMAT0022943 |
| 27 | hsa-miR-6887-5p | MIMAT0027674 |
| 28 | hsa-miR-1231 | MIMAT0005586 |
| 29 | hsa-miR-5572 | MIMAT0022260 |
| 30 | hsa-miR-6738-5p | MIMAT0027377 |
| 31 | hsa-miR-6784-5p | MIMAT0027468 |
| 32 | hsa-miR-6791-5p | MIMAT0027482 |
| 33 | hsa-miR-6749-5p | MIMAT0027398 |
| 34 | hsa-miR-6741-5p | MIMAT0027383 |
| 35 | hsa-miR-128-1-5p | MIMAT0026477 |
| 36 | hsa-miR-4419b | MIMAT0019034 |
| 37 | hsa-miR-6746-5p | MIMAT0027392 |
| 38 | hsa-miR-3184-5p | MIMAT0015064 |
| 39 | hsa-miR-3679-5p | MIMAT0018104 |
| 40 | hsa-miR-7110-5p | MIMAT0028117 |
| 41 | hsa-miR-4516 | MIMAT0019053 |
| 42 | hsa-miR-6717-5p | MIMAT0025846 |
| 43 | hsa-miR-6826-5p | MIMAT0027552 |
| 44 | hsa-miR-4433b-3p | MIMAT0030414 |
| 45 | hsa-miR-3679-3p | MIMAT0018105 |
| 46 | hsa-miR-3135b | MIMAT0018985 |
| 47 | hsa-miR-3622a-5p | MIMAT0018003 |
| 48 | hsa-miR-711 | MIMAT0012734 |
| 49 | hsa-miR-4467 | MIMAT0018994 |
| 50 | hsa-miR-6857-5p | MIMAT0027614 |
| 51 | hsa-miR-6515-3p | MIMAT0025487 |
| 52 | hsa-miR-1225-5p | MIMAT0005572 |
| 53 | hsa-miR-187-5p | MIMAT0004561 |
| 54 | hsa-miR-3185 | MIMAT0015065 |
| 55 | hsa-miR-642b-3p | MIMAT0018444 |
| 56 | hsa-miR-1249 | MIMAT0005901 |
| 57 | hsa-miR-744-5p | MIMAT0004945 |
| 58 | hsa-miR-4442 | MIMAT0018960 |
| 59 | hsa-miR-1228-3p | MIMAT0005583 |
| 60 | hsa-miR-939-5p | MIMAT0004982 |
| 61 | hsa-miR-6845-5p | MIMAT0027590 |
| 62 | hsa-miR-887-3p | MIMAT0004951 |
| 63 | hsa-miR-7845-5p | MIMAT0030420 |
| 64 | hsa-miR-6729-5p | MIMAT0027359 |
| 65 | hsa-miR-4632-5p | MIMAT0022977 |
| 66 | hsa-miR-615-5p | MIMAT0004804 |
| 67 | hsa-miR-6724-5p | MIMAT0025856 |
| 68 | hsa-miR-4728-5p | MIMAT0019849 |
| 69 | hsa-miR-6732-5p | MIMAT0027365 |
| 70 | hsa-miR-6816-5p | MIMAT0027532 |
| 71 | hsa-miR-4695-5p | MIMAT0019788 |
| 72 | hsa-miR-6088 | MIMAT0023713 |
| 73 | hsa-miR-7975 | MIMAT0031178 |
| 74 | hsa-miR-3197 | MIMAT0015082 |
| 75 | hsa-miR-6125 | MIMAT0024598 |
| 76 | hsa-miR-4433-3p | MIMAT0018949 |
| 77 | hsa-miR-6727-5p | MIMAT0027355 |
| 78 | hsa-miR-4706 | MIMAT0019806 |
| 79 | hsa-miR-7847-3p | MIMAT0030422 |
| 80 | hsa-miR-6805-3p | MIMAT0027511 |
| 81 | hsa-miR-6766-3p | MIMAT0027433 |
| 82 | hsa-miR-1913 | MIMAT0007888 |
| 83 | hsa-miR-4649-5p | MIMAT0019711 |
| 84 | hsa-miR-602 | MIMAT0003270 |
| 85 | hsa-miR-3663-3p | MIMAT0018085 |
| 86 | hsa-miR-6893-5p | MIMAT0027686 |
| 87 | hsa-miR-6861-5p | MIMAT0027623 |
| 88 | hsa-miR-4449 | MIMAT0018968 |
| 89 | hsa-miR-6842-5p | MIMAT0027586 |
| 90 | hsa-miR-4454 | MIMAT0018976 |
| 91 | hsa-miR-5195-3p | MIMAT0021127 |
| 92 | hsa-miR-663b | MIMAT0005867 |
| 93 | hsa-miR-6765-5p | MIMAT0027430 |
| 94 | hsa-miR-4513 | MIMAT0019050 |
| 95 | hsa-miR-614 | MIMAT0003282 |
| 96 | hsa-miR-6785-5p | MIMAT0027470 |
| 97 | hsa-miR-6777-5p | MIMAT0027454 |
| 98 | hsa-miR-940 | MIMAT0004983 |
| 99 | hsa-miR-4741 | MIMAT0019871 |
| 100 | hsa-miR-6870-5p | MIMAT0027640 |
| 101 | hsa-miR-6131 | MIMAT0024615 |
| 102 | hsa-miR-150-3p | MIMAT0004610 |
| 103 | hsa-miR-4707-5p | MIMAT0019807 |
| 104 | hsa-miR-1915-3p | MIMAT0007892 |
| 105 | hsa-miR-3937 | MIMAT0018352 |
| 106 | hsa-miR-937-5p | MIMAT0022938 |
| 107 | hsa-miR-4443 | MIMAT0018961 |
| 108 | hsa-miR-1914-3p | MIMAT0007890 |
| 109 | hsa-miR-3620-5p | MIMAT0022967 |
| 110 | hsa-miR-1268b | MIMAT0018925 |
| 111 | hsa-miR-1227-5p | MIMAT0022941 |
| 112 | hsa-miR-6880-5p | MIMAT0027660 |
| 113 | hsa-miR-4417 | MIMAT0018929 |
| 114 | hsa-miR-6802-5p | MIMAT0027504 |

TABLE 1-continued

| SEQ ID NO: | Gene name | miRBase registration No. |
|---|---|---|
| 115 | hsa-miR-6769a-5p | MIMAT0027438 |
| 116 | hsa-miR-663a | MIMAT0003326 |
| 117 | hsa-miR-6721-5p | MIMAT0025852 |
| 118 | hsa-miR-4532 | MIMAT0019071 |
| 119 | hsa-miR-7977 | MIMAT0031180 |
| 120 | hsa-miR-92b-5p | MIMAT0004792 |
| 121 | hsa-miR-371a-5p | MIMAT0004687 |
| 122 | hsa-miR-6126 | MIMAT0024599 |
| 123 | hsa-miR-4734 | MIMAT0019859 |
| 124 | hsa-miR-4665-3p | MIMAT0019740 |
| 125 | hsa-miR-423-5p | MIMAT0004748 |
| 126 | hsa-miR-1469 | MIMAT0007347 |
| 127 | hsa-miR-4675 | MIMAT0019757 |
| 128 | hsa-miR-1915-5p | MIMAT0007891 |
| 129 | hsa-miR-6716-5p | MIMAT0025844 |
| 130 | hsa-miR-718 | MIMAT0012735 |
| 131 | hsa-miR-4281 | MIMAT0016907 |
| 132 | hsa-miR-6820-5p | MIMAT0027540 |
| 133 | hsa-miR-6795-5p | MIMAT0027490 |
| 134 | hsa-miR-6779-5p | MIMAT0027458 |
| 135 | hsa-miR-7109-5p | MIMAT0028115 |
| 136 | hsa-miR-6798-5p | MIMAT0027496 |
| 137 | hsa-miR-4648 | MIMAT0019710 |
| 138 | hsa-miR-8059 | MIMAT0030986 |
| 139 | hsa-miR-6765-3p | MIMAT0027431 |
| 140 | hsa-miR-6132 | MIMAT0024616 |
| 141 | hsa-miR-4492 | MIMAT0019027 |
| 142 | hsa-miR-7107-5p | MIMAT0028111 |
| 143 | hsa-miR-3195 | MIMAT0015079 |
| 144 | hsa-miR-3180 | MIMAT0018178 |
| 145 | hsa-miR-296-3p | MIMAT0004679 |
| 146 | hsa-miR-564 | MIMAT0003228 |
| 147 | hsa-miR-1268a | MIMAT0005922 |
| 148 | hsa-miR-6848-5p | MIMAT0027596 |
| 149 | hsa-miR-762 | MIMAT0010313 |
| 150 | hsa-miR-2861 | MIMAT0013802 |
| 151 | hsa-miR-1203 | MIMAT0005866 |
| 152 | hsa-miR-1260b | MIMAT0015041 |
| 153 | hsa-miR-4476 | MIMAT0019003 |
| 154 | hsa-miR-6885-5p | MIMAT0027670 |
| 155 | hsa-miR-6769b-5p | MIMAT0027620 |
| 156 | hsa-miR-23b-3p | MIMAT0000418 |
| 157 | hsa-miR-1343-5p | MIMAT0027038 |
| 158 | hsa-miR-3621 | MIMAT0018002 |
| 159 | hsa-miR-4688 | MIMAT0019777 |
| 160 | hsa-miR-4286 | MIMAT0016916 |
| 161 | hsa-miR-4640-5p | MIMAT0019699 |
| 162 | hsa-miR-4739 | MIMAT0019868 |
| 163 | hsa-miR-1260a | MIMAT0005911 |
| 164 | hsa-miR-4276 | MIMAT0016904 |
| 165 | hsa-miR-7106-5p | MIMAT0028109 |
| 166 | hsa-miR-128-2-5p | MIMAT0031095 |
| 167 | hsa-miR-125a-3p | MIMAT0004602 |
| 168 | hsa-miR-92a-2-5p | MIMAT0004508 |
| 169 | hsa-miR-486-3p | MIMAT0004762 |
| 170 | hsa-miR-3196 | MIMAT0015080 |
| 171 | hsa-miR-211-3p | MIMAT0022694 |
| 172 | hsa-miR-4271 | MIMAT0016901 |
| 173 | hsa-miR-6851-5p | MIMAT0027602 |
| 174 | hsa-miR-149-3p | MIMAT0004609 |
| 175 | hsa-miR-4667-5p | MIMAT0019743 |
| 176 | hsa-miR-135a-3p | MIMAT0004595 |
| 177 | hsa-miR-4486 | MIMAT0019020 |
| 178 | hsa-miR-4697-5p | MIMAT0019791 |
| 179 | hsa-miR-4725-3p | MIMAT0019844 |
| 180 | hsa-miR-6510-5p | MIMAT0025476 |
| 181 | hsa-miR-5001-5p | MIMAT0021021 |
| 182 | hsa-miR-4673 | MIMAT0019755 |
| 183 | hsa-miR-4466 | MIMAT0018993 |
| 184 | hsa-miR-23a-3p | MIMAT0000078 |
| 185 | hsa-miR-3656 | MIMAT0018076 |
| 186 | hsa-miR-6782-5p | MIMAT0027464 |
| 187 | hsa-miR-4689 | MIMAT0019778 |
| 188 | hsa-miR-451a | MIMAT0001631 |
| 189 | hsa-miR-4446-3p | MIMAT0018965 |
| 190 | hsa-miR-3180-3p | MIMAT0015058 |
| 191 | hsa-miR-642a-3p | MIMAT0020924 |
| 192 | hsa-miR-6889-5p | MIMAT0027678 |
| 193 | hsa-miR-3178 | MIMAT0015055 |
| 194 | hsa-miR-4665-5p | MIMAT0019739 |
| 195 | hsa-miR-6722-3p | MIMAT0025854 |
| 196 | hsa-miR-30c-1-3p | MIMAT0004674 |
| 197 | hsa-miR-4507 | MIMAT0019044 |
| 198 | hsa-miR-3141 | MIMAT0015010 |
| 199 | hsa-miR-1199-5p | MIMAT0031119 |
| 200 | hsa-mir-4257 | MI0015856 |
| 201 | hsa-mir-6726 | MI0022571 |
| 202 | hsa-mir-1343 | MI0017320 |
| 203 | hsa-mir-1247 | MI0006382 |
| 204 | hsa-mir-6787 | MI0022632 |
| 205 | hsa-mir-6875 | MI0022722 |
| 206 | hsa-mir-1225 | MI0006311 |
| 207 | hsa-mir-8063 | MI0025899 |
| 208 | hsa-mir-6781 | MI0022626 |
| 209 | hsa-mir-4746 | MI0017385 |
| 210 | hsa-mir-1908 | MI0008329 |
| 211 | hsa-mir-6756 | MI0022601 |
| 212 | hsa-mir-204 | MI0000284 |
| 213 | hsa-mir-4651 | MI0017279 |
| 214 | hsa-mir-6757 | MI0022602 |
| 215 | hsa-mir-6825 | MI0022670 |
| 216 | hsa-mir-7108 | MI0022959 |
| 217 | hsa-mir-4792 | MI0017439 |
| 218 | hsa-mir-7641-1 | MI0024975 |
| 219 | hsa-mir-7641-2 | MI0024976 |
| 220 | hsa-miR-3188 | MI0014232 |
| 221 | hsa-miR-3131 | MI0014151 |
| 222 | hsa-mir-6780b | MI0022681 |
| 223 | hsa-mir-8069 | MI0025905 |
| 224 | hsa-mir-6840 | MI0022686 |
| 225 | hsa-mir-8072 | MI0025908 |
| 226 | hsa-mir-1233-1 | MI0006323 |
| 227 | hsa-mir-1233-2 | MI0015973 |
| 228 | hsa-mir-6887 | MI0022734 |
| 229 | hsa-mir-1231 | MI0006321 |
| 230 | hsa-mir-5572 | MI0019117 |
| 231 | hsa-mir-6738 | MI0022583 |
| 232 | hsa-mir-6784 | MI0022629 |
| 233 | hsa-mir-6791 | MI0022636 |
| 234 | hsa-mir-6749 | MI0022594 |
| 235 | hsa-mir-6741 | MI0022586 |
| 236 | hsa-mir-128-1 | MI0000447 |
| 237 | hsa-mir-4419b | MI0016861 |
| 238 | hsa-mir-6746 | MI0022591 |
| 239 | hsa-mir-3184 | MI0014226 |
| 240 | hsa-mir-3679 | MI0016080 |
| 241 | hsa-mir-7110 | MI0022961 |
| 242 | hsa-mir-4516 | MI0016882 |
| 243 | hsa-mir-6717 | MI0022551 |
| 244 | hsa-mir-6826 | MI0022671 |
| 245 | hsa-mir-4433b | MI0025511 |
| 246 | hsa-mir-3135b | MI0016809 |
| 247 | hsa-mir-3622a | MI0016013 |
| 248 | hsa-mir-711 | MI0012488 |
| 249 | hsa-mir-4467 | MI0016818 |
| 250 | hsa-mir-6857 | MI0022703 |
| 251 | hsa-mir-6515 | MI0022227 |
| 252 | hsa-mir-187 | MI0000274 |
| 253 | hsa-mir-3185 | MI0014227 |
| 254 | hsa-mir-642b | MI0016685 |
| 255 | hsa-mir-1249 | MI0006384 |
| 256 | hsa-mir-744 | MI0005559 |
| 257 | hsa-mir-4442 | MI0016785 |
| 258 | hsa-mir-1228 | MI0006318 |
| 259 | hsa-mir-939 | MI0005761 |
| 260 | hsa-mir-6845 | MI0022691 |
| 261 | hsa-mir-887 | MI0005562 |
| 262 | hsa-mir-7845 | MI0025515 |
| 263 | hsa-mir-6729 | MI0022574 |
| 264 | hsa-mir-4632 | MI0017259 |
| 265 | hsa-mir-615 | MI0003628 |
| 266 | hsa-mir-6724 | MI0022559 |
| 267 | hsa-mir-4728 | MI0017365 |
| 268 | hsa-mir-6732 | MI0022577 |

TABLE 1-continued

| SEQ ID NO: | Gene name | miRBase registration No. |
|---|---|---|
| 269 | hsa-mir-6816 | MI0022661 |
| 270 | hsa-mir-4695 | MI0017328 |
| 271 | hsa-mir-6088 | MI0020365 |
| 272 | hsa-mir-7975 | MI0025751 |
| 273 | hsa-mir-3197 | MI0014245 |
| 274 | hsa-mir-6125 | MI0021259 |
| 275 | hsa-mir-4433 | MI0016773 |
| 276 | hsa-mir-6727 | MI0022572 |
| 277 | hsa-mir-4706 | MI0017339 |
| 278 | hsa-mir-7847 | MI0025517 |
| 279 | hsa-mir-6805 | MI0022650 |
| 280 | hsa-mir-6766 | MI0022611 |
| 281 | hsa-mir-1913 | MI0008334 |
| 282 | hsa-mir-4649 | MI0017276 |
| 283 | hsa-mir-602 | MI0003615 |
| 284 | hsa-mir-3663 | MI0016064 |
| 285 | hsa-mir-6893 | MI0022740 |
| 286 | hsa-mir-6861 | MI0022708 |
| 287 | hsa-mir-4449 | MI0016792 |
| 288 | hsa-mir-6842 | MI0022688 |
| 289 | hsa-mir-4454 | MI0016800 |
| 290 | hsa-mir-5195 | MI0018174 |
| 291 | hsa-mir-663b | MI0006336 |
| 292 | hsa-mir-6765 | MI0022610 |
| 293 | hsa-mir-4513 | MI0016879 |
| 294 | hsa-mir-614 | MI0003627 |
| 295 | hsa-mir-6785 | MI0022630 |
| 296 | hsa-mir-6777 | MI0022622 |
| 297 | hsa-mir-940 | MI0005762 |
| 298 | hsa-mir-4741 | MI0017379 |
| 299 | hsa-mir-6870 | MI0022717 |
| 300 | hsa-mir-6131 | MI0021276 |
| 301 | hsa-mir-150 | MI0000479 |
| 302 | hsa-mir-4707 | MI0017340 |
| 303 | hsa-mir-1915 | MI0008336 |
| 304 | hsa-mir-3937 | MI0016593 |
| 305 | hsa-mir-937 | MI0005759 |
| 306 | hsa-mir-4443 | MI0016786 |
| 307 | hsa-mir-1914 | MI0008335 |
| 308 | hsa-mir-3620 | MI0016011 |
| 309 | hsa-mir-1268b | MI0016748 |
| 310 | hsa-mir-1227 | MI0006316 |
| 311 | hsa-mir-6880 | MI0022727 |
| 312 | hsa-mir-4417 | MI0016753 |
| 313 | hsa-mir-6802 | MI0022647 |
| 314 | hsa-mir-6769a | MI0022614 |
| 315 | hsa-mir-663a | MI0003672 |
| 316 | hsa-mir-6721 | MI0022556 |
| 317 | hsa-mir-4532 | MI0016899 |
| 318 | hsa-mir-7977 | MI0025753 |
| 319 | hsa-mir-92b | MI0003560 |
| 320 | hsa-mir-371a | MI0000779 |
| 321 | hsa-mir-6126 | MI0021260 |
| 322 | hsa-mir-4734 | MI0017371 |
| 323 | hsa-mir-4665 | MI0017295 |
| 324 | hsa-mir-423 | MI0001445 |
| 325 | hsa-mir-1469 | MI0007074 |
| 326 | hsa-mir-4675 | MI0017306 |
| 327 | hsa-mir-6716 | MI0022550 |
| 328 | hsa-mir-718 | MI0012489 |
| 329 | hsa-mir-4281 | MI0015885 |
| 330 | hsa-mir-6820 | MI0022665 |
| 331 | hsa-mir-6795 | MI0022640 |
| 332 | hsa-mir-6779 | MI0022624 |
| 333 | hsa-mir-7109 | MI0022960 |
| 334 | hsa-mir-6798 | MI0022643 |
| 335 | hsa-mir-4648 | MI0017275 |
| 336 | hsa-mir-8059 | MI0025895 |
| 337 | hsa-mir-6132 | MI0021277 |
| 338 | hsa-mir-4492 | MI0016854 |
| 339 | hsa-mir-7107 | MI0022958 |
| 340 | hsa-mir-3195 | MI0014240 |
| 341 | hsa-mir-3180-4 | MI0016408 |
| 342 | hsa-mir-3180-5 | MI0016409 |
| 343 | hsa-mir-296 | MI0000747 |
| 344 | hsa-mir-564 | MI0003570 |
| 345 | hsa-mir-1268a | MI0006405 |
| 346 | hsa-mir-6848 | MI0022694 |
| 347 | hsa-mir-762 | MI0003892 |
| 348 | hsa-mir-2861 | MI0013006 |
| 349 | hsa-mir-1203 | MI0006335 |
| 350 | hsa-mir-1260b | MI0014197 |
| 351 | hsa-mir-4476 | MI0016828 |
| 352 | hsa-mir-6885 | MI0022732 |
| 353 | hsa-mir-6769b | MI0022706 |
| 354 | hsa-mir-23b | MI0000439 |
| 355 | hsa-mir-3621 | MI0016012 |
| 356 | hsa-mir-4688 | MI0017321 |
| 357 | hsa-mir-4286 | MI0015894 |
| 358 | hsa-mir-4640 | MI0017267 |
| 359 | hsa-mir-4739 | MI0017377 |
| 360 | hsa-mir-1260a | MI0006394 |
| 361 | hsa-mir-4276 | MI0015882 |
| 362 | hsa-mir-7106 | MI0022957 |
| 363 | hsa-mir-128-2 | MI0000727 |
| 364 | hsa-mir-125a | MI0000469 |
| 365 | hsa-mir-92a-2 | MI0000094 |
| 366 | hsa-mir-486 | MI0002470 |
| 367 | hsa-mir-486-2 | MI0023622 |
| 368 | hsa-mir-3196 | MI0014241 |
| 369 | hsa-mir-211 | MI0000287 |
| 370 | hsa-mir-4271 | MI0015879 |
| 371 | hsa-mir-6851 | MI0022697 |
| 372 | hsa-mir-149 | MI0000478 |
| 373 | hsa-mir-4667 | MI0017297 |
| 374 | hsa-mir-135a-1 | MI0000452 |
| 375 | hsa-mir-4486 | MI0016847 |
| 376 | hsa-mir-4697 | MI0017330 |
| 377 | hsa-mir-4725 | MI0017362 |
| 378 | hsa-mir-6510 | MI0022222 |
| 379 | hsa-mir-5001 | MI0017867 |
| 380 | hsa-mir-4673 | MI0017304 |
| 381 | hsa-mir-4466 | MI0016817 |
| 382 | hsa-mir-23a | MI0000079 |
| 383 | hsa-mir-3656 | MI0016056 |
| 384 | hsa-mir-6782 | MI0022627 |
| 385 | hsa-mir-4689 | MI0017322 |
| 386 | hsa-mir-451a | MI0001729 |
| 387 | hsa-mir-4446 | MI0016789 |
| 388 | hsa-mir-3180-1 | MI0014214 |
| 389 | hsa-mir-3180-2 | MI0014215 |
| 390 | hsa-mir-3180-3 | MI0014217 |
| 391 | hsa-mir-642a | MI0003657 |
| 392 | hsa-mir-6889 | MI0022736 |
| 393 | hsa-mir-3178 | MI0014212 |
| 394 | hsa-mir-6722 | MI0022557 |
| 395 | hsa-mir-30c-1 | MI0000736 |
| 396 | hsa-mir-4507 | MI0016871 |
| 397 | hsa-mir-3141 | MI0014165 |
| 398 | hsa-mir-1199 | MI0020340 |
| 399 | isomiR example 1 of SEQ ID NO: 3 | — |
| 400 | isomiR example 2 of SEQ ID NO: 3 | — |
| 401 | isomiR example 1 of SEQ ID NO: 4 | — |
| 402 | isomiR example 2 of SEQ ID NO: 4 | — |
| 403 | isomiR example 1 of SEQ ID NO: 11 | — |
| 404 | isomiR example 2 of SEQ ID NO: 11 | — |
| 405 | isomiR example 1 of SEQ ID NO: 13 | — |
| 406 | isomiR example 2 of SEQ ID NO: 13 | — |
| 407 | isomiR example 1 of SEQ ID NO: 14 | — |
| 408 | isomiR example 2 of SEQ ID NO: 14 | — |
| 409 | isomiR example 1 of SEQ ID NO: 18 | — |
| 410 | isomiR example 2 of SEQ ID NO: 18 | — |
| 411 | isomiR example 1 of SEQ ID NO: 20 | — |
| 412 | isomiR example 2 of SEQ ID NO: 20 | — |
| 413 | isomiR example 1 of SEQ ID NO: 21 | — |
| 414 | isomiR example 2 of SEQ ID NO: 21 | — |
| 415 | isomiR example 1 of SEQ ID NO: 26 | — |
| 416 | isomiR example 2 of SEQ ID NO: 26 | — |
| 417 | isomiR example 1 of SEQ ID NO: 29 | — |
| 418 | isomiR example 2 of SEQ ID NO: 29 | — |
| 419 | isomiR example 1 of SEQ ID NO: 35 | — |
| 420 | isomiR example 2 of SEQ ID NO: 35 | — |
| 421 | isomiR example 1 of SEQ ID NO: 36 | — |
| 422 | isomiR example 2 of SEQ ID NO: 36 | — |

TABLE 1-continued

| SEQ ID NO: | Gene name | miRBase registration No. |
|---|---|---|
| 423 | isomiR example 1 of SEQ ID NO: 39 | — |
| 424 | isomiR example 2 of SEQ ID NO: 39 | — |
| 425 | isomiR example 1 of SEQ ID NO: 41 | — |
| 426 | isomiR example 2 of SEQ ID NO: 41 | — |
| 427 | isomiR example 1 of SEQ ID NO: 42 | — |
| 428 | isomiR example 2 of SEQ ID NO: 42 | — |
| 429 | isomiR example 1 of SEQ ID NO: 45 | — |
| 430 | isomiR example 2 of SEQ ID NO: 45 | — |
| 431 | isomiR example 1 of SEQ ID NO: 46 | — |
| 432 | isomiR example 2 of SEQ ID NO: 46 | — |
| 433 | isomiR example 1 of SEQ ID NO: 47 | — |
| 434 | isomiR example 2 of SEQ ID NO: 47 | — |
| 435 | isomiR example 1 of SEQ ID NO: 48 | — |
| 436 | isomiR example 2 of SEQ ID NO: 48 | — |
| 437 | isomiR example 1 of SEQ ID NO: 49 | — |
| 438 | isomiR example 2 of SEQ ID NO: 49 | — |
| 439 | isomiR example 1 of SEQ ID NO: 51 | — |
| 440 | isomiR example 2 of SEQ ID NO: 51 | — |
| 441 | isomiR example 1 of SEQ ID NO: 53 | — |
| 442 | isomiR example 2 of SEQ ID NO: 53 | — |
| 443 | isomiR example 1 of SEQ ID NO: 54 | — |
| 444 | isomiR example 2 of SEQ ID NO: 54 | — |
| 445 | isomiR example 1 of SEQ ID NO: 55 | — |
| 446 | isomiR example 2 of SEQ ID NO: 55 | — |
| 447 | isomiR example 1 of SEQ ID NO: 56 | — |
| 448 | isomiR example 2 of SEQ ID NO: 56 | — |
| 449 | isomiR example 1 of SEQ ID NO: 57 | — |
| 450 | isomiR example 2 of SEQ ID NO: 57 | — |
| 451 | isomiR example 1 of SEQ ID NO: 58 | — |
| 452 | isomiR example 2 of SEQ ID NO: 58 | — |
| 453 | isomiR example 1 of SEQ ID NO: 59 | — |
| 454 | isomiR example 2 of SEQ ID NO: 59 | — |
| 455 | isomiR example 1 of SEQ ID NO: 60 | — |
| 456 | isomiR example 2 of SEQ ID NO: 60 | — |
| 457 | isomiR example 1 of SEQ ID NO: 62 | — |
| 458 | isomiR example 2 of SEQ ID NO: 62 | — |
| 459 | isomiR example 1 of SEQ ID NO: 65 | — |
| 460 | isomiR example 2 of SEQ ID NO: 65 | — |
| 461 | isomiR example 1 of SEQ ID NO: 66 | — |
| 462 | isomiR example 2 of SEQ ID NO: 66 | — |
| 463 | isomiR example 1 of SEQ ID NO: 67 | — |
| 464 | isomiR example 2 of SEQ ID NO: 67 | — |
| 465 | isomiR example 1 of SEQ ID NO: 68 | — |
| 466 | isomiR example 2 of SEQ ID NO: 68 | — |
| 467 | isomiR example 1 of SEQ ID NO: 71 | — |
| 468 | isomiR example 2 of SEQ ID NO: 71 | — |
| 469 | isomiR example 1 of SEQ ID NO: 72 | — |
| 470 | isomiR example 2 of SEQ ID NO: 72 | — |
| 471 | isomiR example 1 of SEQ ID NO: 73 | — |
| 472 | isomiR example 2 of SEQ ID NO: 73 | — |
| 473 | isomiR example 1 of SEQ ID NO: 74 | — |
| 474 | isomiR example 2 of SEQ ID NO: 74 | — |
| 475 | isomiR example 1 of SEQ ID NO: 75 | — |
| 476 | isomiR example 2 of SEQ ID NO: 75 | — |
| 477 | isomiR example 1 of SEQ ID NO: 76 | — |
| 478 | isomiR example 2 of SEQ ID NO: 76 | — |
| 479 | isomiR example 1 of SEQ ID NO: 78 | — |
| 480 | isomiR example 2 of SEQ ID NO: 78 | — |
| 481 | isomiR example 1 of SEQ ID NO: 82 | — |
| 482 | isomiR example 2 of SEQ ID NO: 82 | — |
| 483 | isomiR example 1 of SEQ ID NO: 83 | — |
| 484 | isomiR example 2 of SEQ ID NO: 83 | — |
| 485 | isomiR example 1 of SEQ ID NO: 88 | — |
| 486 | isomiR example 2 of SEQ ID NO: 88 | — |
| 487 | isomiR example 1 of SEQ ID NO: 90 | — |
| 488 | isomiR example 2 of SEQ ID NO: 90 | — |
| 489 | isomiR example 1 of SEQ ID NO: 91 | — |
| 490 | isomiR example 2 of SEQ ID NO: 91 | — |
| 491 | isomiR example 1 of SEQ ID NO: 92 | — |
| 492 | isomiR example 2 of SEQ ID NO: 92 | — |
| 493 | isomiR example 1 of SEQ ID NO: 94 | — |
| 494 | isomiR example 2 of SEQ ID NO: 94 | — |
| 495 | isomiR example 1 of SEQ ID NO: 95 | — |
| 496 | isomiR example 2 of SEQ ID NO: 95 | — |
| 497 | isomiR example 1 of SEQ ID NO: 98 | — |
| 498 | isomiR example 2 of SEQ ID NO: 98 | — |
| 499 | isomiR example 1 of SEQ ID NO: 99 | — |
| 500 | isomiR example 2 of SEQ ID NO: 99 | — |
| 501 | isomiR example 1 of SEQ ID NO: 101 | — |
| 502 | isomiR example 2 of SEQ ID NO: 101 | — |
| 503 | isomiR example 1 of SEQ ID NO: 102 | — |
| 504 | isomiR example 2 of SEQ ID NO: 102 | — |
| 505 | isomiR example 1 of SEQ ID NO: 103 | — |
| 506 | isomiR example 2 of SEQ ID NO: 103 | — |
| 507 | isomiR example 1 of SEQ ID NO: 104 | — |
| 508 | isomiR example 2 of SEQ ID NO: 104 | — |
| 509 | isomiR example 1 of SEQ ID NO: 106 | — |
| 510 | isomiR example 2 of SEQ ID NO: 106 | — |
| 511 | isomiR example 1 of SEQ ID NO: 107 | — |
| 512 | isomiR example 2 of SEQ ID NO: 107 | — |
| 513 | isomiR example 1 of SEQ ID NO: 108 | — |
| 514 | isomiR example 2 of SEQ ID NO: 108 | — |
| 515 | isomiR example 1 of SEQ ID NO: 109 | — |
| 516 | isomiR example 2 of SEQ ID NO: 109 | — |
| 517 | isomiR example 1 of SEQ ID NO: 110 | — |
| 518 | isomiR example 2 of SEQ ID NO: 110 | — |
| 519 | isomiR example 1 of SEQ ID NO: 113 | — |
| 520 | isomiR example 2 of SEQ ID NO: 113 | — |
| 521 | isomiR example 1 of SEQ ID NO: 116 | — |
| 522 | isomiR example 2 of SEQ ID NO: 116 | — |
| 523 | isomiR example 1 of SEQ ID NO: 117 | — |
| 524 | isomiR example 2 of SEQ ID NO: 117 | — |
| 525 | isomiR example 1 of SEQ ID NO: 118 | — |
| 526 | isomiR example 2 of SEQ ID NO: 118 | — |
| 527 | isomiR example 1 of SEQ ID NO: 120 | — |
| 528 | isomiR example 2 of SEQ ID NO: 120 | — |
| 529 | isomiR example 1 of SEQ E) NO: 121 | — |
| 530 | isomiR example 2 of SEQ E) NO: 121 | — |
| 531 | isomiR example 1 of SEQ ID NO: 122 | — |
| 532 | isomiR example 2 of SEQ ID NO: 122 | — |
| 533 | isomiR example 1 of SEQ ID NO: 123 | — |
| 534 | isomiR example 2 of SEQ ID NO: 123 | — |
| 535 | isomiR example 1 of SEQ ID NO: 125 | — |
| 536 | isomiR example 2 of SEQ ID NO: 125 | — |
| 537 | isomiR example 1 of SEQ ID NO: 128 | — |
| 538 | isomiR example 2 of SEQ ID NO: 128 | — |
| 539 | isomiR example 1 of SEQ ID NO: 129 | — |
| 540 | isomiR example 2 of SEQ ID NO: 129 | — |
| 541 | isomiR example 1 of SEQ ID NO: 130 | — |
| 542 | isomiR example 2 of SEQ ID NO: 130 | — |
| 543 | isomiR example 1 of SEQ ID NO: 131 | — |
| 544 | isomiR example 2 of SEQ ID NO: 131 | — |
| 545 | isomiR example 1 of SEQ ID NO: 137 | — |
| 546 | isomiR example 2 of SEQ ID NO: 137 | — |
| 547 | isomiR example 1 of SEQ ID NO: 140 | — |
| 548 | isomiR example 2 of SEQ ID NO: 140 | — |
| 549 | isomiR example 1 of SEQ ID NO: 141 | — |
| 550 | isomiR example 2 of SEQ ID NO: 141 | — |
| 551 | isomiR example 1 of SEQ ID NO: 143 | — |
| 552 | isomiR example 2 of SEQ ID NO: 143 | — |
| 553 | isomiR example 1 of SEQ ID NO: 144 | — |
| 554 | isomiR example 2 of SEQ ID NO: 144 | — |
| 555 | isomiR example 1 of SEQ ID NO: 145 | — |
| 556 | isomiR example 2 of SEQ ID NO: 145 | — |
| 557 | isomiR example 1 of SEQ ID NO: 146 | — |
| 558 | isomiR example 2 of SEQ ID NO: 146 | — |
| 559 | isomiR example 1 of SEQ ID NO: 147 | — |
| 560 | isomiR example 2 of SEQ ID NO: 147 | — |
| 561 | isomiR example 1 of SEQ ID NO: 150 | — |
| 562 | isomiR example 2 of SEQ ID NO: 150 | — |
| 563 | isomiR example 1 of SEQ ID NO: 152 | — |
| 564 | isomiR example 2 of SEQ ID NO: 152 | — |
| 565 | isomiR example 1 of SEQ ID NO: 153 | — |
| 566 | isomiR example 2 of SEQ ID NO: 153 | — |
| 567 | isomiR example 1 of SEQ ID NO: 156 | — |
| 568 | isomiR example 2 of SEQ ID NO: 156 | — |
| 569 | isomiR example 1 of SEQ ID NO: 159 | — |
| 570 | isomiR example 2 of SEQ ID NO: 159 | — |
| 571 | isomiR example 1 of SEQ ID NO: 160 | — |
| 572 | isomiR example 2 of SEQ ID NO: 160 | — |
| 573 | isomiR example 1 of SEQ ID NO: 161 | — |
| 574 | isomiR example 2 of SEQ ID NO: 161 | — |
| 575 | isomiR example 1 of SEQ ID NO: 162 | — |
| 576 | isomiR example 2 of SEQ ID NO: 162 | — |

TABLE 1-continued

| SEQ ID NO: | Gene name | miRBase registration No. |
|---|---|---|
| 577 | isomiR example 1 of SEQ ID NO: 163 | — |
| 578 | isomiR example 2 of SEQ ID NO: 163 | — |
| 579 | isomiR example 1 of SEQ ID NO: 166 | — |
| 580 | isomiR example 2 of SEQ ID NO: 166 | — |
| 581 | isomiR example 1 of SEQ ID NO: 167 | — |
| 582 | isomiR example 2 of SEQ ID NO: 167 | — |
| 583 | isomiR example 1 of SEQ ID NO: 168 | — |
| 584 | isomiR example 2 of SEQ ID NO: 168 | — |
| 585 | isomiR example 1 of SEQ ID NO: 169 | — |
| 586 | isomiR example 2 of SEQ ID NO: 169 | — |
| 587 | isomiR example 1 of SEQ ID NO: 170 | — |
| 588 | isomiR example 2 of SEQ ID NO: 170 | — |
| 589 | isomiR example 1 of SEQ ID NO: 171 | — |
| 590 | isomiR example 2 of SEQ ID NO: 171 | — |
| 591 | isomiR example 1 of SEQ ID NO: 172 | — |
| 592 | isomiR example 2 of SEQ ID NO: 172 | — |
| 593 | isomiR example 1 of SEQ ID NO: 174 | — |
| 594 | isomiR example 2 of SEQ ID NO: 174 | — |
| 595 | isomiR example 1 of SEQ ID NO: 175 | — |
| 596 | isomiR example 2 of SEQ ID NO: 175 | — |
| 597 | isomiR example 1 of SEQ ID NO: 176 | — |
| 598 | isomiR example 2 of SEQ ID NO: 176 | — |
| 599 | isomiR example 1 of SEQ ID NO: 177 | — |
| 600 | isomiR example 2 of SEQ ID NO: 177 | — |
| 601 | isomiR example 1 of SEQ ID NO: 179 | — |
| 602 | isomiR example 2 of SEQ ID NO: 179 | — |
| 603 | isomiR example 1 of SEQ ID NO: 180 | — |
| 604 | isomiR example 2 of SEQ ID NO: 180 | — |
| 605 | isomiR example 1 of SEQ ID NO: 181 | — |
| 606 | isomiR example 2 of SEQ ID NO: 181 | — |
| 607 | isomiR example 1 of SEQ ID NO: 182 | — |
| 608 | isomiR example 2 of SEQ ID NO: 182 | — |
| 609 | isomiR example 1 of SEQ ID NO: 183 | — |
| 610 | isomiR example 2 of SEQ ID NO: 183 | — |
| 611 | isomiR example 1 of SEQ ID NO: 184 | — |
| 612 | isomiR example 2 of SEQ ID NO: 184 | — |
| 613 | isomiR example 1 of SEQ ID NO: 185 | — |
| 614 | isomiR example 2 of SEQ ID NO: 185 | — |
| 615 | isomiR example 1 of SEQ ID NO: 187 | — |
| 616 | isomiR example 2 of SEQ ID NO: 187 | — |
| 617 | isomiR example 1 of SEQ ID NO: 188 | — |
| 618 | isomiR example 2 of SEQ ID NO: 188 | — |
| 619 | isomiR example 1 of SEQ ID NO: 189 | — |
| 620 | isomiR example 2 of SEQ ID NO: 189 | — |
| 621 | isomiR example 1 of SEQ ID NO: 190 | — |
| 622 | isomiR example 2 of SEQ ID NO: 190 | — |
| 623 | isomiR example 1 of SEQ ID NO: 191 | — |
| 624 | isomiR example 2 of SEQ ID NO: 191 | — |
| 625 | isomiR example 1 of SEQ ID NO: 193 | — |
| 626 | isomiR example 2 of SEQ ID NO: 193 | — |
| 627 | isomiR example 1 of SEQ ID NO: 194 | — |
| 628 | isomiR example 2 of SEQ ID NO: 194 | — |
| 629 | isomiR example 1 of SEQ ID NO: 196 | — |
| 630 | isomiR example 2 of SEQ ID NO: 196 | — |
| 631 | isomiR example 1 of SEQ ID NO: 197 | — |
| 632 | isomiR example 2 of SEQ ID NO: 197 | — |
| 633 | isomiR example 1 of SEQ ID NO: 198 | — |
| 634 | isomiR example 2 of SEQ ID NO: 198 | — |
| 635 | hsa-miR-6794-5p | MIMAT0027488 |
| 636 | hsa-miR-6774-5p | MIMAT0027448 |
| 637 | hsa-miR-4707-3p | MIMAT0019808 |
| 638 | hsa-miR-4534 | MIMAT0019073 |
| 639 | hsa-miR-4294 | MIMAT0016849 |
| 640 | hsa-miR-6850-5p | MIMAT0027600 |
| 641 | hsa-miR-6089 | MIMAT0023714 |
| 642 | hsa-miR-671-5p | MIMAT0003880 |
| 643 | hsa-mir-6794 | MI0022639 |
| 644 | hsa-mir-6774 | MI0022619 |
| 645 | hsa-mir-4707 | MI0017340 |
| 646 | hsa-mir-4534 | MI0016901 |
| 647 | hsa-mir-4294 | MI0015827 |
| 648 | hsa-mir-6850 | MI0022696 |
| 649 | hsa-mir-6089-1 | MI0020366 |
| 650 | hsa-mir-6089-2 | MI0023563 |
| 651 | hsa-mir-671 | MI0003760 |
| 652 | isomiR example 1 of SEQ ID NO: 637 | — |
| 653 | isomiR example 2 of SEQ ID NO: 637 | — |
| 654 | isomiR example 1 of SEQ ID NO: 641 | — |
| 655 | isomiR example 2 of SEQ ID NO: 641 | — |
| 656 | isomiR example 1 of SEQ ID NO: 642 | — |
| 657 | isomiR example 2 of SEQ ID NO: 642 | — |

The present specification encompasses the contents described in the specifications and/or drawings of Japanese Patent Application Nos. 2014-123224 and 2015-071485 from which the present application claims priority.

Advantageous Effects of Invention

According to the present invention, stomach cancer can be detected easily and in high accuracy.

For example, the presence or absence of stomach cancer in a patient(s) can be easily detected by using, as an indicator(s), the measurement values of several miRNAs in blood, serum, and/or plasma of the patient(s), which can be collected with limited invasiveness.

BRIEF DESCRIPTION OF DRAWINGS

FIG. 1 This figure shows the relationship between the nucleotide sequences of hsa-miR-1225-3p represented by SEQ ID NO: 7 and hsa-miR-1225-5p represented by SEQ ID NO: 52, which are produced from a precursor hsa-mir-1225 represented by SEQ ID NO: 206.

DESCRIPTION OF EMBODIMENTS

Figure 2:
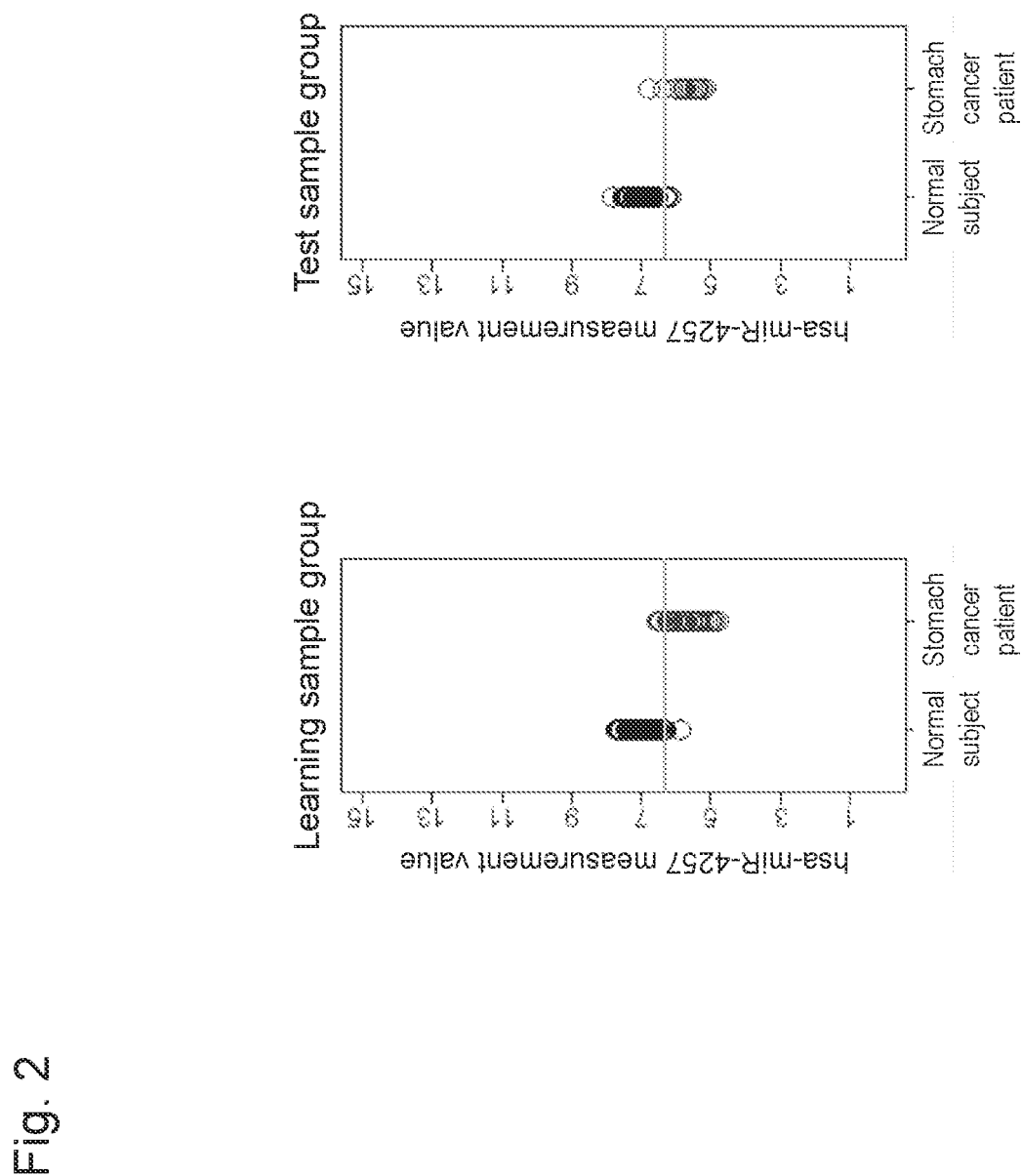
FIG. 2 Left diagram: the measurement values of hsa-miR-4257 (SEQ ID NO: 1) in healthy subjects (100 persons) and stomach cancer patients (34 persons) selected as a training cohort were each plotted on the ordinate. The horizontal line in the diagram depicts a threshold (6.29) that was optimized by Fisher's discriminant analysis and discriminated between the two groups. Right diagram: the measurement values of hsa-miR-4257 (SEQ ID NO: 1) in healthy subjects (50 persons) and stomach cancer patients (16 persons) selected as a validation cohort were each plotted on the ordinate. The horizontal line in the diagram depicts the threshold (6.29) that was set in the training cohort and discriminated between the two groups.

Hereinafter, the present invention will be further described in detail.

1. Target Nucleic Acid for Stomach Cancer

Primary target nucleic acids as a stomach cancer marker(s) for detecting the presence and/or absence of stomach cancer or stomach cancer cells using the nucleic acid probe(s) or the primer(s) for the detection of stomach cancer defined above according to the present invention comprises at least one or more miRNAs selected from the group consisting of hsa-miR-4257, hsa-miR-6726-5p, hsa-miR-1343-3p, hsa-miR-1247-3p, hsa-miR-6787-5p, hsa-miR-6875-5p, hsa-miR-1225-3p, hsa-miR-8063, hsa-miR-6781-5p, hsa-miR-4746-3p, hsa-miR-1908-5p, hsa-miR-6756-5p, hsa-miR-204-3p, hsa-miR-4651, hsa-miR-6757-5p, hsa-miR-6825-5p, hsa-miR-7108-5p, hsa-miR-4792, hsa-miR-7641, hsa-miR-3188, hsa-miR-3131, hsa-miR-6780b-5p, hsa-miR-8069, hsa-miR-6840-3p, hsa-miR-8072, hsa-miR-1233-5p, hsa-miR-6887-5p, hsa-miR-1231, hsa-miR-5572, hsa-miR-6738-5p, hsa-miR-6784-5p, hsa-miR-6791-5p, hsa-miR-6749-5p, hsa-miR-6741-5p, hsa-miR-128-1-5p, hsa-miR-4419b, hsa-miR-6746-5p, hsa-miR-3184-5p, hsa-miR-3679-5p, hsa-miR-7110-5p, hsa-miR-4516, hsa-miR-6717-5p, hsa-miR-6826-5p, hsa-miR-4433b-3p, hsa-miR-3679-3p, hsa-miR-3135b, hsa-miR-3622a-5p, hsa-miR-711, hsa-miR-4467, hsa-miR-6857-5p, hsa-miR-6515-3p, hsa-miR-1225-5p, hsa-miR-187-5p, hsa-miR-3185, hsa-miR-642b-3p, hsa-miR-1249, hsa-miR-744-5p, hsa-miR-4442, hsa-miR-1228-3p, hsa-miR-939-5p, hsa-miR-6845-5p, hsa-miR-887-3p, hsa-miR-7845-5p, hsa-miR-6729-5p, hsa-miR-4632-5p, hsa-miR-615-5p, hsa-miR-6724-5p, hsa-miR-4728-5p, hsa-miR-6732-5p, hsa-miR-6816-5p, hsa-miR-4695-5p, hsa-miR-6088, hsa-miR-7975, hsa-miR-3197, hsa-miR-6125, hsa-miR-4433-3p, hsa-miR-6727-5p, hsa-miR-4706, hsa-miR-7847-3p, hsa-miR-6805-3p, hsa-miR-6766-3p, hsa-miR-1913, hsa-miR-4649-5p, hsa-miR-602, hsa-miR-3663-3p, hsa-miR-6893-5p, hsa-miR-6861-5p, hsa-miR-4449, hsa-miR-6842-5p, hsa-miR-4454, hsa-miR-5195-3p, hsa-miR-663b, hsa-miR-6765-5p, hsa-miR-4513, hsa-miR-614, hsa-miR-6785-5p, hsa-miR-6777-5p, hsa-miR-940, hsa-miR-4741, hsa-miR-6870-5p, hsa-miR-6131, hsa-miR-150-3p, hsa-miR-4707-5p, hsa-miR-1915-3p, hsa-miR-3937, hsa-miR-937-5p, hsa-miR-4443, hsa-miR-1914-3p, hsa-miR-3620-5p, hsa-miR-1268b, hsa-miR-1227-5p, hsa-miR-6880-5p, hsa-miR-4417, hsa-miR-6802-5p, hsa-miR-6769a-5p, hsa-miR-663a, hsa-miR-6721-5p, hsa-miR-4532, hsa-miR-7977, hsa-miR-92b-5p, hsa-miR-371a-5p, hsa-miR-6126, hsa-miR-4734, hsa-miR-4665-3p, hsa-miR-423-5p, hsa-miR-1469, hsa-miR-4675, hsa-miR-1915-5p, hsa-miR-6716-5p, hsa-miR-718, hsa-miR-4281, hsa-miR-6820-5p, hsa-miR-6795-5p, hsa-miR-6779-5p, hsa-miR-7109-5p, hsa-miR-6798-5p, hsa-miR-4648, hsa-miR-8059, hsa-miR-6765-3p, hsa-miR-6132, hsa-miR-4492, hsa-miR-7107-5p, hsa-miR-3195, hsa-miR-3180, hsa-miR-296-3p, hsa-miR-564, hsa-miR-1268a, hsa-miR-6848-5p, hsa-miR-762, hsa-miR-2861, hsa-miR-1203, hsa-miR-1260b, hsa-miR-4476, hsa-miR-6885-5p, hsa-miR-6769b-5p, hsa-miR-23b-3p, hsa-miR-1343-5p, hsa-miR-3621, hsa-miR-4688, hsa-miR-4286, hsa-miR-4640-5p, hsa-miR-4739, hsa-miR-1260a, hsa-miR-4276, hsa-miR-7106, hsa-miR-6794-5p, hsa-miR-6774-5p, hsa-miR-4707-3p, hsa-miR-4534, hsa-miR-4294, hsa-miR-6850-5p, hsa-miR-6089 and hsa-miR-671-5p. Furthermore, at least one or more miRNAs selected from the group consisting of other stomach cancer markers that can be combined with these miRNAs, i.e., hsa-miR-128-2-5p, hsa-miR-125a-3p, hsa-miR-92a-2-5p, and hsa-miR-486-3p can also be preferably used as a target nucleic acid. Moreover, at least one or more miRNAs selected from the group consisting of other stomach cancer markers that can be combined with these miRNAs, i.e., hsa-miR-3196, hsa-miR-211-3p, hsa-miR-4271, hsa-miR-6851-5p, hsa-miR-149-3p, hsa-miR-4667-5p, hsa-miR-135a-3p, hsa-miR-4486, hsa-miR-4697-5p, hsa-miR-4725-3p, hsa-miR-6510-5p, hsa-miR-5001-5p, hsa-miR-4673, hsa-miR-4466, hsa-miR-23a-3p, hsa-miR-3656, hsa-miR-6782-5p, hsa-miR-4689, hsa-miR-451a, hsa-miR-4446-3p, hsa-miR-3180-3p, hsa-miR-642a-3p, hsa-miR-6889-5p, hsa-miR-3178, hsa-miR-4665-5p, hsa-miR-6722-3p, hsa-miR-30c-1-3p, hsa-miR-4507, hsa-miR-3141 and hsa-miR-1199-5p can also be preferably used as a target nucleic acid(s).

These miRNAs include, for example, a human gene comprising a nucleotide sequence represented by any of SEQ ID NOs: 1 to 199 and 635 to 642 (i.e., hsa-miR-4257, hsa-miR-6726-5p, hsa-miR-1343-3p, hsa-miR-1247-3p, hsa-miR-6787-5p, hsa-miR-6875-5p, hsa-miR-1225-3p, hsa-miR-8063, hsa-miR-6781-5p, hsa-miR-4746-3p, hsa-miR-1908-5p, hsa-miR-6756-5p, hsa-miR-204-3p, hsa-miR-4651, hsa-miR-6757-5p, hsa-miR-6825-5p, hsa-miR-7108-5p, hsa-miR-4792, hsa-miR-7641, hsa-miR-3188, hsa-miR-3131, hsa-miR-6780b-5p, hsa-miR-8069, hsa-miR-6840-3p, hsa-miR-8072, hsa-miR-1233-5p, hsa-miR-6887-5p, hsa-miR-1231, hsa-miR-5572, hsa-miR-6738-5p, hsa-miR-6784-5p, hsa-miR-6791-5p, hsa-miR-6749-5p, hsa-miR-6741-5p, hsa-miR-128-1-5p, hsa-miR-4419b, hsa-miR-6746-5p, hsa-miR-3184-5p, hsa-miR-3679-5p, hsa-miR-7110-5p, hsa-miR-4516, hsa-miR-6717-5p, hsa-miR-6826-5p, hsa-miR-4433b-3p, hsa-miR-3679-3p, hsa-miR-3135b, hsa-miR-3622a-5p, hsa-miR-711, hsa-miR-4467, hsa-miR-6857-5p, hsa-miR-6515-3p, hsa-miR-1225-5p, hsa-miR-187-5p, hsa-miR-3185, hsa-miR-642b-3p, hsa-miR-1249, hsa-miR-744-5p, hsa-miR-4442, hsa-miR-1228-3p, hsa-miR-939-5p, hsa-miR-6845-5p, hsa-miR-887-3p, hsa-miR-7845-5p, hsa-miR-6729-5p, hsa-miR-4632-5p, hsa-miR-615-5p, hsa-miR-6724-5p, hsa-miR-4728-5p, hsa-miR-6732-5p, hsa-miR-6816-5p, hsa-miR-4695-5p, hsamiR-6088, hsa-miR-7975, hsa-miR-3197, hsa-miR-6125, hsa-miR-4433-3p, hsa-miR-6727-5p, hsa-miR-4706, hsa-miR-7847-3p, hsa-miR-6805-3p, hsa-miR-6766-3p, hsa-miR-1913, hsa-miR-4649-5p, hsa-miR-602, hsa-miR-3663-3p, hsa-miR-6893-5p, hsa-miR-6861-5p, hsa-miR-4449, hsa-miR-6842-5p, hsa-miR-4454, hsa-miR-5195-3p, hsa-miR-663b, hsa-miR-6765-5p, hsa-miR-4513, hsa-miR-614, hsa-miR-6785-5p, hsa-miR-6777-5p, hsa-miR-940, hsa-miR-4741, hsa-miR-6870-5p, hsa-miR-6131, hsa-miR-150-3p, hsa-miR-4707-5p, hsa-miR-1915-3p, hsa-miR-3937, hsa-miR-937-5p, hsa-miR-4443, hsa-miR-1914-3p, hsa-miR-3620-5p, hsa-miR-1268b, hsa-miR-1227-5p, hsa-miR-6880-5p, hsa-miR-4417, hsa-miR-6802-5p, hsa-miR-6769a-5p, hsa-miR-663a, hsa-miR-6721-5p, hsa-miR-4532, hsa-miR-7977, hsa-miR-92b-5p, hsa-miR-371a-5p, hsa-miR-6126, hsa-miR-4734, hsa-miR-4665-3p, hsa-miR-423-5p, hsa-miR-1469, hsa-miR-4675, hsa-miR-1915-5p, hsa-miR-6716-5p, hsa-miR-718, hsa-miR-4281, hsa-miR-6820-5p, hsa-miR-6795-5p, hsa-miR-6779-5p, hsa-miR-7109-5p, hsa-miR-6798-5p, hsa-miR-4648, hsa-miR-8059, hsa-miR-6765-3p, hsa-miR-6132, hsa-miR-4492, hsa-miR-7107-5p, hsa-miR-3195, hsa-miR-3180, hsa-miR-296-3p, hsa-miR-564, hsa-miR-1268a, hsa-miR-6848-5p, hsa-miR-762, hsa-miR-2861, hsa-miR-1203, hsa-miR-1260b, hsa-miR-4476, hsa-miR-6885-5p, hsa-miR-6769b-5p, hsa-miR-23b-3p, hsa-miR-1343-5p, hsa-miR-3621, hsa-miR-4688, hsa-miR-4286, hsa-miR-4640-5p, hsa-miR-4739, hsa-miR-1260a, hsa-miR-4276, hsa-miR-7106, hsa-miR-6794-5p, hsa-miR-6774-5p, hsa-miR-4707-3p, hsa-miR-4534, hsa-miR-4294, hsa-miR-6850-5p, hsa-miR-6089, hsa-miR-671-5p, hsa-miR-128-2-5p, hsa-miR-125a-3p, hsa-miR-92a-2-5p, hsa-miR-486-3p, hsa-miR-3196, hsa-miR-211-3p, hsa-miR-4271, hsa-miR-6851-5p, hsa-miR-149-3p, hsa-miR-4667-5p, hsa-miR-135a-3p, hsa-miR-4486, hsa-miR-4697-5p, hsa-miR-4725-3p, hsa-miR-6510-5p, hsa-miR-5001-5p, hsa-miR-4673, hsa-miR-4466, hsa-miR-23a-3p, hsa-miR-3656, hsa-miR-6782-5p, hsa-miR-4689, hsa-miR-451a, hsa-miR-4446-3p, hsa-miR-3180-3p, hsa-miR-642a-3p, hsa-miR-6889-5p, hsa-miR-3178, hsa-miR-4665-5p, hsa-miR-6722-3p, hsa-miR-30c-1-3p, hsa-miR-4507, hsa-miR-3141 and hsa-miR-1199-5p, respectively), a congener thereof, a transcript thereof, and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 657 or a transcript thereof, more preferably the transcript, i.e., a miRNA or its precursor RNA (pri-miRNA or pre-miRNA).

The first target gene is the hsa-miR-4257 gene, a congener thereof, a transcript thereof, or a variant or a derivative thereof. None of the previously known reports show that change in the expression of the gene or the transcript thereof can serve as a marker for stomach cancer.

The second target gene is the hsa-miR-6726-5p gene, a congener thereof, a transcript thereof, or a variant or a derivative thereof. None of the previously known reports show that change in the expression of the gene or the transcript thereof can serve as a marker for stomach cancer.

The third target gene is the hsa-miR-1343-3p gene, a congener thereof, a transcript thereof, or a variant or a derivative thereof. None of the previously known reports show that change in the expression of the gene or the transcript thereof can serve as a marker for stomach cancer.

The fourth target gene is the hsa-miR-1247-3p gene, a congener thereof, a transcript thereof, or a variant or a derivative thereof. None of the previously known reports show that change in the expression of the gene or the transcript thereof can serve as a marker for stomach cancer.

The fifth target gene is the hsa-miR-6787-5p gene, a congener thereof, a transcript thereof, or a variant or a derivative thereof. None of the previously known reports show that change in the expression of the gene or the transcript thereof can serve as a marker for stomach cancer.

The sixth target gene is the hsa-miR-6875-5p gene, a congener thereof, a transcript thereof, or a variant or a derivative thereof. None of the previously known reports show that change in the expression of the gene or the transcript thereof can serve as a marker for stomach cancer.

The seventh target gene is the hsa-miR-1225-3p gene, a congener thereof, a transcript thereof, or a variant or a derivative thereof. None of the previously known reports show that change in the expression of the gene or the transcript thereof can serve as a marker for stomach cancer.

The eighth target gene is the hsa-miR-8063 gene, a congener thereof, a transcript thereof, or a variant or a derivative thereof. None of the previously known reports show that change in the expression of the gene or the transcript thereof can serve as a marker for stomach cancer.

The ninth target gene is the hsa-miR-6781-5p gene, a congener thereof, a transcript thereof, or a variant or a derivative thereof. None of the previously known reports show that change in the expression of the gene or the transcript thereof can serve as a marker for stomach cancer.

The 10th target gene is the hsa-miR-4746-3p gene, a congener thereof, a transcript thereof, or a variant or a derivative thereof. None of the previously known reports show that change in the expression of the gene or the transcript thereof can serve as a marker for stomach cancer.

The 11th target gene is the hsa-miR-1908-5p gene, a congener thereof, a transcript thereof, or a variant or a derivative thereof. None of the previously known reports show that change in the expression of the gene or the transcript thereof can serve as a marker for stomach cancer.

The 12th target gene is the hsa-miR-6756-5p gene, a congener thereof, a transcript thereof, or a variant or a derivative thereof. None of the previously known reports show that change in the expression of the gene or the transcript thereof can serve as a marker for stomach cancer.

The 13th target gene is the hsa-miR-204-3p gene, a congener thereof, a transcript thereof, or a variant or a derivative thereof. None of the previously known reports show that change in the expression of the gene or the transcript thereof can serve as a marker for stomach cancer.

The 14th target gene is the hsa-miR-4651 gene, a congener thereof, a transcript thereof, or a variant or a derivative thereof. None of the previously known reports show that change in the expression of the gene or the transcript thereof can serve as a marker for stomach cancer.

The 15th target gene is the hsa-miR-6757-5p gene, a congener thereof, a transcript thereof, or a variant or a derivative thereof. None of the previously known reports show that change in the expression of the gene or the transcript thereof can serve as a marker for stomach cancer.

The 16th target gene is the hsa-miR-6825-5p gene, a congener thereof, a transcript thereof, or a variant or a derivative thereof. None of the previously known reports show that change in the expression of the gene or the transcript thereof can serve as a marker for stomach cancer.

The 17th target gene is the hsa-miR-7108-5p gene, a congener thereof, a transcript thereof, or a variant or a derivative thereof. None of the previously known reports show that change in the expression of the gene or the transcript thereof can serve as a marker for stomach cancer.

The 18th target gene is the hsa-miR-4792 gene, a congener thereof, a transcript thereof, or a variant or a derivative thereof. None of the previously known reports show that change in the expression of the gene or the transcript thereof can serve as a marker for stomach cancer.

The 19th target gene is the hsa-miR-7641 gene, a congener thereof, a transcript thereof, or a variant or a derivative thereof. None of the previously known reports show that change in the expression of the gene or the transcript thereof can serve as a marker for stomach cancer.

The 20th target gene is the hsa-miR-3188 gene, a congener thereof, a transcript thereof, or a variant or a derivative thereof. None of the previously known reports show that change in the expression of the gene or the transcript thereof can serve as a marker for stomach cancer.

The 21st target gene is the hsa-miR-3131 gene, a congener thereof, a transcript thereof, or a variant or a derivative thereof. None of the previously known reports show that change in the expression of the gene or the transcript thereof can serve as a marker for stomach cancer.

The 22nd target gene is the hsa-miR-6780b-5p gene, a congener thereof, a transcript thereof, or a variant or a derivative thereof. None of the previously known reports show that change in the expression of the gene or the transcript thereof can serve as a marker for stomach cancer.

The 23rd target gene is the hsa-miR-8069 gene, a congener thereof, a transcript thereof, or a variant or a derivative thereof. None of the previously known reports show that change in the expression of the gene or the transcript thereof can serve as a marker for stomach cancer.

The 24th target gene is the hsa-miR-6840-3p gene, a congener thereof, a transcript thereof, or a variant or a derivative thereof. None of the previously known reports show that change in the expression of the gene or the transcript thereof can serve as a marker for stomach cancer.

The 25th target gene is the hsa-miR-8072 gene, a congener thereof, a transcript thereof, or a variant or a derivative thereof. None of the previously known reports show that change in the expression of the gene or the transcript thereof can serve as a marker for stomach cancer.

The 26th target gene is the hsa-miR-1233-5p gene, a congener thereof, a transcript thereof, or a variant or a derivative thereof. None of the previously known reports show that change in the expression of the gene or the transcript thereof can serve as a marker for stomach cancer.

The 27th target gene is the hsa-miR-6887-5p gene, a congener thereof, a transcript thereof, or a variant or a derivative thereof. None of the previously known reports show that change in the expression of the gene or the transcript thereof can serve as a marker for stomach cancer.

The 28th target gene is the hsa-miR-1231 gene, a congener thereof, a transcript thereof, or a variant or a derivative thereof. None of the previously known reports show that change in the expression of the gene or the transcript thereof can serve as a marker for stomach cancer.

The 29th target gene is the hsa-miR-5572 gene, a congener thereof, a transcript thereof, or a variant or a derivative thereof. None of the previously known reports show that change in the expression of the gene or the transcript thereof can serve as a marker for stomach cancer.

The 30th target gene is the hsa-miR-6738-5p gene, a congener thereof, a transcript thereof, or a variant or a derivative thereof. None of the previously known reports show that change in the expression of the gene or the transcript thereof can serve as a marker for stomach cancer.

The 31st target gene is the hsa-miR-6784-5p gene, a congener thereof, a transcript thereof, or a variant or a derivative thereof. None of the previously known reports show that change in the expression of the gene or the transcript thereof can serve as a marker for stomach cancer.

The 32nd target gene is the hsa-miR-6791-5p gene, a congener thereof, a transcript thereof, or a variant or a derivative thereof. None of the previously known reports show that change in the expression of the gene or the transcript thereof can serve as a marker for stomach cancer.

The 33rd target gene is the hsa-miR-6749-5p gene, a congener thereof, a transcript thereof, or a variant or a derivative thereof. None of the previously known reports show that change in the expression of the gene or the transcript thereof can serve as a marker for stomach cancer.

The 34th target gene is the hsa-miR-6741-5p gene, a congener thereof, a transcript thereof, or a variant or a derivative thereof. None of the previously known reports show that change in the expression of the gene or the transcript thereof can serve as a marker for stomach cancer.

The 35th target gene is the hsa-miR-128-1-5p gene, a congener thereof, a transcript thereof, or a variant or a derivative thereof. None of the previously known reports show that change in the expression of the gene or the transcript thereof can serve as a marker for stomach cancer.

The 36th target gene is the hsa-miR-4419b gene, a congener thereof, a transcript thereof, or a variant or a derivative thereof. None of the previously known reports show that change in the expression of the gene or the transcript thereof can serve as a marker for stomach cancer.

The 37th target gene is the hsa-miR-6746-5p gene, a congener thereof, a transcript thereof, or a variant or a derivative thereof. None of the previously known reports show that change in the expression of the gene or the transcript thereof can serve as a marker for stomach cancer.

The 38th target gene is the hsa-miR-3184-5p gene, a congener thereof, a transcript thereof, or a variant or a derivative thereof. None of the previously known reports show that change in the expression of the gene or the transcript thereof can serve as a marker for stomach cancer.

The 39th target gene is the hsa-miR-3679-5p gene, a congener thereof, a transcript thereof, or a variant or a derivative thereof. None of the previously known reports show that change in the expression of the gene or the transcript thereof can serve as a marker for stomach cancer.

The 40th target gene is the hsa-miR-7110-5p gene, a congener thereof, a transcript thereof, or a variant or a derivative thereof. None of the previously known reports show that change in the expression of the gene or the transcript thereof can serve as a marker for stomach cancer.

The 41st target gene is the hsa-miR-4516 gene, a congener thereof, a transcript thereof, or a variant or a derivative thereof. None of the previously known reports show that change in the expression of the gene or the transcript thereof can serve as a marker for stomach cancer.

The 42nd target gene is the hsa-miR-6717-5p gene, a congener thereof, a transcript thereof, or a variant or a derivative thereof. None of the previously known reports show that change in the expression of the gene or the transcript thereof can serve as a marker for stomach cancer.

The 43rd target gene is the hsa-miR-6826-5p gene, a congener thereof, a transcript thereof, or a variant or a derivative thereof. None of the previously known reports show that change in the expression of the gene or the transcript thereof can serve as a marker for stomach cancer.

The 44th target gene is the hsa-miR-4433b-3p gene, a congener thereof, a transcript thereof, or a variant or a derivative thereof. None of the previously known reports show that change in the expression of the gene or the transcript thereof can serve as a marker for stomach cancer.

The 45th target gene is the hsa-miR-3679-3p gene, a congener thereof, a transcript thereof, or a variant or a derivative thereof. None of the previously known reports show that change in the expression of the gene or the transcript thereof can serve as a marker for stomach cancer.

The 46th target gene is the hsa-miR-3135b gene, a congener thereof, a transcript thereof, or a variant or a derivative thereof. None of the previously known reports show that change in the expression of the gene or the transcript thereof can serve as a marker for stomach cancer.

The 47th target gene is the hsa-miR-3622a-5p gene, a congener thereof, a transcript thereof, or a variant or a derivative thereof. None of the previously known reports show that change in the expression of the gene or the transcript thereof can serve as a marker for stomach cancer.

The 48th target gene is the hsa-miR-711 gene, a congener thereof, a transcript thereof, or a variant or a derivative thereof. None of the previously known reports show that change in the expression of the gene or the transcript thereof can serve as a marker for stomach cancer.

The 49th target gene is the hsa-miR-4467 gene, a congener thereof, a transcript thereof, or a variant or a derivative thereof. None of the previously known reports show that change in the expression of the gene or the transcript thereof can serve as a marker for stomach cancer.

The 50th target gene is the hsa-miR-6857-5p gene, a congener thereof, a transcript thereof, or a variant or a derivative thereof. None of the previously known reports show that change in the expression of the gene or the transcript thereof can serve as a marker for stomach cancer.

The 51st target gene is the hsa-miR-6515-3p gene, a congener thereof, a transcript thereof, or a variant or a derivative thereof. None of the previously known reports show that change in the expression of the gene or the transcript thereof can serve as a marker for stomach cancer.

The 52nd target gene is the hsa-miR-1225-5p gene, a congener thereof, a transcript thereof, or a variant or a derivative thereof. None of the previously known reports show that change in the expression of the gene or the transcript thereof can serve as a marker for stomach cancer.

The 53rd target gene is the hsa-miR-187-5p gene, a congener thereof, a transcript thereof, or a variant or a derivative thereof. None of the previously known reports show that change in the expression of the gene or the transcript thereof can serve as a marker for stomach cancer.

The 54th target gene is the hsa-miR-3185 gene, a congener thereof, a transcript thereof, or a variant or a derivative thereof. None of the previously known reports show that change in the expression of the gene or the transcript thereof can serve as a marker for stomach cancer.

The 55th target gene is the hsa-miR-642b-3p gene, a congener thereof, a transcript thereof, or a variant or a derivative thereof. None of the previously known reports show that change in the expression of the gene or the transcript thereof can serve as a marker for stomach cancer.

The 56th target gene is the hsa-miR-1249 gene, a congener thereof, a transcript thereof, or a variant or a derivative thereof. None of the previously known reports show that change in the expression of the gene or the transcript thereof can serve as a marker for stomach cancer.

The 57th target gene is the hsa-miR-744-5p gene, a congener thereof, a transcript thereof, or a variant or a derivative thereof. None of the previously known reports show that change in the expression of the gene or the transcript thereof can serve as a marker for stomach cancer.

The 58th target gene is the hsa-miR-4442 gene, a congener thereof, a transcript thereof, or a variant or a derivative thereof. None of the previously known reports show that change in the expression of the gene or the transcript thereof can serve as a marker for stomach cancer.

The 59th target gene is the hsa-miR-1228-3p gene, a congener thereof, a transcript thereof, or a variant or a derivative thereof. None of the previously known reports show that change in the expression of the gene or the transcript thereof can serve as a marker for stomach cancer.

The 60th target gene is the hsa-miR-939-5p gene, a congener thereof, a transcript thereof, or a variant or a derivative thereof. None of the previously known reports show that change in the expression of the gene or the transcript thereof can serve as a marker for stomach cancer.

The 61st target gene is the hsa-miR-6845-5p gene, a congener thereof, a transcript thereof, or a variant or a derivative thereof. None of the previously known reports show that change in the expression of the gene or the transcript thereof can serve as a marker for stomach cancer.

The 62nd target gene is the hsa-miR-887-3p gene, a congener thereof, a transcript thereof, or a variant or a derivative thereof. None of the previously known reports show that change in the expression of the gene or the transcript thereof can serve as a marker for stomach cancer.

The 63rd target gene is the hsa-miR-7845-5p gene, a congener thereof, a transcript thereof, or a variant or a derivative thereof. None of the previously known reports show that change in the expression of the gene or the transcript thereof can serve as a marker for stomach cancer.

The 64th target gene is the hsa-miR-6729-5p gene, a congener thereof, a transcript thereof, or a variant or a derivative thereof. None of the previously known reports show that change in the expression of the gene or the transcript thereof can serve as a marker for stomach cancer.

The 65th target gene is the hsa-miR-4632-5p gene, a congener thereof, a transcript thereof, or a variant or a derivative thereof. None of the previously known reports show that change in the expression of the gene or the transcript thereof can serve as a marker for stomach cancer.

The 66th target gene is the hsa-miR-615-5p gene, a congener thereof, a transcript thereof, or a variant or a derivative thereof. None of the previously known reports show that change in the expression of the gene or the transcript thereof can serve as a marker for stomach cancer.

The 67th target gene is the hsa-miR-6724-5p gene, a congener thereof, a transcript thereof, or a variant or a derivative thereof. None of the previously known reports show that change in the expression of the gene or the transcript thereof can serve as a marker for stomach cancer.

The 68th target gene is the hsa-miR-4728-5p gene, a congener thereof, a transcript thereof, or a variant or a derivative thereof. None of the previously known reports show that change in the expression of the gene or the transcript thereof can serve as a marker for stomach cancer.

The 69th target gene is the hsa-miR-6732-5p gene, a congener thereof, a transcript thereof, or a variant or a derivative thereof. None of the previously known reports show that change in the expression of the gene or the transcript thereof can serve as a marker for stomach cancer.

The 70th target gene is the hsa-miR-6816-5p gene, a congener thereof, a transcript thereof, or a variant or a derivative thereof. None of the previously known reports show that change in the expression of the gene or the transcript thereof can serve as a marker for stomach cancer.

The 71st target gene is the hsa-miR-4695-5p gene, a congener thereof, a transcript thereof, or a variant or a derivative thereof. None of the previously known reports show that change in the expression of the gene or the transcript thereof can serve as a marker for stomach cancer.

The 72nd target gene is the hsa-miR-6088 gene, a congener thereof, a transcript thereof, or a variant or a derivative thereof. None of the previously known reports show that change in the expression of the gene or the transcript thereof can serve as a marker for stomach cancer.

The 73rd target gene is the hsa-miR-7975 gene, a congener thereof, a transcript thereof, or a variant or a derivative thereof. None of the previously known reports show that change in the expression of the gene or the transcript thereof can serve as a marker for stomach cancer.

The 74th target gene is the hsa-miR-3197 gene, a congener thereof, a transcript thereof, or a variant or a derivative thereof. None of the previously known reports show that change in the expression of the gene or the transcript thereof can serve as a marker for stomach cancer.

The 75th target gene is the hsa-miR-6125 gene, a congener thereof, a transcript thereof, or a variant or a derivative thereof. None of the previously known reports show that change in the expression of the gene or the transcript thereof can serve as a marker for stomach cancer.

The 76th target gene is the hsa-miR-4433-3p gene, a congener thereof, a transcript thereof, or a variant or a derivative thereof. None of the previously known reports show that change in the expression of the gene or the transcript thereof can serve as a marker for stomach cancer.

The 77th target gene is the hsa-miR-6727-5p gene, a congener thereof, a transcript thereof, or a variant or a derivative thereof. None of the previously known reports show that change in the expression of the gene or the transcript thereof can serve as a marker for stomach cancer.

The 78th target gene is the hsa-miR-4706 gene, a congener thereof, a transcript thereof, or a variant or a derivative thereof. None of the previously known reports show that change in the expression of the gene or the transcript thereof can serve as a marker for stomach cancer.

The 79th target gene is the hsa-miR-7847-3p gene, a congener thereof, a transcript thereof, or a variant or a derivative thereof. None of the previously known reports show that change in the expression of the gene or the transcript thereof can serve as a marker for stomach cancer.

The 80th target gene is the hsa-miR-6805-3p gene, a congener thereof, a transcript thereof, or a variant or a derivative thereof. None of the previously known reports show that change in the expression of the gene or the transcript thereof can serve as a marker for stomach cancer.

The 81st target gene is the hsa-miR-6766-3p gene, a congener thereof, a transcript thereof, or a variant or a derivative thereof. None of the previously known reports show that change in the expression of the gene or the transcript thereof can serve as a marker for stomach cancer.

The 82nd target gene is the hsa-miR-1913 gene, a congener thereof, a transcript thereof, or a variant or a derivative thereof. None of the previously known reports show that change in the expression of the gene or the transcript thereof can serve as a marker for stomach cancer.

The 83rd target gene is the hsa-miR-4649-5p gene, a congener thereof, a transcript thereof, or a variant or a derivative thereof. None of the previously known reports show that change in the expression of the gene or the transcript thereof can serve as a marker for stomach cancer.

The 84th target gene is the hsa-miR-602 gene, a congener thereof, a transcript thereof, or a variant or a derivative thereof. None of the previously known reports show that change in the expression of the gene or the transcript thereof can serve as a marker for stomach cancer.

The 85th target gene is the hsa-miR-3663-3p gene, a congener thereof, a transcript thereof, or a variant or a derivative thereof. None of the previously known reports show that change in the expression of the gene or the transcript thereof can serve as a marker for stomach cancer.

The 86th target gene is the hsa-miR-6893-5p gene, a congener thereof, a transcript thereof, or a variant or a derivative thereof. None of the previously known reports show that change in the expression of the gene or the transcript thereof can serve as a marker for stomach cancer.

The 87th target gene is the hsa-miR-6861-5p gene, a congener thereof, a transcript thereof, or a variant or a derivative thereof. None of the previously known reports show that change in the expression of the gene or the transcript thereof can serve as a marker for stomach cancer.

The 88th target gene is the hsa-miR-4449 gene, a congener thereof, a transcript thereof, or a variant or a derivative thereof. None of the previously known reports show that change in the expression of the gene or the transcript thereof can serve as a marker for stomach cancer.

The 89th target gene is the hsa-miR-6842-5p gene, a congener thereof, a transcript thereof, or a variant or a derivative thereof. None of the previously known reports show that change in the expression of the gene or the transcript thereof can serve as a marker for stomach cancer.

The 90th target gene is the hsa-miR-4454 gene, a congener thereof, a transcript thereof, or a variant or a derivative thereof. None of the previously known reports show that change in the expression of the gene or the transcript thereof can serve as a marker for stomach cancer.

The 91st target gene is the hsa-miR-5195-3p gene, a congener thereof, a transcript thereof, or a variant or a derivative thereof. None of the previously known reports show that change in the expression of the gene or the transcript thereof can serve as a marker for stomach cancer.

The 92nd target gene is the hsa-miR-663b gene, a congener thereof, a transcript thereof, or a variant or a derivative thereof. None of the previously known reports show that change in the expression of the gene or the transcript thereof can serve as a marker for stomach cancer.

The 93rd target gene is the hsa-miR-6765-5p gene, a congener thereof, a transcript thereof, or a variant or a derivative thereof. None of the previously known reports show that change in the expression of the gene or the transcript thereof can serve as a marker for stomach cancer.

The 94th target gene is the hsa-miR-4513 gene, a congener thereof, a transcript thereof, or a variant or a derivative thereof. None of the previously known reports show that change in the expression of the gene or the transcript thereof can serve as a marker for stomach cancer.

The 95th target gene is the hsa-miR-614 gene, a congener thereof, a transcript thereof, or a variant or a derivative thereof. None of the previously known reports show that change in the expression of the gene or the transcript thereof can serve as a marker for stomach cancer.

The 96th target gene is the hsa-miR-6785-5p gene, a congener thereof, a transcript thereof, or a variant or a derivative thereof. None of the previously known reports show that change in the expression of the gene or the transcript thereof can serve as a marker for stomach cancer.

The 97th target gene is the hsa-miR-6777-5p gene, a congener thereof, a transcript thereof, or a variant or a derivative thereof. None of the previously known reports show that change in the expression of the gene or the transcript thereof can serve as a marker for stomach cancer.

The 98th target gene is the hsa-miR-940 gene, a congener thereof, a transcript thereof, or a variant or a derivative thereof. None of the previously known reports show that change in the expression of the gene or the transcript thereof can serve as a marker for stomach cancer.

The 99th target gene is the hsa-miR-4741 gene, a congener thereof, a transcript thereof, or a variant or a derivative thereof. None of the previously known reports show that change in the expression of the gene or the transcript thereof can serve as a marker for stomach cancer.

The 100th target gene is the hsa-miR-6870-5p gene, a congener thereof, a transcript thereof, or a variant or a derivative thereof. None of the previously known reports show that change in the expression of the gene or the transcript thereof can serve as a marker for stomach cancer.

The 101st target gene is the hsa-miR-6131 gene, a congener thereof, a transcript thereof, or a variant or a derivative thereof. None of the previously known reports show that change in the expression of the gene or the transcript thereof can serve as a marker for stomach cancer.

The 102nd target gene is the hsa-miR-150-3p gene, a congener thereof, a transcript thereof, or a variant or a derivative thereof. None of the previously known reports show that change in the expression of the gene or the transcript thereof can serve as a marker for stomach cancer.

The 103rd target gene is the hsa-miR-4707-5p gene, a congener thereof, a transcript thereof, or a variant or a derivative thereof. None of the previously known reports show that change in the expression of the gene or the transcript thereof can serve as a marker for stomach cancer.

The 104th target gene is the hsa-miR-1915-3p gene, a congener thereof, a transcript thereof, or a variant or a derivative thereof. None of the previously known reports show that change in the expression of the gene or the transcript thereof can serve as a marker for stomach cancer.

The 105th target gene is the hsa-miR-3937 gene, a congener thereof, a transcript thereof, or a variant or a derivative thereof. None of the previously known reports show that change in the expression of the gene or the transcript thereof can serve as a marker for stomach cancer.

The 106th target gene is the hsa-miR-937-5p gene, a congener thereof, a transcript thereof, or a variant or a derivative thereof. None of the previously known reports show that change in the expression of the gene or the transcript thereof can serve as a marker for stomach cancer.

The 107th target gene is the hsa-miR-4443 gene, a congener thereof, a transcript thereof, or a variant or a derivative thereof. None of the previously known reports show that change in the expression of the gene or the transcript thereof can serve as a marker for stomach cancer.

The 108th target gene is the hsa-miR-1914-3p gene, a congener thereof, a transcript thereof, or a variant or a derivative thereof. None of the previously known reports show that change in the expression of the gene or the transcript thereof can serve as a marker for stomach cancer.

The 109th target gene is the hsa-miR-3620-5p gene, a congener thereof, a transcript thereof, or a variant or a derivative thereof. None of the previously known reports show that change in the expression of the gene or the transcript thereof can serve as a marker for stomach cancer.

The 110th target gene is the hsa-miR-1268b gene, a congener thereof, a transcript thereof, or a variant or a derivative thereof. None of the previously known reports show that change in the expression of the gene or the transcript thereof can serve as a marker for stomach cancer.

The 111th target gene is the hsa-miR-1227-5p gene, a congener thereof, a transcript thereof, or a variant or a derivative thereof. None of the previously known reports show that change in the expression of the gene or the transcript thereof can serve as a marker for stomach cancer.

The 112th target gene is the hsa-miR-6880-5p gene, a congener thereof, a transcript thereof, or a variant or a derivative thereof. None of the previously known reports show that change in the expression of the gene or the transcript thereof can serve as a marker for stomach cancer.

The 113th target gene is the hsa-miR-4417 gene, a congener thereof, a transcript thereof, or a variant or a derivative thereof. None of the previously known reports show that change in the expression of the gene or the transcript thereof can serve as a marker for stomach cancer.

The 114th target gene is the hsa-miR-6802-5p gene, a congener thereof, a transcript thereof, or a variant or a derivative thereof. None of the previously known reports show that change in the expression of the gene or the transcript thereof can serve as a marker for stomach cancer.

The 115th target gene is the hsa-miR-6769a-5p gene, a congener thereof, a transcript thereof, or a variant or a derivative thereof. None of the previously known reports show that change in the expression of the gene or the transcript thereof can serve as a marker for stomach cancer.

The 116th target gene is the hsa-miR-663a gene, a congener thereof, a transcript thereof, or a variant or a derivative thereof. None of the previously known reports show that change in the expression of the gene or the transcript thereof can serve as a marker for stomach cancer.

The 117th target gene is the hsa-miR-6721-5p gene, a congener thereof, a transcript thereof, or a variant or a derivative thereof. None of the previously known reports show that change in the expression of the gene or the transcript thereof can serve as a marker for stomach cancer.

The 118th target gene is the hsa-miR-4532 gene, a congener thereof, a transcript thereof, or a variant or a derivative thereof. None of the previously known reports show that change in the expression of the gene or the transcript thereof can serve as a marker for stomach cancer.

The 119th target gene is the hsa-miR-7977 gene, a congener thereof, a transcript thereof, or a variant or a derivative thereof. None of the previously known reports show that change in the expression of the gene or the transcript thereof can serve as a marker for stomach cancer.

The 120th target gene is the hsa-miR-92b-5p gene, a congener thereof, a transcript thereof, or a variant or a derivative thereof. None of the previously known reports show that change in the expression of the gene or the transcript thereof can serve as a marker for stomach cancer.

The 121st target gene is the hsa-miR-371a-5p gene, a congener thereof, a transcript thereof, or a variant or a derivative thereof. None of the previously known reports show that change in the expression of the gene or the transcript thereof can serve as a marker for stomach cancer.

The 122nd target gene is the hsa-miR-6126 gene, a congener thereof, a transcript thereof, or a variant or a derivative thereof. None of the previously known reports show that change in the expression of the gene or the transcript thereof can serve as a marker for stomach cancer.

The 123rd target gene is the hsa-miR-4734 gene, a congener thereof, a transcript thereof, or a variant or a derivative thereof. None of the previously known reports show that change in the expression of the gene or the transcript thereof can serve as a marker for stomach cancer.

The 124th target gene is the hsa-miR-4665-3p gene, a congener thereof, a transcript thereof, or a variant or a derivative thereof. None of the previously known reports show that change in the expression of the gene or the transcript thereof can serve as a marker for stomach cancer.

The 125th target gene is the hsa-miR-423-5p gene, a congener thereof, a transcript thereof, or a variant or a derivative thereof. None of the previously known reports show that change in the expression of the gene or the transcript thereof can serve as a marker for stomach cancer.

The 126th target gene is the hsa-miR-1469 gene, a congener thereof, a transcript thereof, or a variant or a derivative thereof. None of the previously known reports show that change in the expression of the gene or the transcript thereof can serve as a marker for stomach cancer.

The 127th target gene is the hsa-miR-4675 gene, a congener thereof, a transcript thereof, or a variant or a derivative thereof. None of the previously known reports show that change in the expression of the gene or the transcript thereof can serve as a marker for stomach cancer.

The 128th target gene is the hsa-miR-1915-5p gene, a congener thereof, a transcript thereof, or a variant or a derivative thereof. None of the previously known reports show that change in the expression of the gene or the transcript thereof can serve as a marker for stomach cancer.

The 129th target gene is the hsa-miR-6716-5p gene, a congener thereof, a transcript thereof, or a variant or a derivative thereof. None of the previously known reports show that change in the expression of the gene or the transcript thereof can serve as a marker for stomach cancer.

The 130th target gene is the hsa-miR-718 gene, a congener thereof, a transcript thereof, or a variant or a derivative thereof. None of the previously known reports show that change in the expression of the gene or the transcript thereof can serve as a marker for stomach cancer.

The 131st target gene is the hsa-miR-4281 gene, a congener thereof, a transcript thereof, or a variant or a derivative thereof. None of the previously known reports show that change in the expression of the gene or the transcript thereof can serve as a marker for stomach cancer.

The 132nd target gene is the hsa-miR-6820-5p gene, a congener thereof, a transcript thereof, or a variant or a derivative thereof. None of the previously known reports show that change in the expression of the gene or the transcript thereof can serve as a marker for stomach cancer.

The 133rd target gene is the hsa-miR-6795-5p gene, a congener thereof, a transcript thereof, or a variant or a derivative thereof. None of the previously known reports show that change in the expression of the gene or the transcript thereof can serve as a marker for stomach cancer.

The 134th target gene is the hsa-miR-6779-5p gene, a congener thereof, a transcript thereof, or a variant or a derivative thereof. None of the previously known reports show that change in the expression of the gene or the transcript thereof can serve as a marker for stomach cancer.

The 135th target gene is the hsa-miR-7109-5p gene, a congener thereof, a transcript thereof, or a variant or a derivative thereof. None of the previously known reports show that change in the expression of the gene or the transcript thereof can serve as a marker for stomach cancer.

The 136th target gene is the hsa-miR-6798-5p gene, a congener thereof, a transcript thereof, or a variant or a derivative thereof. None of the previously known reports show that change in the expression of the gene or the transcript thereof can serve as a marker for stomach cancer.

The 137th target gene is the hsa-miR-4648 gene, a congener thereof, a transcript thereof, or a variant or a derivative thereof. None of the previously known reports show that change in the expression of the gene or the transcript thereof can serve as a marker for stomach cancer.

The 138th target gene is the hsa-miR-8059 gene, a congener thereof, a transcript thereof, or a variant or a derivative thereof. None of the previously known reports show that change in the expression of the gene or the transcript thereof can serve as a marker for stomach cancer.

The 139th target gene is the hsa-miR-6765-3p gene, a congener thereof, a transcript thereof, or a variant or a derivative thereof. None of the previously known reports show that change in the expression of the gene or the transcript thereof can serve as a marker for stomach cancer.

The 140th target gene is the hsa-miR-6132 gene, a congener thereof, a transcript thereof, or a variant or a derivative thereof. None of the previously known reports show that change in the expression of the gene or the transcript thereof can serve as a marker for stomach cancer.

The 141st target gene is the hsa-miR-4492 gene, a congener thereof, a transcript thereof, or a variant or a derivative thereof. None of the previously known reports show that change in the expression of the gene or the transcript thereof can serve as a marker for stomach cancer.

The 142nd target gene is the hsa-miR-7107-5p gene, a congener thereof, a transcript thereof, or a variant or a derivative thereof. None of the previously known reports show that change in the expression of the gene or the transcript thereof can serve as a marker for stomach cancer.

The 143rd target gene is the hsa-miR-3195 gene, a congener thereof, a transcript thereof, or a variant or a derivative thereof. None of the previously known reports show that change in the expression of the gene or the transcript thereof can serve as a marker for stomach cancer.

The 144th target gene is the hsa-miR-3180 gene, a congener thereof, a transcript thereof, or a variant or a derivative thereof. None of the previously known reports show that change in the expression of the gene or the transcript thereof can serve as a marker for stomach cancer.

The 145th target gene is the hsa-miR-296-3p gene, a congener thereof, a transcript thereof, or a variant or a derivative thereof. None of the previously known reports show that change in the expression of the gene or the transcript thereof can serve as a marker for stomach cancer.

The 146th target gene is the hsa-miR-564 gene, a congener thereof, a transcript thereof, or a variant or a derivative thereof. None of the previously known reports show that change in the expression of the gene or the transcript thereof can serve as a marker for stomach cancer.

The 147th target gene is the hsa-miR-1268a gene, a congener thereof, a transcript thereof, or a variant or a derivative thereof. None of the previously known reports show that change in the expression of the gene or the transcript thereof can serve as a marker for stomach cancer.

The 148th target gene is the hsa-miR-6848-5p gene, a congener thereof, a transcript thereof, or a variant or a derivative thereof. None of the previously known reports show that change in the expression of the gene or the transcript thereof can serve as a marker for stomach cancer.

The 149th target gene is the hsa-miR-762 gene, a congener thereof, a transcript thereof, or a variant or a derivative thereof. None of the previously known reports show that change in the expression of the gene or the transcript thereof can serve as a marker for stomach cancer.

The 150th target gene is the hsa-miR-2861 gene, a congener thereof, a transcript thereof, or a variant or a derivative thereof. None of the previously known reports show that change in the expression of the gene or the transcript thereof can serve as a marker for stomach cancer.

The 151st target gene is the hsa-miR-1203 gene, a congener thereof, a transcript thereof, or a variant or a derivative The 152nd target gene is the hsa-miR-1260b gene, a congener thereof, a transcript thereof, or a variant or a derivative thereof. None of the previously known reports show that change in the expression of the gene or the transcript thereof can serve as a marker for stomach cancer.

The 153rd target gene is the hsa-miR-4476 gene, a congener thereof, a transcript thereof, or a variant or a derivative thereof. None of the previously known reports show that change in the expression of the gene or the transcript thereof can serve as a marker for stomach cancer.

The 154th target gene is the hsa-miR-6885-5p gene, a congener thereof, a transcript thereof, or a variant or a derivative thereof. None of the previously known reports show that change in the expression of the gene or the transcript thereof can serve as a marker for stomach cancer.

The 155th target gene is the hsa-miR-6769b-5p gene, a congener thereof, a transcript thereof, or a variant or a derivative thereof. None of the previously known reports show that change in the expression of the gene or the transcript thereof can serve as a marker for stomach cancer.

The 156th target gene is the hsa-miR-23b-3p gene, a congener thereof, a transcript thereof, or a variant or a derivative thereof. None of the previously known reports show that change in the expression of the gene or the transcript thereof can serve as a marker for stomach cancer.

The 157th target gene is the hsa-miR-1343-5p gene, a congener thereof, a transcript thereof, or a variant or a derivative thereof. None of the previously known reports show that change in the expression of the gene or the transcript thereof can serve as a marker for stomach cancer.

The 158th target gene is the hsa-miR-3621 gene, a congener thereof, a transcript thereof, or a variant or a derivative thereof. None of the previously known reports show that change in the expression of the gene or the transcript thereof can serve as a marker for stomach cancer.

The 159th target gene is the hsa-miR-4688 gene, a congener thereof, a transcript thereof, or a variant or a derivative thereof. None of the previously known reports show that change in the expression of the gene or the transcript thereof can serve as a marker for stomach cancer.

The 160th target gene is the hsa-miR-4286 gene, a congener thereof, a transcript thereof, or a variant or a derivative thereof. None of the previously known reports show that change in the expression of the gene or the transcript thereof can serve as a marker for stomach cancer.

The 161st target gene is the hsa-miR-4640-5p gene, a congener thereof, a transcript thereof, or a variant or a derivative thereof. None of the previously known reports show that change in the expression of the gene or the transcript thereof can serve as a marker for stomach cancer.

The 162nd target gene is the hsa-miR-4739 gene, a congener thereof, a transcript thereof, or a variant or a derivative thereof. None of the previously known reports show that change in the expression of the gene or the transcript thereof can serve as a marker for stomach cancer.

The 163rd target gene is the hsa-miR-1260a gene, a congener thereof, a transcript thereof, or a variant or a derivative thereof. None of the previously known reports show that change in the expression of the gene or the transcript thereof can serve as a marker for stomach cancer.

The 164th target gene is the hsa-miR-4276 gene, a congener thereof, a transcript thereof, or a variant or a derivative thereof. None of the previously known reports show that change in the expression of the gene or the transcript thereof can serve as a marker for stomach cancer.

The 165th target gene is the hsa-miR-7106-5p gene, a congener thereof, a transcript thereof, or a variant or a derivative thereof. None of the previously known reports show that change in the expression of the gene or the transcript thereof can serve as a marker for stomach cancer.

The 166th target gene is the hsa-miR-128-2-5p gene, a congener thereof, a transcript thereof, or a variant or a derivative thereof. The previously known report shows that change in the expression of the hsa-miR-128b (hsa-miR-128-2-3p) gene, which is derived from the same precursor, or the transcript thereof can serve as a marker for stomach cancer (Patent Literature 2).

The 167th target gene is the hsa-miR-125a-3p gene, a congener thereof, a transcript thereof, or a variant or a derivative thereof. The previously known report shows that change in the expression of the gene or the transcript thereof can serve as a marker for stomach cancer (Patent Literature 1).

The 168th target gene is the hsa-miR-92a-2-5p gene, a congener thereof, a transcript thereof, or a variant or a derivative thereof. The previously known report shows that change in the expression of the hsa-miR-92-2 (hsa-miR-92a-2-3p) gene, which is derived from the same precursor, or the transcript thereof can serve as a marker for stomach cancer (Patent Literature 2).

The 169th target gene is the hsa-miR-486-3p gene, a congener thereof, a transcript thereof, or a variant or a derivative thereof. The previously known report shows that change in the expression of the hsa-miR-486-5p gene, which is derived from the same precursor, or the transcript thereof can serve as a marker for stomach cancer (Patent Literature 3).

The 170th target gene is the hsa-miR-3196 gene, a congener thereof, a transcript thereof, or a variant or a derivative thereof. None of the previously known reports show that change in the expression of the gene or the transcript thereof can serve as a marker for stomach cancer.

The 171st target gene is the hsa-miR-211-3p gene, a congener thereof, a transcript thereof, or a variant or a derivative thereof. The previously known report shows that change in the expression of the hsa-miR-211 (hsa-miR-211-5p) gene, which is derived from the same precursor, or the transcript thereof can serve as a marker for stomach cancer (Patent Literature 2).

The 172nd target gene is the hsa-miR-4271 gene, a congener thereof, a transcript thereof, or a variant or a derivative thereof. None of the previously known reports show that change in the expression of the gene or the transcript thereof can serve as a marker for stomach cancer.

The 173rd target gene is the hsa-miR-6851-5p gene, a congener thereof, a transcript thereof, or a variant or a derivative thereof. None of the previously known reports show that change in the expression of the gene or the transcript thereof can serve as a marker for stomach cancer.

The 174th target gene is the hsa-miR-149-3p gene, a congener thereof, a transcript thereof, or a variant or a derivative thereof. None of the previously known reports show that change in the expression of the gene or the transcript thereof can serve as a marker for stomach cancer.

The 175th target gene is the hsa-miR-4667-5p gene, a congener thereof, a transcript thereof, or a variant or a derivative thereof. None of the previously known reports show that change in the expression of the gene or the transcript thereof can serve as a marker for stomach cancer.

The 176th target gene is the hsa-miR-135a-3p gene, a congener thereof, a transcript thereof, or a variant or a derivative thereof. None of the previously known reports show that change in the expression of the gene or the transcript thereof can serve as a marker for stomach cancer.

The 177th target gene is the hsa-miR-4486 gene, a congener thereof, a transcript thereof, or a variant or a derivative thereof. None of the previously known reports show that change in the expression of the gene or the transcript thereof can serve as a marker for stomach cancer.

The 178th target gene is the hsa-miR-4697-5p gene, a congener thereof, a transcript thereof, or a variant or a derivative thereof. None of the previously known reports show that change in the expression of the gene or the transcript thereof can serve as a marker for stomach cancer.

The 179th target gene is the hsa-miR-4725-3p gene, a congener thereof, a transcript thereof, or a variant or a derivative thereof. None of the previously known reports show that change in the expression of the gene or the transcript thereof can serve as a marker for stomach cancer.

The 180th target gene is the hsa-miR-6510-5p gene, a congener thereof, a transcript thereof, or a variant or a derivative thereof. None of the previously known reports show that change in the expression of the gene or the transcript thereof can serve as a marker for stomach cancer.

The 181st target gene is the hsa-miR-5001-5p gene, a congener thereof, a transcript thereof, or a variant or a derivative thereof. None of the previously known reports show that change in the expression of the gene or the transcript thereof can serve as a marker for stomach cancer.

The 182nd target gene is the hsa-miR-4673 gene, a congener thereof, a transcript thereof, or a variant or a derivative thereof. None of the previously known reports show that change in the expression of the gene or the transcript thereof can serve as a marker for stomach cancer.

The 183rd target gene is the hsa-miR-4466 gene, a congener thereof, a transcript thereof, or a variant or a derivative thereof. None of the previously known reports show that change in the expression of the gene or the transcript thereof can serve as a marker for stomach cancer.

The 184th target gene is the hsa-miR-23a-3p gene, a congener thereof, a transcript thereof, or a variant or a derivative thereof. The previously known report shows that change in the expression of the gene or the transcript thereof can serve as a marker for stomach cancer (Patent Literature 2).

The 185th target gene is the hsa-miR-3656 gene, a congener thereof, a transcript thereof, or a variant or a derivative thereof. None of the previously known reports show that change in the expression of the gene or the transcript thereof can serve as a marker for stomach cancer.

The 186th target gene is the hsa-miR-6782-5p gene, a congener thereof, a transcript thereof, or a variant or a derivative thereof. None of the previously known reports show that change in the expression of the gene or the transcript thereof can serve as a marker for stomach cancer.

The 187th target gene is the hsa-miR-4689 gene, a congener thereof, a transcript thereof, or a variant or a derivative thereof. None of the previously known reports show that change in the expression of the gene or the transcript thereof can serve as a marker for stomach cancer.

The 188th target gene is the hsa-miR-451a gene, a congener thereof, a transcript thereof, or a variant or a derivative thereof. The previously known report shows that change in the expression of the gene or the transcript thereof can serve as a marker for stomach cancer (Patent Literature 3).

The 189th target gene is the hsa-miR-4446-3p gene, a congener thereof, a transcript thereof, or a variant or a derivative thereof. None of the previously known reports show that change in the expression of the gene or the transcript thereof can serve as a marker for stomach cancer.

The 190th target gene is the hsa-miR-3180-3p gene, a congener thereof, a transcript thereof, or a variant or a derivative thereof. None of the previously known reports show that change in the expression of the gene or the transcript thereof can serve as a marker for stomach cancer.

The 191st target gene is the hsa-miR-642a-3p gene, a congener thereof, a transcript thereof, or a variant or a derivative thereof. None of the previously known reports show that change in the expression of the gene or the transcript thereof can serve as a marker for stomach cancer.

The 192nd target gene is the hsa-miR-6889-5p gene, a congener thereof, a transcript thereof, or a variant or a derivative thereof. None of the previously known reports show that change in the expression of the gene or the transcript thereof can serve as a marker for stomach cancer.

The 193rd target gene is the hsa-miR-3178 gene, a congener thereof, a transcript thereof, or a variant or a derivative thereof. None of the previously known reports show that change in the expression of the gene or the transcript thereof can serve as a marker for stomach cancer.

The 194th target gene is the hsa-miR-4665-5p gene, a congener thereof, a transcript thereof, or a variant or a derivative thereof. None of the previously known reports show that change in the expression of the gene or the transcript thereof can serve as a marker for stomach cancer.

The 195th target gene is the hsa-miR-6722-3p gene, a congener thereof, a transcript thereof, or a variant or a derivative thereof. None of the previously known reports show that change in the expression of the gene or the transcript thereof can serve as a marker for stomach cancer.

The 196th target gene is the hsa-miR-30c-1-3p gene, a congener thereof, a transcript thereof, or a variant or a derivative thereof. The previously known report shows that change in the expression of the hsa-miR-30c (hsa-miR-30c-1-5p) gene, which is derived from the same precursor, or the transcript thereof can serve as a marker for stomach cancer (Patent Literature 2).

The 197th target gene is the hsa-miR-4507 gene, a congener thereof, a transcript thereof, or a variant or a derivative thereof. None of the previously known reports show that change in the expression of the gene or the transcript thereof can serve as a marker for stomach cancer.

The 198th target gene is the hsa-miR-3141 gene, a congener thereof, a transcript thereof, or a variant or a derivative thereof. None of the previously known reports show that change in the expression of the gene or the transcript thereof can serve as a marker for stomach cancer.

The 199th target gene is the hsa-miR-1199-5p gene, a congener thereof, a transcript thereof, or a variant or a derivative thereof. None of the previously known reports show that change in the expression of the gene or the transcript thereof can serve as a marker for stomach cancer.

The 200th target gene is the hsa-miR-6794-5p gene, a congener thereof, a transcript thereof, or a variant or a derivative thereof. None of the previously known reports show that change in the expression of the gene or the transcript thereof can serve as a marker for stomach cancer.

The 201st target gene is the hsa-miR-6774-5p gene, a congener thereof, a transcript thereof, or a variant or a derivative thereof. None of the previously known reports show that change in the expression of the gene or the transcript thereof can serve as a marker for stomach cancer.

The 202nd target gene is the hsa-miR-4707-3p gene, a congener thereof, a transcript thereof, or a variant or a derivative thereof. None of the previously known reports show that change in the expression of the gene or the transcript thereof can serve as a marker for stomach cancer.

The 203rd target gene is the hsa-miR-4534 gene, a congener thereof, a transcript thereof, or a variant or a derivative thereof. None of the previously known reports show that change in the expression of the gene or the transcript thereof can serve as a marker for stomach cancer.

The 204th target gene is the hsa-miR-4294 gene, a congener thereof, a transcript thereof, or a variant or a derivative thereof. None of the previously known reports show that change in the expression of the gene or the transcript thereof can serve as a marker for stomach cancer.

The 205th target gene is the hsa-miR-6850-5p gene, a congener thereof, a transcript thereof, or a variant or a derivative thereof. None of the previously known reports show that change in the expression of the gene or the transcript thereof can serve as a marker for stomach cancer.

The 206th target gene is the hsa-miR-6089 gene, a congener thereof, a transcript thereof, or a variant or a derivative thereof. None of the previously known reports show that change in the expression of the gene or the transcript thereof can serve as a marker for stomach cancer.

The 207th target gene is the hsa-miR-671-5p gene, a congener thereof, a transcript thereof, or a variant or a derivative thereof. None of the previously known reports show that change in the expression of the gene or the transcript thereof can serve as a marker for stomach cancer.

2. Nucleic Acid Probe or Primer for Detection of Stomach Cancer

In the present invention, a nucleic acid(s) capable of specifically binding to any of the target nucleic acid(s) as the stomach cancer marker(s) described above can be used as a nucleic acid(s), for example, a nucleic acid probe(s) or a primer(s), for the detection or diagnosis of stomach cancer.

In the present invention, the nucleic acid probe(s) or the primer(s) that can be used for detecting stomach cancer or for diagnosing stomach cancer enables qualitative and/or quantitative measurement of the presence, expression level, or abundance of any of the target nucleic acids as the stomach cancer markers described above, for example: human-derived hsa-miR-4257, hsa-miR-6726-5p, hsa-miR-1343-3p, hsa-miR-1247-3p, hsa-miR-6787-5p, hsa-miR-6875-5p, hsa-miR-1225-3p, hsa-miR-8063, hsa-miR-6781-5p, hsa-miR-4746-3p, hsa-miR-1908-5p, hsa-miR-6756-5p, hsa-miR-204-3p, hsa-miR-4651, hsa-miR-6757-5p, hsa-miR-6825-5p, hsa-miR-7108-5p, hsa-miR-4792, hsa-miR-7641, hsa-miR-3188, hsa-miR-3131, hsa-miR-6780b-5p, hsa-miR-8069, hsa-miR-6840-3p, hsa-miR-8072, hsa-miR-1233-5p, hsa-miR-6887-5p, hsa-miR-1231, hsa-miR-5572, hsa-miR-6738-5p, hsa-miR-6784-5p, hsa-miR-6791-5p, hsa-miR-6749-5p, hsa-miR-6741-5p, hsa-miR-128-1-5p, hsa-miR-4419b, hsa-miR-6746-5p, hsa-miR-3184-5p, hsa-miR-3679-5p, hsa-miR-7110-5p, hsa-miR-4516, hsa-miR-6717-5p, hsa-miR-6826-5p, hsa-miR-4433b-3p, hsa-miR-3679-3p, hsa-miR-3135b, hsa-miR-3622a-5p, hsa-miR-711, hsa-miR-4467, hsa-miR-6857-5p, hsa-miR-6515-3p, hsa-miR-1225-5p, hsa-miR-187-5p, hsa-miR-3185, hsa-miR-642b-3p, hsa-miR-1249, hsa-miR-744-5p, hsa-miR-4442, hsa-miR-1228-3p, hsa-miR-939-5p, hsa-miR-6845-5p, hsa-miR-887-3p, hsa-miR-7845-5p, hsa-miR-6729-5p, hsa-miR-4632-5p, hsa-miR-615-5p, hsa-miR-6724-5p, hsa-miR-4728-5p, hsa-miR-6732-5p, hsa-miR-6816-5p, hsa-miR-4695-5p, hsa-miR-6088, hsa-miR-7975, hsa-miR-3197, hsa-miR-6125, hsa-miR-4433-3p, hsa-miR-6727-5p, hsa-miR-4706, hsa-miR-7847-3p, hsa-miR-6805-3p, hsa-miR-6766-3p, hsa-miR-1913, hsa-miR-4649-5p, hsa-miR-602, hsa-miR-3663-3p, hsa-miR-6893-5p, hsa-miR-6861-5p, hsa-miR-4449, hsa-miR-6842-5p, hsa-miR-4454, hsa-miR-5195-3p, hsa-miR-663b, hsa-miR-6765-5p, hsa-miR-4513, hsa-miR-614, hsa-miR-6785-5p, hsa-miR-6777-5p, hsa-miR-940, hsa-miR-4741, hsa-miR-6870-5p, hsa-miR-6131, hsa-miR-150-3p, hsa-miR-4707-5p, hsa-miR-1915-3p, hsa-miR-3937, hsa-miR-937-5p, hsa-miR-4443, hsa-miR-1914-3p, hsa-miR-3620-5p, hsa-miR-1268b, hsa-miR-1227-5p, hsa-miR-6880-5p, hsa-miR-4417, hsa-miR-6802-5p, hsa-miR-6769a-5p, hsa-miR-663a, hsa-miR-6721-5p, hsa-miR-4532, hsa-miR-7977, hsa-miR-92b-5p, hsa-miR-371a-5p, hsa-miR-6126, hsa-miR-4734, hsa-miR-4665-3p, hsa-miR-423-5p, hsa-miR-1469, hsa-miR-4675, hsa-miR-1915-5p, hsa-miR-6716-5p, hsa-miR-718, hsa-miR-4281, hsa-miR-6820-5p, hsa-miR-6795-5p, hsa-miR-6779-5p, hsa-miR-7109-5p, hsa-miR-6798-5p, hsa-miR-4648, hsa-miR-8059, hsa-miR-6765-3p, hsa-miR-6132, hsa-miR-4492, hsa-miR-7107-5p, hsa-miR-3195, hsa-miR-3180, hsa-miR-296-3p, hsa-miR-564, hsa-miR-1268a, hsa-miR-6848-5p, hsa-miR-762, hsa-miR-2861, hsa-miR-1203, hsa-miR-1260b, hsa-miR-4476, hsa-miR-6885-5p, hsa-miR-6769b-5p, hsa-miR-23b-3p, hsa-miR-1343-5p, hsa-miR-3621, hsa-miR-4688, hsa-miR-4286, hsa-miR-4640-5p, hsa-miR-4739, hsa-miR-1260a, hsa-miR-4276, hsa-miR-7106, hsa-miR-6794-5p, hsa-miR-6774-5p, hsa-miR-4707-3p, hsa-miR-4534, hsa-miR-4294, hsa-miR-6850-5p, hsa-miR-6089 and hsa-miR-671-5p or a combination thereof, congeners thereof, transcripts thereof, or variants or derivatives thereof; and, optionally combined therewith, hsa-miR-128-2-5p, hsa-miR-125a-3p, hsa-miR-92a-2-5p, and hsa-miR-486-3p or a combination thereof, congeners thereof, transcripts thereof, or variants or derivatives thereof; and, optionally combined therewith, hsa-miR-3196, hsa-miR-211-3p, hsa-miR-4271, hsa-miR-6851-5p, hsa-miR-149-3p, hsa-miR-4667-5p, hsa-miR-135a-3p, hsa-miR-4486, hsa-miR-4697-5p, hsa-miR-4725-3p, hsa-miR-6510-5p, hsa-miR-5001-5p, hsa-miR-4673, hsa-miR-4466, hsa-miR-23a-3p, hsa-miR-3656, hsa-miR-6782-5p, hsa-miR-4689, hsa-miR-451a, hsa-miR-4446-3p, hsa-miR-3180-3p, hsa-miR-642a-3p, hsa-miR-6889-5p, hsa-miR-3178, hsa-miR-4665-5p, hsa-miR-6722-3p, hsa-miR-30c-1-3p, hsa-miR-4507, hsa-miR-3141 and hsa-miR-1199-5p or a combination thereof, congeners thereof, transcripts thereof, or variants or derivatives thereof.

The expression level of each target nucleic acid described above is increased or decreased (hereinafter, referred to as "increased/decreased") depending on the type of the target nucleic acid in a subject having stomach cancer as compared with a healthy subject. Hence, the nucleic acid of the present invention can be effectively used for measuring the expression level of the target nucleic acid described above in a body fluid derived from a subject (e.g., a human) suspected of having stomach cancer and a body fluid derived from a healthy subject and thereby detecting stomach cancer by the comparison thereof.

The nucleic acid probe(s) or the primer(s) that can be used in the present invention is a nucleic acid probe(s) capable of specifically binding to at least one polynucleotide consisting of a nucleotide sequence represented by any of SEQ ID NOs: 1 to 165 and 635 to 642, or a primer for amplifying at least one polynucleotide consisting of a nucleotide sequence represented by any of SEQ ID NOs: 1 to 165 and 635 to 642.

The nucleic acid probe(s) or the primer(s) that can be used in the present invention may further comprise a nucleic acid probe capable of specifically binding to at least one polynucleotide consisting of a nucleotide sequence represented by any of SEQ ID NOs: 166 to 169, or a primer for amplifying at least one polynucleotide consisting of a nucleotide sequence represented by any of SEQ ID NOs: 166 to 169.

The nucleic acid probe(s) or the primer(s) that can be used in the present invention may further comprise a nucleic acid probe capable of specifically binding to at least one polynucleotide consisting of a nucleotide sequence represented by any of SEQ ID NOs: 170 to 199, or a primer for amplifying at least one polynucleotide consisting of a nucleotide sequence represented by any of SEQ ID NOs: 170 to 199.

Specifically, these nucleic acid probes or primers comprise a combination of one or more polynucleotides selected from a group of polynucleotides comprising nucleotide sequences represented by any of SEQ ID NOs: 1 to 657, or nucleotide sequences derived from the nucleotide sequences by the replacement of u with t, and a group of complementary polynucleotides thereof, a group of polynucleotides respectively hybridizing under stringent conditions (mentioned later) to DNAs consisting of nucleotide sequences complementary to these nucleotide sequences, and a group of complementary polynucleotides thereof, and a group of polynucleotides comprising 15 or more, preferably 17 or more consecutive nucleotides in the nucleotide sequences of these polynucleotide groups. These polynucleotides can be used as nucleic acid probes and primers for detecting the stomach cancer markers as target nucleic acids.

More specifically, examples of the nucleic acid probe(s) or the primer(s) that can be used in the present invention include one or more polynucleotides selected from the group consisting of the following polynucleotides (a) to (e):

(a) a polynucleotide consisting of a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 165 and 635 to 642, (c) a polynucleotide consisting of a nucleotide sequence complementary to a nucleotide sequence represented by any of SEQ ID NOs: 1 to 165 and 635 to 642, or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 165 and 635 to 642, or a nucleotide sequence derived from the nucleotide sequence by the replacement of u with t, and (e) a polynucleotide hybridizing under stringent conditions to any of the polynucleotides (a) to (d).

In addition to at least one or more polynucleotides selected from the group consisting of the polynucleotides (a) to (e), the nucleic acid probe(s) or the primer(s) that can be used in the present invention may further comprise polynucleotides selected from the group consisting of the following polynucleotides (f) to (j):

(f) a polynucleotide consisting of a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 166 to 169, (h) a polynucleotide consisting of a nucleotide sequence complementary to a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 166 to 169 or a nucleotide sequence derived from the nucleotide sequence by the replacement of u with t, and (j) a polynucleotide hybridizing under stringent conditions to any of the polynucleotides (f) to (i).

In addition to at least one or more polynucleotide(s) selected from the group consisting of the polynucleotides (a) to (j), the nucleic acid probe(s) or the primer(s) that can be used in the present invention may further comprise polynucleotides selected from the group consisting of the following polynucleotides (k) to (o):

(k) a polynucleotide consisting of a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 170 to 199, (m) a polynucleotide consisting of a nucleotide sequence complementary to a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 170 to 199 or a nucleotide sequence derived from the nucleotide sequence by the replacement of u with t, and (o) a polynucleotide hybridizing under stringent conditions to any of the polynucleotides (k) to (n).

For the above-mentioned polynucleotides, the "fragment thereof comprising 15 or more consecutive nucleotides" can comprise, but not limited to, the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, or the like, in the nucleotide sequence of each polynucleotide.

These polynucleotides or fragments thereof used in the present invention may each be DNA or may each be RNA.

The polynucleotides that can be used in the present invention can each be prepared by use of a general technique such as a DNA recombination technique, PCR, or a method using an automatic DNA/RNA synthesizer.

The DNA recombination technique and the PCR method may employ a technique described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-4257, hsa-miR-6726-5p, hsa-miR-1343-3p, hsa-miR-1247-3p, hsa-miR-6787-5p, hsa-miR-6875-5p, hsa-miR-1225-3p, hsa-miR-8063, hsa-miR-6781-5p, hsa-miR-4746-3p, hsa-miR-1908-5p, hsa-miR-6756-5p, hsa-miR-204-3p, hsa-miR-4651, hsa-miR-6757-5p, hsa-miR-6825-5p, hsa-miR-7108-5p, hsa-miR-4792, hsa-miR-7641, hsa-miR-3188, hsa-miR-3131, hsa-miR-6780b-5p, hsa-miR-8069, hsa-miR-6840-3p, hsa-miR-8072, hsa-miR-1233-5p, hsa-miR-6887-5p, hsa-miR-1231, hsa-miR-5572, hsa-miR-6738-5p, hsa-miR-6784-5p, hsa-miR-6791-5p, hsa-miR-6749-5p, hsa-miR-6741-5p, hsa-miR-128-1-5p, hsa-miR-4419b, hsa-miR-6746-5p, hsa-miR-3184-5p, hsa-miR-3679-5p, hsa-miR-7110-5p, hsa-miR-4516, hsa-miR-6717-5p, hsa-miR-6826-5p, hsa-miR-4433b-3p, hsa-miR-3679-3p, hsa-miR-3135b, hsa-miR-3622a-5p, hsa-miR-711, hsa-miR-4467, hsa-miR-6857-5p, hsa-miR-6515-3p, hsa-miR-1225-5p, hsa-miR-187-5p, hsa-miR-3185, hsa-miR-642b-3p, hsa-miR-1249, hsa-miR-744-5p, hsa-miR-4442, hsa-miR-1228-3p, hsa-miR-939-5p, hsa-miR-6845-5p, hsa-miR-887-3p, hsa-miR-7845-5p, hsa-miR-6729-5p, hsa-miR-4632-5p, hsa-miR-615-5p, hsa-miR-6724-5p, hsa-miR-4728-5p, hsa-miR-6732-5p, hsa-miR-6816-5p, hsa-miR-4695-5p, hsa-miR-6088, hsa-miR-7975, hsa-miR-3197, hsa-miR-6125, hsa-miR-4433-3p, hsa-miR-6727-5p, hsa-miR-4706, hsa-miR-7847-3p, hsa-miR-6805-3p, hsa-miR-6766-3p, hsa-miR-1913, hsa-miR-4649-5p, hsa-miR-602, hsa-miR-3663-3p, hsa-miR-6893-5p, hsa-miR-6861-5p, hsa-miR-4449, hsa-miR-6842-5p, hsa-miR-4454, hsa-miR-5195-3p, hsa-miR-663b, hsa-miR-6765-5p, hsa-miR-4513, hsa-miR-614, hsa-miR-6785-5p, hsa-miR-6777-5p, hsa-miR-940, hsa-miR-4741, hsa-miR-6870-5p, hsa-miR-6131, hsa-miR-150-3p, hsa-miR-4707-5p, hsa-miR-1915-3p, hsa-miR-3937, hsa-miR-937-5p, hsa-miR-4443, hsa-miR-1914-3p, hsa-miR-3620-5p, hsa-miR-1268b, hsa-miR-1227-5p, hsa-miR-6880-5p, hsa-miR-4417, hsa-miR-6802-5p, hsa-miR-6769a-5p, hsa-miR-663a, hsa-miR-6721-5p, hsa-miR-4532, hsa-miR-7977, hsa-miR-92b-5p, hsa-miR-371a-5p, hsa-miR-6126, hsa-miR-4734, hsa-miR-4665-3p, hsa-miR-423-5p, hsa-miR-1469, hsa-miR-4675, hsa-miR-1915-5p, hsa-miR-6716-5p, hsa-miR-718, hsa-miR-4281, hsa-miR-6820-5p, hsa-miR-6795-5p, hsa-miR-6779-5p, hsa-miR-7109-5p, hsa-miR-6798-5p, hsa-miR-4648, hsa-miR-8059, hsa-miR-6765-3p, hsa-miR-6132, hsa-miR-4492, hsa-miR-7107-5p, hsa-miR-3195, hsa-miR-3180, hsa-miR-296-3p, hsa-miR-564, hsa-miR-1268a, hsa-miR-6848-5p, hsa-miR-762, hsa-miR-2861, hsa-miR-1203, hsa-miR-1260b, hsa-miR-4476, hsa-miR-6885-5p, hsa-miR-6769b-5p, hsa-miR-23b-3p, hsa-miR-1343-5p, hsa-miR-3621, hsa-miR-4688, hsa-miR-4286, hsa-miR-4640-5p, hsa-miR-4739, hsa-miR-1260a, hsa-miR-4276, hsa-miR-7106, hsa-miR-6794-5p, hsa-miR-6774-5p, hsa-miR-4707-3p, hsa-miR-4534, hsa-miR-4294, hsa-miR-6850-5p, hsa-miR-6089 and hsa-miR-671-5p, hsa-miR-128-2-5p, hsa-miR-125a-3p, hsa-miR-92a-2-5p, hsa-miR-486-3p, hsa-miR-3196, hsa-miR-211-3p, hsa-miR-4271, hsa-miR-6851-5p, hsa-miR-149-3p, hsa-miR-4667-5p, hsa-miR-135a-3p, hsa-miR-4486, hsa-miR-4697-5p, hsa-miR-4725-3p, hsa-miR-6510-5p, hsa-miR-5001-5p, hsa-miR-4673, hsa-miR-4466, hsa-miR-23a-3p, hsa-miR-3656, hsa-miR-6782-5p, hsa-miR-4689, hsa-miR-451a, hsa-miR-4446-3p, hsa-miR-3180-3p, hsa-miR-642a-3p, hsa-miR-6889-5p, hsa-miR-3178, hsa-miR-4665-5p, hsa-miR-6722-3p, hsa-miR-30c-1-3p, hsa-miR-4507, hsa-miR-3141 and hsa-miR-1199-5p represented by SEQ ID NOs: 1 to 199 and 635 to 642 are known in the art, and their acquisition methods are also known as mentioned above. Therefore, each polynucleotide that can be used as a nucleic acid probe(s) or a primer(s) in the present invention can be prepared by cloning the gene.

Such a nucleic acid probe(s) or a primer(s) can be chemically synthesized using an automatic DNA synthesizer. In general, a phosphoramidite method is used in this synthesis, and single-stranded DNA up to approximately 100 nucleotides can be automatically synthesized by this method. The automatic DNA synthesizer is commercially available from, for example, Polygen GmbH, ABI, or Applied Biosystems, Inc.

Alternatively, the polynucleotide of the present invention can also be prepared by a cDNA cloning method. The cDNA cloning technique may employ, for example, microRNA Cloning Kit Wako.

In this context, the sequences of the nucleic acid probe(s) and the primer(s) for detecting the polynucleotide consisting of a nucleotide sequence represented by any of SEQ ID NOs: 1 to 199 and 635 to 642 do not exist as miRNAs or precursors thereof in the living body or in vivo. For example, the nucleotide sequences represented by SEQ ID NO: 7 and SEQ ID NO: 52 are produced from the precursor represented by SEQ ID NO: 206. This precursor has a hairpin-like structure as shown in FIG. 1, and the nucleotide sequences represented by SEQ ID NO: 7 and SEQ ID NO: 52 have mismatch sequences with each other. As such, a nucleotide sequence completely complementary to the nucleotide sequence represented by SEQ ID NO: 7 or SEQ ID NO: 52 is not naturally produced in vivo. Therefore, the nucleic acid probe and the primer for detecting the nucleotide sequence represented by any of SEQ ID NOs: 1 to 199 and 635 to 642 each have an artificial nucleotide sequence that does not exist in the living body or in vivo.

3. Kit or Device for Detection of Stomach Cancer

The present invention also provides a kit or a device for the detection of stomach cancer, comprising one or more polynucleotides (which may include a variant, a fragment, or a derivative thereof; hereinafter, also referred to as a polynucleotide for detection) that can be used as a nucleic acid probe(s) or a primer(s) in the present invention for measuring a target nucleic acid(s) as a stomach cancer marker(s).

The target nucleic acid(s) as a stomach cancer marker(s) according to the present invention is selected from the following group 1:

miR-4257, miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR-4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-1915-5p, miR-6716-5p, miR-718, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-6848-5p, miR-762, miR-2861, miR-1203, miR-1260b, miR-4476, miR-6885-5p, miR-6769b-5p, miR-23b-3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p.

Additional target nucleic acid(s) that may be optionally used in the measurement is preferably selected from the following group 2: miR-128-2-5p, miR-125a-3p, miR-92a-2-5p, and miR-486-3p. Additional target nucleic acid(s) that may be optionally further used in the measurement is preferably selected from the following group 3: miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141 and miR-1199-5p.

The kit or the device of the present invention comprises a nucleic acid(s) capable of specifically binding to any of the target nucleic acids as the stomach cancer markers described above, preferably one or more polynucleotides selected from the nucleic acid probes or the primers described in the preceding Section 2, specifically, the polynucleotides described in the preceding Section 2 or variant(s) thereof.

Specifically, the kit or the device of the present invention can comprise at least one or more polynucleotides comprising (or consisting of) a nucleotide sequence represented by any of SEQ ID NOs: 1 to 165 and 635 to 642 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotides comprising (or consisting of) a nucleotide sequence represented by any of SEQ ID NOs: 166 to 169 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotides comprising (or consisting of) a nucleotide sequence represented by any of SEQ ID NOs: 170 to 199 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment(s) that can be contained in the kit or the device of the present invention is, for example, one or more, preferably two or more polynucleotides selected from the group consisting of the following polynucleotides (1) to (3):

(1) a polynucleotide comprising 15 or more consecutive nucleotides that are from a nucleotide sequence derived from a nucleotide sequence represented by any of SEQ ID NOs: 1 to 165 and 635 to 642 by the replacement of u with t, or a complementary sequence thereof;

(2) a polynucleotide comprising 15 or more consecutive nucleotides that are from a nucleotide sequence derived from a nucleotide sequence represented by any of SEQ ID NOs: 166 to 169 by the replacement of u with t, or a complementary sequence thereof; and (3) a polynucleotide comprising 15 or more consecutive nucleotides that are from a nucleotide sequence derived from a nucleotide sequence represented by any of SEQ ID NOs: 170 to 199 by the replacement of u with t, or a complementary sequence thereof.

In a preferred embodiment, the polynucleotide is a polynucleotide consisting of a nucleotide sequence represented by any of SEQ ID NOs: 1 to 165 and 635 to 642 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 166 to 169 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 170 to 199 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

Specific examples of the aforementioned polynucleotide combination as target nucleic acids for the kit or the device of the present invention can include combinations of the polynucleotides consisting of nucleotide sequences represented by SEQ ID NOs shown in Table 1 (SEQ ID NOs: 1 to 199 and 635 to 642 corresponding to the miRNA markers in Table 1). However, these are given merely for illustrative purposes, and all of various other possible combinations are included in the present invention.

The combination of the target nucleic acids for the kit or the device for discriminating a stomach cancer patient from a healthy subject according to the present invention is desirably, for example, a combination of two or more polynucleotides consisting of the nucleotide sequences represented by SEQ ID NOs shown in Table 1. Usually, a combination of two of these polynucleotides can produce adequate performance.

The specific combination of two polynucleotides consisting of the nucleotide sequences or the complementary sequences thereof for discriminating a stomach cancer patient from a healthy subject is preferably a combination comprising at least one or more of the newly found polynucleotides consisting of the nucleotide sequences represented by SEQ ID NOs: 1 to 165 and 635 to 642, among the combinations of two of the aforementioned polynucleotides consisting of the nucleotide sequences represented by SEQ ID NOs: 1 to 199 and 635 to 642.

The combination of polynucleotides with cancer type specificity capable of discriminating a stomach cancer patient not only from a healthy subject but also from other cancer patients is preferably, for example, a combination of multiple polynucleotides comprising at least one polynucleotide selected from the group consisting of polynucleotides of SEQ ID NOs: 9, 13, 21, 27, 34, 36, 66, 75, 95, 98, 108, 130, 135, 143, 155, 183, 185, 187, 191, 193, 194, 635, 636, 637, 638, 639, 640, 641 and 642 (hereinafter, this group is referred to as "cancer type-specific polynucleotide group 1"), with any of the polynucleotides of the other SEQ ID NOs.

The combination of polynucleotides with cancer type specificity capable of discriminating a stomach cancer patient not only from a healthy subject but also from other cancer patients is more preferably a combination of multiple polynucleotides selected from the cancer type-specific polynucleotide group 1.

The combination of polynucleotides with cancer type specificity capable of discriminating a stomach cancer patient not only from a healthy subject but also from other cancer patients is more preferably a combination comprising at least one or more polynucleotides selected from the group consisting of polynucleotides of SEQ ID NOs: 21, 34, 36, 98, and 155 (hereinafter, this group is referred to as "cancer type-specific polynucleotide group 2") included in the cancer type-specific polynucleotide group 1, among the combinations of multiple polynucleotides selected from the cancer type-specific polynucleotide group 1.

The number of the polynucleotides with cancer type specificity may be 2, 3, 4, 5, 6, 7, 8, 9, 10 or more in the combination and is more preferably 6 or more in the combination. Usually, the combination of 6 of these polynucleotides can produce adequate performance.

Non-limiting examples of the combination of the polynucleotide consisting of the nucleotide sequence represented by SEQ ID NO: 21 or a complementary sequence thereof with polynucleotides consisting of nucleotide sequences represented by SEQ ID NOs of five polynucleotides selected from the cancer type-specific polynucleotide group 1 or complementary sequences thereof are listed below.

(1) a combination of SEQ ID NOs: 9, 21, 36, 98, 130, and 637 (markers: hsa-miR-6781-5p, hsa-miR-3131, hsa-miR-4419b, hsa-miR-940, hsa-miR-718, and hsa-miR-4707-3p);

(2) a combination of SEQ ID NOs: 9, 21, 34, 36, 98, and 637 (markers: hsa-miR-6781-5p, hsa-miR-3131, hsa-miR-6741-5p, hsa-miR-4419b, hsa-miR-940, and hsa-miR-4707-3p);

(3) a combination of SEQ ID NOs: 9, 21, 34, 36, 98, and 155 (markers: hsa-miR-6781-5p, hsa-miR-3131, hsa-miR-6741-5p, hsa-miR-4419b, hsa-miR-940, and hsa-miR-6769b-5p);

(4) a combination of SEQ ID NOs: 21, 36, 75, 98, 155, and 635 (markers: hsa-miR-3131, hsa-miR-4419b, hsa-miR-6125, hsa-miR-940, hsa-miR-6769b-5p, and hsa-miR-6794-5p); and (5) a combination of SEQ ID NOs: 9, 21, 36, 98, 108, and 155 (markers: hsa-miR-6781-5p, hsa-miR-3131, hsa-miR-4419b, hsa-miR-940, hsa-miR-1914-3p, and hsa-miR-6769b-5p).

Non-limiting examples of the combination of the polynucleotide consisting of the nucleotide sequence represented by SEQ ID NO: 34 or a complementary sequence thereof with polynucleotides consisting of nucleotide sequences represented by SEQ ID NOs of five polynucleotides selected from the cancer type-specific polynucleotide group 1 or complementary sequences thereof are further listed.

(1) a combination of SEQ ID NOs: 34, 36, 143, 155, 187, and 635 (markers: hsa-miR-6741-5p, hsa-miR-4419b, hsa-miR-3195, hsa-miR-6769b-5p, hsa-miR-4689, and hsa-miR-6794-5p);

(2) a combination of SEQ ID NOs: 9, 34, 36, 66, 98, and 187 (markers: hsa-miR-6781-5p, hsa-miR-6741-5p, hsa-miR-4419b, hsa-miR-615-5p, hsa-miR-940, and hsa-miR-4689);

(3) a combination of SEQ ID NOs: 9, 34, 36, 98, 187, and 637 (markers: hsa-miR-6781-5p, hsa-miR-6741-5p, hsa-miR-4419b, hsa-miR-940, hsa-miR-4689, and hsa-miR-4707-3p);

(4) a combination of SEQ ID NOs: 9, 34, 36, 98, 185, and 637 (markers: hsa-miR-6781-5p, hsa-miR-6741-5p, hsa-miR-4419b, hsa-miR-940, hsa-miR-3656, and hsa-miR-4707-3p); and (5) a combination of SEQ ID NOs: 9, 34, 36, 98, 637, and 639 (markers: hsa-miR-6781-5p, hsa-miR-6741-5p, hsa-miR-4419b, hsa-miR-940, hsa-miR-4707-3p, and hsa-miR-4294).

Non-limiting examples of the combination of the polynucleotide consisting of the nucleotide sequence represented by SEQ ID NO: 36 or a complementary sequence thereof with polynucleotides consisting of nucleotide sequences represented by SEQ ID NOs of five polynucleotides selected from the cancer type-specific polynucleotide group 1 or complementary sequences thereof are further listed.

(1) a combination of SEQ ID NOs: 9, 36, 98, 108, 638, and 639 (markers: hsa-miR-6781-5p, hsa-miR-4419b, hsa-miR-940, hsa-miR-1914-3p, hsa-miR-4534, and hsa-miR-4294);

(2) a combination of SEQ ID NOs: 36, 98, 155, 194, 635, and 642 (markers: hsa-miR-4419b, hsa-miR-940, hsa-miR-6769b-5p, hsa-miR-4665-5p, hsa-miR-6794-5p, and hsa-miR-671-5p);

(3) a combination of SEQ ID NOs: 9, 34, 36, 75, 98, and 637 (markers: hsa-miR-6781-5p, hsa-miR-6741-5p, hsa-miR-4419b, hsa-miR-6125, hsa-miR-940, and hsa-miR-4707-3p);

(4) a combination of SEQ ID NOs: 21, 36, 98, 155, 185, and 635 (markers: hsa-miR-3131, hsa-miR-4419b, hsa-miR-940, hsa-miR-6769b-5p, hsa-miR-3656, and hsa-miR-6794-5p); and (5) a combination of SEQ ID NOs: 9, 36, 98, 108, 155, and 635 (markers: hsa-miR-6781-5p, hsa-miR-4419b, hsa-miR-940, hsa-miR-1914-3p, hsa-miR-6769b-5p, and hsa-miR-6794-5p).

Non-limiting examples of the combination of the polynucleotide consisting of the nucleotide sequence represented by SEQ ID NO: 98 or a complementary sequence thereof with polynucleotides consisting of nucleotide sequences represented by SEQ ID NOs of five polynucleotides selected from the cancer type-specific polynucleotide group 1 or complementary sequences thereof are further listed.

(1) a combination of SEQ ID NOs: 9, 36, 98, 130, 194, and 637 (markers: hsa-miR-6781-5p, hsa-miR-4419b, hsa-miR-940, hsa-miR-718, hsa-miR-4665-5p, and hsa-miR-4707-3p);

(2) a combination of SEQ ID NOs: 21, 36, 98, 108, 155, and 635 (markers: hsa-miR-3131, hsa-miR-4419b, hsa-miR-940, hsa-miR-1914-3p, hsa-miR-6769b-5p, and hsa-miR-6794-5p);

(3) a combination of SEQ ID NOs: 9, 36, 98, 108, 155, and 639 (markers: hsa-miR-6781-5p, hsa-miR-4419b, hsa-miR-940, hsa-miR-1914-3p, hsa-miR-6769b-5p, and hsa-miR-4294);

(4) a combination of SEQ ID NOs: 9, 36, 98, 155, 187, and 639 (markers: hsa-miR-6781-5p, hsa-miR-4419b, hsa-miR-940, hsa-miR-6769b-5p, hsa-miR-4689, and hsa-miR-4294); and (5) a combination of SEQ ID NOs: 9, 36, 98, 155, 187, and 637 (markers: hsa-miR-6781-5p, hsa-miR-4419b, hsa-miR-940, hsa-miR-6769b-5p, hsa-miR-4689, and hsa-miR-4707-3p).

Non-limiting examples of the combination of the polynucleotide consisting of the nucleotide sequence represented by SEQ ID NO: 155 or a complementary sequence thereof with polynucleotides consisting of nucleotide sequences represented by SEQ ID NOs of five polynucleotides selected from the cancer type-specific polynucleotide group 1 or complementary sequences thereof are further listed.

(1) a combination of SEQ ID NOs: 9, 36, 75, 98, 155, and 635 (markers: hsa-miR-6781-5p, hsa-miR-4419b, hsa-miR-6125, hsa-miR-940, hsa-miR-6769b-5p, and hsa-miR-6794-5p);

(2) a combination of SEQ ID NOs: 36, 98, 130, 155, 185, and 635 (markers: hsa-miR-4419b, hsa-miR-940, hsa-miR-718, hsa-miR-6769b-5p, hsa-miR-3656, and hsa-miR-6794-5p);

(3) a combination of SEQ ID NOs: 9, 13, 143, 155, 194, and 639 (markers: hsa-miR-6781-5p, hsa-miR-204-3p, hsa-miR-3195, hsa-miR-6769b-5p, hsa-miR-4665-5p, and hsa-miR-4294);

(4) a combination of SEQ ID NOs: 9, 13, 34, 36, 98, and 155 (markers: hsa-miR-6781-5p, hsa-miR-204-3p, hsa-miR-6741-5p, hsa-miR-4419b, hsa-miR-940, and hsa-miR-6769b-5p); and (5) a combination of SEQ ID NOs: 36, 98, 108, 155, 193, and 635 (markers: hsa-miR-4419b, hsa-miR-940, hsa-miR-1914-3p, hsa-miR-6769b-5p, hsa-miR-3178, and hsa-miR-6794-5p).

The kit or the device of the present invention can also comprise a polynucleotide(s) that is already known or that will be found in the future, to enable detection of stomach cancer, in addition to the polynucleotide(s) (which may include a variant(s), a fragment(s), and a derivative(s)) as described above according to the present invention.

The kit of the present invention can also comprise an antibody for measuring a marker(s) for stomach cancer examination known in the art, such as CEA, or CA19-9, in addition to the polynucleotide(s) according to the present invention as described above, and a variant(s) thereof or a fragment(s) thereof.

These polynucleotides contained in the kit of the present invention may be packaged in different containers either individually or in any combination.

The kit of the present invention may comprise a kit for extracting a nucleic acid(s) (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or the device of the present invention comprises nucleic acids capable of specifically binding to the polynucleotides of at least one or more, preferably at least two or more, more preferably at least three or more, most preferably at least five or more to all of the stomach cancer marker miRNAs, respectively, of the group 1 described above. The kit or the device of the present invention can optionally further comprise nucleic acids capable of specifically binding to the polynucleotides of at least one or more, preferably at least two or more, more preferably at least three or more, most preferably at least five or more to all of the stomach cancer marker miRNAs, respectively, of the group 2 described above. The kit or the device of the present invention can optionally further comprise nucleic acids capable of specifically binding to the polynucleotides of at least one or more, preferably at least two or more, more preferably at least three or more, most preferably at least five or more to all of the stomach cancer marker miRNAs, respectively, of the group 3 described above.

The kit or the device of the present invention can be used for detecting stomach cancer as described in the Section 4 below.

4. Method for Detecting Stomach Cancer

The present invention further provides a method for detecting stomach cancer, comprising using the kit or the device of the present invention (comprising the nucleic acid(s) that can be used in the present invention) described in the preceding Section 3 above to measure an expression level(s) of one or more stomach cancer-derived genes represented by: an expression level(s) of stomach cancer-derived gene(s) selected from the following group: miR-4257, miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR-4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-1915-5p, miR-6716-5p, miR-718, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-6848-5p, miR-762, miR-2861, miR-1203, miR-1260b, miR-4476, miR-6885-5p, miR-6769b-5p, miR-23b-3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p; and optionally an expression level(s) of stomach cancer-derived gene(s) selected from the following group: miR-128-2-5p, miR-125a-3p, miR-92a-2-5p, and miR-486-3p; and optionally an expression level(s) of stomach cancer-derived gene(s) selected from the following group: miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141 and miR-1199-5p in a sample in vitro, further comparing, for example, the expression level(s) of the gene(s) in the sample (e.g., blood, serum, or plasma) collected from a subject suspected of having stomach cancer with a control expression level in the sample collected from a healthy subject (including a non-stomach cancer patient), and evaluating the subject as having stomach cancer when the expression level of the target nucleic acid is statistically significantly different between the samples.

This method of the present invention enables a limitedly invasive, early diagnosis of cancer with high sensitivity and specificity and thereby brings about early treatment and improved prognosis. In addition, exacerbation of the disease or the effectiveness of surgical, radiotherapeutic, and chemotherapeutic treatments can be monitored.

The method for extracting the stomach cancer-derived gene(s) from the sample such as blood, serum, or plasma according to the present invention is particularly preferably prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizol™ (Life Technologies Corp.) may be used. The stomach cancer-derived gene(s) may be prepared by the addition of a reagent for RNA extraction containing acidic phenol, such as Trizol (Life Technologies Corp.) or Isogen (Nippon Gene Co., Ltd.). Alternatively, a kit such as miRNeasy™ Mini Kit (Qiagen N.V.) may be used, though the method is not limited thereto.

The present invention also provides use of the kit or the device of the present invention for detecting in vitro an expression product(s) of a stomach cancer-derived miRNA gene(s) in a sample derived from a subject.

In the method of the present invention, the kit or the device described above comprises a single polynucleotide or any possible combination of polynucleotides that can be used in the present invention as described above.

In the detection or (genetic) diagnosis of stomach cancer according to the present invention, each polynucleotide contained in the kit or the device of the present invention can be used as a probe or a primer. In the case of using the polynucleotide as a primer, TaqMan™ MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of stomach cancer or the detection of the presence or absence of stomach cancer. Specifically, the detection of stomach cancer using the kit or the device can be performed by detecting in vitro an expression level(s) of a gene(s) using the nucleic acid probe(s) or the primer(s) contained in the kit or the device in a sample such as blood, serum, plasma, or urine from a subject suspected of having stomach cancer. The subject suspected of having stomach cancer can be evaluated as having stomach cancer when the expression level(s) of a target miRNA marker(s) measured using polynucleotide(s) (including a variant(s), a fragment(s), and a derivative(s) thereof) consisting of a nucleotide sequence(s) represented by at least one or more of SEQ ID NOs: 1 to 165 and 635 to 642 or a complementary sequence(s) thereof, optionally a nucleotide sequence(s) represented by one or more of SEQ ID NOs: 166 to 169 or a complementary sequence(s) thereof, and optionally a nucleotide sequence(s) represented by one or more of SEQ ID NOs: 170 to 199 or a complementary sequence(s) thereof in the sample such as blood, serum, plasma, or urine of the subject is statistically significantly different from the expression level(s) thereof in the sample such as blood, serum, or plasma, or urine of a healthy subject.

The method of the present invention can be combined with gastric X-ray examination and gastroscopy as well as a diagnostic imaging method such as CT, PET, or MRI. The method of the present invention is capable of specifically detecting stomach cancer and can substantially discriminate stomach cancer from other cancers.

The method for detecting the absence of an expression product(s) of a stomach cancer-derived gene(s) or the presence of the expression product(s) of a stomach cancer-derived gene(s) in a sample using the kit or the device of the present invention comprises collecting a body fluid such as blood, serum, plasma, or urine of a subject, and measuring the expression level(s) of the target gene(s) contained therein using one or more polynucleotide(s) (including a variant(s), a fragment(s), and a derivative(s)) selected from the polynucleotide group of the present invention, to evaluate the presence or absence of stomach cancer or to detect stomach cancer. Using the method for detecting stomach cancer according to the present invention, for example, the presence or absence of amelioration of the disease or the degree of amelioration thereof in a stomach cancer patient to whom a therapeutic drug for the amelioration of the disease is administered can be also evaluated or diagnosed.

The method of the present invention can comprise, for example, the following steps (a), (b), and (c):
(a) contacting a sample derived from a subject with a polynucleotide(s) in the kit or the device of the present invention in vitro;
(b) measuring an expression level(s) of the target nucleic acid(s) in the sample using the polynucleotide(s) as a nucleic acid probe(s) or a primer(s); and
(c) evaluating the presence or absence of stomach cancer (cells) in the subject on the basis of the result in the step (b).

Specifically, the present invention provides a method for detecting stomach cancer, comprising measuring an expression level(s) of a target nucleic acid(s) in a sample of a subject using a nucleic acid(s) capable of specifically binding to at least one or more (preferably at least two or more) polynucleotide(s) selected from the group consisting of miR-4257, miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR-4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-1915-5p, miR-6716-5p, miR-718, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-6848-5p, miR-762, miR-2861, miR-1203, miR-1260b, miR-4476, miR-6885-5p, miR-6769b-5p, miR-23b-3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p and evaluating in vitro whether or not the subject has stomach cancer using the measured expression level(s) and a control expression level(s) of a healthy subject measured in the same way as above.

The term "evaluation" used herein is evaluation support based on results of in vitro examination, not physician's judgment.

As described above, as for the target nucleic acids in a preferred embodiment of the method of the present invention, specifically, miR-4257 is hsa-miR-4257, miR-6726-5p is hsa-miR-6726-5p, miR-1343-3p is hsa-miR-1343-3p, miR-1247-3p is hsa-miR-1247-3p, miR-6787-5p is hsa-miR-6787-5p, miR-6875-5p is hsa-miR-6875-5p, miR-1225-3p is hsa-miR-1225-3p, miR-8063 is hsa-miR-8063, miR-6781-5p is hsa-miR-6781-5p, miR-4746-3p is hsa-miR-4746-3p, miR-1908-5p is hsa-miR-1908-5p, miR-6756-5p is hsa-miR-6756-5p, miR-204-3p is hsa-miR-204-3p, miR-4651 is hsa-miR-4651, miR-6757-5p is hsa-miR-6757-5p, miR-6825-5p is hsa-miR-6825-5p, miR-7108-5p is hsa-miR-7108-5p, miR-4792 is hsa-miR-4792, miR-7641 is hsa-miR-7641, miR-3188 is hsa-miR-3188, miR-3131 is hsa-miR-3131, miR-6780b-5p is hsa-miR-6780b-5p, miR-8069 is hsa-miR-8069, miR-6840-3p is hsa-miR-6840-3p, miR-8072 is hsa-miR-8072, miR-1233-5p is hsa-miR-1233-5p, miR-6887-5p is hsa-miR-6887-5p, miR-1231 is hsa-miR-1231, miR-5572 is hsa-miR-5572, miR-6738-5p is hsa-miR-6738-5p, miR-6784-5p is hsa-miR-6784-5p, miR-6791-5p is hsa-miR-6791-5p, miR-6749-5p is hsa-miR-6749-5p, miR-6741-5p is hsa-miR-6741-5p, miR-128-1-5p is hsa-miR-128-1-5p, miR-4419b is hsa-miR-4419b, miR-6746-5p is hsa-miR-6746-5p, miR-3184-5p is hsa-miR-3184-5p, miR-3679-5p is hsa-miR-3679-5p, miR-7110-5p is hsa-miR-7110-5p, miR-4516 is hsa-miR-4516, miR-6717-5p is hsa-miR-6717-5p, miR-6826-5p is hsa-miR-6826-5p, miR-4433b-3p is hsa-miR-4433b-3p, miR-3679-3p is hsa-miR-3679-3p, miR-3135b is hsa-miR-3135b, miR-3622a-5p is hsa-miR-3622a-5p, miR-711 is hsa-miR-711, miR-4467 is hsa-miR-4467, miR-6857-5p is hsa-miR-6857-5p, miR-6515-3p is hsa-miR-6515-3p, miR-1225-5p is hsa-miR-1225-5p, miR-187-5p is hsa-miR-187-5p, miR-3185 is hsa-miR-3185, miR-642b-3p is hsa-miR-642b-3p, miR-1249 is hsa-miR-1249, miR-744-5p is hsa-miR-744-5p, miR-4442 is hsa-miR-4442, miR-1228-3p is hsa-miR-1228-3p, miR-939-5p is hsa-miR-939-5p, miR-6845-5p is hsa-miR-6845-5p, miR-887-3p is hsa-miR-887-3p, miR-7845-5p is hsamiR-7845-5p, miR-6729-5p is hsa-miR-6729-5p, miR-4632-5p is hsa-miR-4632-5p, miR-615-5p is hsa-miR-615-5p, miR-6724-5p is hsa-miR-6724-5p, miR-4728-5p is hsa-miR-4728-5p, miR-6732-5p is hsa-miR-6732-5p, miR-6816-5p is hsa-miR-6816-5p, miR-4695-5p is hsa-miR-4695-5p, miR-6088 is hsa-miR-6088, miR-7975 is hsa-miR-7975, miR-3197 is hsa-miR-3197, miR-6125 is hsa-miR-6125, miR-4433-3p is hsa-miR-4433-3p, miR-6727-5p is hsa-miR-6727-5p, miR-4706 is hsa-miR-4706, miR-7847-3p is hsa-miR-7847-3p, miR-6805-3p is hsa-miR-6805-3p, miR-6766-3p is hsa-miR-6766-3p, miR-1913 is hsa-miR-1913, miR-4649-5p is hsa-miR-4649-5p, miR-602 is hsa-miR-602, miR-3663-3p is hsa-miR-3663-3p, miR-6893-5p is hsa-miR-6893-5p, miR-6861-5p is hsa-miR-6861-5p, miR-4449 is hsa-miR-4449, miR-6842-5p is hsa-miR-6842-5p, miR-4454 is hsa-miR-4454, miR-5195-3p is hsa-miR-5195-3p, miR-663b is hsa-miR-663b, miR-6765-5p is hsa-miR-6765-5p, miR-4513 is hsa-miR-4513, miR-614 is hsa-miR-614, miR-6785-5p is hsa-miR-6785-5p, miR-6777-5p is hsa-miR-6777-5p, miR-940 is hsa-miR-940, miR-4741 is hsa-miR-4741, miR-6870-5p is hsa-miR-6870-5p, miR-6131 is hsa-miR-6131, miR-150-3p is hsa-miR-150-3p, miR-4707-5p is hsa-miR-4707-5p, miR-1915-3p is hsa-miR-1915-3p, miR-3937 is hsa-miR-3937, miR-937-5p is hsa-miR-937-5p, miR-4443 is hsa-miR-4443, miR-1914-3p is hsa-miR-1914-3p, miR-3620-5p is hsa-miR-3620-5p, miR-1268b is hsa-miR-1268b, miR-1227-5p is hsa-miR-1227-5p, miR-6880-5p is hsa-miR-6880-5p, miR-4417 is hsa-miR-4417, miR-6802-5p is hsa-miR-6802-5p, miR-6769a-5p is hsa-miR-6769a-5p, miR-663a is hsa-miR-663a, miR-6721-5p is hsa-miR-6721-5p, miR-4532 is hsa-miR-4532, miR-7977 is hsa-miR-7977, miR-92b-5p is hsa-miR-92b-5p, miR-371a-5p is hsa-miR-371a-5p, miR-6126 is hsa-miR-6126, miR-4734 is hsa-miR-4734, miR-4665-3p is hsa-miR-4665-3p, miR-423-5p is hsa-miR-423-5p, miR-1469 is hsa-miR-1469, miR-4675 is hsa-miR-4675, miR-1915-5p is hsa-miR-1915-5p, miR-6716-5p is hsa-miR-6716-5p, miR-718 is hsa-miR-718, miR-4281 is hsa-miR-4281, miR-6820-5p is hsa-miR-6820-5p, miR-6795-5p is hsa-miR-6795-5p, miR-6779-5p is hsa-miR-6779-5p, miR-7109-5p is hsa-miR-7109-5p, miR-6798-5p is hsa-miR-6798-5p, miR-4648 is hsa-miR-4648, miR-8059 is hsa-miR-8059, miR-6765-3p is hsa-miR-6765-3p, miR-6132 is hsa-miR-6132, miR-4492 is hsa-miR-4492, miR-7107-5p is hsa-miR-7107-5p, miR-3195 is hsa-miR-3195, miR-3180 is hsa-miR-3180, miR-296-3p is hsa-miR-296-3p, miR-564 is hsa-miR-564, miR-1268a is hsa-miR-1268a, miR-6848-5p is hsa-miR-6848-5p, miR-762 is hsa-miR-762, miR-2861 is hsa-miR-2861, miR-1203 is hsa-miR-1203, miR-1260b is hsa-miR-1260b, miR-4476 is hsa-miR-4476, miR-6885-5p is hsa-miR-6885-5p, miR-6769b-5p is hsa-miR-6769b-5p, miR-23b-3p is hsa-miR-23b-3p, miR-1343-5p is hsa-miR-1343-5p, miR-3621 is hsa-miR-3621, miR-4688 is hsa-miR-4688, miR-4286 is hsa-miR-4286, miR-4640-5p is hsa-miR-4640-5p, miR-4739 is hsa-miR-4739, miR-1260a is hsa-miR-1260a, miR-4276 is hsa-miR-4276, miR-7106-5p is hsa-miR-7106-5p, miR-6794-5p is hsa-miR-6794-5p, miR-6774-5p is hsa-miR-6774-5p, miR-4707-3p is hsa-miR-4707-3p, miR-4534 is hsa-miR-4534, miR-4294 is hsa-miR-4294, miR-6850-5p is hsa-miR-6850-5p, miR-6089 is hsa-miR-6089, and miR-671-5p is hsa-miR-671-5p.

In a preferred embodiment of the method of the present invention, specifically, the nucleic acid(s) (specifically, probe(s) or primer(s)) is selected from the group consisting of the following polynucleotides (a) to (e):

(a) a polynucleotide consisting of a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 165 and 635 to 642, (c) a polynucleotide consisting of a nucleotide sequence complementary to a nucleotide sequence represented by any of SEQ ID NOs: 1 to 165 and 635 to 642 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 165 and 635 to 642 or a nucleotide sequence derived from the nucleotide sequence by the replacement of u with t, and (e) a polynucleotide hybridizing under stringent conditions to any of the polynucleotides (a) to (d).

The method of the present invention can further employ a nucleic acid(s) capable of specifically binding to at least one or more polynucleotides selected from miR-128-2-5p, miR-125a-3p, miR-92a-2-5p, and miR-486-3p.

In a preferred embodiment, as for such a nucleic acid, specifically, miR-128-2-5p is hsa-miR-128-2-5p, miR-125a-3p is hsa-miR-125a-3p, miR-92a-2-5p is hsa-miR-92a-2-5p, and miR-486-3p is hsa-miR-486-3p.

In a preferred embodiment, such a nucleic acid(s) is specifically selected from the group consisting of the following polynucleotides (f) to (j):

(f) a polynucleotide consisting of a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 166 to 169, (h) a polynucleotide consisting of a nucleotide sequence complementary to a nucleotide sequence represented by any of SEQ ID NOs: 166 to 169 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 166 to 169 or a nucleotide sequence derived from the nucleotide sequence by the replacement of u with t, and (j) a polynucleotide hybridizing under stringent conditions to any of the polynucleotides (f) to (i).

The method of the present invention can further employ a nucleic acid(s) capable of specifically binding to at least one or more polynucleotides selected from the group consisting of miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141, and miR-1199-5p.

In a preferred embodiment, as for such a nucleic acid, specifically, miR-3196 is hsa-miR-3196, miR-211-3p is hsamiR-211-3p, miR-4271 is hsa-miR-4271, miR-6851-5p is hsa-miR-6851-5p, miR-149-3p is hsa-miR-149-3p, miR-4667-5p is hsa-miR-4667-5p, miR-135a-3p is hsa-miR-135a-3p, miR-4486 is hsa-miR-4486, miR-4697-5p is hsa-miR-4697-5p, miR-4725-3p is hsa-miR-4725-3p, miR-6510-5p is hsa-miR-6510-5p, miR-5001-5p is hsa-miR-5001-5p, miR-4673 is hsa-miR-4673, miR-4466 is hsa-miR-4466, miR-23a-3p is hsa-miR-23a-3p, miR-3656 is hsa-miR-3656, miR-6782-5p is hsa-miR-6782-5p, miR-4689 is hsa-miR-4689, miR-451a is hsa-miR-451a, miR-4446-3p is hsa-miR-4446-3p, miR-3180-3p is hsa-miR-3180-3p, miR-642a-3p is hsa-miR-642a-3p, miR-6889-5p is hsa-miR-6889-5p, miR-3178 is hsa-miR-3178, miR-4665-5p is hsa-miR-4665-5p, miR-6722-3p is hsa-miR-6722-3p, miR-30c-1-3p is hsa-miR-30c-1-3p, miR-4507 is hsa-miR-4507, miR-3141 is hsa-miR-3141, and miR-1199-5p is hsa-miR-1199-5p.

Specifically, the nucleic acid(s) further used is a polynucleotide(s) selected from the group consisting of the following polynucleotides (k) to (o):

(k) a polynucleotide consisting of a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 170 to 199, (m) a polynucleotide consisting of a nucleotide sequence complementary to a nucleotide sequence represented by any of SEQ ID NOs: 170 to 199 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 170 to 199 or a nucleotide sequence derived from the nucleotide sequence by the replacement of u with t, and (o) a polynucleotide hybridizing under stringent conditions to any of the polynucleotides (k) to (n).

Examples of the sample used in the method of the present invention can include samples prepared from a living tissue (preferably a stomach tissue) or a body fluid such as blood, serum, plasma, or urine from the subject. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

The subject used herein refers to a mammal, for example, a human, a monkey, a mouse or a rat without any limitation, and is preferably a human.

The steps of the method of the present invention can be changed according to the type of the sample to be assayed.

In the case of using RNA as an analyte, the detection of stomach cancer (cells) can comprise, for example, the following steps (a), (b), and (c):

(a) binding RNA(s) prepared from the sample of the subject or a complementary polynucleotide(s) (cDNA(s)) transcribed therefrom to a polynucleotide(s) in the kit or the device of the present invention;

(b) measuring the sample-derived RNA or the cDNA(s) synthesized from the RNA, bound with the polynucleotide by hybridization using the polynucleotide as a nucleic acid probe(s) or by quantitative RT-PCR using the polynucleotide(s) as a primer(s); and (c) evaluating the presence or absence of stomach cancer (or stomach cancer-derived gene expression) on the basis of the measurement results of the step (b).

For example, various hybridization methods can be used for detecting, examining, evaluating, or diagnosing stomach cancer (or stomach cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe(s) that can be used in the present invention. Specific examples thereof can include a method which comprises labeling the nucleic acid probe (or a complementary strand) with a radioisotope ($^{32}$P, $^{33}$P, $^{35}$S, etc.), a fluorescent material, or the like, hybridizing the labeled product with the tissue-derived RNA of the subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises preparing cDNA from the tissue-derived RNA of the subject according to a routine method, hybridizing a pair of primers (consisting of a plus strand and a reverse strand binding to the cDNA) of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention is attached to a substrate (solid phase) is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes these arrays. 3D-Gene™ Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on nucleic acid probes using an image detector (examples thereof can include Typhoon 9410 (GE Healthcare) and 3D-Gene™ scanner (Toray Industries, Inc.)).

The "stringent conditions" used herein are, as mentioned above, conditions under which a nucleic acid probe hybridizes to its target sequence to a larger extent (e.g., a measurement value equal to or larger than "(a mean of background measurement values)+(a standard deviation of the background measurement values)×2") than that for other sequences.

The stringent conditions are defined by hybridization and subsequent washing conditions. Examples of the hybridization conditions include, but not limited to, 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably involve 3 to 10×SSC and 0.1 to 1% SDS. Examples of the conditions for the washing, following the hybridization, which is another condition to define the stringent conditions, can include conditions involving continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using a polynucleotide fragment(s) in the kit of the present invention as a primer(s) include treatment for approximately 15 seconds to 1 minute at 5 to 10° C. plus a Tm value calculated from the sequence(s) of the primer(s), using a PCR buffer having composition such as 10 mM Tris-HCL (pH 8.3), 50 mM KCL, and 1 to 2 mM $MgCl_2$. Examples of the method for calculating such a Tm value include Tm value=2 (the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan® MicroRNA Assays (Life Technologies Corp.); LNA®-based MicroRNA PCR (Exiqon); or Ncode® miRNA qRT-PCT kit (Invitrogen Corp.) may be used.

For the calculation of gene expression levels according to the present invention, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$ or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring a target gene or gene expression level(s) in a sample derived from a subject using the polynucleotide(s), the kit, or the device (e.g., chip) for detection of the present invention, or a combination thereof, preparing a discriminant (discriminant function) with gene expression levels in a sample derived from a stomach cancer patient and a sample derived from a healthy subject as supervising samples, and determining or evaluating the presence and/or absence of the stomach cancer-derived gene(s) in the sample.

Specifically, the present invention further provides the method comprising: a first step of measuring in vitro an expression level(s) of a target gene(s) (target nucleic acid) in multiple samples that were known to be able to determine or evaluate the presence and/or absence of the stomach cancer-derived gene(s) in the samples, using the polynucleotide(s), the kit, or the device (e.g., chip) for detection of the present invention, or a combination thereof; a second step of constructing a discriminant with the measurement values of the expression level(s) of the target gene(s) that was obtained in the first step as supervising samples; a third step of measuring in vitro an expression level(s) of the target gene(s) in a sample derived from a subject in the same way as in the first step; and a fourth step of substituting the measurement value(s) of the expression level(s) of the target gene(s) obtained in the third step into the discriminant obtained in the second step, and determining or evaluating the presence or absence of the stomach cancer-derived gene(s) in the sample on the basis of the results obtained from the discriminant, wherein the target gene(s) can be detected using the polynucleotide(s) or using a polynucleotide(s) for the detection, that was contained in the polynucleotide, the kit or the device (e.g., chip). In this context, the discriminant can be prepared by use of Fisher's discriminant analysis, non-linear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In Formula 1, x represents an explanatory variable, w represents a coefficient of the explanatory variable, and w0 represents a constant term.

$$f(x) = w_0 + \sum_{i=1}^{n} w_i x_i \quad \text{Formula 1}$$

Values obtained from the discriminant are referred to as discriminant scores. The measurement values of a newly offered data set can be substituted as explanatory variables into the discriminant to determine clusters on the basis of the signs of the discriminant scores.

The Fisher's discriminant analysis, one type of linear discriminant analysis, is a dimension reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer., 2002). In the Fisher's discriminant analysis, direction w of projection is determined so as to maximize Formula 2. In Formula 2, μ represents an average input, ng represents the number of data associate with class g, and μg represents an average input of the data associate with class g. The numerator and the denominator are the interclass variance and the intraclass variance, respectively, when each data is projected in the direction of the vector w. Discriminant coefficient wi is determined by maximizing this ratio (Takafumi Kanamori et al., "Pattern Recognition", Kyoritsu Shuppan Co., Ltd. (2009); and Richard O. et al., Pattern Classification Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)} \quad \text{Formula 2}$$

$$\text{subject to } \mu = \sum_{i=1}^{n} \frac{x_i}{n}, \mu_g = \sum_{i:u_i=g}^{n} \frac{x_i}{n_g}$$

The Mahalanobis' distance is calculated according to Formula 3 in consideration of data correlation and can be used as nonlinear discriminant analysis for determining a cluster in which a data point belongs to, based on a short Mahalanobis' distance from the data point to that cluster. In Formula 3, μ represents a central vector of each cluster, and S-1 represents an inverse matrix of the variance-covariance matrix of the cluster. The central vector is calculated from explanatory variable x, and an average vector, a median value vector, or the like can be used.

$$D(x, \mu) = \{(x - \mu)^t S^{-1}(x - \mu)\}^{\frac{1}{2}} \quad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be substituted as explanatory variables into the discriminant to determine classes. In this respect, the result of the discriminant analysis may be classes, may be a probability of data to be classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, comprises preparing a hyperplane by supervising a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a stomach cancer patient group and a healthy subject group. For example, stomach tissue examination can be used for each subject to be confirmed either as a stomach cancer patient or a healthy subject.

Next, a data set consisting of comprehensive gene expression levels of serum-derived samples of the two divided groups (hereinafter, this data set is referred to as a training cohort) is prepared, and a C-SVC discriminant is determined by using genes that were found to differ clearly in their gene expression levels between the two groups as explanatory variables and using this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_{a} \frac{1}{2} a^T Q a - e^T a \quad \text{Formula 4}$$

$$\text{subject to } y^T a = 0, 0 \le a_i \le C, i = 1, \ldots, l,$$

Formula 5 is a finally obtained discriminant, and a group in which the data point belongs to can be determined on the basis of the sign of a value obtained according to the discriminant. In this formula, x represents a support vector, y represents a label indicating the association of a group, a represents the corresponding coefficient, b represents a constant term, and K represents a kernel function.

$$f(x) = \text{sgn}\left(\sum_{i=1}^{l} y_i a_i K(x_i, x) + b\right) \quad \text{Formula 5}$$

For example, a RBF kernel defined by Formula 6 can be used as the kernel function. In this formula, x represents a support vector, and γ represents a kernel parameter for adjusting the complexity of the hyperplane.

$$K(x_i, x_j) = \exp(-r\|x_i - x_j\|^2), r<0 \quad \text{Formula 6}$$

In addition, an approach such as neural network, k-nearest neighbor algorithms, decision trees, or logistic regression analysis can be selected as a method for determining or evaluating the presence and/or absence of expression of a stomach cancer-derived target gene(s) in a sample derived from a subject, or for evaluating the expression level thereof by comparison with a control derived from a healthy subject.

The method of the present invention can comprise, for example, the following steps (a), (b), and (c):

(a) measuring an expression level(s) of a target gene(s) in tissues containing stomach cancer-derived genes derived from stomach cancer patients and/or samples already known to be tissues containing no stomach cancer-derived gene(s) derived from healthy subjects, using the polynucleotide(s), the kit, or the device (e.g., DNA chip) for detection according to the present invention;

(b) preparing the discriminants of Formulas 1 to 3, 5, and 6 described above from the measurement values of the expression level measured in the step (a); and (c) measuring an expression level(s) of the target gene(s) in a sample derived from a subject using the polynucleotide(s), the kit, or the device (e.g., DNA chip) for diagnosis (detection) according to the present invention, substituting the obtained measurement value(s) into the discriminants prepared in the step (b), and determining or evaluating the presence and/or absence of the stomach cancer-derived target gene(s) in the sample, or evaluating the expression level(s) thereof by comparison with a healthy subject-derived control, on the basis of the obtained results. In this context, in the discriminants of Formulas 1 to 3, 5, and 6, x represents an explanatory variable and includes a value obtained by measuring a polynucleotide(s) selected from the polynucleotides described in the Section 2 above, or any fragment thereof, etc. Specifically, the explanatory variable for discriminating a stomach cancer patient from a healthy subject according to the present invention is a gene expression level(s) selected from, for example, the following expression levels (1) to (3):

(1) a gene expression level(s) in the serum of a stomach cancer patient or a healthy subject measured by any DNA comprising 15 or more consecutive nucleotides in a nucleotide sequence represented by any of SEQ ID NOs: 1 to 165 and 635 to 642 or a complementary sequence thereof, (2) a gene expression level(s) in the serum of a stomach cancer patient or a healthy subject measured by any DNA comprising 15 or more consecutive nucleotides in a nucleotide sequence represented by any of SEQ ID NOs: 166 to 169 or a complementary sequence thereof, and (3) a gene expression level(s) in the serum of a stomach cancer patient or a healthy subject measured by any DNA comprising 15 or more consecutive nucleotides in a nucleotide sequence represented by any of SEQ ID NOs: 170 to 199 or a complementary sequence thereof.

As described above, for the method for determining or evaluating the presence and/or absence of a stomach cancer-derived gene(s) in a sample derived from a subject, the preparation of a discriminant requires a discriminant prepared in a training cohort. For enhancing the accuracy of the discriminant, it is necessary for the discriminant to use genes that show clear difference between two groups in the training cohort.

Each gene that is used for an explanatory variable in a discriminant is preferably determined as follows. First, comprehensive gene expression levels of a stomach cancer patient group and comprehensive gene expression levels of a healthy subject group in a training cohort are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of a stomach cancer patient group and gene expression levels of a healthy subject group may be calculated to select a gene that is used for an explanatory variable in a discriminant. Alternatively, ROC curves may be prepared using gene expression levels of a stomach cancer patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discriminant accuracy include a method of constructing a discriminant in every combination of genes that satisfy the significance level of P value, and a method of repetitively evaluating a discriminant while increasing the number of genes for use one by one in a descending order of difference in gene expression level (Furey T S. et al., 2000, Bioinformatics., Vol. 16, p. 906-14). A gene expression level of another independent stomach cancer patient or healthy subject is substituted as an explanatory variable into this discriminant to calculate discriminant results of the group to which this independent stomach cancer patient or healthy subject associate. Specifically, the found gene set for diagnosis and the discriminant constructed using the gene set for diagnosis can be evaluated in an independent sample cohort to find a more universal gene set for diagnosis capable of detecting stomach cancer and a more universal method for discriminating stomach cancer.

Split-sample method is preferably used for evaluating the discriminant performance (generality) of the discriminant. Specifically, a data set is divided into a training cohort and a validation cohort, and gene selection by a statistical test and discriminant preparation are performed in the training cohort. Accuracy, sensitivity, and specificity are calculated using a result of discriminating a validation cohort according to the discriminant and a true group to which the validation cohort associate, to evaluate the performance of the discriminant. On the other hand, instead of dividing a data set, the gene selection by a statistical test and discriminant preparation may be performed using all of samples, and accuracy, sensitivity, and specificity can be calculated by the discriminant analysis of a newly prepared samples for evaluation of the performance of the discriminant.

The present invention provides a polynucleotide(s) for detection or for disease diagnosis useful in the diagnosis and treatment of stomach cancer, a method for detecting stomach cancer using the polynucleotide(s), and a kit and a device for the detection of stomach cancer, comprising the polynucleotide(s). Particularly, in order to select a gene(s) for diagnosis and prepare a discriminant so as to exhibit accuracy beyond a stomach cancer diagnosis method using existing tumor markers CEA and CA19-9, a gene set for diagnosis and a discriminant for the method of the present invention, that exhibit accuracy beyond CEA and CA19-9, can be constructed, for example, by comparing expressed genes in serum derived from a patient confirmed to be negative using CEA and CA19-9 but finally found to have stomach cancer by detailed examination such as computed tomography using a contrast medium, with genes expressed in serum derived from a patient having no stomach cancer.

For example, the gene set for diagnosis is set to any combination selected from one or two or more of the polynucleotides based on a nucleotide sequence(s) represented by any of SEQ ID NOs: 1 to 165 and 635 to 642 or a complementary sequence(s) thereof as described above; and optionally one or two or more of the polynucleotides based on a nucleotide sequence(s) represented by any of SEQ ID NOs: 166 to 169 or a complementary sequence(s) thereof; and optionally one or two or more of the polynucleotides based on a nucleotide sequence represented by any of SEQ ID NOs: 170 to 199 or a complementary sequence thereof. Further, a discriminant is constructed using expression levels of the gene set for diagnosis in samples derived from class I stomach cancer patients and samples derived from class II healthy subjects as a result of tissue diagnosis. As a result, the presence or absence of stomach cancer-derived genes in an unknown sample can be determined with 100% accuracy at the maximum by measuring expression levels of the gene set for diagnosis in an unknown sample.

EXAMPLES

Hereinafter, the present invention will be described further specifically with reference to Examples below. However, the scope of the present invention is not intended to be limited by these Examples.

Reference Example 1

<Collection of samples from stomach cancer patient and healthy subject>

Serum was collected using VENOJECT II vacuum blood collecting tube VP-AS109K60 (Terumo Corp.) from each of 100 healthy subjects and 34 stomach cancer patients (19 cases with stage IA, 5 cases with stage IB, 2 cases with stage IIA, 2 cases with stage IIB, 3 cases with stage IIIA, and 3 cases with stage IIIC) with no primary cancer found in areas other than stomach cancer after acquisition of informed consent, and used as a training cohort. Likewise, serum was collected using VENOJECT II vacuum blood collecting tube VP-AS109K60 (Terumo Corp.) from each of 50 healthy subjects and 16 stomach cancer patients (9 cases with stage IA, 2 cases with stage IB, 2 cases with stage IIA, 1 case with stage IIB, 1 case with stage IIIA, and 1 case with stage IIIC) with no primary cancer found in areas other than stomach cancer after acquisition of informed consent, and used as a validation cohort.

<Extraction of Total RNA>

Total RNA was obtained from 300 μL of the serum sample obtained from each of 200 persons in total of 150 healthy subjects and 50 stomach cancer patients included in the training cohort and the validation cohort, using a reagent for RNA extraction in 3D-Gene™ RNA extraction reagent from liquid sample kit (Toray Industries, Inc.) according to the protocol provided by the manufacturer.

<Measurement of Gene Expression Level> miRNAs in the total RNA obtained from the serum samples of each of 200 persons in total of 150 healthy subjects and 50 stomach cancer patients included in the training cohort and the validation cohort were fluorescently labeled using 3D-Gene™ miRNA Labeling kit (Toray Industries, Inc.) according to the protocol (ver 2.20) provided by the manufacturer. The oligo DNA chip used was 3D-Gene™ Human miRNA Oligo chip (Toray Industries, Inc.) with attached probes having sequences complementary to 2,555 miRNAs among the miRNAs registered in miR-Base Release 20. Hybridization between the miRNAs in the total RNA and the probes on the DNA chip under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained in the 50 stomach cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Sample from Patient with Cancer Other than Stomach Cancers>

Serum was collected using VENOJECT II vacuum blood collecting tube VP-AS109K60 (Terumo Corp.) from each of 63 pancreatic cancer patients, 65 bile duct cancer patients, 35 colorectal cancer patients, 32 liver cancer patients, and 17 benign pancreaticobiliary disease patients with no cancer found in other organs after acquisition of informed consent, and used as a training cohort together with the samples of 34 stomach cancer patients and 102 healthy subjects of Reference Example 1. Likewise, serum was collected using VENOJECT II vacuum blood collecting tube VP-AS109K60 (Terumo Corp.) from each of 37 pancreatic cancer patients, 33 bile duct cancer patients, 15 colorectal cancer patients, 20 liver cancer patients, and 4 benign pancreaticobiliary disease patients with no cancer found in other organs after acquisition of informed consent, and used as a validation cohort together with the samples of 16 stomach cancer patients with no cancer found in areas other than stomach cancer and 48 healthy subjects of Reference Example 1. Subsequent operations were conducted in the same way as in Reference Example 1.

Example 1

<Selection of Gene Markers Using the Training Cohort, and Method for Evaluating Stomach Cancer Discriminant Performance of Single Gene Marker Using the Validation Cohort>

In this Example, a gene marker for discriminating a stomach cancer patient from a healthy subject was selected from the training cohort and studied in samples of the validation cohort independent of the training cohort, for a method for evaluating the stomach cancer discriminant performance of each selected gene marker alone.

Specifically, first, the miRNA expression levels of the training cohort and the validation cohort obtained in the preceding Reference Examples were combined and normalized by quantile normalization.

Next, genes for diagnosis were selected using the training cohort. Here, in order to acquire diagnostic markers with higher reliability, only genes having the expression level of $2^6$ or higher in 50% or more of the samples in either of the stomach cancer patient group of the training cohort or the healthy subject group of the training cohort were selected. In order to further acquire statistically significant genes for discriminating a stomach cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant. The result is described in Table 2.

In this way, polynucleotides consisting of hsa-miR-4257, hsa-miR-6726-5p, hsa-miR-1343-3p, hsa-miR-1247-3p, hsa-miR-6787-5p, hsa-miR-6875-5p, hsa-miR-1225-3p, hsa-miR-8063, hsa-miR-6781-5p, hsa-miR-4746-3p, hsa-miR-1908-5p, hsa-miR-6756-5p, hsa-miR-204-3p, hsa-miR-4651, hsa-miR-6757-5p, hsa-miR-6825-5p, hsa-miR-7108-5p, hsa-miR-4792, hsa-miR-7641, hsa-miR-3188, hsa-miR-3131, hsa-miR-6780b-5p, hsa-miR-8069, hsa-miR-6840-3p, hsa-miR-8072, hsa-miR-1233-5p, hsa-miR-6887-5p, hsa-miR-1231, hsa-miR-5572, hsa-miR-6738-5p, hsa-miR-6784-5p, hsa-miR-6791-5p, hsa-miR-6749-5p, hsa-miR-6741-5p, hsa-miR-128-1-5p, hsa-miR-4419b, hsa-miR-6746-5p, hsa-miR-3184-5p, hsa-miR-3679-5p, hsa-miR-7110-5p, hsa-miR-4516, hsa-miR-6717-5p, hsa-miR-6826-5p, hsa-miR-4433b-3p, hsa-miR-3679-3p, hsa-miR-3135b, hsa-miR-3622a-5p, hsa-miR-711, hsa-miR-4467, hsa-miR-6857-5p, hsa-miR-6515-3p, hsa-miR-1225-5p, hsa-miR-187-5p, hsa-miR-3185, hsa-miR-642b-3p, hsa-miR-1249, hsa-miR-744-5p, hsa-miR-4442, hsa-miR-1228-3p, hsa-miR-939-5p, hsa-miR-6845-5p, hsa-miR-887-3p, hsa-miR-7845-5p, hsa-miR-6729-5p, hsa-miR-4632-5p, hsa-miR-615-5p, hsa-miR-6724-5p, hsa-miR-4728-5p, hsa-miR-6732-5p, hsa-miR-6816-5p, hsa-miR-4695-5p, hsa-miR-6088, hsa-miR-7975, hsa-miR-3197, hsa-miR-6125, hsa-miR-4433-3p, hsa-miR-6727-5p, hsa-miR-4706, hsa-miR-7847-3p, hsa-miR-6805-3p, hsa-miR-6766-3p, hsa-miR-1913, hsa-miR-4649-5p, hsa-miR-602, hsa-miR-3663-3p, hsa-miR-6893-5p, hsa-miR-6861-5p, hsa-miR-4449, hsa-miR-6842-5p, hsa-miR-4454, hsa-miR-5195-3p, hsa-miR-663b, hsa-miR-6765-5p, hsa-miR-4513, hsa-miR-614, hsa-miR-6785-5p, hsa-miR-6777-5p, hsa-miR-940, hsa-miR-4741, hsa-miR-6870-5p, hsa-miR-6131, hsa-miR-150-3p, hsa-miR-4707-5p, hsa-miR-1915-3p, hsa-miR-3937, hsa-miR-937-5p, hsa-miR-4443, hsa-miR-1914-3p, hsa-miR-3620-5p, hsa-miR-1268b, hsa-miR-1227-5p, hsa-miR-6880-5p, hsa-miR-4417, hsa-miR-6802-5p, hsa-miR-6769a-5p, hsa-miR-663a, hsa-miR-6721-5p, hsa-miR-4532, hsa-miR-7977, hsa-miR-92b-5p, hsa-miR-371a-5p, hsa-miR-6126, hsa-miR-4734, hsa-miR-4665-3p, hsa-miR-423-5p, hsa-miR-1469, hsa-miR-4675, hsa-miR-1915-5p, hsa-miR-6716-5p, hsa-miR-718, hsa-miR-4281, hsa-miR-6820-5p, hsa-miR-6795-5p, hsa-miR-6779-5p, hsa-miR-7109-5p, hsa-miR-6798-5p, hsa-miR-4648, hsa-miR-8059, hsa-miR-6765-3p, hsa-miR-6132, hsa-miR-4492, hsa-miR-7107-5p, hsa-miR-3195, hsa-miR-3180, hsa-miR-296-3p, hsa-miR-564, hsa-miR-1268a, hsa-miR-6848-5p, hsa-miR-762, hsa-miR-2861, hsa-miR-1203, hsa-miR-1260b, hsa-miR-4476, hsa-miR-6885-5p, hsa-miR-6769b-5p, hsa-miR-23b-3p, hsa-miR-1343-5p, hsa-miR-3621, hsa-miR-4688, hsa-miR-4286, hsa-miR-4640-5p, hsa-miR-4739, hsa-miR-1260a, hsa-miR-4276, hsa-miR-7106, hsa-miR-128-2-5p, hsa-miR-125a-3p, hsa-miR-92a-2-5p and hsa-miR-486-3p genes, and the nucleotide sequences of SEQ ID NOs: 1 to 169 related thereto were found.

Among them, genes newly found as markers for examining the presence or absence of stomach cancer are polynucleotides consisting of the nucleotide sequences represented by SEQ ID NOs: 1 to 165.

A discriminant for determining the presence or absence of stomach cancer was further prepared by Fisher's discriminant analysis with the expression levels of these genes as indicators. Specifically, any newly found polynucleotide consisting of a nucleotide sequence represented by any of SEQ ID NOs: 1 to 169 in the training cohort was applied for Formula 2 to construct a discriminant. Calculated accuracy, sensitivity, and specificity are shown in Table 3. In this respect, a discriminant coefficient and a constant term are shown in Table 4. In this context, all of the polynucleotides consisting of the nucleotide sequences represented by SEQ ID NOs: 1 to 169 were selected as markers capable of determining all of papillary adenocarcinoma, tubular adenocarcinoma (3 cases), low differentiated adenocarcinoma, signet-ring cell carcinoma, and mucinous carcinoma, which are main types of stomach cancer.

Next, accuracy, sensitivity, and specificity in the validation cohort were calculated using the discriminant thus prepared, and the discriminant performance of the selected polynucleotides was validated using independent samples (Table 3). For example, the expression level measurement value of the nucleotide sequence represented by SEQ ID NO: 1 was compared between the healthy subjects (100 persons) and the stomach cancer patients (34 persons) in the training cohort. As a result, the gene expression level measurement values were found to be significantly lower in the stomach cancer patient group than in the healthy subject group (see the left diagram of FIG. 2). These results were also reproducible in the healthy subjects (50 persons) and the stomach cancer patients (16 persons) in the validation cohort (see the right diagram of FIG. 2). Likewise, the results obtained about the other polynucleotides shown in SEQ ID NOs: 2 to 169 showed that the gene expression level measurement values were significantly lower (−) or higher (+) in the stomach cancer patient group than in the healthy subject group (Table 2). These results were able to be validated in the validation cohort. For example, as for this nucleotide sequence represented by SEQ ID NO: 1, the number of correctly or incorrectly identified samples in the detection of stomach cancer was calculated using the threshold (6.29) that was set in the training cohort and discriminated between the groups. As a result, 14 true positives, 49 true negatives, 1 false positive, and 2 false negatives were obtained. From these values, 95.5% accuracy, 87.5% sensitivity, and 98% specificity were obtained as the detection performance. In this way, the detection performance was calculated as to all of the polynucleotides shown in SEQ ID NOs: 1 to 169, and described in Table 3. The polynucleotides consisting of the nucleotide sequences represented by SEQ ID NOs: 1 to 169 shown in Table 3, exhibited sensitivity of 87.5%, 93.8%, 93.8%, 81.2%, 93.8%, 87.5%, 87.5%, 81.2%, 68.8%, 87.5%, 75.0%, 81.2%, 87.5%, 75.0%, 81.2%, 93.8%, 68.8%, 81.2%, 56.2%, 68.8%, 87.5%, 56.2%, 62.5%, 62.5%, 62.5%, 75.0%, 56.2%, 87.5%, 93.8%, 62.5%, 87.5%, 62.5%, 68.8%, 81.2%, 81.2%, 62.5%, 81.2%, 81.2%, 62.5%, 87.5%, 62.5%, 75.0%, 56.2%, 75.0%, 62.5%, 56.2%, 68.8%, 62.5%, 56.2%, 93.8%, 62.5%, 62.5%, 56.2%, 81.2%, 68.8%, 56.2%, 43.8%, 75.0%, 75.0%, 68.8%, 81.2%, 75.0%, 68.8%, 68.8%, 43.8%, 62.5%, 50.0%, 50.0%, 62.5%, 62.5%, 50.0%, 68.8%, 37.5%, 50.0%, 37.5%, 68.8%, 68.8%, 56.2%, 12.5%, 75.0%, 50.0%, 50.0%, 37.5%, 68.8%, 25.0%, 81.2%, 43.8%, 56.2%, 62.5%, 37.5%, 43.8%, 43.8%, 37.5%, 43.8%, 31.2%, 43.8%, 50.0%, 25%, 43.8%, 37.5%, 37.5%, 31.2%, 25.0%, 25.0%, 56.2%, 31.2%, 43.8%, 56.2%, 50.0%, 37.5%, 31.2%, 31.2%, 37.5%, 50.0%, 12.5%, 31.2%, 56.2%, 18.8%, 43.8%, 18.8%, 37.5%, 31.2%, 37.5%, 50.0%, 50.0%, 12.5%, 31.2%, 31.2%, 31.2%, 31.2%, 50.0%, 37.5%, 18.8%, 37.5%, 50.0%, 43.8%, 18.8%, 43.8%, 31.2%, 18.8%, 50.0%, 25.0%, 31.2%, 31.2%, 18.8%, 43.8%, 6.2%, 25.0%, 12.5%, 31.2%, 12.5%, 18.8%, 37.5%, 6.2%, 31.2%, 6.2%, 18.8%, 6.2%, 18.8%, 6.2%, 12.5%, 18.8%, 6.2%, 12.5%, 6.2%, 50.0%, 68.8%, 31.2%, and 25.0%, respectively, in the validation cohort. As seen from Comparative Example mentioned later, the existing markers CEA and CA19-9 had sensitivity of 12.5% (when the abnormal value of CEA was defined as 5 ng/ml or higher) and 12.5% (when the abnormal value of CA19-9 was defined as 37 U/ml or higher), respectively, in the validation cohort, demonstrating that all of the polynucleotides consisting of the nucleotide sequences represented by SEQ ID NOs: 1 to 169 can discriminate, each alone, stomach cancer in the validation cohort with sensitivity beyond CEA and CA19-9.

For example, 4 polynucleotides consisting of the nucleotide sequences represented by SEQ ID NOs: 3, 5, 21, and 28 were able to correctly determine stomach cancer as to 9 stage IA stomach cancer samples contained in the validation cohort. Thus, these polynucleotides can detect even early stomach cancer and contribute to the early diagnosis of stomach cancer.

Example 2

<Method for Evaluating Stomach Cancer Discriminant Performance by Combination of Multiple Gene Markers Using Samples in the Validation Cohort>

In this Example, a method for evaluating stomach cancer discriminant performance by a combination of the gene markers selected in Example 1 was studied. Specifically, Fisher's discriminant analysis was conducted as to 14,190 combinations of two expression level measurement values comprising at least one or more of the expression level measurement values of the newly found polynucleotides consisting of the nucleotide sequences represented by SEQ ID NOs: 1 to 165 among any of the polynucleotides consisting of the nucleotide sequences represented by SEQ ID NOs: 1 to 169 selected in Example 1, to construct a discriminant for determining the presence or absence of stomach cancer. Next, accuracy, sensitivity, and specificity in the validation cohort were calculated using the discriminant thus prepared, and the discriminant performance of the selected polynucleotides was validated using the independent samples.

Figure 3:
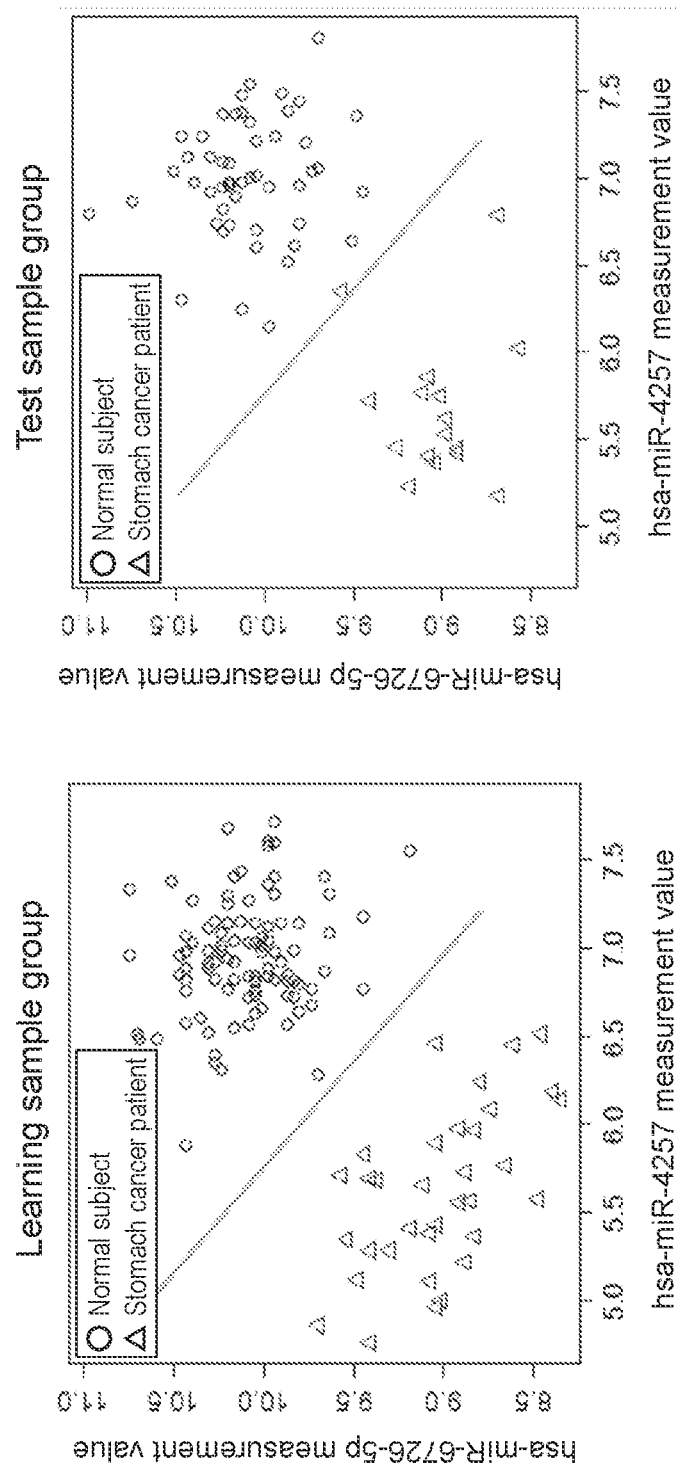
FIG. 3 Left diagram: the measurement values of hsa-miR-4257 (SEQ ID NO: 1) in healthy subjects (100 persons, circles) and stomach cancer patients (34 persons, triangles) selected as a training cohort were each plotted on the abscissa against their measurement values of hsa-miR-6726-5p (SEQ ID NO: 2) on the ordinate. The line in the diagram depicts a discriminant function (0=0.83x+y−14.78) that was optimized by Fisher's discriminant analysis and discriminated between the two groups. Right diagram: the measurement values of hsa-miR-4257 (SEQ ID NO: 1) in healthy subjects (50 persons, circles) and stomach cancer patients (16 persons, triangles) selected as a validation cohort were each plotted on the abscissa against their measurement values of hsa-miR-6726-5p (SEQ ID NO: 2) on the ordinate. The line in the diagram depicts the threshold (0=0.83x+y−14.78) that was set for the training cohort and discriminated between the two groups.

For example, the expression level measurement values of the nucleotide sequences represented by SEQ ID NO: 1 and SEQ ID NO: 2 were compared between the healthy subjects (100 persons) and the stomach cancer patients (34 persons) in the training cohort. As a result, a scatter diagram that significantly separated the expression level measurement values of the stomach cancer patient group from those of the healthy subject group was obtained (see the left diagram of FIG. 3). These results were also reproducible in the healthy subjects (50 persons) and the stomach cancer patients (16 persons) in the validation cohort (see the right diagram of FIG. 3). Likewise, a scatter diagram that significantly separated the gene expression level measurement values of the stomach cancer patient group from those of the healthy subject group was also obtained as to the other combinations of two expression level measurement values comprising at least one or more of the expression level measurement values of the newly found polynucleotides consisting of the nucleotide sequences represented by SEQ ID NOs: 1 to 165 among the polynucleotides consisting of the nucleotide sequences represented by SEQ ID NOs: 1 to 169. These results were able to be validated in the validation cohort. For example, as for these nucleotide sequences represented by SEQ ID NO: 1 and SEQ ID NO: 2, the number of samples that were correctly or incorrectly identified in the detection of stomach cancer was calculated using the function (0=0.83x+y−14.78) that was set in the training cohort and discriminated between the two groups. As a result, 15 true positives, 50 true negatives, 0 false positives, and 1 false negative were obtained. From these values, 98.5% accuracy, 93.8% sensitivity, and 100% specificity were obtained as the detection performance. In this way, the detection performance was calculated as to all of the combinations of two expression level measurement values comprising at least one or more of the expression level measurement values of any of the newly found polynucleotides consisting of the nucleotide sequences represented by SEQ ID NOs: 1 to 165 among the polynucleotides consisting of the nucleotide sequences represented by SEQ ID NOs: 1 to 169. Among them, 168 combinations comprising the expression level measurement value of the polynucleotide consisting of the nucleotide sequence represented by SEQ ID NO: 1 and the detection performance thereof were described in Table 6 as an example. For example, a combination of the expression level measurement values of the polynucleotides consisting of the nucleotide sequences represented by SEQ ID NOs: 1 and 14 exhibited sensitivity of 100% in the validation cohort. Also, all of combinations of two polynucleotides consisting of nucleotide sequences represented by SEQ ID NO: 1 and any of SEQ ID NOs: 2, 4, 14, 17, 22, 24, 27, 32, 39, 43, 46, 48, 53, 65, 66, 67, 78, 89, 91, 98, 99, 113, 116, 122, 129, 141, 144, 148, 150, 154, and 156 exhibited specificity of 100%. 14,159 combinations of the expression level measurement values of polynucleotides having sensitivity beyond the existing marker CEA or CA19-9 (both 12.5% in Table 5) were obtained in the validation cohort. All of the nucleotide sequences 1 to 165 described in Table 2 obtained in Example 1 were employed at least once in these combinations. These results demonstrated that the combined use of two of the polynucleotides consisting of the nucleotide sequences represented by SEQ ID NOs: 1 to 165 can also discriminate stomach cancer with excellent performance beyond the existing marker. Thus, the combinations of two expression level measurement values of the polynucleotides consisting of the nucleotide sequences also produced excellent stomach cancer detection sensitivity.

Markers for the detection of stomach cancer with better sensitivity are obtained by further combining 3, 4, 5, 6, 7, 8, 9, 10 or more of the expression level measurement values of the polynucleotides consisting of the nucleotide sequences represented by SEQ ID NOs: 1 to 169. For example, the newly found polynucleotides consisting of the nucleotide sequences represented by SEQ ID NOs: 1 to 165 among the polynucleotides consisting of the nucleotide sequences represented by SEQ ID NOs: 1 to 169 selected in Example 1 were measured to obtain their expression levels between the healthy subject group and the stomach cancer group in the validation cohort. All of the polynucleotides were ranked in the descending order of their P values based on the Student's t-test which indicates statistical significance of difference between groups (i.e., one having the lowest P value was ranked in the first place), and stomach cancer detection sensitivity was evaluated using combinations of one or more polynucleotides to which the polynucleotides were added one by one from the top to the bottom according to the rank. In short, the order in which the polynucleotides were combined in this evaluation is in reverse in terms of SEQ ID NOs from SEQ ID NO: 165 to SEQ ID NOs: 164, 163, . . . shown in Table 2. As a result, the sensitivity in the validation cohort was 6.2% for 1 polynucleotide (SEQ ID NO: 165), 62.5% for 2 polynucleotides (SEQ ID NOs: 165 and 164), 68.8% for 4 polynucleotides (SEQ ID NOs: 162 to 165), 75.0% for 8 polynucleotides (SEQ ID NOs: 158 to 165), 87.5% for 13 polynucleotides (SEQ ID NOs: 153 to 165), 93.8% for 15 polynucleotides (SEQ ID NOs: 151 to 165), 100% for 23 polynucleotides (SEQ ID NOs: 143 to 165), 100% for 50 polynucleotides (SEQ ID NOs: 116 to 165), 100% for 80 polynucleotides (SEQ ID NOs: 86 to 165), 100% for 100 polynucleotides (SEQ ID NOs: 66 to 165), 100% for 150 polynucleotides (SEQ ID NOs: 16 to 165), and 100% for 165 polynucleotides (SEQ ID NOs: 1 to 165).

These results demonstrated that a combination of multiple polynucleotides can produce higher stomach cancer discriminant performance than that of each polynucleotide alone or a combination of a fewer number of polynucleotides. In this context, the combinations of multiple polynucleotides are not limited to the combinations of the polynucleotides added in the order of statistically significant difference as described above, and any combination of multiple polynucleotides can be used in the detection of stomach cancer.

From these results, it can be concluded that all of the polynucleotides consisting of the nucleotide sequences represented by SEQ ID NOs: 1 to 169 serve as excellent markers for the detection of stomach cancer.

TABLE 2

| SEQ ID NO: | Gene name | P value after Bonferroni correction | Expression level in stomach cancer patient relative to healthy subject |
|---|---|---|---|
| 1 | hsa-miR-4257 | 1.77.E−35 | − |
| 2 | hsa-miR-6726-5p | 1.21.E−34 | − |
| 3 | hsa-miR-1343-3p | 2.35.E−27 | − |
| 4 | hsa-miR-1247-3p | 1.41.E−25 | + |
| 5 | hsa-miR-6787-5p | 9.96.E−25 | − |
| 6 | hsa-miR-6875-5p | 3.18.E−23 | + |
| 7 | hsa-miR-1225-3p | 4.17.E−23 | + |
| 8 | hsa-miR-8063 | 1.39.E−22 | − |
| 9 | hsa-miR-6781-5p | 4.80.E−22 | + |
| 10 | hsa-miR-4746-3p | 7.08.E−22 | + |
| 11 | hsa-miR-1908-5p | 1.66.E−21 | + |
| 12 | hsa-miR-6756-5p | 2.78.E−21 | − |
| 13 | hsa-miR-204-3p | 3.60.E−21 | − |
| 14 | hsa-miR-4651 | 3.74.E−21 | − |
| 15 | hsa-miR-6757-5p | 5.50.E−21 | − |
| 16 | hsa-miR-6825-5p | 7.04.E−20 | + |
| 17 | hsa-miR-7108-5p | 8.87.E−20 | + |
| 18 | hsa-miR-4792 | 1.50.E−19 | + |
| 19 | hsa-miR-7641 | 2.77.E−19 | − |
| 20 | hsa-miR-3188 | 4.51.E−19 | + |
| 21 | hsa-miR-3131 | 1.03.E−18 | − |
| 22 | hsa-miR-6780b-5p | 1.44.E−18 | + |
| 23 | hsa-miR-8069 | 2.56.E−18 | + |
| 24 | hsa-miR-6840-3p | 3.01.E−18 | − |
| 25 | hsa-miR-8072 | 4.25.E−18 | + |
| 26 | hsa-miR-1233-5p | 2.25.E−17 | − |
| 27 | hsa-miR-6887-5p | 4.74.E−17 | − |
| 28 | hsa-miR-1231 | 5.08.E−17 | + |
| 29 | hsa-miR-5572 | 1.08.E−16 | + |
| 30 | hsa-miR-6738-5p | 1.16.E−16 | − |
| 31 | hsa-miR-6784-5p | 1.68.E−16 | + |
| 32 | hsa-miR-6791-5p | 3.16.E−16 | + |
| 33 | hsa-miR-6749-5p | 3.69.E−16 | − |
| 34 | hsa-miR-6741-5p | 5.38.E−16 | − |
| 35 | hsa-miR-128-1-5p | 1.67.E−15 | + |
| 36 | hsa-miR-4419b | 2.16.E−15 | − |
| 37 | hsa-miR-6746-5p | 2.49.E−15 | − |
| 38 | hsa-miR-3184-5p | 2.56.E−15 | + |
| 39 | hsa-miR-3679-5p | 2.88.E−15 | + |
| 40 | hsa-miR-7110-5p | 3.95.E−15 | + |
| 41 | hsa-miR-4516 | 4.43.E−15 | − |
| 42 | hsa-miR-6717-5p | 4.77.E−15 | − |
| 43 | hsa-miR-6826-5p | 4.94.E−15 | − |
| 44 | hsa-miR-4433b-3p | 5.34.E−15 | + |
| 45 | hsa-miR-3679-3p | 2.55.E−14 | + |
| 46 | hsa-miR-3135b | 3.35.E−14 | − |
| 47 | hsa-miR-3622a-5p | 4.36.E−14 | − |
| 48 | hsa-miR-711 | 5.86.E−14 | + |
| 49 | hsa-miR-4467 | 7.26.E−14 | + |
| 50 | hsa-miR-6857-5p | 2.73.E−13 | + |
| 51 | hsa-miR-6515-3p | 3.28.E−13 | + |
| 52 | hsa-miR-1225-5p | 4.67.E−13 | + |
| 53 | hsa-miR-187-5p | 5.39.E−13 | − |
| 54 | hsa-miR-3185 | 6.80.E−13 | + |
| 55 | hsa-miR-642b-3p | 8.60.E−13 | − |
| 56 | hsa-miR-1249 | 1.16.E−12 | + |
| 57 | hsa-miR-744-5p | 2.15.E−12 | + |
| 58 | hsa-miR-4442 | 3.26.E−12 | − |
| 59 | hsa-miR-1228-3p | 4.54.E−12 | + |
| 60 | hsa-miR-939-5p | 7.77.E−12 | + |
| 61 | hsa-miR-6845-5p | 9.25.E−12 | + |
| 62 | hsa-miR-887-3p | 1.35.E−11 | + |
| 63 | hsa-miR-7845-5p | 1.81.E−11 | + |
| 64 | hsa-miR-6729-5p | 2.80.E−11 | + |
| 65 | hsa-miR-4632-5p | 6.45.E−11 | + |
| 66 | hsa-miR-615-5p | 7.56.E−11 | − |
| 67 | hsa-miR-6724-5p | 8.75.E−11 | + |
| 68 | hsa-miR-4728-5p | 1.05.E−10 | − |
| 69 | hsa-miR-6732-5p | 1.23.E−10 | + |
| 70 | hsa-miR-6816-5p | 1.35.E−10 | + |
| 71 | hsa-miR-4695-5p | 4.88.E−10 | + |
| 72 | hsa-miR-6088 | 5.46.E−10 | − |
| 73 | hsa-miR-7975 | 5.48.E−10 | − |
| 74 | hsa-miR-3197 | 5.56.E−10 | + |
| 75 | hsa-miR-6125 | 6.01.E−10 | + |
| 76 | hsa-miR-4433-3p | 6.04.E−10 | + |
| 77 | hsa-miR-6727-5p | 8.92.E−10 | − |

TABLE 2-continued

| SEQ ID NO: | Gene name | P value after Bonferroni correction | Expression level in stomach cancer patient relative to healthy subject |
|---|---|---|---|
| 78 | hsa-miR-4706 | 1.09.E-09 | - |
| 79 | hsa-miR-7847-3p | 1.25.E-09 | - |
| 80 | hsa-miR-6805-3p | 1.57.E-09 | + |
| 81 | hsa-miR-6766-3p | 1.95.E-09 | + |
| 82 | hsa-miR-1913 | 2.12.E-09 | + |
| 83 | hsa-miR-4649-5p | 2.42.E-09 | - |
| 84 | hsa-miR-602 | 2.50.E-09 | + |
| 85 | hsa-miR-3663-3p | 2.83.E-09 | - |
| 86 | hsa-miR-6893-5p | 3.40.E-09 | - |
| 87 | hsa-miR-6861-5p | 3.53.E-09 | - |
| 88 | hsa-miR-4449 | 4.40.E-09 | + |
| 89 | hsa-miR-6842-5p | 4.48.E-09 | + |
| 90 | hsa-miR-4454 | 4.77.E-09 | - |
| 91 | hsa-miR-5195-3p | 6.01.E-09 | - |
| 92 | hsa-miR-663b | 9.12.E-09 | - |
| 93 | hsa-miR-6765-5p | 2.06.E-08 | + |
| 94 | hsa-miR-4513 | 2.61.E-08 | - |
| 95 | hsa-miR-614 | 4.92.E-08 | - |
| 96 | hsa-miR-6785-5p | 5.85.E-08 | - |
| 97 | hsa-miR-6777-5p | 6.02.E-08 | - |
| 98 | hsa-miR-940 | 8.08.E-08 | + |
| 99 | hsa-miR-4741 | 9.53.E-08 | + |
| 100 | hsa-miR-6870-5p | 1.07.E-07 | + |
| 101 | hsa-miR-6131 | 1.21.E-07 | - |
| 102 | hsa-miR-150-3p | 1.31.E-07 | - |
| 103 | hsa-miR-4707-5p | 1.70.E-07 | + |
| 104 | hsa-miR-1915-3p | 2.00.E-07 | + |
| 105 | hsa-miR-3937 | 2.17.E-07 | + |
| 106 | hsa-miR-937-5p | 2.85.E-07 | - |
| 107 | hsa-miR-4443 | 3.12.E-07 | + |
| 108 | hsa-miR-1914-3p | 3.23.E-07 | - |
| 109 | hsa-miR-3620-5p | 3.97.E-07 | + |
| 110 | hsa-miR-1268b | 5.51.E-07 | + |
| 111 | hsa-miR-1227-5p | 8.69.E-07 | + |
| 112 | hsa-miR-6880-5p | 9.59.E-07 | + |
| 113 | hsa-miR-4417 | 1.28.E-06 | + |
| 114 | hsa-miR-6802-5p | 1.30.E-06 | - |
| 115 | hsa-miR-6769a-5p | 1.32.E-06 | - |
| 116 | hsa-miR-663a | 1.42.E-06 | + |
| 117 | hsa-miR-6721-5p | 1.73.E-06 | + |
| 118 | hsa-miR-4532 | 2.01.E-06 | - |
| 119 | hsa-miR-7977 | 2.27.E-06 | - |
| 120 | hsa-miR-92b-5p | 2.37.E-06 | + |
| 121 | hsa-miR-371a-5p | 2.37.E-06 | - |
| 122 | hsa-miR-6126 | 2.47.E-06 | + |
| 123 | hsa-miR-4734 | 2.53.E-06 | + |
| 124 | hsa-miR-4665-3p | 2.71.E-06 | + |
| 125 | hsa-miR-423-5p | 4.04.E-06 | - |
| 126 | hsa-miR-1469 | 8.08.E-06 | + |
| 127 | hsa-miR-4675 | 8.36.E-06 | - |
| 128 | hsa-miR-1915-5p | 8.49.E-06 | - |
| 129 | hsa-miR-6716-5p | 9.56.E-06 | + |
| 130 | hsa-miR-718 | 1.59.E-05 | + |
| 131 | hsa-miR-4281 | 1.59.E-05 | - |
| 132 | hsa-miR-6820-5p | 1.88.E-05 | - |
| 133 | hsa-miR-6795-5p | 3.14.E-05 | - |
| 134 | hsa-miR-6779-5p | 3.55.E-05 | - |
| 135 | hsa-miR-7109-5p | 4.02.E-05 | - |
| 136 | hsa-miR-6798-5p | 4.28.E-05 | + |
| 137 | hsa-miR-4648 | 6.38.E-05 | + |
| 138 | hsa-miR-8059 | 7.15.E-05 | - |
| 139 | hsa-miR-6765-3p | 8.47.E-05 | - |
| 140 | hsa-miR-6132 | 1.28.E-04 | + |
| 141 | hsa-miR-4492 | 1.51.E-04 | + |
| 142 | hsa-miR-7107-5p | 1.64.E-04 | - |
| 143 | hsa-miR-3195 | 1 73.E-04 | + |
| 144 | hsa-miR-3180 | 2.82.E-04 | + |
| 145 | hsa-miR-296-3p | 2.89.E-04 | - |
| 146 | hsa-miR-564 | 4.75.E-04 | - |
| 147 | hsa-miR-1268a | 5.55.E-04 | + |
| 148 | hsa-miR-6848-5p | 6.07.E-04 | + |
| 149 | hsa-miR-762 | 8.99.E-04 | + |
| 150 | hsa-miR-2861 | 1.57.E-03 | - |
| 151 | hsa-miR-1203 | 1.91.E-03 | + |
| 152 | hsa-miR-1260b | 2.01.E-03 | - |
| 153 | hsa-miR-4476 | 2.45.E-03 | - |
| 154 | hsa-miR-6885-5p | 2.83.E-03 | - |
| 155 | hsa-miR-6769b-5p | 2.84.E-03 | - |
| 156 | hsa-miR-23b-3p | 2.87.E-03 | - |
| 157 | hsa-miR-1343-5p | 3.95.E-03 | + |
| 158 | hsa-miR-3621 | 4.31.E-03 | - |
| 159 | hsa-miR-4688 | 4.77.E-03 | - |
| 160 | hsa-miR-4286 | 4.90.E-03 | - |
| 161 | hsa-miR-4640-5p | 6.06.E-03 | + |
| 162 | hsa-miR-4739 | 6.13.E-03 | + |
| 163 | hsa-miR-1260a | 7.24.E-03 | - |
| 164 | hsa-miR-4276 | 8.00.E-03 | + |
| 165 | hsa-miR-7106-5p | 9.50.E-03 | - |
| 166 | hsa-miR-128-2-5p | 1.79.E-09 | - |
| 167 | lisa-miR-125a-3p | 1.81.E-09 | - |
| 168 | hsa-miR-92a-2-5p | 2.01.E-05 | + |
| 169 | hsa-miR-486-3p | 2.60.E-03 | - |

TABLE 3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 95.5 | 85.3 | 99.0 | 95.5 | 87.5 | 98.0 |
| 2 | 94.8 | 88.2 | 97.0 | 97.0 | 93.8 | 98.0 |
| 3 | 97.0 | 91.2 | 99.0 | 97.0 | 93.8 | 98.0 |
| 4 | 93.3 | 82.4 | 97.0 | 90.9 | 81.2 | 94.0 |
| 5 | 93.3 | 79.4 | 98.0 | 97.0 | 93.8 | 98.0 |
| 6 | 94.0 | 91.2 | 95.0 | 87.9 | 87.5 | 88.0 |
| 7 | 92.5 | 82.4 | 96.0 | 97.0 | 87.5 | 100.0 |
| 8 | 90.3 | 88.2 | 91.0 | 90.9 | 81.2 | 94.0 |
| 9 | 94.8 | 85.3 | 98.0 | 86.4 | 68.8 | 92.0 |
| 10 | 91.0 | 76.5 | 96.0 | 95.5 | 87.5 | 98.0 |
| 11 | 90.3 | 82.4 | 93.0 | 89.4 | 75.0 | 94.0 |
| 12 | 90.3 | 73.5 | 96.0 | 87.9 | 81.2 | 90.0 |
| 13 | 91.0 | 73.5 | 97.0 | 81.8 | 87.5 | 80.0 |
| 14 | 91.8 | 79.4 | 96.0 | 92.4 | 75.0 | 98.0 |
| 15 | 90.3 | 76.5 | 95.0 | 95.5 | 81.2 | 100.0 |
| 16 | 88.1 | 82.4 | 90.0 | 92.4 | 93.8 | 92.0 |
| 17 | 88.1 | 73.5 | 93.0 | 83.3 | 68.8 | 88.0 |
| 18 | 92.5 | 88.2 | 94.0 | 93.9 | 81.2 | 98.0 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 19 | 88.1 | 73.5 | 93.0 | 83.3 | 56.2 | 92.0 |
| 20 | 91.8 | 85.3 | 94.0 | 90.9 | 68.8 | 98.0 |
| 21 | 91.8 | 76.5 | 97.0 | 95.5 | 87.5 | 98.0 |
| 22 | 88.8 | 70.6 | 95.0 | 89.4 | 56.2 | 100.0 |
| 23 | 88.1 | 67.6 | 95.0 | 87.9 | 62.5 | 96.0 |
| 24 | 87.3 | 64.7 | 95.0 | 87.9 | 62.5 | 96.0 |
| 25 | 88.1 | 61.8 | 97.0 | 83.3 | 62.5 | 90.0 |
| 26 | 90.3 | 76.5 | 95.0 | 89.4 | 75.0 | 94.0 |
| 27 | 91.0 | 67.6 | 99.0 | 89.4 | 56.2 | 100.0 |
| 28 | 90.3 | 79.4 | 94.0 | 90.9 | 87.5 | 92.0 |
| 29 | 85.8 | 79.4 | 88.0 | 90.9 | 93.8 | 90.0 |
| 30 | 89.6 | 76.5 | 94.0 | 86.4 | 62.5 | 94.0 |
| 31 | 85.1 | 73.5 | 89.0 | 87.9 | 87.5 | 88.0 |
| 32 | 85.1 | 67.6 | 91.0 | 89.4 | 62.5 | 98.0 |
| 33 | 87.3 | 61.8 | 96.0 | 90.9 | 68.8 | 98.0 |
| 34 | 90.3 | 70.6 | 97.0 | 89.4 | 81.2 | 92.0 |
| 35 | 89.6 | 82.4 | 92.0 | 84.8 | 81.2 | 86.0 |
| 36 | 90.3 | 73.5 | 96.0 | 89.4 | 62.5 | 98.0 |
| 37 | 90.3 | 70.6 | 97.0 | 92.4 | 81.2 | 96.0 |
| 38 | 87.3 | 82.4 | 89.0 | 90.9 | 81.2 | 94.0 |
| 39 | 90.3 | 76.5 | 95.0 | 90.9 | 62.5 | 100.0 |
| 40 | 87.3 | 76.5 | 91.0 | 89.4 | 87.5 | 90.0 |
| 41 | 90.3 | 61.8 | 100.0 | 90.9 | 62.5 | 100.0 |
| 42 | 90.3 | 61.8 | 100.0 | 93.9 | 75.0 | 100.0 |
| 43 | 90.3 | 67.6 | 98.0 | 89.4 | 56.2 | 100.0 |
| 44 | 87.3 | 73.5 | 92.0 | 81.8 | 75.0 | 84.0 |
| 45 | 90.3 | 82.4 | 93.0 | 83.3 | 62.5 | 90.0 |
| 46 | 90.3 | 70.6 | 97.0 | 87.9 | 56.2 | 98.0 |
| 47 | 85.1 | 47.1 | 98.0 | 90.9 | 68.8 | 98.0 |
| 48 | 86.6 | 64.7 | 94.0 | 89.4 | 62.5 | 98.0 |
| 49 | 83.6 | 73.5 | 87.0 | 86.4 | 56.2 | 96.0 |
| 50 | 90.3 | 79.4 | 94.0 | 95.5 | 93.8 | 96.0 |
| 51 | 84.3 | 61.8 | 92.0 | 77.3 | 62.5 | 82.0 |
| 52 | 87.3 | 64.7 | 95.0 | 84.8 | 62.5 | 92.0 |
| 53 | 84.3 | 52.9 | 95.0 | 87.9 | 56.2 | 98.0 |
| 54 | 85.8 | 67.6 | 92.0 | 90.9 | 81.2 | 94.0 |
| 55 | 87.3 | 64.7 | 95.0 | 90.9 | 68.8 | 98.0 |
| 56 | 86.5 | 67.6 | 92.9 | 80.3 | 56.2 | 88.0 |
| 57 | 83.6 | 52.9 | 94.0 | 84.8 | 43.8 | 98.0 |
| 58 | 85.8 | 70.6 | 91.0 | 87.9 | 75.0 | 92.0 |
| 59 | 84.3 | 55.9 | 94.0 | 86.4 | 75.0 | 90.0 |
| 60 | 82.8 | 73.5 | 86.0 | 83.3 | 68.8 | 88.0 |
| 61 | 85.1 | 52.9 | 96.0 | 87.9 | 81.2 | 90.0 |
| 62 | 82.8 | 61.8 | 90.0 | 84.8 | 75.0 | 88.0 |
| 63 | 85.1 | 58.8 | 94.0 | 86.4 | 68.8 | 92.0 |
| 64 | 79.9 | 50.0 | 90.0 | 81.8 | 68.8 | 86.0 |
| 65 | 88.1 | 61.8 | 97.0 | 84.8 | 43.8 | 98.0 |
| 66 | 83.6 | 41.2 | 98.0 | 89.4 | 62.5 | 98.0 |
| 67 | 82.8 | 55.9 | 92.0 | 78.8 | 50.0 | 88.0 |
| 68 | 78.4 | 44.1 | 90.0 | 81.8 | 50.0 | 92.0 |
| 69 | 82.1 | 61.8 | 89.0 | 80.3 | 62.5 | 86.0 |
| 70 | 82.1 | 58.8 | 90.0 | 84.8 | 62.5 | 92.0 |
| 71 | 79.9 | 47.1 | 91.0 | 83.3 | 50.0 | 94.0 |
| 72 | 79.9 | 50.0 | 90.0 | 86.4 | 68.8 | 92.0 |
| 73 | 80.6 | 41.2 | 94.0 | 78.8 | 37.5 | 92.0 |
| 74 | 85.8 | 61.8 | 94.0 | 83.3 | 50.0 | 94.0 |
| 75 | 81.3 | 44.1 | 94.0 | 81.8 | 37.5 | 96.0 |
| 76 | 81.3 | 61.8 | 88.0 | 83.3 | 68.8 | 88.0 |
| 77 | 86.6 | 67.6 | 93.0 | 90.9 | 68.8 | 98.0 |
| 78 | 85.1 | 58.8 | 94.0 | 84.8 | 56.2 | 94.0 |
| 79 | 85.1 | 44.1 | 99.0 | 78.8 | 12.5 | 100.0 |
| 80 | 79.9 | 50.0 | 90.0 | 89.4 | 75.0 | 94.0 |
| 81 | 82.8 | 47.1 | 95.0 | 80.3 | 50.0 | 90.0 |
| 82 | 82.1 | 55.9 | 91.0 | 78.5 | 50.0 | 87.8 |
| 83 | 84.3 | 50.0 | 96.0 | 81.8 | 37.5 | 96.0 |
| 84 | 82.8 | 52.9 | 93.0 | 87.9 | 68.8 | 94.0 |
| 85 | 82.8 | 47.1 | 95.0 | 78.8 | 25.0 | 96.0 |
| 86 | 85.8 | 52.9 | 97.0 | 92.4 | 81.2 | 96.0 |
| 87 | 84.3 | 50.0 | 96.0 | 81.8 | 43.8 | 94.0 |
| 88 | 80.6 | 38.2 | 95.0 | 86.4 | 56.2 | 96.0 |
| 89 | 81.3 | 41.2 | 95.0 | 87.9 | 62.5 | 96.0 |
| 90 | 81.3 | 47.1 | 93.0 | 78.8 | 37.5 | 92.0 |
| 91 | 82.1 | 47.1 | 94.0 | 81.8 | 43.8 | 94.0 |
| 92 | 83.6 | 47.1 | 96.0 | 86.4 | 43.8 | 100.0 |
| 93 | 82.8 | 47.1 | 95.0 | 80.3 | 37.5 | 94.0 |

TABLE 3-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 94 | 79.1 | 29.4 | 96.0 | 83.3 | 43.8 | 96.0 |
| 95 | 76.9 | 38.2 | 90.0 | 78.8 | 31.2 | 94.0 |
| 96 | 81.3 | 44.1 | 94.0 | 83.3 | 43.8 | 96.0 |
| 97 | 79.9 | 38.2 | 94.0 | 83.3 | 50.0 | 94.0 |
| 98 | 80.6 | 44.1 | 93.0 | 78.8 | 25.0 | 96.0 |
| 99 | 82.1 | 50.0 | 93.0 | 80.3 | 43.8 | 92.0 |
| 100 | 81.3 | 38.2 | 96.0 | 84.8 | 37.5 | 100.0 |
| 101 | 85.1 | 50.0 | 97.0 | 83.3 | 37.5 | 98.0 |
| 102 | 80.6 | 29.4 | 98.0 | 77.3 | 31.2 | 92.0 |
| 103 | 76.1 | 32.4 | 91.0 | 75.8 | 25.0 | 92.0 |
| 104 | 84.3 | 50.0 | 96.0 | 80.3 | 25.0 | 98.0 |
| 105 | 79.1 | 38.2 | 93.0 | 84.8 | 56.2 | 94.0 |
| 106 | 82.8 | 44.1 | 96.0 | 81.8 | 31.2 | 98.0 |
| 107 | 82.1 | 44.1 | 95.0 | 83.3 | 43.8 | 96.0 |
| 108 | 81.3 | 47.1 | 93.0 | 80.3 | 56.2 | 88.0 |
| 109 | 79.9 | 38.2 | 94.0 | 81.8 | 50.0 | 92.0 |
| 110 | 74.6 | 32.4 | 89.0 | 72.7 | 37.5 | 84.0 |
| 111 | 81.3 | 44.1 | 94.0 | 75.8 | 31.2 | 90.0 |
| 112 | 82.8 | 47.1 | 95.0 | 80.3 | 31.2 | 96.0 |
| 113 | 81.3 | 35.3 | 97.0 | 81.8 | 37.5 | 96.0 |
| 114 | 86.6 | 52.9 | 98.0 | 86.4 | 50.0 | 98.0 |
| 115 | 79.1 | 38.2 | 93.0 | 75.8 | 12.5 | 96.0 |
| 116 | 81.3 | 41.2 | 95.0 | 78.8 | 31.2 | 94.0 |
| 117 | 76.9 | 38.2 | 90.0 | 80.3 | 56.2 | 88.0 |
| 118 | 81.3 | 38.2 | 96.0 | 75.8 | 18.8 | 94.0 |
| 119 | 78.4 | 35.3 | 93.0 | 81.8 | 43.8 | 94.0 |
| 120 | 78.4 | 38.2 | 92.0 | 78.8 | 18.8 | 98.0 |
| 121 | 79.1 | 35.3 | 94.0 | 75.8 | 37.5 | 88.0 |
| 122 | 78.4 | 38.2 | 92.0 | 81.8 | 31.2 | 98.0 |
| 123 | 78.4 | 32.4 | 94.0 | 80.3 | 37.5 | 94.0 |
| 124 | 87.3 | 52.9 | 99.0 | 86.4 | 50.0 | 98.0 |
| 125 | 76.9 | 32.4 | 92.0 | 75.8 | 50.0 | 84.0 |
| 126 | 78.4 | 29.4 | 95.0 | 71.2 | 12.5 | 90.0 |
| 127 | 80.6 | 41.2 | 94.0 | 83.3 | 31.2 | 100.0 |
| 128 | 79.9 | 32.4 | 96.0 | 78.8 | 31.2 | 94.0 |
| 129 | 77.6 | 26.5 | 95.0 | 77.3 | 31.2 | 92.0 |
| 130 | 76.1 | 26.5 | 93.0 | 75.8 | 31.2 | 90.0 |
| 131 | 78.4 | 35.3 | 93.0 | 84.8 | 50.0 | 96.0 |
| 132 | 80.6 | 29.4 | 98.0 | 77.3 | 37.5 | 90.0 |
| 133 | 79.9 | 23.5 | 99.0 | 80.3 | 18.8 | 100.0 |
| 134 | 75.4 | 32.4 | 90.0 | 83.3 | 37.5 | 98.0 |
| 135 | 73.9 | 23.5 | 91.0 | 80.3 | 50.0 | 90.0 |
| 136 | 78.4 | 44.1 | 90.0 | 74.2 | 43.8 | 84.0 |
| 137 | 73.9 | 20.6 | 92.0 | 80.3 | 18.8 | 100.0 |
| 138 | 79.1 | 29.4 | 96.0 | 81.8 | 43.8 | 94.0 |
| 139 | 82.1 | 41.2 | 96.0 | 80.3 | 31.2 | 96.0 |
| 140 | 79.9 | 29.4 | 97.0 | 78.8 | 18.8 | 98.0 |
| 141 | 79.1 | 32.4 | 95.0 | 81.8 | 50.0 | 92.0 |
| 142 | 75.4 | 29.4 | 91.0 | 75.8 | 25.0 | 92.0 |
| 143 | 78.4 | 38.2 | 92.0 | 77.3 | 31.2 | 92.0 |
| 144 | 79.9 | 32.4 | 96.0 | 81.8 | 31.2 | 98.0 |
| 145 | 81.2 | 27.3 | 99.0 | 77.3 | 18.8 | 96.0 |
| 146 | 81.3 | 35.3 | 97.0 | 84.8 | 43.8 | 98.0 |
| 147 | 73.1 | 14.7 | 93.0 | 71.2 | 6.2 | 92.0 |
| 148 | 77.6 | 23.5 | 96.0 | 78.8 | 25.0 | 96.0 |
| 149 | 77.6 | 23.5 | 96.0 | 72.3 | 12.5 | 91.8 |
| 150 | 77.6 | 23.5 | 96.0 | 80.3 | 31.2 | 96.0 |
| 151 | 74.6 | 14.7 | 95.0 | 78.8 | 12.5 | 100.0 |
| 152 | 79.9 | 32.4 | 96.0 | 75.8 | 18.8 | 94.0 |
| 153 | 76.1 | 20.6 | 95.0 | 78.8 | 37.5 | 92.0 |
| 154 | 81.3 | 32.4 | 98.0 | 75.8 | 6.2 | 98.0 |
| 155 | 76.9 | 20.6 | 96.0 | 81.8 | 31.2 | 98.0 |
| 156 | 79.1 | 23.5 | 98.0 | 72.7 | 6.2 | 94.0 |
| 157 | 82.1 | 35.3 | 98.0 | 80.3 | 18.8 | 100.0 |
| 158 | 74.6 | 11.8 | 96.0 | 74.2 | 6.2 | 96.0 |
| 159 | 77.6 | 20.6 | 97.0 | 78.8 | 18.8 | 98.0 |
| 160 | 75.4 | 20.6 | 94.0 | 71.2 | 6.2 | 92.0 |
| 161 | 78.4 | 26.5 | 96.0 | 78.8 | 12.5 | 100.0 |
| 162 | 79.1 | 20.6 | 99.0 | 78.8 | 18.8 | 98.0 |
| 163 | 76.1 | 20.6 | 95.0 | 72.7 | 6.2 | 94.0 |
| 164 | 76.9 | 14.7 | 98.0 | 78.8 | 12.5 | 100.0 |
| 165 | 74.6 | 8.8 | 97.0 | 75.8 | 6.2 | 98.0 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 166 | 85.1 | 52.9 | 96.0 | 87.9 | 50.0 | 100.0 |
| 167 | 85.8 | 50.0 | 98.0 | 89.4 | 68.8 | 96.0 |
| 168 | 80.6 | 41.2 | 94.0 | 77.3 | 31.2 | 92.0 |
| 169 | 80.6 | 32.4 | 97.0 | 81.8 | 25.0 | 100.0 |

TABLE 4

| SEQ ID NO: | Discriminant coefficient | Constant term |
|---|---|---|
| 1 | 2.731 | 17.177 |
| 2 | 3.324 | 31.765 |
| 3 | 1.836 | 12.851 |
| 4 | 4.010 | 25.699 |
| 5 | 3.767 | 31.391 |
| 6 | 3.829 | 35.096 |
| 7 | 3.144 | 17.990 |
| 8 | 2.726 | 21.913 |
| 9 | 5.443 | 57.639 |
| 10 | 2.686 | 18.095 |
| 11 | 4.398 | 51.318 |
| 12 | 5.286 | 43.176 |
| 13 | 1.921 | 24.270 |
| 14 | 5.407 | 58.548 |
| 15 | 2.820 | 19.731 |
| 16 | 2.197 | 14.682 |
| 17 | 4.707 | 43.642 |
| 18 | 2.022 | 13.892 |
| 19 | 1.268 | 8.665 |
| 20 | 3.417 | 21.034 |
| 21 | 2.266 | 15.207 |
| 22 | 3.039 | 27.590 |
| 23 | 7.728 | 99.955 |
| 24 | 3.052 | 26.321 |
| 25 | 5.366 | 66.791 |
| 26 | 2.810 | 30.883 |
| 27 | 2.291 | 13.933 |
| 28 | 3.580 | 23.815 |
| 29 | 2.466 | 16.690 |
| 30 | 3.715 | 25.964 |
| 31 | 3.866 | 49.046 |
| 32 | 4.847 | 44.998 |
| 33 | 4.518 | 44.908 |
| 34 | 4.174 | 28.253 |
| 35 | 2.781 | 21.080 |
| 36 | 2.163 | 12.587 |
| 37 | 2.399 | 14.923 |
| 38 | 2.387 | 19.533 |
| 39 | 2.662 | 18.538 |
| 40 | 1.844 | 14.656 |
| 41 | 4.162 | 54.280 |
| 42 | 1.861 | 10.860 |
| 43 | 1.882 | 10.852 |
| 44 | 3.955 | 32.182 |
| 45 | 3.509 | 21.353 |
| 46 | 2.764 | 21.183 |
| 47 | 2.237 | 12.508 |
| 48 | 3.474 | 29.057 |
| 49 | 2.348 | 23.412 |
| 50 | 1.601 | 8.585 |
| 51 | 4.385 | 29.783 |
| 52 | 3.501 | 25.951 |
| 53 | 2.121 | 20.821 |
| 54 | 2.398 | 17.081 |
| 55 | 2.333 | 21.669 |
| 56 | 3.979 | 23.944 |
| 57 | 2.618 | 18.423 |
| 58 | 3.487 | 32.829 |
| 59 | 4.222 | 26.720 |
| 60 | 2.479 | 18.929 |
| 61 | 3.944 | 38.152 |
| 62 | 2.371 | 17.392 |
| 63 | 2.987 | 20.097 |
| 64 | 9.232 | 116.333 |
| 65 | 4.246 | 34.038 |
| 66 | 1.900 | 12.014 |
| 67 | 4.891 | 49.041 |
| 68 | 5.062 | 35.194 |
| 69 | 3.378 | 28.973 |
| 70 | 4.587 | 46.523 |
| 71 | 4.446 | 33.529 |
| 72 | 3.367 | 33.945 |
| 73 | 2.155 | 21.186 |
| 74 | 2.768 | 26.384 |
| 75 | 5.220 | 62.722 |
| 76 | 3.883 | 28.652 |
| 77 | 5.643 | 71.747 |
| 78 | 3.610 | 27.579 |
| 79 | 2.457 | 15.182 |
| 80 | 2.520 | 19.029 |
| 81 | 3.853 | 22.961 |
| 82 | 3.525 | 21.894 |
| 83 | 2.531 | 25.858 |
| 84 | 3.041 | 19.506 |
| 85 | 3.868 | 46.680 |
| 86 | 2.117 | 17.685 |
| 87 | 3.724 | 26.711 |
| 88 | 3.680 | 23.968 |
| 89 | 3.374 | 20.135 |
| 90 | 2.196 | 25.309 |
| 91 | 2.976 | 20.156 |
| 92 | 2.933 | 25.402 |
| 93 | 5.009 | 53.145 |
| 94 | 2.567 | 14.765 |
| 95 | 1.729 | 11.402 |
| 96 | 2.393 | 21.401 |
| 97 | 3.112 | 20.031 |
| 98 | 3.065 | 19.720 |
| 99 | 3.850 | 38.303 |
| 100 | 3.191 | 23.796 |
| 101 | 1.739 | 18.155 |
| 102 | 1.790 | 11.695 |
| 103 | 4.223 | 31.086 |
| 104 | 3.902 | 43.384 |
| 105 | 4.394 | 38.067 |
| 106 | 3.808 | 31.650 |
| 107 | 2.442 | 15.680 |
| 108 | 4.742 | 35.456 |
| 109 | 4.065 | 32.357 |
| 110 | 3.132 | 31.233 |
| 111 | 6.253 | 59.917 |
| 112 | 2.144 | 16.593 |
| 113 | 5.077 | 41.640 |
| 114 | 4.331 | 36.232 |
| 115 | 4.104 | 26.007 |
| 116 | 4.365 | 44.632 |
| 117 | 4.092 | 30.958 |
| 118 | 3.410 | 40.413 |
| 119 | 2.277 | 22.244 |
| 120 | 3.385 | 27.099 |
| 121 | 3.662 | 26.864 |
| 122 | 3.020 | 32.940 |
| 123 | 5.127 | 61.295 |
| 124 | 2.499 | 14.725 |

TABLE 4-continued

| SEQ ID NO: | Discriminant coefficient | Constant term |
|---|---|---|
| 125 | 2.372 | 17.057 |
| 126 | 5.371 | 54.883 |
| 127 | 2.882 | 21.683 |
| 128 | 1.355 | 8.339 |
| 129 | 3.793 | 24.904 |
| 130 | 3.673 | 25.051 |
| 131 | 3.824 | 44.211 |
| 132 | 2.858 | 20.620 |
| 133 | 2.687 | 15.927 |
| 134 | 6.294 | 44.652 |
| 135 | 5.392 | 39.920 |
| 136 | 2.883 | 30.122 |
| 137 | 1.419 | 8.435 |
| 138 | 3.372 | 25.593 |
| 139 | 1.616 | 14.087 |
| 140 | 3.505 | 27.638 |
| 141 | 5.430 | 57.153 |
| 142 | 4.737 | 36.945 |
| 143 | 4.079 | 33.703 |
| 144 | 4.615 | 40.322 |
| 145 | 1.899 | 11.130 |
| 146 | 1.461 | 8.484 |
| 147 | 3.248 | 36.484 |
| 148 | 4.537 | 33.621 |
| 149 | 6.451 | 87.375 |
| 150 | 5.814 | 72.020 |
| 151 | 2.391 | 14.618 |
| 152 | 2.345 | 19.966 |
| 153 | 1.746 | 12.413 |
| 154 | 2.794 | 30.977 |
| 155 | 3.878 | 24.272 |
| 156 | 1.014 | 5.894 |
| 157 | 3.451 | 35.923 |
| 158 | 4.810 | 57.343 |
| 159 | 3.755 | 26.714 |
| 160 | 2.474 | 18.364 |
| 161 | 4.014 | 31.043 |
| 162 | 3.561 | 40.868 |
| 163 | 2.408 | 16.644 |
| 164 | 1.795 | 10.022 |
| 165 | 2.135 | 12.545 |
| 166 | 2.652 | 28.430 |
| 167 | 1.220 | 7.446 |
| 168 | 2.017 | 19.036 |
| 169 | 2.835 | 22.505 |

TABLE 5-1

| Training cohort | | | |
|---|---|---|---|
| Sample name | Cancer stage | CEA | CA19-9 |
| SC03 | IA | 2.9(−) | 77.4(+) |
| SC04 | IA | 2.9(−) | 0.1(−) |
| SC05 | IA | 2.9(−) | 21.8(−) |
| SC06 | IA | 1.7(−) | 41.9(+) |
| SC07 | IB | 1.5(−) | 25.1(−) |
| SC09 | IA | 2.3(−) | 17.5(−) |
| SC10 | IIB | 1.2(−) | 10.0(−) |
| SC12 | IA | 3.3(−) | 8.5(−) |
| SC13 | IA | 3.4(−) | 8.2(−) |
| SC15 | IA | 3.7(−) | 6.3(−) |
| SC17 | IIB | 2.8(−) | 4.3(−) |
| SC18 | IB | 6.9(+) | 20.2(−) |
| SC19 | IA | 3.1(−) | 5.0(−) |
| SC20 | IIIC | 3.3(−) | 20.1(−) |
| SC23 | IB | 2.5(−) | 0.1(−) |
| SC24 | IA | 3.1(−) | 43.2(−) |
| SC25 | IIIA | 2.6(−) | 16.4(−) |
| SC26 | IA | 0.9(−) | 7.3(−) |
| SC27 | IA | 2.0(−) | 9.2(−) |
| SC29 | IIA | 1.3(−) | 35.6(−) |
| SC30 | IA | 2.8(−) | 0.1(−) |
| SC31 | IA | 2.4(−) | 14.0(−) |
| SC32 | IA | 4.0(−) | 10.5(−) |
| SC34 | IA | 2.4(−) | 17.0(−) |
| SC36 | IIIC | 1.5(−) | 14.1(−) |
| SC38 | IA | 4.8(−) | 47.6(+) |
| SC40 | IIA | 1.7(−) | 29.4(−) |
| SC41 | IA | 0.3(−) | 10.9(−) |
| SC42 | IIIA | 2.2(−) | 12.2(−) |
| SC45 | IIIC | 0.8(−) | 6.5(−) |
| SC47 | IB | 1.3(−) | 26.3(−) |
| SC48 | IIIA | 1.9(−) | 6.3(−) |
| SC49 | IA | 2.9(−) | 41.1(+) |
| SC50 | IB | 1.4(−) | 11.4(−) |

TABLE 5-2

| Validation cohort | | | |
|---|---|---|---|
| Sample name | Cancer stage | CEA | CA19/9 |
| SC01 | IA | 3.7(−) | 0.1(−) |
| SC02 | IA | 4.9(−) | 65.2(+) |
| SC08 | IA | 1.1(−) | 9.9(−) |
| SC11 | IA | 1.8(−) | 9.4(−) |
| SC14 | IB | 2.0(−) | 26.1(−) |
| SC16 | IA | 3.1(−) | 9.5(−) |
| SC21 | IIA | 0.7(−) | 9.1(−) |
| SC22 | IA | 1.4(−) | 6.0(−) |
| SC28 | IA | 3.3(−) | 6.6(−) |
| SC33 | IIIA | 5.6(+) | 14.7(−) |
| SC35 | IA | 3.7(−) | 7.8(−) |
| SC37 | IIB | 4.2(−) | 0.1(−) |
| SC39 | IIC | 17.5(+) | 7.0(−) |
| SC43 | IIA | 4.6(−) | 10.1(−) |
| SC44 | IA | 1.8(−) | 5.8(−) |
| SC46 | IB | 2.7(−) | 37.1(+) |

For CEA, 5 ng/mL or lower was indicated as "−", and for A19-9, 37 U/mL or lower was indicated as "−", while values exceeding these were indicated as "+".

TABLE 6

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_2 | 100.0 | 100.0 | 100.0 | 98.5 | 93.8 | 100.0 |
| 1_3 | 97.8 | 94.1 | 99.0 | 95.5 | 87.5 | 98.0 |
| 1_4 | 98.5 | 94.1 | 100.0 | 98.5 | 93.8 | 100.0 |
| 1_5 | 96.3 | 88.2 | 99.0 | 95.5 | 87.5 | 98.0 |
| 1_6 | 97.0 | 91.2 | 99.0 | 93.9 | 87.5 | 96.0 |
| 1_7 | 96.3 | 91.2 | 98.0 | 95.5 | 87.5 | 98.0 |
| 1_8 | 95.5 | 88.2 | 98.0 | 95.5 | 87.5 | 98.0 |
| 1_9 | 97.0 | 91.2 | 99.0 | 95.5 | 87.5 | 98.0 |

TABLE 6-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 1_10 | 97.0 | 91.2 | 99.0 | 95.5 | 87.5 | 98.0 |
| 1_11 | 96.3 | 88.2 | 99.0 | 95.5 | 87.5 | 98.0 |
| 1_12 | 96.3 | 88.2 | 99.0 | 93.9 | 87.5 | 96.0 |
| 1_13 | 100.0 | 100.0 | 100.0 | 93.9 | 93.8 | 94.0 |
| 1_14 | 97.8 | 94.1 | 99.0 | 100.0 | 100.0 | 100.0 |
| 1_15 | 95.5 | 85.3 | 99.0 | 95.5 | 87.5 | 98.0 |
| 1_16 | 96.3 | 88.2 | 99.0 | 95.5 | 87.5 | 98.0 |
| 1_17 | 96.3 | 91.2 | 98.0 | 95.5 | 81.2 | 100.0 |
| 1_18 | 96.3 | 88.2 | 99.0 | 95.5 | 87.5 | 98.0 |
| 1_19 | 100.0 | 100.0 | 100.0 | 95.5 | 87.5 | 98.0 |
| 1_20 | 96.3 | 88.2 | 99.0 | 95.5 | 87.5 | 98.0 |
| 1_21 | 95.5 | 85.3 | 99.0 | 95.5 | 87.5 | 98.0 |
| 1_22 | 97.8 | 91.2 | 100.0 | 95.5 | 81.2 | 100.0 |
| 1_23 | 99.3 | 97.1 | 100.0 | 95.5 | 87.5 | 98.0 |
| 1_24 | 96.3 | 88.2 | 99.0 | 97.0 | 87.5 | 100.0 |
| 1_25 | 99.3 | 97.1 | 100.0 | 95.5 | 87.5 | 98.0 |
| 1_26 | 96.3 | 88.2 | 99.0 | 93.9 | 87.5 | 96.0 |
| 1_27 | 96.3 | 88.2 | 99.0 | 97.0 | 87.5 | 100.0 |
| 1_28 | 96.3 | 88.2 | 99.0 | 97.0 | 93.8 | 98.0 |
| 1_29 | 95.5 | 88.2 | 98.0 | 95.5 | 87.5 | 98.0 |
| 1_30 | 95.5 | 88.2 | 98.0 | 95.5 | 87.5 | 98.0 |
| 1_31 | 96.3 | 88.2 | 99.0 | 93.9 | 87.5 | 96.0 |
| 1_32 | 96.3 | 88.2 | 99.0 | 97.0 | 87.5 | 100.0 |
| 1_33 | 96.3 | 88.2 | 99.0 | 95.5 | 87.5 | 98.0 |
| 1_34 | 96.3 | 88.2 | 99.0 | 95.5 | 87.5 | 98.0 |
| 1_35 | 96.3 | 88.2 | 99.0 | 95.5 | 87.5 | 98.0 |
| 1_36 | 96.3 | 88.2 | 99.0 | 95.5 | 87.5 | 98.0 |
| 1_37 | 96.3 | 88.2 | 99.0 | 95.5 | 87.5 | 98.0 |
| 1_38 | 96.3 | 88.2 | 99.0 | 95.5 | 87.5 | 98.0 |
| 1_39 | 96.3 | 88.2 | 99.0 | 97.0 | 87.5 | 100.0 |
| 1_40 | 95.5 | 88.2 | 98.0 | 95.5 | 87.5 | 98.0 |
| 1_41 | 95.5 | 85.3 | 99.0 | 95.5 | 87.5 | 98.0 |
| 1_42 | 95.5 | 85.3 | 99.0 | 95.5 | 87.5 | 98.0 |
| 1_43 | 95.5 | 85.3 | 99.0 | 97.0 | 87.5 | 100.0 |
| 1_44 | 95.5 | 88.2 | 98.0 | 93.9 | 87.5 | 96.0 |
| 1_45 | 97.8 | 94.1 | 99.0 | 95.5 | 87.5 | 98.0 |
| 1_46 | 97.0 | 91.2 | 99.0 | 97.0 | 87.5 | 100.0 |
| 1_47 | 97.0 | 94.1 | 98.0 | 97.0 | 93.8 | 98.0 |
| 1_48 | 96.3 | 88.2 | 99.0 | 97.0 | 87.5 | 100.0 |
| 1_49 | 97.8 | 91.2 | 100.0 | 93.9 | 87.5 | 96.0 |
| 1_50 | 95.5 | 85.3 | 99.0 | 95.5 | 87.5 | 98.0 |
| 1_51 | 98.5 | 97.1 | 99.0 | 95.5 | 87.5 | 98.0 |
| 1_52 | 95.5 | 85.3 | 99.0 | 95.5 | 87.5 | 98.0 |
| 1_53 | 95.5 | 85.3 | 99.0 | 97.0 | 87.5 | 100.0 |
| 1_54 | 95.5 | 85.3 | 99.0 | 95.5 | 87.5 | 98.0 |
| 1_55 | 96.3 | 88.2 | 99.0 | 95.5 | 87.5 | 98.0 |
| 1_56 | 97.7 | 94.1 | 99.0 | 95.5 | 87.5 | 98.0 |
| 1_57 | 97.8 | 91.2 | 100.0 | 97.0 | 93.8 | 98.0 |
| 1_58 | 95.5 | 88.2 | 98.0 | 93.9 | 87.5 | 96.0 |
| 1_59 | 97.0 | 94.1 | 98.0 | 93.9 | 87.5 | 96.0 |
| 1_60 | 94.8 | 85.3 | 98.0 | 95.5 | 87.5 | 98.0 |
| 1_61 | 95.5 | 85.3 | 99.0 | 97.0 | 93.8 | 98.0 |
| 1_62 | 96.3 | 88.2 | 99.0 | 95.5 | 87.5 | 98.0 |
| 1_63 | 96.3 | 88.2 | 99.0 | 95.5 | 87.5 | 98.0 |
| 1_64 | 96.3 | 88.2 | 99.0 | 95.5 | 87.5 | 98.0 |
| 1_65 | 96.3 | 88.2 | 99.0 | 97.0 | 87.5 | 100.0 |
| 1_66 | 97.0 | 91.2 | 99.0 | 97.0 | 87.5 | 100.0 |
| 1_67 | 95.5 | 88.2 | 98.0 | 97.0 | 87.5 | 100.0 |
| 1_68 | 95.5 | 85.3 | 99.0 | 95.5 | 87.5 | 98.0 |
| 1_69 | 95.5 | 88.2 | 98.0 | 95.5 | 87.5 | 98.0 |
| 1_70 | 96.3 | 88.2 | 99.0 | 95.5 | 87.5 | 98.0 |
| 1_71 | 96.3 | 88.2 | 99.0 | 95.5 | 87.5 | 98.0 |
| 1_72 | 95.5 | 85.3 | 99.0 | 95.5 | 87.5 | 98.0 |
| 1_73 | 95.5 | 85.3 | 99.0 | 95.5 | 87.5 | 98.0 |
| 1_74 | 95.5 | 85.3 | 99.0 | 95.5 | 87.5 | 98.0 |
| 1_75 | 98.5 | 94.1 | 100.0 | 95.5 | 87.5 | 98.0 |
| 1_76 | 95.5 | 85.3 | 99.0 | 93.9 | 87.5 | 96.0 |
| 1_77 | 95.5 | 85.3 | 99.0 | 95.5 | 87.5 | 98.0 |
| 1_78 | 96.3 | 88.2 | 99.0 | 98.5 | 93.8 | 100.0 |
| 1_79 | 97.0 | 91.2 | 99.0 | 95.5 | 87.5 | 98.0 |
| 1_80 | 95.5 | 88.2 | 98.0 | 95.5 | 87.5 | 98.0 |
| 1_81 | 97.0 | 91.2 | 99.0 | 95.5 | 87.5 | 98.0 |
| 1_82 | 95.5 | 85.3 | 99.0 | 95.4 | 87.5 | 98.0 |
| 1_83 | 96.3 | 88.2 | 99.0 | 95.5 | 87.5 | 98.0 |
| 1_84 | 94.8 | 82.4 | 99.0 | 95.5 | 87.5 | 98.0 |

TABLE 6-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 1_85 | 96.3 | 88.2 | 99.0 | 95.5 | 87.5 | 98.0 |
| 1_86 | 99.3 | 97.1 | 100.0 | 95.5 | 93.8 | 96.0 |
| 1_87 | 95.5 | 85.3 | 99.0 | 95.5 | 87.5 | 98.0 |
| 1_88 | 96.3 | 88.2 | 99.0 | 95.5 | 87.5 | 98.0 |
| 1_89 | 96.3 | 88.2 | 99.0 | 97.0 | 87.5 | 100.0 |
| 1_90 | 95.5 | 85.3 | 99.0 | 95.5 | 87.5 | 98.0 |
| 1_91 | 96.3 | 91.2 | 98.0 | 97.0 | 87.5 | 100.0 |
| 1_92 | 96.3 | 88.2 | 99.0 | 95.5 | 87.5 | 98.0 |
| 1_93 | 96.3 | 88.2 | 99.0 | 95.5 | 87.5 | 98.0 |
| 1_94 | 96.3 | 88.2 | 99.0 | 95.5 | 87.5 | 98.0 |
| 1_95 | 96.3 | 88.2 | 99.0 | 95.5 | 87.5 | 98.0 |
| 1_96 | 95.5 | 85.3 | 99.0 | 95.5 | 87.5 | 98.0 |
| 1_97 | 97.0 | 91.2 | 99.0 | 95.5 | 87.5 | 98.0 |
| 1_98 | 95.5 | 91.2 | 97.0 | 97.0 | 87.5 | 100.0 |
| 1_99 | 95.5 | 85.3 | 99.0 | 97.0 | 87.5 | 100.0 |
| 1_100 | 96.3 | 88.2 | 99.0 | 95.5 | 87.5 | 98.0 |
| 1_101 | 96.3 | 88.2 | 99.0 | 95.5 | 87.5 | 98.0 |
| 1_102 | 99.3 | 97.1 | 100.0 | 97.0 | 93.8 | 98.0 |
| 1_103 | 95.5 | 85.3 | 99.0 | 95.5 | 87.5 | 98.0 |
| 1_104 | 95.5 | 85.3 | 99.0 | 93.9 | 87.5 | 96.0 |
| 1_105 | 95.5 | 85.3 | 99.0 | 95.5 | 87.5 | 98.0 |
| 1_106 | 96.3 | 88.2 | 99.0 | 95.5 | 87.5 | 98.0 |
| 1_107 | 96.3 | 88.2 | 99.0 | 95.5 | 87.5 | 98.0 |
| 1_108 | 97.0 | 91.2 | 99.0 | 93.9 | 87.5 | 96.0 |
| 1_109 | 95.5 | 85.3 | 99.0 | 95.5 | 87.5 | 98.0 |
| 1_110 | 96.3 | 88.2 | 99.0 | 95.5 | 87.5 | 98.0 |
| 1_111 | 96.3 | 88.2 | 99.0 | 95.5 | 87.5 | 98.0 |
| 1_112 | 95.5 | 85.3 | 99.0 | 95.5 | 87.5 | 98.0 |
| 1_113 | 97.0 | 91.2 | 99.0 | 98.5 | 93.8 | 100.0 |
| 1_114 | 95.5 | 85.3 | 99.0 | 95.5 | 87.5 | 98.0 |
| 1_115 | 95.5 | 85.3 | 99.0 | 95.5 | 87.5 | 98.0 |
| 1_116 | 96.3 | 91.2 | 98.0 | 98.5 | 93.8 | 100.0 |
| 1_117 | 96.3 | 88.2 | 99.0 | 95.5 | 87.5 | 98.0 |
| 1_118 | 96.3 | 88.2 | 99.0 | 95.5 | 87.5 | 98.0 |
| 1_119 | 95.5 | 85.3 | 99.0 | 95.5 | 87.5 | 98.0 |
| 1_120 | 97.0 | 91.2 | 99.0 | 95.5 | 87.5 | 98.0 |
| 1_121 | 96.3 | 88.2 | 99.0 | 95.5 | 87.5 | 98.0 |
| 1_122 | 96.3 | 88.2 | 99.0 | 97.0 | 87.5 | 100.0 |
| 1_123 | 97.8 | 91.2 | 100.0 | 97.0 | 93.8 | 98.0 |
| 1_124 | 95.5 | 85.3 | 99.0 | 95.5 | 87.5 | 98.0 |
| 1_125 | 98.5 | 94.1 | 100.0 | 97.0 | 93.8 | 98.0 |
| 1_126 | 97.0 | 91.2 | 99.0 | 97.0 | 93.8 | 98.0 |
| 1_127 | 96.3 | 88.2 | 99.0 | 95.5 | 87.5 | 98.0 |
| 1_128 | 96.3 | 88.2 | 99.0 | 95.5 | 87.5 | 98.0 |
| 1_129 | 97.0 | 91.2 | 99.0 | 97.0 | 87.5 | 100.0 |
| 1_130 | 96.3 | 88.2 | 99.0 | 95.5 | 87.5 | 98.0 |
| 1_131 | 96.3 | 88.2 | 99.0 | 95.5 | 87.5 | 98.0 |
| 1_132 | 97.0 | 91.2 | 99.0 | 95.5 | 87.5 | 98.0 |
| 1_133 | 96.3 | 88.2 | 99.0 | 95.5 | 87.5 | 98.0 |
| 1_134 | 96.3 | 88.2 | 99.0 | 95.5 | 87.5 | 98.0 |
| 1_135 | 96.3 | 88.2 | 99.0 | 97.0 | 93.8 | 98.0 |
| 1_136 | 95.5 | 85.3 | 99.0 | 95.5 | 87.5 | 98.0 |
| 1_137 | 95.5 | 85.3 | 99.0 | 97.0 | 93.8 | 98.0 |
| 1_138 | 96.3 | 88.2 | 99.0 | 95.5 | 87.5 | 98.0 |
| 1_139 | 95.5 | 85.3 | 99.0 | 95.5 | 87.5 | 98.0 |
| 1_140 | 97.0 | 91.2 | 99.0 | 95.5 | 87.5 | 98.0 |
| 1_141 | 95.5 | 85.3 | 99.0 | 98.5 | 93.8 | 100.0 |
| 1_142 | 97.8 | 91.2 | 100.0 | 93.9 | 87.5 | 96.0 |
| 1_143 | 95.5 | 85.3 | 99.0 | 95.5 | 87.5 | 98.0 |
| 1_144 | 96.3 | 88.2 | 99.0 | 97.0 | 87.5 | 100.0 |
| 1_145 | 96.2 | 87.9 | 99.0 | 95.5 | 87.5 | 98.0 |
| 1_146 | 99.3 | 97.1 | 100.0 | 97.0 | 93.8 | 98.0 |
| 1_147 | 96.3 | 88.2 | 99.0 | 95.5 | 87.5 | 98.0 |
| 1_148 | 96.3 | 88.2 | 99.0 | 98.5 | 93.8 | 100.0 |
| 1_149 | 95.5 | 85.3 | 99.0 | 95.4 | 87.5 | 98.0 |
| 1_150 | 97.0 | 91.2 | 99.0 | 97.0 | 87.5 | 100.0 |
| 1_151 | 95.5 | 88.2 | 98.0 | 95.5 | 87.5 | 98.0 |
| 1_152 | 95.5 | 85.3 | 99.0 | 95.5 | 87.5 | 98.0 |
| 1_153 | 99.3 | 97.1 | 100.0 | 97.0 | 93.8 | 98.0 |
| 1_154 | 96.3 | 88.2 | 99.0 | 97.0 | 87.5 | 100.0 |
| 1_155 | 96.3 | 88.2 | 99.0 | 95.5 | 87.5 | 98.0 |
| 1_156 | 96.3 | 88.2 | 99.0 | 97.0 | 87.5 | 100.0 |
| 1_157 | 96.3 | 88.2 | 99.0 | 97.0 | 93.8 | 98.0 |
| 1_158 | 95.5 | 85.3 | 99.0 | 95.5 | 87.5 | 98.0 |
| 1_159 | 95.5 | 85.3 | 99.0 | 95.5 | 87.5 | 98.0 |

TABLE 6-continued

|         | Training cohort | | | Validation cohort | | |
|---------|---|---|---|---|---|---|
| SEQ ID NO: | Accuracy (%) | Sensitivity (%) | Specificity (%) | Accuracy (%) | Sensitivity (%) | Specificity (%) |
| 1_160 | 95.5 | 85.3 | 99.0 | 95.5 | 87.5 | 98.0 |
| 1_161 | 95.5 | 85.3 | 99.0 | 95.5 | 87.5 | 98.0 |
| 1_162 | 96.3 | 88.2 | 99.0 | 95.5 | 87.5 | 98.0 |
| 1_163 | 95.5 | 85.3 | 99.0 | 95.5 | 87.5 | 98.0 |
| 1_164 | 96.3 | 88.2 | 99.0 | 95.5 | 87.5 | 98.0 |
| 1_165 | 97.8 | 94.1 | 99.0 | 95.5 | 87.5 | 98.0 |
| 1_166 | 96.3 | 88.2 | 99.0 | 95.5 | 87.5 | 98.0 |
| 1_167 | 98.5 | 97.1 | 99.0 | 97.0 | 93.8 | 98.0 |
| 1_168 | 97.0 | 91.2 | 99.0 | 95.5 | 87.5 | 98.0 |
| 1_169 | 96.3 | 88.2 | 99.0 | 95.5 | 87.5 | 98.0 |

Example 3

<Selection of Gene Markers Using all Samples and Method for Evaluating Stomach Cancer Discriminant Performance of Acquired Gene Markers>

In this Example, the samples of the training cohort and the validation cohort used in Examples 1 and 2 described above were integrated, and selection of a gene marker and evaluation of its stomach cancer discriminant performance were conducted using all of the samples.

Specifically, the expression levels in the sera of the 50 stomach cancer patients and the 150 healthy subject miRNAs obtained in the preceding Reference Examples were normalized by quantile normalization. In order to acquire diagnosis markers with higher reliability, only genes having a gene expression level of $2^6$ or higher in 50% or more of the samples in either of the stomach cancer patient group or the healthy subject group were selected in the gene marker selection. In order to further acquire statistical significance for discriminating a stomach cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant and described in Table 7. In this way, hsa-miR-3196, hsa-miR-211-3p, hsa-miR-4271, hsa-miR-6851-5p, hsa-miR-149-3p, hsa-miR-4667-5p, hsa-miR-135a-3p, hsa-miR-4486, hsa-miR-4697-5p, hsa-miR-4725-3p, hsa-miR-6510-5p, hsa-miR-5001-5p, hsa-miR-4673, hsa-miR-4466, hsa-miR-23a-3p, hsa-miR-3656, hsa-miR-6782-5p, hsa-miR-4689, hsa-miR-451a, hsa-miR-4446-3p, hsa-miR-3180-3p, hsa-miR-642a-3p, hsa-miR-6889-5p, hsa-miR-3178, hsa-miR-4665-5p, hsa-miR-6722-3p, hsa-miR-30c-1-3p, hsa-miR-4507, hsa-miR-3141 and hsa-miR-1199-5p genes, and the nucleotide sequences of SEQ ID NOs: 170 to 199 related thereto were found in addition to the genes described in Table 2. As with the nucleotide sequences shown in SEQ ID NOs: 1 to 169, the results obtained about the polynucleotides shown in SEQ ID NOs: 170 to 199 also showed that the measurement values were significantly lower (−) or higher (+) in the stomach cancer patient group than in the healthy subject group (Table 7). These results were able to be validated in the validation cohort. Thus, the presence or absence of stomach cancer in the newly obtained samples can be determined by the methods described in Examples 1 and 2 by using, alone or in combination, the gene expression level measurement values described in Table 7.

TABLE 7

| SEQ ID NO: | Gene name | P value after Bonferroni correction | Expression level in stomach cancer patient relative to healthy subject |
|---|---|---|---|
| 1 | hsa-miR-4257 | 1.17.E−53 | − |
| 2 | hsa-miR-6726-5p | 1.13.E−52 | − |
| 3 | hsa-niiR-1343-3p | 1.41.E−44 | − |
| 4 | hsa-miR-1247-3p | 5.94.E−35 | + |
| 5 | hsa-miR-6787-5p | 2.22.E−39 | − |
| 6 | hsa-miR-6875-5p | 1.92.E−30 | + |
| 7 | hsa-miR-1225-3p | 6.99.E−36 | + |
| 8 | hsa-miR-8063 | 7.15.E−31 | − |
| 9 | hsa-miR-6781-5p | 4.27.E−31 | + |
| 10 | hsa-miR-4746-3p | 1.93.E−35 | + |
| 11 | hsa-miR-1908-5p | 1.34.E−32 | + |
| 12 | hsa-miR-6756-5p | 2.25.E−28 | − |
| 13 | hsa-miR-204-3p | 5.11.E−30 | − |
| 14 | hsa-miR-4651 | 2.11.E−33 | − |
| 15 | hsa-miR-6757-5p | 2.11.E−34 | − |
| 16 | hsa-miR-6825-5p | 1.20.E−31 | + |
| 17 | hsa-miR-7108-5p | 3.88.E−25 | + |
| 18 | hsa-miR-4792 | 5.31.E−29 | + |
| 19 | hsa-miR-7641 | 1.72.E−27 | − |
| 20 | hsa-miR-3188 | 3.58.E−30 | + |
| 21 | hsa-miR-3131 | 3.98.E−33 | − |
| 22 | hsa-miR-6780b-5p | 4.88.E−28 | + |
| 23 | hsa-miR-8069 | 7.94.E−21 | + |
| 24 | hsa-miR-6840-3p | 4.43.E−23 | − |
| 25 | hsa-miR-8072 | 1.55.E−23 | + |
| 26 | hsa-miR-1233-5p | 3.51.E−26 | − |
| 27 | hsa-miR-6887-5p | 1.34.E−24 | − |
| 28 | hsa-miR-1231 | 9.31.E−26 | + |
| 29 | hsa-miR-5572 | 3.97.E−25 | + |
| 30 | hsa-miR-6738-5p | 2.02.E−21 | − |
| 31 | hsa-miR-6784-5p | 1.03.E−23 | + |
| 32 | hsa-miR-6791-5p | 2.63.E−22 | + |
| 33 | hsa-miR-6749-5p | 6.36.E−23 | − |
| 34 | hsa-miR-6741-5p | 6.07.E−23 | − |
| 35 | hsa-miR-128-1-5p | 3.13.E−20 | + |
| 36 | hsa-miR-4419b | 9.02.E−24 | − |
| 37 | hsa-miR-6746-5p | 1.60.E−25 | − |
| 38 | hsa-miR-3184-5p | 1.38.E−23 | + |
| 39 | hsa-miR-3679-5p | 6.33.E−26 | − |
| 40 | hsa-miR-7110-5p | 3.06.E−24 | + |
| 41 | hsa-miR-4516 | 1.26.E−23 | − |
| 42 | hsa-miR-6717-5p | 6.77.E−26 | − |
| 43 | hsa-miR-6826-5p | 8.66.E−25 | − |
| 44 | hsa-miR-4433b-3p | 5.71.E−19 | + |
| 45 | hsa-miR-3679-3p | 2.22.E−19 | + |
| 46 | hsa-miR-3135b | 7.59.E−15 | − |
| 47 | hsa-miR-3622a-5p | 4.66.E−24 | − |
| 48 | hsa-miR-711 | 9.88.E−22 | + |
| 49 | hsa-miR-4467 | 3.85.E−21 | − |
| 50 | hsa-miR-6857-5p | 1.03.E−19 | + |
| 51 | hsa-miR-6515-3p | 5.53.E−16 | + |
| 52 | hsa-miR-1225-5p | 2.33.E−19 | + |
| 53 | hsa-miR-187-5 p | 1.31.E−20 | − |
| 54 | hsa-miR-3185 | 1.30.E−19 | + |

TABLE 7-continued

| SEQ ID NO: | Gene name | P value after Bonferroni correction | Expression level in stomach cancer patient relative to healthy subject |
|---|---|---|---|
| 55 | hsa-miR-642b-3p | 2.56.E-18 | − |
| 56 | hsa-miR-1249 | 5.41.E-19 | + |
| 57 | hsa-miR-744-5p | 9.41.E-20 | + |
| 58 | hsa-miR-4442 | 1.75.E-17 | − |
| 59 | hsa-miR-1228-3p | 1.10.E-19 | + |
| 60 | hsa-miR-939-5p | 1.54.E-16 | + |
| 61 | hsa-miR-6845-5p | 5.15.E-20 | + |
| 62 | hsa-miR-887-3p | 2.86.E-15 | + |
| 63 | hsa-miR-7845-5p | 3.21.E-16 | + |
| 64 | hsa-miR-6729-5p | 6.04.E-16 | + |
| 65 | hsa-miR-4632-5p | 7.17.E-16 | + |
| 66 | hsa-miR-615-5p | 3.13.E-17 | − |
| 67 | hsa-miR-6724-5p | 6.37.E-15 | + |
| 68 | hsa-miR-4728-5p | 1.26.E-16 | − |
| 69 | hsa-miR-6732-5p | 5.05.E-14 | + |
| 70 | hsa-miR-6816-5p | 8.52.E-17 | + |
| 71 | hsa-miR-4695-5p | 2.40.E-14 | + |
| 72 | hsa-miR-6088 | 7.13.E-16 | − |
| 73 | hsa-miR-7975 | 1.51.E-14 | − |
| 74 | hsa-miR-3197 | 5.56.E-16 | + |
| 75 | hsa-miR-6125 | 2.29.E-15 | + |
| 76 | hsa-miR-4433-3p | 1.66.E-13 | + |
| 77 | hsa-miR-6727-5p | 1.77.E-15 | − |
| 78 | hsa-miR-4706 | 2.89.E-15 | + |
| 79 | hsa-miR-7847-3p | 1.35.E-14 | − |
| 80 | hsa-miR-6805-3p | 5.87.E-17 | + |
| 81 | hsa-miR-6766-3p | 1.02.E-14 | + |
| 82 | hsa-miR-1913 | 6.53.E-14 | + |
| 83 | hsa-miR-4649-5p | 1.20.E-13 | − |
| 84 | hsa-miR-602 | 3.43.E-17 | + |
| 85 | hsa-miR-3663-3p | 2.10.E-13 | − |
| 86 | hsa-miR-6893-5p | 3.43.E-17 | − |
| 87 | hsa-miR-6861-5p | 4.41.E-14 | − |
| 88 | hsa-miR-4449 | 2.00.E-16 | + |
| 89 | hsa-miR-6842-5p | 1.49.E-15 | + |
| 90 | hsa-miR-4454 | 1.57.E-13 | − |
| 91 | hsa-miR-5195-3p | 6.87.E-14 | − |
| 92 | hsa-miR-663b | 1.51.E-12 | − |
| 93 | hsa-miR-6765-5p | 5.17.E-11 | + |
| 94 | hsa-miR-4513 | 3.77.E-14 | − |
| 95 | hsa-miR-614 | 1.11.E-11 | − |
| 96 | hsa-miR-6785-5p | 6.54.E-12 | − |
| 97 | hsa-miR-6777-5p | 2.92.E-14 | − |
| 98 | hsa-miR-940 | 1.38.E-13 | + |
| 99 | hsa-miR-4741 | 2.04.E-12 | + |
| 100 | hsa-miR-6870-5p | 4.12.E-14 | + |
| 101 | hsa-miR-6131 | 1.02.E-12 | − |
| 102 | hsa-miR-150-3p | 1.47.E-10 | − |
| 103 | hsa-miR-4707-5p | 8.76.E-12 | + |
| 104 | hsa-miR-1915-3p | 4.55.E-13 | + |
| 105 | hsa-miR-3937 | 6.01.E-12 | + |
| 106 | hsa-miR-937-5p | 3.22.E-11 | − |
| 107 | hsa-miR-4443 | 3.16.E-10 | + |
| 108 | hsa-miR-1914-3p | 7.61.E-11 | − |
| 109 | hsa-miR-3620-5p | 7.63 E-11 | + |
| 110 | hsa-miR-1268b | 2.01.E-09 | + |
| 111 | hsa-miR-1227-5p | 3.14.E-10 | + |
| 112 | hsa-miR-6880-5p | 3.80.E-09 | + |
| 113 | hsa-miR-4417 | 7.19.E-10 | + |
| 114 | hsa-miR-6802-5p | 4.37.E-11 | − |
| 115 | hsa-miR-6769a-5p | 3.34.E-09 | − |
| 116 | hsa-miR-663a | 7.98.E-11 | + |
| 117 | hsa-miR-6721-5p | 1.38.E-09 | + |
| 118 | hsa-miR-4532 | 9.58.E-08 | − |
| 119 | hsa-miR-7977 | 9.99.E-11 | − |
| 120 | hsa-miR-92b-5p | 1.77.E-08 | + |
| 121 | hsa-miR-371a-5p | 8.63.E-09 | − |
| 122 | hsa-miR-6126 | 1.93.E-10 | + |
| 123 | hsa-miR-4734 | 3.27.E-09 | + |
| 124 | hsa-miR-4665-3p | 6.99.E-14 | + |
| 125 | hsa-miR-423-5p | 1.58.E-08 | − |
| 126 | hsa-miR-1469 | 8.71.E-07 | + |
| 127 | hsa-miR-4675 | 2.67.E-10 | − |
| 128 | hsa-miR-1915-5p | 1.06.E-08 | − |
| 129 | hsa-miR-6716-5p | 7.56.E-09 | + |
| 130 | hsa-miR-718 | 1.99.E-09 | + |
| 131 | hsa-miR-4281 | 9.46.E-11 | − |
| 132 | hsa-miR-6820-5p | 1.42.E-08 | − |
| 133 | hsa-miR-6795-5p | 4.38.E-10 | − |
| 134 | hsa-miR-6779-5p | 2.99.E-08 | − |
| 135 | hsa-miR-7109-5p | 7.06.E-08 | − |
| 136 | hsa-miR-6798-5p | 7.93.E-07 | + |
| 137 | hsa-miR-4648 | 2.21.E-09 | + |
| 138 | hsa-miR-8059 | 1.44.E-08 | − |
| 139 | hsa-miR-6765-3p | 6.59.E-08 | − |
| 140 | hsa-miR-6132 | 3.82.E-06 | + |
| 141 | hsa-miR-4492 | 1.34.E-08 | + |
| 142 | hsa-miR-7107-5p | 1.84.E-06 | − |
| 143 | hsa-miR-3195 | 6.91.E-08 | + |
| 144 | hsa-miR-3180 | 1.11.E-07 | + |
| 145 | hsa-miR-296-3p | 2.56.E-06 | − |
| 146 | hsa-miR-564 | 1.32.E-07 | − |
| 147 | hsa-miR-1268a | 1.25.E-04 | + |
| 148 | hsa-miR-6848-5p | 2.82.E-06 | + |
| 149 | hsa-miR-762 | 5.66.E-04 | + |
| 150 | hsa-miR-2861 | 1.45.E-06 | − |
| 151 | hsa-miR-1203 | 7.90.E-07 | + |
| 152 | hsa-miR-1260b | 2.26.E-04 | − |
| 153 | hsa-miR-4476 | 5.95.E-06 | − |
| 154 | hsa-miR-6885-5p | 5.73.E-05 | − |
| 155 | hsa-miR-6769b-5p | 1.91.E-07 | − |
| 156 | hsa-miR-23b-3p | 1.38.E-05 | − |
| 157 | hsa-miR-1343-5p | 7.73.E-06 | + |
| 158 | hsa-miR-3621 | 3.64.E-05 | − |
| 159 | hsa-miR-4688 | 1.47.E-05 | − |
| 160 | hsa-miR-4286 | 3.79.E-03 | − |
| 161 | hsa-miR-4640-5p | 1.79.E-05 | + |
| 162 | hsa-miR-4739 | 2.45.E-05 | + |
| 163 | hsa-miR-1260a | 7.35.E-04 | − |
| 164 | hsa-miR-4276 | 3.45.E-07 | + |
| 165 | hsa-miR-7106-5p | 4.60.E-04 | − |
| 166 | hsa-miR-128-2-5p | 1.05.E-13 | − |
| 167 | lisa-miR-125a-3p | 2.30.E-15 | − |
| 168 | hsa-miR-92a-2-5p | 5.42.E-09 | + |
| 169 | hsa-miR-486-3p | 2.00.E-05 | − |
| 170 | hsa-miR-3196 | 2.06.E-06 | + |
| 171 | hsa-miR-211-3p | 2.03.E-05 | − |
| 172 | hsa-miR-4271 | 2.31.E-05 | − |
| 173 | hsa-miR-6851-5p | 2.68.E-05 | + |
| 174 | hsa-miR-149-3p | 2.75.E-05 | − |
| 175 | hsa-miR-4667-5p | 4.05.E-05 | + |
| 176 | hsa-miR-135a-3p | 4.28.E-05 | + |
| 177 | hsa-miR-4486 | 6.68.E-05 | + |
| 178 | hsa-miR-4697-5p | 7.18.E-05 | − |
| 179 | hsa-miR-4725-3p | 8.16.E-05 | + |
| 180 | hsa-miR-6510-5p | 8.18.E-05 | + |
| 181 | hsa-miR-5001-5p | 1.92.E-04 | − |
| 182 | hsa-miR-4673 | 2.32.E-04 | + |
| 183 | hsa-miR-4466 | 3.06.E-04 | − |
| 184 | hsa-miR-23a-3p | 5.28.E-04 | − |
| 185 | hsa-miR-3656 | 5.41.E-04 | + |
| 186 | hsa-miR-6782-5p | 7.05.E-04 | + |
| 187 | hsa-miR-4689 | 1.01.E-03 | − |
| 188 | hsa-miR-451a | 1.22.E-03 | − |
| 189 | hsa-miR-4446-3p | 1.51.E-03 | − |
| 190 | hsa-miR-3180-3p | 1.64.E-03 | + |
| 191 | hsa-miR-642a-3p | 1.80.E-03 | − |
| 192 | hsa-miR-6889-5p | 1.91.E-03 | + |
| 193 | hsa-miR-3178 | 2.08.E-03 | + |
| 194 | hsa-miR-4665-5p | 2.84.E-03 | − |
| 195 | hsa-miR-6722-3p | 3.22.E-03 | + |
| 196 | hsa-miR-30c-1-3p | 4.13.E-03 | + |
| 197 | hsa-miR-4507 | 6.12.E-03 | + |
| 198 | hsa-miR-3141 | 6.13.E-03 | + |
| 199 | hsa-miR-1199-5p | 7.28.E-03 | − |

Example 4

<Method for Evaluating Stomach Cancer-Specific Discriminant Performance by Combination of Multiple Gene Markers Using Samples of Validation Cohort>

In this Example, gene markers for diagnosis were selected by comparing gene expression levels of miRNAs in sera of stomach cancer patients with that of a control group consisting of healthy subjects, pancreatic cancer patients, bile duct cancer patients, colorectal cancer patients, liver cancer patients, and benign pancreaticobiliary disease patients in the same way as the method described in Example 1 using the gene markers selected in Example 1 with respect to the training cohort as the sample group described in Reference Example 2. The polynucleotides consisting of the nucleotide sequences represented by SEQ ID NOs: 635 to 642 thus selected were further combined therewith to study a method for evaluating stomach cancer-specific discriminant performance.

Specifically, first, the miRNA expression levels in the training cohort and the validation cohort obtained in Reference Example 2 mentioned above were combined and normalized by quantile normalization. Next, Fisher's discriminant analysis was conducted as to combinations of 1 to 6 expression level measurement values comprising at least one or more of the expression level measurement values of the polynucleotides consisting of the nucleotide sequences represented by SEQ ID NOs: 1 to 165 and 635 to 642, to construct a discriminant for determining the presence or absence of stomach cancer. Next, accuracy, sensitivity, and specificity in the validation cohort were calculated using the discriminant thus prepared, with the stomach cancer patient group as a positive sample group and, on the other hand, the healthy subject group, the pancreatic cancer patient group, the bile duct cancer patient group, the colorectal cancer patient group, the liver cancer patient group, and the benign pancreaticobiliary disease patient group as a negative sample groups. The discriminant performance of the selected polynucleotides was validated using the independent samples.

Most of polynucleotides consisting of the nucleotide sequences represented by any of these SEQ ID NOs (SEQ ID NOs: 1 to 165 and 635 to 642 corresponding to the miRNA markers of Table 1) or complementary sequences thereof mentioned above were able to provide relatively high accuracy, sensitivity, and specificity in the determination of the presence or absence of stomach cancer, and furthermore, were able to specifically discriminate stomach cancer from the other cancers. For example, among the combinations of multiple polynucleotides selected from the group consisting of polynucleotides consisting of the nucleotide sequences represented by SEQ ID NOs: 9, 13, 21, 27, 34, 36, 66, 75, 95, 98, 108, 130, 135, 143, 155, 183, 185, 187, 191, 193, 194, 635, 636, 637, 638, 639, 640, 641 and 642 or complementary sequences thereof (the cancer type-specific polynucleotide group 1) as polynucleotides capable of specifically binding to target markers, combinations comprising at least one or more polynucleotides selected from the group consisting of polynucleotides consisting of the nucleotide sequences represented by SEQ ID NOs: 21, 34, 36, 98, and 155 or complementary sequences thereof (the cancer type-specific polynucleotide group 2) included in the cancer type-specific polynucleotide group 1 were able to specifically discriminate stomach cancer from the other cancers with high accuracy.

The number of the aforementioned polynucleotides with cancer type specificity in the combination can be 2, 3, 4, 5, 6, 7, 8, 9, 10 or more for the combination. The combinations of 6 or more of these polynucleotides were able to exhibit discriminant accuracy of 80% or higher.

Specifically, the discriminant accuracy of the measurement using the polynucleotide consisting of the nucleotide sequence represented by SEQ ID NO: 21 or a complementary sequence thereof is shown in Table 8-1. The measurement using the polynucleotide consisting of the nucleotide sequence represented by SEQ ID NO: 21 or a complementary sequence thereof exhibited the highest accuracy of 79.8% in the training cohort and accuracy of 83.8% in the validation cohort. Also, for example, the measurement using the combinations of two polynucleotides comprising at least one polynucleotide consisting of the nucleotide sequence represented by SEQ ID NO: 21 or a complementary sequence thereof exhibited the highest accuracy of 82.4% in the training cohort and accuracy of 80.9% in the validation cohort. Furthermore, for example, the measurement using the combinations of three polynucleotides comprising at least one polynucleotide consisting of the nucleotide sequence represented by SEQ ID NO: 21 or a complementary sequence thereof exhibited the highest accuracy of 84.1% in the training cohort and accuracy of 83.8% in the validation cohort. Furthermore, for example, the measurement using the combinations of four polynucleotides comprising at least one polynucleotide consisting of the nucleotide sequence represented by SEQ ID NO: 21 or a complementary sequence thereof exhibited the highest accuracy of 85.9% in the training cohort and accuracy of 82.7% in the validation cohort. Furthermore, for example, the measurement using the combinations of five polynucleotides comprising at least one polynucleotide consisting of the nucleotide sequence represented by SEQ ID NO: 21 or a complementary sequence thereof exhibited the highest accuracy of 87.9% in the training cohort and accuracy of 88.4% in the validation cohort. Furthermore, for example, the measurement using the combinations of six polynucleotides comprising at least one polynucleotide consisting of the nucleotide sequence represented by SEQ ID NO: 21 or a complementary sequence thereof exhibited the highest accuracy of 87.0% in the training cohort and accuracy of 87.3% in the validation cohort.

Specifically, the discriminant accuracy of the measurement using the polynucleotide consisting of the nucleotide sequence represented by SEQ ID NO: 34 or a complementary sequence thereof is shown in Table 8-2. The measurement using the polynucleotide consisting of the nucleotide sequence represented by SEQ ID NO: 34 or a complementary sequence thereof exhibited the highest accuracy of 62.8% in the training cohort and accuracy of 60.7% in the validation cohort. Also, for example, the measurement using the combinations of two polynucleotides comprising at least one polynucleotide consisting of the nucleotide sequence represented by SEQ ID NO: 34 or a complementary sequence thereof exhibited the highest accuracy of 81.0% in the training cohort and accuracy of 82.1% in the validation cohort. Furthermore, for example, the measurement using the combinations of three polynucleotides comprising at least one polynucleotide consisting of the nucleotide sequence represented by SEQ ID NO: 34 or a complementary sequence thereof exhibited the highest accuracy of 84.4% in the training cohort and accuracy of 82.1% in the validation cohort. Furthermore, for example, the measurement using the combinations of four polynucleotides comprising at least one polynucleotide consisting of the nucleotide sequence represented by SEQ ID NO: 34 or a complementary sequence thereof exhibited the highest accuracy of 87.0% in the training cohort and accuracy of 88.4% in the validation cohort. Furthermore, for example, the measurement using the combinations of five polynucleotides comprising at least one polynucleotide consisting of the nucleotide sequence represented by SEQ ID NO: 34 or a complementary sequence thereof exhibited the highest accuracy of 88.2% in the training cohort and accuracy of 87.9% in the validation cohort. Furthermore, for example, the measurement using the combinations of six polynucleotides comprising at least one polynucleotide consisting of the nucleotide sequence represented by SEQ ID NO: 34 or a complementary sequence thereof exhibited the highest accuracy of 87.3% in the training cohort and accuracy of 88.4% in the validation cohort.

Specifically, the discriminant accuracy of the measurement using the polynucleotide consisting of the nucleotide sequence represented by SEQ ID NO: 36 or a complementary sequence thereof is shown in Table 8-3. The measurement using the polynucleotide consisting of the nucleotide sequence represented by SEQ ID NO: 36 or a complementary sequence thereof exhibited the highest accuracy of 78.7% in the training cohort and accuracy of 78.6% in the validation cohort. Also, for example, the measurement using the combinations of two polynucleotides comprising at least one polynucleotide consisting of the nucleotide sequence represented by SEQ ID NO: 36 or a complementary sequence thereof exhibited the highest accuracy of 82.7% in the training cohort and accuracy of 82.7% in the validation cohort. Furthermore, for example, the measurement using the combinations of three polynucleotides comprising at least one polynucleotide consisting of the nucleotide sequence represented by SEQ ID NO: 36 or a complementary sequence thereof exhibited the highest accuracy of 85.0% in the training cohort and accuracy of 86.7% in the validation cohort. Furthermore, for example, the measurement using the combinations of four polynucleotides comprising at least one polynucleotide consisting of the nucleotide sequence represented by SEQ ID NO: 36 or a complementary sequence thereof exhibited the highest accuracy of 87.0% in the training cohort and accuracy of 85.5% in the validation cohort. Furthermore, for example, the measurement using the combinations of five polynucleotides comprising at least one polynucleotide consisting of the nucleotide sequence represented by SEQ ID NO: 36 or a complementary sequence thereof exhibited the highest accuracy of 87.9% in the training cohort and accuracy of 86.1% in the validation cohort. Furthermore, for example, the measurement using the combinations of six polynucleotides comprising at least one polynucleotide consisting of the nucleotide sequence represented by SEQ ID NO: 36 or a complementary sequence thereof exhibited the highest accuracy of 87.3% in the training cohort and accuracy of 87.9% in the validation cohort.

Specifically, the discriminant accuracy of the measurement using the polynucleotide consisting of the nucleotide sequence represented by SEQ ID NO: 98 or a complementary sequence thereof is shown in Table 8-4. The measurement using the polynucleotide consisting of the nucleotide sequence represented by SEQ ID NO: 98 or a complementary sequence thereof exhibited the highest accuracy of 70.9% in the training cohort and accuracy of 70.5% in the validation cohort. Also, for example, the measurement using the combinations of two polynucleotides comprising at least one polynucleotide consisting of the nucleotide sequence represented by SEQ ID NO: 98 or a complementary sequence thereof exhibited the highest accuracy of 82.4% in the training cohort and accuracy of 82.1% in the validation cohort. Furthermore, for example, the measurement using the combinations of three polynucleotides comprising at least one polynucleotide consisting of the nucleotide sequence represented by SEQ ID NO: 98 or a complementary sequence thereof exhibited the highest accuracy of 84.1% in the training cohort and accuracy of 85.5% in the validation cohort. Furthermore, for example, the measurement using the combinations of four polynucleotides comprising at least one polynucleotide consisting of the nucleotide sequence represented by SEQ ID NO: 98 or a complementary sequence thereof exhibited the highest accuracy of 86.7% in the training cohort and accuracy of 89.6% in the validation cohort. Furthermore, for example, the measurement using the combinations of five polynucleotides comprising at least one polynucleotide consisting of the nucleotide sequence represented by SEQ ID NO: 98 or a complementary sequence thereof exhibited the highest accuracy of 88.2% in the training cohort and accuracy of 87.9% in the validation cohort. Furthermore, for example, the measurement using the combinations of six polynucleotides comprising at least one polynucleotide consisting of the nucleotide sequence represented by SEQ ID NO: 98 or a complementary sequence thereof exhibited the highest accuracy of 87.9% in the training cohort and accuracy of 88.4% in the validation cohort.

Specifically, the discriminant accuracy of the measurement using the polynucleotide consisting of the nucleotide sequence represented by SEQ ID NO: 155 or a complementary sequence thereof is shown in Table 8-5. The measurement using the polynucleotide consisting of the nucleotide sequence represented by SEQ ID NO: 155 or a complementary sequence thereof exhibited the highest accuracy of 67.1% in the training cohort and accuracy of 69.9% in the validation cohort. Also, for example, the measurement using the combinations of two polynucleotides comprising at least one polynucleotide consisting of the nucleotide sequence represented by SEQ ID NO: 155 or a complementary sequence thereof exhibited the highest accuracy of 81.6% in the training cohort and accuracy of 75.7% in the validation cohort. Furthermore, for example, the measurement using the combinations of three polynucleotides comprising at least one polynucleotide consisting of the nucleotide sequence represented by SEQ ID NO: 155 or a complementary sequence thereof exhibited the highest accuracy of 84.4% in the training cohort and accuracy of 85.0% in the validation cohort. Furthermore, for example, the measurement using the combinations of four polynucleotides comprising at least one polynucleotide consisting of the nucleotide sequence represented by SEQ ID NO: 155 or a complementary sequence thereof exhibited the highest accuracy of 87.0% in the training cohort and accuracy of 89.0% in the validation cohort. Furthermore, for example, the measurement using the combinations of five polynucleotides comprising at least one polynucleotide consisting of the nucleotide sequence represented by SEQ ID NO: 155 or a complementary sequence thereof exhibited the highest accuracy of 88.2% in the training cohort and accuracy of 87.3% in the validation cohort. Furthermore, for example, the measurement using the combinations of six polynucleotides comprising at least one polynucleotide consisting of the nucleotide sequence represented by SEQ ID NO: 155 or a complementary sequence thereof exhibited the highest accuracy of 88.2% in the training cohort and accuracy of 89.6% in the validation cohort.

Figure 4:
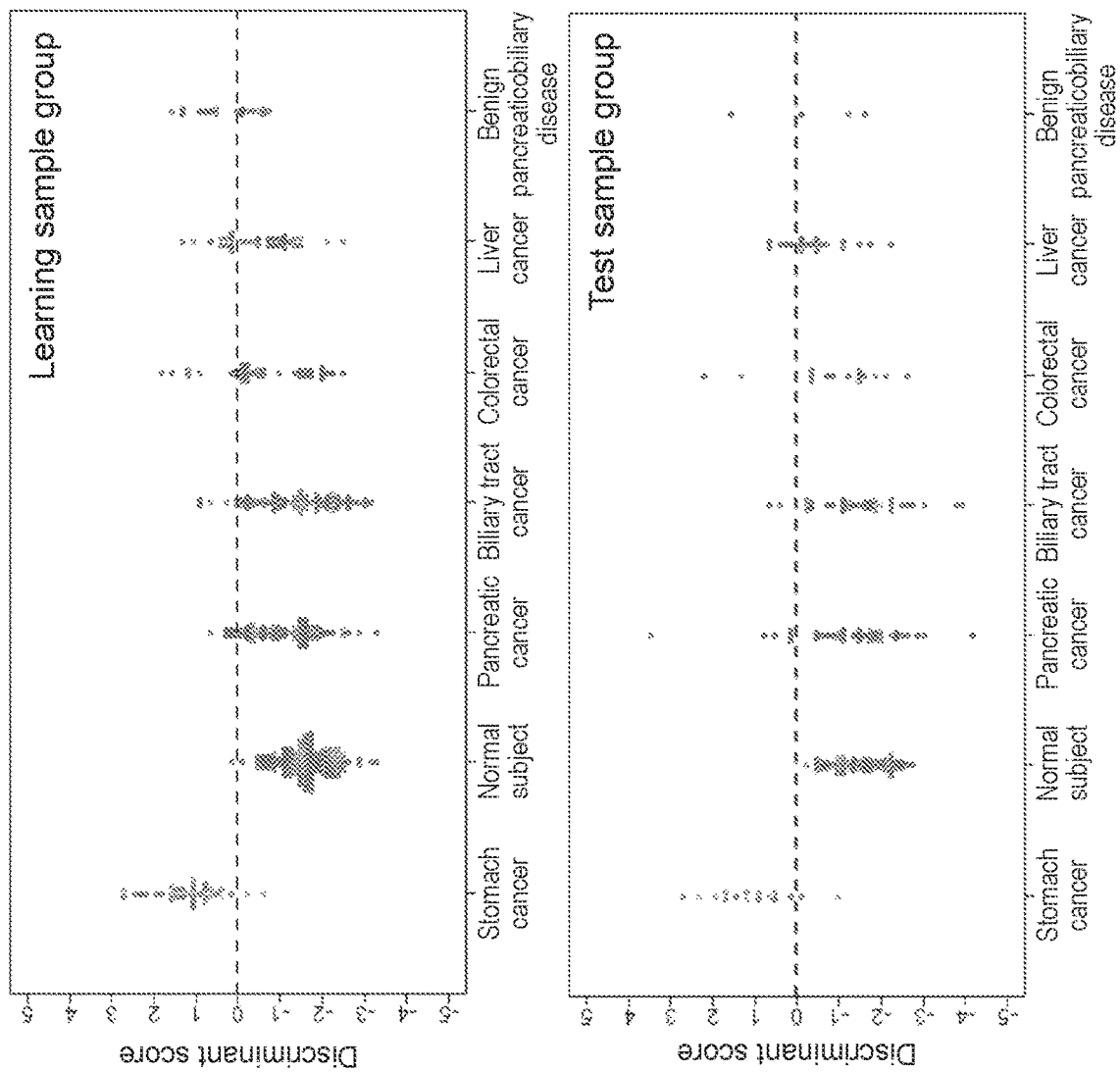
FIG. 4 Upper diagram: a discriminant (2.51×hsa-miR-6781-5p−0.63×hsa-miR-4419b+0.98×hsa-miR-940+0.63×hsa-miR-4294−0.70×hsa-miR-6769b-5p+0.85×hsa-miR-1914-3p−37.81) was prepared by use of Fisher's discriminant analysis from the measurement values of hsa-miR-6781-5p (SEQ ID NO: 9), hsa-miR-204-3p (SEQ ID NO: 13), hsa-miR-3195 (SEQ ID NO: 143), hsa-miR-6769b-5p (SEQ ID NO: 155), hsa-miR-4665-5p (SEQ ID NO: 194), and hsa-miR-4294 (SEQ ID NO: 639) in 34 stomach cancer patients, 102 healthy subjects, 63 pancreatic cancer patients, 65 bile duct cancer patients, 35 colorectal cancer patients, 32 liver cancer patients, and 17 benign pancreaticobiliary disease patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared from the training cohort as to the measurement values of hsa-miR-6781-5p (SEQ ID NO: 9), hsa-miR-204-3p (SEQ ID NO: 13), hsa-miR-3195 (SEQ ID NO: 143), hsa-miR-6769b-5p (SEQ ID NO: 155), hsa-miR-4665-5p (SEQ ID NO: 194), and hsa-miR-4294 (SEQ ID NO: 639) in 16 stomach cancer patients, 48 healthy subjects, 37 pancreatic cancer patients, 33 bile duct cancer patients, 15 colorectal cancer patients, 20 liver cancer patients, and 4 benign pancreaticobiliary disease patients selected as a validation cohort were plotted on the ordinate against the sample groups on the abscissa. The dotted line in the diagram depicts the discriminant boundary that offered a discriminant score of 0 and discriminated between both of the groups.

The expression level measurement values of the nucleotide sequences represented by SEQ ID NOs: 9, 13, 143, 155, 194, and 639 were compared among 34 stomach cancer patients, 102 healthy subjects, 63 pancreatic cancer patients, 65 bile duct cancer patients, 35 colorectal cancer patients, 32 liver cancer patients, and 17 benign pancreaticobiliary disease patients in the training cohort. As a result, a scatter diagram that significantly separated the discriminant score of the stomach cancer patient group from the discriminant scores of the other groups was obtained in the training cohort (see the upper diagram of FIG. 4). These results were also reproducible for the validation cohort (see the lower diagram of FIG. 4).

TABLE 8-1

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 21 | 79.8 | 82.4 | 79.6 | 83.8 | 81.2 | 84.1 |
| 9_21 | 82.4 | 97.1 | 80.8 | 80.9 | 81.2 | 80.9 |
| 9_21_34 | 84.1 | 91.2 | 83.4 | 83.8 | 75 | 84.7 |
| 9_21_34_36 | 85.9 | 91.2 | 85.3 | 82.7 | 68.8 | 84.1 |
| 9_21_34_36_98 | 87.9 | 97.1 | 86.9 | 88.4 | 81.2 | 89.2 |
| 9_21_36_98_130_637 | 83.6 | 100 | 81.8 | 85 | 87.5 | 84.7 |
| 9_21_34_36_98_637 | 87 | 94.1 | 86.3 | 87.3 | 87.5 | 87.3 |
| 9_21_34_36_98_155 | 86.7 | 97.1 | 85.6 | 89 | 81.2 | 89.8 |
| 21_36_75_98_155_635 | 83 | 97.1 | 81.5 | 87.9 | 87.5 | 87.9 |
| 9_21_36_98_108_155 | 86.7 | 100 | 85.3 | 86.7 | 81.2 | 87.3 |

TABLE 8-2

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 34 | 62.8 | 67.6 | 62.3 | 60.7 | 81.2 | 58.6 |
| 21_34 | 81 | 82.4 | 80.8 | 82.1 | 81.2 | 82.2 |
| 9_34_36 | 84.4 | 94.1 | 83.4 | 82.1 | 68.8 | 83.4 |
| 9_34_36_98 | 87 | 97.1 | 85.9 | 88.4 | 87.5 | 88.5 |
| 9_34_36_98_635 | 88.2 | 97.1 | 87.2 | 87.9 | 87.5 | 87.9 |
| 34_36_143_155_187_635 | 86.2 | 94.1 | 85.3 | 86.1 | 87.5 | 86 |
| 9_34_36_66_98_187 | 87.3 | 97.1 | 86.3 | 88.4 | 81.2 | 89.2 |
| 9_34_36_98_187_637 | 86.5 | 94.1 | 85.6 | 87.3 | 87.5 | 87.3 |
| 9_34_36_98_185_637 | 86.7 | 97.1 | 85.6 | 86.7 | 87.5 | 86.6 |
| 9_34_36_98_637_639 | 86.5 | 97.1 | 85.3 | 87.9 | 87.5 | 87.9 |

TABLE 8-3

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 36 | 78.7 | 82.4 | 78.3 | 78.6 | 81.2 | 78.3 |
| 9_36 | 82.7 | 97.1 | 81.2 | 82.7 | 75 | 83.4 |
| 9_36_98 | 85 | 100 | 83.4 | 86.7 | 87.5 | 86.6 |
| 9_36_75_98 | 87 | 100 | 85.6 | 85.5 | 81.2 | 86 |
| 9_13_36_108_194 | 87.9 | 94.3 | 87.2 | 86.1 | 75 | 87.3 |
| 9_36_98_108_638_639 | 85.6 | 94.1 | 84.7 | 88.4 | 87.5 | 88.5 |
| 36_98_155_194_635_642 | 85.3 | 100 | 83.7 | 86.1 | 81.2 | 86.6 |
| 9_34_36_75_98_637 | 87.3 | 97.1 | 86.3 | 87.9 | 87.5 | 87.9 |
| 21_36_98_155_185_635 | 83.9 | 97.1 | 82.4 | 89 | 87.5 | 89.2 |
| 9_36_98_108_355_635 | 85.9 | 97.1 | 84.7 | 87.3 | 81.2 | 87.9 |

TABLE 8-4

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 98 | 70.9 | 64.7 | 71.6 | 70.5 | 62.5 | 71.3 |
| 36_98 | 82.4 | 88.2 | 81.8 | 82.1 | 75 | 82.8 |
| 9_98_639 | 84.1 | 91.2 | 83.4 | 85.5 | 81.2 | 86 |
| 9_36_98_194 | 86.7 | 97.1 | 85.6 | 89.6 | 81.2 | 90.4 |
| 9_98_130_135_639 | 88.2 | 97.1 | 87.2 | 87.9 | 100 | 86.6 |
| 9_36_98_130_194_637 | 87.3 | 100 | 85.9 | 89.6 | 87.5 | 89.8 |
| 21_36_98_108_155_635 | 85.6 | 94.1 | 84.7 | 89.6 | 87.5 | 89.8 |
| 9_36_98_108_155_639 | 87.9 | 97.1 | 86.9 | 88.4 | 87.5 | 88.5 |
| 9_36_98_155_187_639 | 87 | 97.1 | 85.9 | 88.4 | 93.8 | 87.9 |
| 9_36_98_155_187_637 | 85.9 | 100 | 84.3 | 85.5 | 81.2 | 86 |

TABLE 8-5

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 155 | 67.1 | 58.8 | 68.1 | 69.9 | 75 | 69.4 |
| 9_155 | 81.6 | 94.1 | 80.2 | 75.7 | 75 | 75.8 |
| 9_155_639 | 84.4 | 97.1 | 83.1 | 85 | 87.5 | 84.7 |
| 9_130_155639 | 87 | 91.2 | 86.6 | 89 | 100 | 87.9 |
| 9_34_130_155_639 | 88.2 | 91.2 | 87.9 | 87.3 | 93.8 | 86.6 |
| 9_36_75_98_155_635 | 85.6 | 100 | 84 | 86.1 | 81.2 | 86.6 |
| 36_98_130_155_185_635 | 85.9 | 94.1 | 85 | 86.1 | 87.5 | 86 |
| 9_13_143_155_194_639 | 88.2 | 94.1 | 87.5 | 89.6 | 87.5 | 89.8 |
| 9_13_34_36_98_155 | 87 | 97.1 | 85.9 | 89 | 81.2 | 89.8 |
| 36_98_108_155_193_635 | 85.3 | 94.1 | 84.3 | 86.7 | 81.2 | 87.3 |

Comparative Example 1

<Stomach Cancer Discriminant Performance of Existing Tumor Markers in Blood>

The concentrations of the existing tumor markers CEA and CA19-9 in blood were measured in the training cohort and the validation cohort obtained in the preceding Reference Examples. When the concentrations of these tumor markers in blood are higher than the reference values described in Kim, H. J. et al., Acta Oncologica, 2009, No. 48, p. 385 to 390 (CEA: 5 ng/mL, CA19-9: 37 U/mL), subjects are usually suspected of having cancer. Thus, whether or not the concentrations of CEA and CA19-9 in blood exceeded their reference values was confirmed for each sample, and the results were assessed for the ability of these tumor markers to detect cancer in stomach cancer patients. The sensitivity of each existing marker in the training cohort and the validation cohort was calculated. The results are shown in Table 5. The sensitivity of CEA and CA19-9 was as low as 2.9% in the training cohort, and was as low as 12.5% and 12.5%, respectively, in the validation cohort, demonstrating that neither of the markers are useful in the detection of stomach cancer (Table 5).

On the other hand, as shown above in Tables 3 and 6 of Examples 1 and 2, it can be concluded that in all of the polynucleotides consisting of the nucleotide sequences represented by SEQ ID NOs: 1 to 169 combinations of 1 or 2 polynucleotides exhibiting sensitivity beyond the existing stomach cancer markers are present, and thus such polynucleotides serve as excellent diagnosis markers.

As shown in these Examples and Comparative Example, the kit, etc., and the method of the present invention can detect stomach cancer with higher sensitivity than the existing tumor markers and therefore permit early detection and treatment of stomach cancer. As a result, improvement in survival rate resulting from reduction in the risk of recurrence, and a therapeutic option of stomach-conserving therapy can also be provided.

INDUSTRIAL APPLICABILITY

According to the present invention, stomach cancer can be effectively detected by a simple and inexpensive method. This enables early detection, diagnosis and treatment of stomach cancer. The method of the present invention can detect stomach cancer with limited invasiveness using the blood of a patient and therefore allows stomach cancer to be detected conveniently and rapidly.

All publications, patents, and patent applications cited herein are incorporated herein by reference in their entirety.

The invention claimed is:

1. A method for detecting stomach cancer in a human subject, comprising:
   measuring an expression level of hsa-miR-718 in a blood, serum or plasma sample from the subject;
   comparing the measured expression level of hsa-miR-718 to a control expression level for a healthy subject;
   detecting an increased level of hsa-miR-718 in the sample from the subject as compared to the control expression level from the sample from the healthy subject;
   wherein the increased level of hsa-miR-718 indicates that the subject has stomach cancer; and
   wherein the method further comprises treating the subject for the stomach cancer or performing a diagnostic procedure on the subject with the stomach cancer;
   wherein the treating comprises surgery, radiotherapy, chemotherapy or a combination thereof; and
   wherein the diagnostic procedure comprises gastric X-ray examination, gastroscopy, or imaging of the stomach.

2. The method according to claim 1, comprising performing the diagnostic procedure on the subject.

3. The method according to claim 1, wherein the expression level of hsa-miR-718 in the sample is measured by using a device comprising a nucleic acid(s) that specifically binds to hsa-miR-718.

4. The method according to claim 3, wherein the device further comprises a nucleic acid(s) capable of specifically binding to one or more polynucleotides selected from the group consisting of the following other stomach cancer markers:
   miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR-4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-6716-5p, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-6848-5p, miR-762, miR-2861, miR-1203, miR-1260b, miR-4476, miR-6885-5p, miR-6769b-5p, miR-23b-3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p; and/or
   miR-128-2-5p, miR-125a-3p, miR-92a-2-5p, miR-486-3p, miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141 and miR-1199-5p.

5. The method according to claim 1, wherein the expression level of hsa-miR-718 in the sample is measured by using a kit comprising a nucleic acid(s) that specifically binds to hsa-miR-718.

6. The method according to claim 5,
   wherein the kit further comprises a nucleic acid(s) capable of specifically binding to one or more polynucleotides selected from the group consisting of following other stomach cancer markers:
   miR-6726-5p, miR-1343-3p, miR-1247-3p, miR-6787-5p, miR-6875-5p, miR-1225-3p, miR-8063, miR-6781-5p, miR-4746-3p, miR-1908-5p, miR-6756-5p, miR-204-3p, miR-4651, miR-6757-5p, miR-6825-5p, miR-7108-5p, miR-4792, miR-7641, miR-3188, miR-3131, miR-6780b-5p, miR-8069, miR-6840-3p, miR-8072, miR-1233-5p, miR-6887-5p, miR-1231, miR-5572, miR-6738-5p, miR-6784-5p, miR-6791-5p, miR-6749-5p, miR-6741-5p, miR-128-1-5p, miR-4419b, miR-6746-5p, miR-3184-5p, miR-3679-5p, miR-7110-5p, miR-4516, miR-6717-5p, miR-6826-5p, miR-4433b-3p, miR-3679-3p, miR-3135b, miR-3622a-5p, miR-711, miR-4467, miR-6857-5p, miR-6515-3p, miR-1225-5p, miR-187-5p, miR-3185, miR-642b-3p, miR-1249, miR-744-5p, miR-4442, miR-1228-3p, miR-939-5p, miR-6845-5p, miR-887-3p, miR-7845-5p, miR-6729-5p, miR-4632-5p, miR-615-5p, miR-6724-5p, miR-4728-5p, miR-6732-5p, miR-6816-5p, miR-4695-5p, miR-6088, miR-7975, miR-3197, miR-6125, miR-4433-3p, miR-6727-5p, miR- 4706, miR-7847-3p, miR-6805-3p, miR-6766-3p, miR-1913, miR-4649-5p, miR-602, miR-3663-3p, miR-6893-5p, miR-6861-5p, miR-4449, miR-6842-5p, miR-4454, miR-5195-3p, miR-663b, miR-6765-5p, miR-4513, miR-614, miR-6785-5p, miR-6777-5p, miR-940, miR-4741, miR-6870-5p, miR-6131, miR-150-3p, miR-4707-5p, miR-1915-3p, miR-3937, miR-937-5p, miR-4443, miR-1914-3p, miR-3620-5p, miR-1268b, miR-1227-5p, miR-6880-5p, miR-4417, miR-6802-5p, miR-6769a-5p, miR-663a, miR-6721-5p, miR-4532, miR-7977, miR-92b-5p, miR-371a-5p, miR-6126, miR-4734, miR-4665-3p, miR-423-5p, miR-1469, miR-4675, miR-6716-5p, miR-4281, miR-6820-5p, miR-6795-5p, miR-6779-5p, miR-7109-5p, miR-6798-5p, miR-4648, miR-8059, miR-6765-3p, miR-6132, miR-4492, miR-7107-5p, miR-3195, miR-3180, miR-296-3p, miR-564, miR-1268a, miR-6848-5p, miR-762, miR-2861, miR-1203, miR-1260b, miR-4476, miR-6885-5p, miR-6769b-5p, miR-23b-3p, miR-1343-5p, miR-3621, miR-4688, miR-4286, miR-4640-5p, miR-4739, miR-1260a, miR-4276, miR-7106-5p, miR-6794-5p, miR-6774-5p, miR-4707-3p, miR-4534, miR-4294, miR-6850-5p, miR-6089 and miR-671-5p; and/or miR-128-2-5p, miR-125a-3p, miR-92a-2-5p, miR-486-3p, miR-3196, miR-211-3p, miR-4271, miR-6851-5p, miR-149-3p, miR-4667-5p, miR-135a-3p, miR-4486, miR-4697-5p, miR-4725-3p, miR-6510-5p, miR-5001-5p, miR-4673, miR-4466, miR-23a-3p, miR-3656, miR-6782-5p, miR-4689, miR-451a, miR-4446-3p, miR-3180-3p, miR-642a-3p, miR-6889-5p, miR-3178, miR-4665-5p, miR-6722-3p, miR-30c-1-3p, miR-4507, miR-3141 and miR-1199-5p.

* * * * *

SEQUENCE LISTING

```
Sequence total quantity: 657
SEQ ID NO: 1              moltype = RNA   length = 18
FEATURE                   Location/Qualifiers
source                    1..18
                          mol_type = transcribed RNA
                          organism = Homo sapiens
SEQUENCE: 1
ccagaggtgg ggactgag                                                         18

SEQ ID NO: 2              moltype = RNA   length = 21
FEATURE                   Location/Qualifiers
source                    1..21
                          mol_type = transcribed RNA
                          organism = Homo sapiens
SEQUENCE: 2
cgggagctgg ggtctgcagg t                                                     21

SEQ ID NO: 3              moltype = RNA   length = 22
FEATURE                   Location/Qualifiers
source                    1..22
                          mol_type = transcribed RNA
                          organism = Homo sapiens
SEQUENCE: 3
ctcctggggc ccgcactctc gc                                                    22

SEQ ID NO: 4              moltype = RNA   length = 24
FEATURE                   Location/Qualifiers
source                    1..24
                          mol_type = transcribed RNA
                          organism = Homo sapiens
SEQUENCE: 4
ccccgggaac gtcgagactg gagc                                                  24

SEQ ID NO: 5              moltype = RNA   length = 22
FEATURE                   Location/Qualifiers
source                    1..22
                          mol_type = transcribed RNA
                          organism = Homo sapiens
SEQUENCE: 5
tggcgggggt agagctggct gc                                                    22

SEQ ID NO: 6              moltype = RNA   length = 21
FEATURE                   Location/Qualifiers
source                    1..21
                          mol_type = transcribed RNA
                          organism = Homo sapiens
SEQUENCE: 6
tgagggaccc aggacaggag a                                                     21

SEQ ID NO: 7              moltype = RNA   length = 22
FEATURE                   Location/Qualifiers
source                    1..22
                          mol_type = transcribed RNA
                          organism = Homo sapiens
SEQUENCE: 7
tgagcccctg tgccgccccc ag                                                    22

SEQ ID NO: 8              moltype = RNA   length = 22
FEATURE                   Location/Qualifiers
source                    1..22
                          mol_type = transcribed RNA
                          organism = Homo sapiens
SEQUENCE: 8
tcaaaatcag gagtcggggc tt                                                    22

SEQ ID NO: 9              moltype = RNA   length = 21
FEATURE                   Location/Qualifiers
source                    1..21
                          mol_type = transcribed RNA
                          organism = Homo sapiens
SEQUENCE: 9
cgggccggag gtcaagggcg t                                                     21

SEQ ID NO: 10             moltype = RNA   length = 21
FEATURE                   Location/Qualifiers
source                    1..21
                          mol_type = transcribed RNA
                          organism = Homo sapiens
```

```
SEQUENCE: 10
agcggtgctc ctgcgggccg a                                              21

SEQ ID NO: 11           moltype = RNA   length = 21
FEATURE                 Location/Qualifiers
source                  1..21
                        mol_type = transcribed RNA
                        organism = Homo sapiens
SEQUENCE: 11
cggcggggac ggcgattggt c                                              21

SEQ ID NO: 12           moltype = RNA   length = 23
FEATURE                 Location/Qualifiers
source                  1..23
                        mol_type = transcribed RNA
                        organism = Homo sapiens
SEQUENCE: 12
agggtggggc tggaggtggg gct                                            23

SEQ ID NO: 13           moltype = RNA   length = 21
FEATURE                 Location/Qualifiers
source                  1..21
                        mol_type = transcribed RNA
                        organism = Homo sapiens
SEQUENCE: 13
gctgggaagg caaagggacg t                                              21

SEQ ID NO: 14           moltype = RNA   length = 20
FEATURE                 Location/Qualifiers
source                  1..20
                        mol_type = transcribed RNA
                        organism = Homo sapiens
SEQUENCE: 14
cggggtgggt gaggtcgggc                                                20

SEQ ID NO: 15           moltype = RNA   length = 22
FEATURE                 Location/Qualifiers
source                  1..22
                        mol_type = transcribed RNA
                        organism = Homo sapiens
SEQUENCE: 15
tagggatggg aggccaggat ga                                             22

SEQ ID NO: 16           moltype = RNA   length = 22
FEATURE                 Location/Qualifiers
source                  1..22
                        mol_type = transcribed RNA
                        organism = Homo sapiens
SEQUENCE: 16
tgggaggtg tggagtcagc at                                              22

SEQ ID NO: 17           moltype = RNA   length = 21
FEATURE                 Location/Qualifiers
source                  1..21
                        mol_type = transcribed RNA
                        organism = Homo sapiens
SEQUENCE: 17
gtgtggccgg caggcgggtg g                                              21

SEQ ID NO: 18           moltype = RNA   length = 18
FEATURE                 Location/Qualifiers
source                  1..18
                        mol_type = transcribed RNA
                        organism = Homo sapiens
SEQUENCE: 18
cggtgagcgc tcgctggc                                                  18

SEQ ID NO: 19           moltype = RNA   length = 19
FEATURE                 Location/Qualifiers
source                  1..19
                        mol_type = transcribed RNA
                        organism = Homo sapiens
SEQUENCE: 19
ttgatctcgg aagctaagc                                                 19

SEQ ID NO: 20           moltype = RNA   length = 23
FEATURE                 Location/Qualifiers
source                  1..23
                        mol_type = transcribed RNA
```

```
                          organism = Homo sapiens
SEQUENCE: 20
agaggctttg tgcggatacg ggg                                               23

SEQ ID NO: 21           moltype = RNA   length = 23
FEATURE                 Location/Qualifiers
source                  1..23
                        mol_type = transcribed RNA
                        organism = Homo sapiens
SEQUENCE: 21
tcgaggactg gtggaagggc ctt                                               23

SEQ ID NO: 22           moltype = RNA   length = 23
FEATURE                 Location/Qualifiers
source                  1..23
                        mol_type = transcribed RNA
                        organism = Homo sapiens
SEQUENCE: 22
tggggaaggc ttggcaggga aga                                               23

SEQ ID NO: 23           moltype = RNA   length = 23
FEATURE                 Location/Qualifiers
source                  1..23
                        mol_type = transcribed RNA
                        organism = Homo sapiens
SEQUENCE: 23
ggatggttgg gggcggtcgg cgt                                               23

SEQ ID NO: 24           moltype = RNA   length = 22
FEATURE                 Location/Qualifiers
source                  1..22
                        mol_type = transcribed RNA
                        organism = Homo sapiens
SEQUENCE: 24
gcccaggact ttgtgcgggg tg                                                22

SEQ ID NO: 25           moltype = RNA   length = 20
FEATURE                 Location/Qualifiers
source                  1..20
                        mol_type = transcribed RNA
                        organism = Homo sapiens
SEQUENCE: 25
ggcggcgggg aggtaggcag                                                   20

SEQ ID NO: 26           moltype = RNA   length = 22
FEATURE                 Location/Qualifiers
source                  1..22
                        mol_type = transcribed RNA
                        organism = Homo sapiens
SEQUENCE: 26
agtgggaggc cagggcacgg ca                                                22

SEQ ID NO: 27           moltype = RNA   length = 23
FEATURE                 Location/Qualifiers
source                  1..23
                        mol_type = transcribed RNA
                        organism = Homo sapiens
SEQUENCE: 27
tgggggaca gatggagagg aca                                                23

SEQ ID NO: 28           moltype = RNA   length = 20
FEATURE                 Location/Qualifiers
source                  1..20
                        mol_type = transcribed RNA
                        organism = Homo sapiens
SEQUENCE: 28
gtgtctgggc ggacagctgc                                                   20

SEQ ID NO: 29           moltype = RNA   length = 21
FEATURE                 Location/Qualifiers
source                  1..21
                        mol_type = transcribed RNA
                        organism = Homo sapiens
SEQUENCE: 29
gttggggtgc agggtctgc t                                                  21

SEQ ID NO: 30           moltype = RNA   length = 23
FEATURE                 Location/Qualifiers
source                  1..23
```

```
                         mol_type = transcribed RNA
                         organism = Homo sapiens
SEQUENCE: 30
cgagggtag aagagcacag ggg                                                 23

SEQ ID NO: 31           moltype = RNA   length = 20
FEATURE                 Location/Qualifiers
source                  1..20
                        mol_type = transcribed RNA
                        organism = Homo sapiens
SEQUENCE: 31
gccggggctt tgggtgaggg                                                    20

SEQ ID NO: 32           moltype = RNA   length = 22
FEATURE                 Location/Qualifiers
source                  1..22
                        mol_type = transcribed RNA
                        organism = Homo sapiens
SEQUENCE: 32
cccctggggc tggcaggcg ga                                                  22

SEQ ID NO: 33           moltype = RNA   length = 22
FEATURE                 Location/Qualifiers
source                  1..22
                        mol_type = transcribed RNA
                        organism = Homo sapiens
SEQUENCE: 33
tcgggcctgg ggttggggga gc                                                 22

SEQ ID NO: 34           moltype = RNA   length = 22
FEATURE                 Location/Qualifiers
source                  1..22
                        mol_type = transcribed RNA
                        organism = Homo sapiens
SEQUENCE: 34
gtgggtgctg gtgggagccg tg                                                 22

SEQ ID NO: 35           moltype = RNA   length = 23
FEATURE                 Location/Qualifiers
source                  1..23
                        mol_type = transcribed RNA
                        organism = Homo sapiens
SEQUENCE: 35
cggggccgta gcactgtctg aga                                                23

SEQ ID NO: 36           moltype = RNA   length = 18
FEATURE                 Location/Qualifiers
source                  1..18
                        mol_type = transcribed RNA
                        organism = Homo sapiens
SEQUENCE: 36
gaggctgaag gaagatgg                                                      18

SEQ ID NO: 37           moltype = RNA   length = 22
FEATURE                 Location/Qualifiers
source                  1..22
                        mol_type = transcribed RNA
                        organism = Homo sapiens
SEQUENCE: 37
ccgggagaag gaggtggcct gg                                                 22

SEQ ID NO: 38           moltype = RNA   length = 24
FEATURE                 Location/Qualifiers
source                  1..24
                        mol_type = transcribed RNA
                        organism = Homo sapiens
SEQUENCE: 38
tgaggggcct cagaccgagc tttt                                               24

SEQ ID NO: 39           moltype = RNA   length = 23
FEATURE                 Location/Qualifiers
source                  1..23
                        mol_type = transcribed RNA
                        organism = Homo sapiens
SEQUENCE: 39
tgaggatatg gcagggaagg gga                                                23

SEQ ID NO: 40           moltype = RNA   length = 21
FEATURE                 Location/Qualifiers
```

```
                              -continued source              1..21
                    mol_type = transcribed RNA
                    organism = Homo sapiens
SEQUENCE: 40
tgggggtgtg gggagagaga g                                              21

SEQ ID NO: 41       moltype = RNA   length = 17
FEATURE             Location/Qualifiers
source              1..17
                    mol_type = transcribed RNA
                    organism = Homo sapiens
SEQUENCE: 41
gggagaaggg tcgggc                                                    17

SEQ ID NO: 42       moltype = RNA   length = 22
FEATURE             Location/Qualifiers
source              1..22
                    mol_type = transcribed RNA
                    organism = Homo sapiens
SEQUENCE: 42
aggcgatgtg gggatgtaga ga                                             22

SEQ ID NO: 43       moltype = RNA   length = 23
FEATURE             Location/Qualifiers
source              1..23
                    mol_type = transcribed RNA
                    organism = Homo sapiens
SEQUENCE: 43
tcaataggaa agaggtggga cct                                            23

SEQ ID NO: 44       moltype = RNA   length = 21
FEATURE             Location/Qualifiers
source              1..21
                    mol_type = transcribed RNA
                    organism = Homo sapiens
SEQUENCE: 44
caggagtggg gggtgggacg t                                              21

SEQ ID NO: 45       moltype = RNA   length = 22
FEATURE             Location/Qualifiers
source              1..22
                    mol_type = transcribed RNA
                    organism = Homo sapiens
SEQUENCE: 45
cttcccccca gtaatcttca tc                                             22

SEQ ID NO: 46       moltype = RNA   length = 22
FEATURE             Location/Qualifiers
source              1..22
                    mol_type = transcribed RNA
                    organism = Homo sapiens
SEQUENCE: 46
ggctggagcg agtgcagtgg tg                                             22

SEQ ID NO: 47       moltype = RNA   length = 22
FEATURE             Location/Qualifiers
source              1..22
                    mol_type = transcribed RNA
                    organism = Homo sapiens
SEQUENCE: 47
caggcacggg agctcaggtg ag                                             22

SEQ ID NO: 48       moltype = RNA   length = 22
FEATURE             Location/Qualifiers
source              1..22
                    mol_type = transcribed RNA
                    organism = Homo sapiens
SEQUENCE: 48
gggacccagg gagagacgta ag                                             22

SEQ ID NO: 49       moltype = RNA   length = 22
FEATURE             Location/Qualifiers
source              1..22
                    mol_type = transcribed RNA
                    organism = Homo sapiens
SEQUENCE: 49
tggcggcggt agttatgggc tt                                             22

SEQ ID NO: 50       moltype = RNA   length = 22
```

```
                            -continued

FEATURE              Location/Qualifiers
source               1..22
                     mol_type = transcribed RNA
                     organism = Homo sapiens
SEQUENCE: 50
ttggggattg ggtcaggcca gt                                              22

SEQ ID NO: 51        moltype = RNA   length = 20
FEATURE              Location/Qualifiers
source               1..20
                     mol_type = transcribed RNA
                     organism = Homo sapiens
SEQUENCE: 51
tctcttcatc tacccccag                                                  20

SEQ ID NO: 52        moltype = RNA   length = 22
FEATURE              Location/Qualifiers
source               1..22
                     mol_type = transcribed RNA
                     organism = Homo sapiens
SEQUENCE: 52
gtgggtacgg cccagtgggg gg                                              22

SEQ ID NO: 53        moltype = RNA   length = 22
FEATURE              Location/Qualifiers
source               1..22
                     mol_type = transcribed RNA
                     organism = Homo sapiens
SEQUENCE: 53
ggctacaaca caggacccgg gc                                              22

SEQ ID NO: 54        moltype = RNA   length = 23
FEATURE              Location/Qualifiers
source               1..23
                     mol_type = transcribed RNA
                     organism = Homo sapiens
SEQUENCE: 54
agaagaaggc ggtcggtctg cgg                                             23

SEQ ID NO: 55        moltype = RNA   length = 22
FEATURE              Location/Qualifiers
source               1..22
                     mol_type = transcribed RNA
                     organism = Homo sapiens
SEQUENCE: 55
agacacattt ggagagggac cc                                              22

SEQ ID NO: 56        moltype = RNA   length = 22
FEATURE              Location/Qualifiers
source               1..22
                     mol_type = transcribed RNA
                     organism = Homo sapiens
SEQUENCE: 56
acgcccttcc cccccttctt ca                                              22

SEQ ID NO: 57        moltype = RNA   length = 22
FEATURE              Location/Qualifiers
source               1..22
                     mol_type = transcribed RNA
                     organism = Homo sapiens
SEQUENCE: 57
tgcggggcta gggctaacag ca                                              22

SEQ ID NO: 58        moltype = RNA   length = 17
FEATURE              Location/Qualifiers
source               1..17
                     mol_type = transcribed RNA
                     organism = Homo sapiens
SEQUENCE: 58
gccggacaag agggagg                                                    17

SEQ ID NO: 59        moltype = RNA   length = 20
FEATURE              Location/Qualifiers
source               1..20
                     mol_type = transcribed RNA
                     organism = Homo sapiens
SEQUENCE: 59
tcacacctgc ctcgccccc                                                  20
```

```
SEQ ID NO: 60           moltype = RNA   length = 24
FEATURE                 Location/Qualifiers
source                  1..24
                        mol_type = transcribed RNA
                        organism = Homo sapiens
SEQUENCE: 60
tggggagctg aggctctggg ggtg                                                24

SEQ ID NO: 61           moltype = RNA   length = 19
FEATURE                 Location/Qualifiers
source                  1..19
                        mol_type = transcribed RNA
                        organism = Homo sapiens
SEQUENCE: 61
cggggccaga gcagagagc                                                      19

SEQ ID NO: 62           moltype = RNA   length = 22
FEATURE                 Location/Qualifiers
source                  1..22
                        mol_type = transcribed RNA
                        organism = Homo sapiens
SEQUENCE: 62
gtgaacgggc gccatcccga gg                                                  22

SEQ ID NO: 63           moltype = RNA   length = 21
FEATURE                 Location/Qualifiers
source                  1..21
                        mol_type = transcribed RNA
                        organism = Homo sapiens
SEQUENCE: 63
aagggacagg gagggtcgtg g                                                   21

SEQ ID NO: 64           moltype = RNA   length = 22
FEATURE                 Location/Qualifiers
source                  1..22
                        mol_type = transcribed RNA
                        organism = Homo sapiens
SEQUENCE: 64
tgggcgaggg cggctgagcg gc                                                  22

SEQ ID NO: 65           moltype = RNA   length = 23
FEATURE                 Location/Qualifiers
source                  1..23
                        mol_type = transcribed RNA
                        organism = Homo sapiens
SEQUENCE: 65
gagggcagcg tgggtgtggc gga                                                 23

SEQ ID NO: 66           moltype = RNA   length = 22
FEATURE                 Location/Qualifiers
source                  1..22
                        mol_type = transcribed RNA
                        organism = Homo sapiens
SEQUENCE: 66
gggggtcccc ggtgctcgga tc                                                  22

SEQ ID NO: 67           moltype = RNA   length = 23
FEATURE                 Location/Qualifiers
source                  1..23
                        mol_type = transcribed RNA
                        organism = Homo sapiens
SEQUENCE: 67
ctgggcccgc ggcgggcgtg ggg                                                 23

SEQ ID NO: 68           moltype = RNA   length = 23
FEATURE                 Location/Qualifiers
source                  1..23
                        mol_type = transcribed RNA
                        organism = Homo sapiens
SEQUENCE: 68
tgggagggga gaggcagcaa gca                                                 23

SEQ ID NO: 69           moltype = RNA   length = 20
FEATURE                 Location/Qualifiers
source                  1..20
                        mol_type = transcribed RNA
                        organism = Homo sapiens
SEQUENCE: 69
taggggtgg caggctggcc                                                      20
```

| | | |
|---|---|---|
| SEQ ID NO: 70<br>FEATURE<br>source | moltype = RNA   length = 21<br>Location/Qualifiers<br>1..21<br>mol_type = transcribed RNA<br>organism = Homo sapiens | |
| SEQUENCE: 70<br>tggggcgggg caggtccctg c | | 21 |
| SEQ ID NO: 71<br>FEATURE<br>source | moltype = RNA   length = 22<br>Location/Qualifiers<br>1..22<br>mol_type = transcribed RNA<br>organism = Homo sapiens | |
| SEQUENCE: 71<br>caggaggcag tgggcgagca gg | | 22 |
| SEQ ID NO: 72<br>FEATURE<br>source | moltype = RNA   length = 20<br>Location/Qualifiers<br>1..20<br>mol_type = transcribed RNA<br>organism = Homo sapiens | |
| SEQUENCE: 72<br>agagatgaag cggggggggcg | | 20 |
| SEQ ID NO: 73<br>FEATURE<br>source | moltype = RNA   length = 18<br>Location/Qualifiers<br>1..18<br>mol_type = transcribed RNA<br>organism = Homo sapiens | |
| SEQUENCE: 73<br>atcctagtca cggcacca | | 18 |
| SEQ ID NO: 74<br>FEATURE<br>source | moltype = RNA   length = 23<br>Location/Qualifiers<br>1..23<br>mol_type = transcribed RNA<br>organism = Homo sapiens | |
| SEQUENCE: 74<br>ggaggcgcag gctcggaaag gcg | | 23 |
| SEQ ID NO: 75<br>FEATURE<br>source | moltype = RNA   length = 20<br>Location/Qualifiers<br>1..20<br>mol_type = transcribed RNA<br>organism = Homo sapiens | |
| SEQUENCE: 75<br>gcggaaggcg gagcggcgga | | 20 |
| SEQ ID NO: 76<br>FEATURE<br>source | moltype = RNA   length = 21<br>Location/Qualifiers<br>1..21<br>mol_type = transcribed RNA<br>organism = Homo sapiens | |
| SEQUENCE: 76<br>acaggagtgg gggtgggaca t | | 21 |
| SEQ ID NO: 77<br>FEATURE<br>source | moltype = RNA   length = 23<br>Location/Qualifiers<br>1..23<br>mol_type = transcribed RNA<br>organism = Homo sapiens | |
| SEQUENCE: 77<br>ctcggggcag gcggctggga gcg | | 23 |
| SEQ ID NO: 78<br>FEATURE<br>source | moltype = RNA   length = 25<br>Location/Qualifiers<br>1..25<br>mol_type = transcribed RNA<br>organism = Homo sapiens | |
| SEQUENCE: 78<br>agcggggagg aagtgggcgc tgctt | | 25 |
| SEQ ID NO: 79<br>FEATURE<br>source | moltype = RNA   length = 21<br>Location/Qualifiers<br>1..21<br>mol_type = transcribed RNA<br>organism = Homo sapiens | |
| SEQUENCE: 79 | | |

-continued

```
cgtggaggac gaggaggagg c                                                  21

SEQ ID NO: 80           moltype = RNA   length = 23
FEATURE                 Location/Qualifiers
source                  1..23
                        mol_type = transcribed RNA
                        organism = Homo sapiens
SEQUENCE: 80
ttgctctgct cccccgcccc cag                                                23

SEQ ID NO: 81           moltype = RNA   length = 22
FEATURE                 Location/Qualifiers
source                  1..22
                        mol_type = transcribed RNA
                        organism = Homo sapiens
SEQUENCE: 81
tgattgtctt cccccaccct ca                                                 22

SEQ ID NO: 82           moltype = RNA   length = 22
FEATURE                 Location/Qualifiers
source                  1..22
                        mol_type = transcribed RNA
                        organism = Homo sapiens
SEQUENCE: 82
tctgcccct ccgctgctgc ca                                                  22

SEQ ID NO: 83           moltype = RNA   length = 24
FEATURE                 Location/Qualifiers
source                  1..24
                        mol_type = transcribed RNA
                        organism = Homo sapiens
SEQUENCE: 83
tgggcgaggg gtgggctctc agag                                               24

SEQ ID NO: 84           moltype = RNA   length = 23
FEATURE                 Location/Qualifiers
source                  1..23
                        mol_type = transcribed RNA
                        organism = Homo sapiens
SEQUENCE: 84
gacacgggcg acagctgcgg ccc                                                23

SEQ ID NO: 85           moltype = RNA   length = 23
FEATURE                 Location/Qualifiers
source                  1..23
                        mol_type = transcribed RNA
                        organism = Homo sapiens
SEQUENCE: 85
tgagcaccac acaggccggg cgc                                                23

SEQ ID NO: 86           moltype = RNA   length = 21
FEATURE                 Location/Qualifiers
source                  1..21
                        mol_type = transcribed RNA
                        organism = Homo sapiens
SEQUENCE: 86
caggcaggtg tagggtggag c                                                  21

SEQ ID NO: 87           moltype = RNA   length = 22
FEATURE                 Location/Qualifiers
source                  1..22
                        mol_type = transcribed RNA
                        organism = Homo sapiens
SEQUENCE: 87
actgggtagg tggggctcca gg                                                 22

SEQ ID NO: 88           moltype = RNA   length = 22
FEATURE                 Location/Qualifiers
source                  1..22
                        mol_type = transcribed RNA
                        organism = Homo sapiens
SEQUENCE: 88
cgtcccgggg ctgcgcgagg ca                                                 22

SEQ ID NO: 89           moltype = RNA   length = 22
FEATURE                 Location/Qualifiers
source                  1..22
                        mol_type = transcribed RNA
                        organism = Homo sapiens
```

```
SEQUENCE: 89
tgggggtggt ctctagccaa gg                                              22

SEQ ID NO: 90           moltype = RNA  length = 20
FEATURE                 Location/Qualifiers
source                  1..20
                        mol_type = transcribed RNA
                        organism = Homo sapiens
SEQUENCE: 90
ggatccgagt cacggcacca                                                 20

SEQ ID NO: 91           moltype = RNA  length = 21
FEATURE                 Location/Qualifiers
source                  1..21
                        mol_type = transcribed RNA
                        organism = Homo sapiens
SEQUENCE: 91
atccagttct ctgagggggc t                                               21

SEQ ID NO: 92           moltype = RNA  length = 22
FEATURE                 Location/Qualifiers
source                  1..22
                        mol_type = transcribed RNA
                        organism = Homo sapiens
SEQUENCE: 92
ggtggcccgg ccgtgcctga gg                                              22

SEQ ID NO: 93           moltype = RNA  length = 25
FEATURE                 Location/Qualifiers
source                  1..25
                        mol_type = transcribed RNA
                        organism = Homo sapiens
SEQUENCE: 93
gtgaggcggg gccaggaggg tgtgt                                           25

SEQ ID NO: 94           moltype = RNA  length = 22
FEATURE                 Location/Qualifiers
source                  1..22
                        mol_type = transcribed RNA
                        organism = Homo sapiens
SEQUENCE: 94
agactgacgg ctggaggccc at                                              22

SEQ ID NO: 95           moltype = RNA  length = 23
FEATURE                 Location/Qualifiers
source                  1..23
                        mol_type = transcribed RNA
                        organism = Homo sapiens
SEQUENCE: 95
gaacgcctgt tcttgccagg tgg                                             23

SEQ ID NO: 96           moltype = RNA  length = 22
FEATURE                 Location/Qualifiers
source                  1..22
                        mol_type = transcribed RNA
                        organism = Homo sapiens
SEQUENCE: 96
tgggagggcg tggatgatgg tg                                              22

SEQ ID NO: 97           moltype = RNA  length = 23
FEATURE                 Location/Qualifiers
source                  1..23
                        mol_type = transcribed RNA
                        organism = Homo sapiens
SEQUENCE: 97
acggggagtc aggcagtggt gga                                             23

SEQ ID NO: 98           moltype = RNA  length = 21
FEATURE                 Location/Qualifiers
source                  1..21
                        mol_type = transcribed RNA
                        organism = Homo sapiens
SEQUENCE: 98
aaggcagggc ccccgctccc c                                               21

SEQ ID NO: 99           moltype = RNA  length = 23
FEATURE                 Location/Qualifiers
source                  1..23
                        mol_type = transcribed RNA
```

```
                                   organism = Homo sapiens
SEQUENCE: 99
cgggctgtcc ggaggggtcg gct                                                   23

SEQ ID NO: 100           moltype = RNA  length = 19
FEATURE                  Location/Qualifiers
source                   1..19
                         mol_type = transcribed RNA
                         organism = Homo sapiens
SEQUENCE: 100
tgggggagat gggggttga                                                        19

SEQ ID NO: 101           moltype = RNA  length = 19
FEATURE                  Location/Qualifiers
source                   1..19
                         mol_type = transcribed RNA
                         organism = Homo sapiens
SEQUENCE: 101
ggctggtcag atgggagtg                                                        19

SEQ ID NO: 102           moltype = RNA  length = 22
FEATURE                  Location/Qualifiers
source                   1..22
                         mol_type = transcribed RNA
                         organism = Homo sapiens
SEQUENCE: 102
ctggtacagg cctgggggac ag                                                    22

SEQ ID NO: 103           moltype = RNA  length = 23
FEATURE                  Location/Qualifiers
source                   1..23
                         mol_type = transcribed RNA
                         organism = Homo sapiens
SEQUENCE: 103
gccccggcgc gggcgggttc tgg                                                   23

SEQ ID NO: 104           moltype = RNA  length = 20
FEATURE                  Location/Qualifiers
source                   1..20
                         mol_type = transcribed RNA
                         organism = Homo sapiens
SEQUENCE: 104
ccccagggcg acgcggcggg                                                       20

SEQ ID NO: 105           moltype = RNA  length = 23
FEATURE                  Location/Qualifiers
source                   1..23
                         mol_type = transcribed RNA
                         organism = Homo sapiens
SEQUENCE: 105
acaggcggct gtagcaatgg ggg                                                   23

SEQ ID NO: 106           moltype = RNA  length = 20
FEATURE                  Location/Qualifiers
source                   1..20
                         mol_type = transcribed RNA
                         organism = Homo sapiens
SEQUENCE: 106
gtgagtcagg gtggggctgg                                                       20

SEQ ID NO: 107           moltype = RNA  length = 17
FEATURE                  Location/Qualifiers
source                   1..17
                         mol_type = transcribed RNA
                         organism = Homo sapiens
SEQUENCE: 107
ttggaggcgt gggtttt                                                          17

SEQ ID NO: 108           moltype = RNA  length = 22
FEATURE                  Location/Qualifiers
source                   1..22
                         mol_type = transcribed RNA
                         organism = Homo sapiens
SEQUENCE: 108
ggaggggtcc cgcactggga gg                                                    22

SEQ ID NO: 109           moltype = RNA  length = 22
FEATURE                  Location/Qualifiers
source                   1..22
```

```
                         mol_type = transcribed RNA
                         organism = Homo sapiens
SEQUENCE: 109
gtgggctggg ctgggctggg cc                                              22

SEQ ID NO: 110           moltype = RNA  length = 20
FEATURE                  Location/Qualifiers
source                   1..20
                         mol_type = transcribed RNA
                         organism = Homo sapiens
SEQUENCE: 110
cgggcgtggt ggtggggggtg                                                20

SEQ ID NO: 111           moltype = RNA  length = 17
FEATURE                  Location/Qualifiers
source                   1..17
                         mol_type = transcribed RNA
                         organism = Homo sapiens
SEQUENCE: 111
gtggggccag gcggtgg                                                    17

SEQ ID NO: 112           moltype = RNA  length = 22
FEATURE                  Location/Qualifiers
source                   1..22
                         mol_type = transcribed RNA
                         organism = Homo sapiens
SEQUENCE: 112
tggtggagga agagggcagc tc                                              22

SEQ ID NO: 113           moltype = RNA  length = 18
FEATURE                  Location/Qualifiers
source                   1..18
                         mol_type = transcribed RNA
                         organism = Homo sapiens
SEQUENCE: 113
ggtgggcttc ccggaggg                                                   18

SEQ ID NO: 114           moltype = RNA  length = 20
FEATURE                  Location/Qualifiers
source                   1..20
                         mol_type = transcribed RNA
                         organism = Homo sapiens
SEQUENCE: 114
ctaggtgggg ggcttgaagc                                                 20

SEQ ID NO: 115           moltype = RNA  length = 21
FEATURE                  Location/Qualifiers
source                   1..21
                         mol_type = transcribed RNA
                         organism = Homo sapiens
SEQUENCE: 115
aggtgggtat ggaggagccc t                                               21

SEQ ID NO: 116           moltype = RNA  length = 22
FEATURE                  Location/Qualifiers
source                   1..22
                         mol_type = transcribed RNA
                         organism = Homo sapiens
SEQUENCE: 116
aggcggggcg ccgcgggacc gc                                              22

SEQ ID NO: 117           moltype = RNA  length = 23
FEATURE                  Location/Qualifiers
source                   1..23
                         mol_type = transcribed RNA
                         organism = Homo sapiens
SEQUENCE: 117
tgggcagggg cttattgtag gag                                             23

SEQ ID NO: 118           moltype = RNA  length = 17
FEATURE                  Location/Qualifiers
source                   1..17
                         mol_type = transcribed RNA
                         organism = Homo sapiens
SEQUENCE: 118
ccccggggag cccggcg                                                    17

SEQ ID NO: 119           moltype = RNA  length = 18
FEATURE                  Location/Qualifiers
```

```
source                    1..18
                          mol_type = transcribed RNA
                          organism = Homo sapiens
SEQUENCE: 119
ttcccagcca acgcacca                                                   18

SEQ ID NO: 120            moltype = RNA   length = 22
FEATURE                   Location/Qualifiers
source                    1..22
                          mol_type = transcribed RNA
                          organism = Homo sapiens
SEQUENCE: 120
agggacggga cgcggtgcag tg                                              22

SEQ ID NO: 121            moltype = RNA   length = 20
FEATURE                   Location/Qualifiers
source                    1..20
                          mol_type = transcribed RNA
                          organism = Homo sapiens
SEQUENCE: 121
actcaaactg tgggggcact                                                 20

SEQ ID NO: 122            moltype = RNA   length = 18
FEATURE                   Location/Qualifiers
source                    1..18
                          mol_type = transcribed RNA
                          organism = Homo sapiens
SEQUENCE: 122
gtgaaggccc ggcggaga                                                   18

SEQ ID NO: 123            moltype = RNA   length = 22
FEATURE                   Location/Qualifiers
source                    1..22
                          mol_type = transcribed RNA
                          organism = Homo sapiens
SEQUENCE: 123
gctgcgggct gcggtcaggg cg                                              22

SEQ ID NO: 124            moltype = RNA   length = 26
FEATURE                   Location/Qualifiers
source                    1..26
                          mol_type = transcribed RNA
                          organism = Homo sapiens
SEQUENCE: 124
ctcggccgcg gcgcgtagcc cccgcc                                          26

SEQ ID NO: 125            moltype = RNA   length = 23
FEATURE                   Location/Qualifiers
source                    1..23
                          mol_type = transcribed RNA
                          organism = Homo sapiens
SEQUENCE: 125
tgaggggcag agagcgagac ttt                                             23

SEQ ID NO: 126            moltype = RNA   length = 22
FEATURE                   Location/Qualifiers
source                    1..22
                          mol_type = transcribed RNA
                          organism = Homo sapiens
SEQUENCE: 126
ctcggcgcgg ggcgcgggct cc                                              22

SEQ ID NO: 127            moltype = RNA   length = 22
FEATURE                   Location/Qualifiers
source                    1..22
                          mol_type = transcribed RNA
                          organism = Homo sapiens
SEQUENCE: 127
ggggctgtga ttgaccagca gg                                              22

SEQ ID NO: 128            moltype = RNA   length = 22
FEATURE                   Location/Qualifiers
source                    1..22
                          mol_type = transcribed RNA
                          organism = Homo sapiens
SEQUENCE: 128
accttgcctt gctgcccggg cc                                              22

SEQ ID NO: 129            moltype = RNA   length = 20
```

```
FEATURE                 Location/Qualifiers
source                  1..20
                        mol_type = transcribed RNA
                        organism = Homo sapiens
SEQUENCE: 129
tgggaatggg ggtaagggcc                                                     20

SEQ ID NO: 130          moltype = RNA   length = 21
FEATURE                 Location/Qualifiers
source                  1..21
                        mol_type = transcribed RNA
                        organism = Homo sapiens
SEQUENCE: 130
cttccgcccc gccgggcgtc g                                                   21

SEQ ID NO: 131          moltype = RNA   length = 18
FEATURE                 Location/Qualifiers
source                  1..18
                        mol_type = transcribed RNA
                        organism = Homo sapiens
SEQUENCE: 131
gggtcccggg gagggggg                                                       18

SEQ ID NO: 132          moltype = RNA   length = 19
FEATURE                 Location/Qualifiers
source                  1..19
                        mol_type = transcribed RNA
                        organism = Homo sapiens
SEQUENCE: 132
tgcggcagag ctggggtca                                                      19

SEQ ID NO: 133          moltype = RNA   length = 24
FEATURE                 Location/Qualifiers
source                  1..24
                        mol_type = transcribed RNA
                        organism = Homo sapiens
SEQUENCE: 133
tgggggggaca ggatgagagg ctgt                                               24

SEQ ID NO: 134          moltype = RNA   length = 21
FEATURE                 Location/Qualifiers
source                  1..21
                        mol_type = transcribed RNA
                        organism = Homo sapiens
SEQUENCE: 134
ctgggagggg ctgggtttgg c                                                   21

SEQ ID NO: 135          moltype = RNA   length = 21
FEATURE                 Location/Qualifiers
source                  1..21
                        mol_type = transcribed RNA
                        organism = Homo sapiens
SEQUENCE: 135
ctgggggggag gagaccctgc t                                                  21

SEQ ID NO: 136          moltype = RNA   length = 23
FEATURE                 Location/Qualifiers
source                  1..23
                        mol_type = transcribed RNA
                        organism = Homo sapiens
SEQUENCE: 136
ccaggggat gggcgagctt ggg                                                  23

SEQ ID NO: 137          moltype = RNA   length = 20
FEATURE                 Location/Qualifiers
source                  1..20
                        mol_type = transcribed RNA
                        organism = Homo sapiens
SEQUENCE: 137
tgtgggactg caaatgggag                                                     20

SEQ ID NO: 138          moltype = RNA   length = 22
FEATURE                 Location/Qualifiers
source                  1..22
                        mol_type = transcribed RNA
                        organism = Homo sapiens
SEQUENCE: 138
ggggaactgt agatgaaaag gc                                                  22
```

```
SEQ ID NO: 139           moltype = RNA  length = 21
FEATURE                  Location/Qualifiers
source                   1..21
                         mol_type = transcribed RNA
                         organism = Homo sapiens
SEQUENCE: 139
tcacctggct ggcccgccca g                                              21

SEQ ID NO: 140           moltype = RNA  length = 19
FEATURE                  Location/Qualifiers
source                   1..19
                         mol_type = transcribed RNA
                         organism = Homo sapiens
SEQUENCE: 140
agcagggctg gggattgca                                                 19

SEQ ID NO: 141           moltype = RNA  length = 17
FEATURE                  Location/Qualifiers
source                   1..17
                         mol_type = transcribed RNA
                         organism = Homo sapiens
SEQUENCE: 141
ggggctgggc gcgcgcc                                                   17

SEQ ID NO: 142           moltype = RNA  length = 22
FEATURE                  Location/Qualifiers
source                   1..22
                         mol_type = transcribed RNA
                         organism = Homo sapiens
SEQUENCE: 142
tcggcctggg gaggaggaag gg                                             22

SEQ ID NO: 143           moltype = RNA  length = 17
FEATURE                  Location/Qualifiers
source                   1..17
                         mol_type = transcribed RNA
                         organism = Homo sapiens
SEQUENCE: 143
cgcgccgggc ccgggtt                                                   17

SEQ ID NO: 144           moltype = RNA  length = 19
FEATURE                  Location/Qualifiers
source                   1..19
                         mol_type = transcribed RNA
                         organism = Homo sapiens
SEQUENCE: 144
tggggcggag cttccggag                                                 19

SEQ ID NO: 145           moltype = RNA  length = 22
FEATURE                  Location/Qualifiers
source                   1..22
                         mol_type = transcribed RNA
                         organism = Homo sapiens
SEQUENCE: 145
gagggttggg tggaggctct cc                                             22

SEQ ID NO: 146           moltype = RNA  length = 19
FEATURE                  Location/Qualifiers
source                   1..19
                         mol_type = transcribed RNA
                         organism = Homo sapiens
SEQUENCE: 146
aggcacggtg tcagcaggc                                                 19

SEQ ID NO: 147           moltype = RNA  length = 18
FEATURE                  Location/Qualifiers
source                   1..18
                         mol_type = transcribed RNA
                         organism = Homo sapiens
SEQUENCE: 147
cgggcgtggt ggtggggg                                                  18

SEQ ID NO: 148           moltype = RNA  length = 23
FEATURE                  Location/Qualifiers
source                   1..23
                         mol_type = transcribed RNA
                         organism = Homo sapiens
SEQUENCE: 148
tgggggctgg gatgggccat ggt                                            23
```

```
SEQ ID NO: 149        moltype = RNA   length = 22
FEATURE               Location/Qualifiers
source                1..22
                      mol_type = transcribed RNA
                      organism = Homo sapiens
SEQUENCE: 149
ggggctgggg ccggggccga gc                                              22

SEQ ID NO: 150        moltype = RNA   length = 19
FEATURE               Location/Qualifiers
source                1..19
                      mol_type = transcribed RNA
                      organism = Homo sapiens
SEQUENCE: 150
ggggcctggc ggtgggcgg                                                  19

SEQ ID NO: 151        moltype = RNA   length = 21
FEATURE               Location/Qualifiers
source                1..21
                      mol_type = transcribed RNA
                      organism = Homo sapiens
SEQUENCE: 151
cccggagcca ggatgcagct c                                               21

SEQ ID NO: 152        moltype = RNA   length = 19
FEATURE               Location/Qualifiers
source                1..19
                      mol_type = transcribed RNA
                      organism = Homo sapiens
SEQUENCE: 152
atcccaccac tgccaccat                                                  19

SEQ ID NO: 153        moltype = RNA   length = 22
FEATURE               Location/Qualifiers
source                1..22
                      mol_type = transcribed RNA
                      organism = Homo sapiens
SEQUENCE: 153
caggaaggat ttagggacag gc                                              22

SEQ ID NO: 154        moltype = RNA   length = 25
FEATURE               Location/Qualifiers
source                1..25
                      mol_type = transcribed RNA
                      organism = Homo sapiens
SEQUENCE: 154
agggggggcac tgcgcaagca aagcc                                          25

SEQ ID NO: 155        moltype = RNA   length = 23
FEATURE               Location/Qualifiers
source                1..23
                      mol_type = transcribed RNA
                      organism = Homo sapiens
SEQUENCE: 155
tggtgggtgg ggaggagaag tgc                                             23

SEQ ID NO: 156        moltype = RNA   length = 21
FEATURE               Location/Qualifiers
source                1..21
                      mol_type = transcribed RNA
                      organism = Homo sapiens
SEQUENCE: 156
atcacattgc caggattac c                                                21

SEQ ID NO: 157        moltype = RNA   length = 22
FEATURE               Location/Qualifiers
source                1..22
                      mol_type = transcribed RNA
                      organism = Homo sapiens
SEQUENCE: 157
tggggagcgg cccccgggtg gg                                              22

SEQ ID NO: 158        moltype = RNA   length = 20
FEATURE               Location/Qualifiers
source                1..20
                      mol_type = transcribed RNA
                      organism = Homo sapiens
SEQUENCE: 158
```

```
cgcgggtcgg ggtctgcagg                                                      20

SEQ ID NO: 159         moltype = RNA   length = 22
FEATURE                Location/Qualifiers
source                 1..22
                       mol_type = transcribed RNA
                       organism = Homo sapiens
SEQUENCE: 159
tagggcagc agaggacctg gg                                                    22

SEQ ID NO: 160         moltype = RNA   length = 17
FEATURE                Location/Qualifiers
source                 1..17
                       mol_type = transcribed RNA
                       organism = Homo sapiens
SEQUENCE: 160
accccactcc tggtacc                                                         17

SEQ ID NO: 161         moltype = RNA   length = 23
FEATURE                Location/Qualifiers
source                 1..23
                       mol_type = transcribed RNA
                       organism = Homo sapiens
SEQUENCE: 161
tgggccaggg agcagctggt ggg                                                  23

SEQ ID NO: 162         moltype = RNA   length = 25
FEATURE                Location/Qualifiers
source                 1..25
                       mol_type = transcribed RNA
                       organism = Homo sapiens
SEQUENCE: 162
aagggaggag gagcggaggg gccct                                                25

SEQ ID NO: 163         moltype = RNA   length = 18
FEATURE                Location/Qualifiers
source                 1..18
                       mol_type = transcribed RNA
                       organism = Homo sapiens
SEQUENCE: 163
atcccacctc tgccacca                                                        18

SEQ ID NO: 164         moltype = RNA   length = 17
FEATURE                Location/Qualifiers
source                 1..17
                       mol_type = transcribed RNA
                       organism = Homo sapiens
SEQUENCE: 164
ctcagtgact catgtgc                                                         17

SEQ ID NO: 165         moltype = RNA   length = 20
FEATURE                Location/Qualifiers
source                 1..20
                       mol_type = transcribed RNA
                       organism = Homo sapiens
SEQUENCE: 165
tgggaggagg ggatcttggg                                                      20

SEQ ID NO: 166         moltype = RNA   length = 23
FEATURE                Location/Qualifiers
source                 1..23
                       mol_type = transcribed RNA
                       organism = Homo sapiens
SEQUENCE: 166
gggggccgat acactgtacg aga                                                  23

SEQ ID NO: 167         moltype = RNA   length = 22
FEATURE                Location/Qualifiers
source                 1..22
                       mol_type = transcribed RNA
                       organism = Homo sapiens
SEQUENCE: 167
acaggtgagg ttcttgggag cc                                                   22

SEQ ID NO: 168         moltype = RNA   length = 22
FEATURE                Location/Qualifiers
source                 1..22
                       mol_type = transcribed RNA
                       organism = Homo sapiens
```

```
SEQUENCE: 168
gggtggggat ttgttgcatt ac                                              22

SEQ ID NO: 169          moltype = RNA   length = 21
FEATURE                 Location/Qualifiers
source                  1..21
                        mol_type = transcribed RNA
                        organism = Homo sapiens
SEQUENCE: 169
cggggcagct cagtacagga t                                               21

SEQ ID NO: 170          moltype = RNA   length = 18
FEATURE                 Location/Qualifiers
source                  1..18
                        mol_type = transcribed RNA
                        organism = Homo sapiens
SEQUENCE: 170
cggggcggca ggggcctc                                                   18

SEQ ID NO: 171          moltype = RNA   length = 21
FEATURE                 Location/Qualifiers
source                  1..21
                        mol_type = transcribed RNA
                        organism = Homo sapiens
SEQUENCE: 171
gcagggacag caaagggtg c                                                21

SEQ ID NO: 172          moltype = RNA   length = 19
FEATURE                 Location/Qualifiers
source                  1..19
                        mol_type = transcribed RNA
                        organism = Homo sapiens
SEQUENCE: 172
gggggaagaa aaggtgggg                                                  19

SEQ ID NO: 173          moltype = RNA   length = 23
FEATURE                 Location/Qualifiers
source                  1..23
                        mol_type = transcribed RNA
                        organism = Homo sapiens
SEQUENCE: 173
aggaggtggt actaggggcc agc                                             23

SEQ ID NO: 174          moltype = RNA   length = 21
FEATURE                 Location/Qualifiers
source                  1..21
                        mol_type = transcribed RNA
                        organism = Homo sapiens
SEQUENCE: 174
agggagggac gggggctgtg c                                               21

SEQ ID NO: 175          moltype = RNA   length = 22
FEATURE                 Location/Qualifiers
source                  1..22
                        mol_type = transcribed RNA
                        organism = Homo sapiens
SEQUENCE: 175
actggggagc agaaggagaa cc                                              22

SEQ ID NO: 176          moltype = RNA   length = 22
FEATURE                 Location/Qualifiers
source                  1..22
                        mol_type = transcribed RNA
                        organism = Homo sapiens
SEQUENCE: 176
tatagggatt ggagccgtgg cg                                              22

SEQ ID NO: 177          moltype = RNA   length = 17
FEATURE                 Location/Qualifiers
source                  1..17
                        mol_type = transcribed RNA
                        organism = Homo sapiens
SEQUENCE: 177
gctgggcgag gctggca                                                    17

SEQ ID NO: 178          moltype = RNA   length = 22
FEATURE                 Location/Qualifiers
source                  1..22
                        mol_type = transcribed RNA
```

```
                                organism = Homo sapiens
SEQUENCE: 178
aggggggcgca gtcactgacg tg                                                 22

SEQ ID NO: 179          moltype = RNA   length = 22
FEATURE                 Location/Qualifiers
source                  1..22
                        mol_type = transcribed RNA
                        organism = Homo sapiens
SEQUENCE: 179
tggggaaggc gtcagtgtcg gg                                                  22

SEQ ID NO: 180          moltype = RNA   length = 22
FEATURE                 Location/Qualifiers
source                  1..22
                        mol_type = transcribed RNA
                        organism = Homo sapiens
SEQUENCE: 180
cagcagggga gagagaggag tc                                                  22

SEQ ID NO: 181          moltype = RNA   length = 24
FEATURE                 Location/Qualifiers
source                  1..24
                        mol_type = transcribed RNA
                        organism = Homo sapiens
SEQUENCE: 181
agggctggac tcagcggcgg agct                                                24

SEQ ID NO: 182          moltype = RNA   length = 22
FEATURE                 Location/Qualifiers
source                  1..22
                        mol_type = transcribed RNA
                        organism = Homo sapiens
SEQUENCE: 182
tccaggcagg agccggactg ga                                                  22

SEQ ID NO: 183          moltype = RNA   length = 18
FEATURE                 Location/Qualifiers
source                  1..18
                        mol_type = transcribed RNA
                        organism = Homo sapiens
SEQUENCE: 183
gggtgcgggc cggcgggg                                                       18

SEQ ID NO: 184          moltype = RNA   length = 21
FEATURE                 Location/Qualifiers
source                  1..21
                        mol_type = transcribed RNA
                        organism = Homo sapiens
SEQUENCE: 184
atcacattgc cagggatttc c                                                   21

SEQ ID NO: 185          moltype = RNA   length = 17
FEATURE                 Location/Qualifiers
source                  1..17
                        mol_type = transcribed RNA
                        organism = Homo sapiens
SEQUENCE: 185
ggcgggtgcg ggggtgg                                                        17

SEQ ID NO: 186          moltype = RNA   length = 25
FEATURE                 Location/Qualifiers
source                  1..25
                        mol_type = transcribed RNA
                        organism = Homo sapiens
SEQUENCE: 186
tagggggtggg ggaattcagg ggtgt                                              25

SEQ ID NO: 187          moltype = RNA   length = 22
FEATURE                 Location/Qualifiers
source                  1..22
                        mol_type = transcribed RNA
                        organism = Homo sapiens
SEQUENCE: 187
ttgaggagac atggtggggg cc                                                  22

SEQ ID NO: 188          moltype = RNA   length = 22
FEATURE                 Location/Qualifiers
source                  1..22
```

| | | |
|---|---|---|
| | mol_type = transcribed RNA organism = Homo sapiens | |
| SEQUENCE: 188 | | |
| aaaccgttac cattactgag tt | | 22 |
| | | |
| SEQ ID NO: 189 | moltype = RNA length = 22 | |
| FEATURE | Location/Qualifiers | |
| source | 1..22 | |
| | mol_type = transcribed RNA organism = Homo sapiens | |
| SEQUENCE: 189 | | |
| cagggctggc agtgacatgg gt | | 22 |
| | | |
| SEQ ID NO: 190 | moltype = RNA length = 22 | |
| FEATURE | Location/Qualifiers | |
| source | 1..22 | |
| | mol_type = transcribed RNA organism = Homo sapiens | |
| SEQUENCE: 190 | | |
| tggggcggag cttccggagg cc | | 22 |
| | | |
| SEQ ID NO: 191 | moltype = RNA length = 22 | |
| FEATURE | Location/Qualifiers | |
| source | 1..22 | |
| | mol_type = transcribed RNA organism = Homo sapiens | |
| SEQUENCE: 191 | | |
| agacacattt ggagagggaa cc | | 22 |
| | | |
| SEQ ID NO: 192 | moltype = RNA length = 23 | |
| FEATURE | Location/Qualifiers | |
| source | 1..23 | |
| | mol_type = transcribed RNA organism = Homo sapiens | |
| SEQUENCE: 192 | | |
| tcggggagtc tggggtccgg aat | | 23 |
| | | |
| SEQ ID NO: 193 | moltype = RNA length = 17 | |
| FEATURE | Location/Qualifiers | |
| source | 1..17 | |
| | mol_type = transcribed RNA organism = Homo sapiens | |
| SEQUENCE: 193 | | |
| ggggcgcggc cggatcg | | 17 |
| | | |
| SEQ ID NO: 194 | moltype = RNA length = 23 | |
| FEATURE | Location/Qualifiers | |
| source | 1..23 | |
| | mol_type = transcribed RNA organism = Homo sapiens | |
| SEQUENCE: 194 | | |
| ctgggggacg cgtgagcgcg agc | | 23 |
| | | |
| SEQ ID NO: 195 | moltype = RNA length = 22 | |
| FEATURE | Location/Qualifiers | |
| source | 1..22 | |
| | mol_type = transcribed RNA organism = Homo sapiens | |
| SEQUENCE: 195 | | |
| tgcaggggtc gggtgggcca gg | | 22 |
| | | |
| SEQ ID NO: 196 | moltype = RNA length = 22 | |
| FEATURE | Location/Qualifiers | |
| source | 1..22 | |
| | mol_type = transcribed RNA organism = Homo sapiens | |
| SEQUENCE: 196 | | |
| ctgggagagg gttgtttact cc | | 22 |
| | | |
| SEQ ID NO: 197 | moltype = RNA length = 20 | |
| FEATURE | Location/Qualifiers | |
| source | 1..20 | |
| | mol_type = transcribed RNA organism = Homo sapiens | |
| SEQUENCE: 197 | | |
| ctgggttggg ctgggctggg | | 20 |
| | | |
| SEQ ID NO: 198 | moltype = RNA length = 19 | |
| FEATURE | Location/Qualifiers | |

```
source                  1..19
                        mol_type = transcribed RNA
                        organism = Homo sapiens
SEQUENCE: 198
gagggcgggt ggaggagga                                                 19

SEQ ID NO: 199          moltype = RNA   length = 20
FEATURE                 Location/Qualifiers
source                  1..20
                        mol_type = transcribed RNA
                        organism = Homo sapiens
SEQUENCE: 199
cctgagcccg ggccgcgcag                                                20

SEQ ID NO: 200          moltype = RNA   length = 86
FEATURE                 Location/Qualifiers
source                  1..86
                        mol_type = transcribed RNA
                        organism = Homo sapiens
SEQUENCE: 200
ggcttagaaa cagtccctag gtaggatttg gggaggagct aagaagcccc tacagggccc    60
agaggtgggg actgagcctt agttgg                                         86

SEQ ID NO: 201          moltype = RNA   length = 61
FEATURE                 Location/Qualifiers
source                  1..61
                        mol_type = transcribed RNA
                        organism = Homo sapiens
SEQUENCE: 201
gggggcggga gctgggtct gcaggttcgc actgatgcct gctcgccctg tctcccgcta     60
g                                                                    61

SEQ ID NO: 202          moltype = RNA   length = 84
FEATURE                 Location/Qualifiers
source                  1..84
                        mol_type = transcribed RNA
                        organism = Homo sapiens
SEQUENCE: 202
gctggcgtcg gtgctgggga gcggcccccg ggtgggcctc tgctctggcc cctcctgggg    60
cccgcactct cgctctgggc ccgc                                           84

SEQ ID NO: 203          moltype = RNA   length = 136
FEATURE                 Location/Qualifiers
source                  1..136
                        mol_type = transcribed RNA
                        organism = Homo sapiens
SEQUENCE: 203
ccgcttgcct cgcccagcgc agccccggcc gctgggcgca cccgtcccgt tcgtcccccgg   60
acgttgctct ctaccccggg aacgtcgaga ctggagcgcc cgaactgagc caccttcgcg   120
gaccccgaga gcggcg                                                   136

SEQ ID NO: 204          moltype = RNA   length = 61
FEATURE                 Location/Qualifiers
source                  1..61
                        mol_type = transcribed RNA
                        organism = Homo sapiens
SEQUENCE: 204
tcggctggcg ggggtagagc tggctgcagg cccggcccct ctcagctgct gccctctcca    60
g                                                                    61

SEQ ID NO: 205          moltype = RNA   length = 72
FEATURE                 Location/Qualifiers
source                  1..72
                        mol_type = transcribed RNA
                        organism = Homo sapiens
SEQUENCE: 205
gagtctgagg gacccaggac aggagaaggc ctatggtgat ttgcattctt cctgccctgg    60
ctccatcctc ag                                                        72

SEQ ID NO: 206          moltype = RNA   length = 90
FEATURE                 Location/Qualifiers
source                  1..90
                        mol_type = transcribed RNA
                        organism = Homo sapiens
SEQUENCE: 206
gtgggtacgg cccagtgggg gggagaggga cacgccctgg gctctgccca gggtgcagcc    60
ggactgactg agcccctgtg ccgcccccag                                     90

SEQ ID NO: 207          moltype = RNA   length = 81
```

| FEATURE | Location/Qualifiers |
|---|---|
| source | 1..81<br>mol_type = transcribed RNA<br>organism = Homo sapiens |

SEQUENCE: 207

```
tagaggcagt ttcaacagat gtgtagactt tgatatgag aaattggttt caaaatcagg    60
agtcggggct ttactgcttt t                                             81
```

| SEQ ID NO: 208 | moltype = RNA  length = 64 |
|---|---|
| FEATURE | Location/Qualifiers |
| source | 1..64<br>mol_type = transcribed RNA<br>organism = Homo sapiens |

SEQUENCE: 208

```
aaccccgggc cggaggtcaa gggcgtcgct tctccctaat gttgcctctt ttccacggcc    60
tcag                                                                 64
```

| SEQ ID NO: 209 | moltype = RNA  length = 71 |
|---|---|
| FEATURE | Location/Qualifiers |
| source | 1..71<br>mol_type = transcribed RNA<br>organism = Homo sapiens |

SEQUENCE: 209

```
gtgtctgtgc cggtcccagg agaacctgca gaggcatcgg gtcagcggtg ctcctgcggg    60
ccgacactca c                                                         71
```

| SEQ ID NO: 210 | moltype = RNA  length = 80 |
|---|---|
| FEATURE | Location/Qualifiers |
| source | 1..80<br>mol_type = transcribed RNA<br>organism = Homo sapiens |

SEQUENCE: 210

```
cgggaatgcc gcggcgggga cggcgattgg tccgtatgtg tggtgccacc ggccgccggc    60
tccgccccgg ccccgccccc                                                80
```

| SEQ ID NO: 211 | moltype = RNA  length = 63 |
|---|---|
| FEATURE | Location/Qualifiers |
| source | 1..63<br>mol_type = transcribed RNA<br>organism = Homo sapiens |

SEQUENCE: 211

```
accctagggt ggggctggag gtggggctga ggctgagtct tcctcccctt cctccctgcc    60
cag                                                                  63
```

| SEQ ID NO: 212 | moltype = RNA  length = 110 |
|---|---|
| FEATURE | Location/Qualifiers |
| source | 1..110<br>mol_type = transcribed RNA<br>organism = Homo sapiens |

SEQUENCE: 212

```
ggctacagtc tttcttcatg tgactcgtgg acttcccttt gtcatcctat gcctgagaat    60
atatgaagga ggctgggaag gcaaagggac gttcaattgt catcactggc              110
```

| SEQ ID NO: 213 | moltype = RNA  length = 73 |
|---|---|
| FEATURE | Location/Qualifiers |
| source | 1..73<br>mol_type = transcribed RNA<br>organism = Homo sapiens |

SEQUENCE: 213

```
cggcgacggc ggggtgggtg aggtcgggcc ccaagactcg gggtttgccg ggcgcctcag    60
ttcaccgcgg ccg                                                       73
```

| SEQ ID NO: 214 | moltype = RNA  length = 69 |
|---|---|
| FEATURE | Location/Qualifiers |
| source | 1..69<br>mol_type = transcribed RNA<br>organism = Homo sapiens |

SEQUENCE: 214

```
gggcttaggg atgggaggcc aggatgaaga ttaatcccta atccccaaca ctggccttgc    60
tatccccag                                                            69
```

| SEQ ID NO: 215 | moltype = RNA  length = 66 |
|---|---|
| FEATURE | Location/Qualifiers |
| source | 1..66<br>mol_type = transcribed RNA<br>organism = Homo sapiens |

SEQUENCE: 215

```
gggcatgggg aggtgtggag tcagcatggg gctaggaggc ccgcgctga cccgccttct     60
ccgcag                                                               66
```

```
SEQ ID NO: 216          moltype = RNA   length = 87
FEATURE                 Location/Qualifiers
source                  1..87
                        mol_type = transcribed RNA
                        organism = Homo sapiens
SEQUENCE: 216
gtgtggccgg caggcgggtg ggcggggcg gccggtggga acccgcccc gccccgcgcc    60
cgcactcacc cgcccgtctc cccacag                                      87

SEQ ID NO: 217          moltype = RNA   length = 74
FEATURE                 Location/Qualifiers
source                  1..74
                        mol_type = transcribed RNA
                        organism = Homo sapiens
SEQUENCE: 217
gcagcccggt gagcgctcgc tggcctggca gtgcgtcgga agaacagggc gggtggggcc    60
gcgcacatct ctgc                                                     74

SEQ ID NO: 218          moltype = RNA   length = 61
FEATURE                 Location/Qualifiers
source                  1..61
                        mol_type = transcribed RNA
                        organism = Homo sapiens
SEQUENCE: 218
tctcgtttga tctcggaagc taagcagggt tgggcctggt tagtacttgg atgggaaact    60
t                                                                   61

SEQ ID NO: 219          moltype = RNA   length = 53
FEATURE                 Location/Qualifiers
source                  1..53
                        mol_type = transcribed RNA
                        organism = Homo sapiens
SEQUENCE: 219
gtttgatctc ggaagctaag cagggtcggg cctggttagt acttggatgg gag           53

SEQ ID NO: 220          moltype = RNA   length = 85
FEATURE                 Location/Qualifiers
source                  1..85
                        mol_type = transcribed RNA
                        organism = Homo sapiens
SEQUENCE: 220
ggcgcctcct gctctgctgt gccgccaggg cctcccctag cgcgccttct ggagaggctt    60
tgtgcggata cggggctgga ggcct                                         85

SEQ ID NO: 221          moltype = RNA   length = 63
FEATURE                 Location/Qualifiers
source                  1..63
                        mol_type = transcribed RNA
                        organism = Homo sapiens
SEQUENCE: 221
gagtcgagga ctggtggaag ggcctttccc ctcagaccaa ggccctggcc ccagcttctt    60
ctc                                                                 63

SEQ ID NO: 222          moltype = RNA   length = 79
FEATURE                 Location/Qualifiers
source                  1..79
                        mol_type = transcribed RNA
                        organism = Homo sapiens
SEQUENCE: 222
cagcctgggg aaggcttggc agggaagaca catgagcagt gcctccactt cacgcctctc    60
ccttgtctcc tttccctag                                                79

SEQ ID NO: 223          moltype = RNA   length = 86
FEATURE                 Location/Qualifiers
source                  1..86
                        mol_type = transcribed RNA
                        organism = Homo sapiens
SEQUENCE: 223
cgcctgagcg tgcagcagga catcttcctg acctggtaat aattaggtga gaaggatggt    60
tgggggcggt cggcgtaact caggga                                        86

SEQ ID NO: 224          moltype = RNA   length = 71
FEATURE                 Location/Qualifiers
source                  1..71
                        mol_type = transcribed RNA
                        organism = Homo sapiens
SEQUENCE: 224
tgaccacccc cgggcaaaga cctgcagatc ccctgttaga gacgggccca ggactttgtg    60
```

```
cggggtgccc a                                                           71

SEQ ID NO: 225          moltype = RNA   length = 80
FEATURE                 Location/Qualifiers
source                  1..80
                        mol_type = transcribed RNA
                        organism = Homo sapiens
SEQUENCE: 225
gcgtcaagat ggcggcgggg aggtaggcag agcaggacgc cgctgctgcc gccgccaccg     60
ccgcctccgc tccagtcgcc                                                 80

SEQ ID NO: 226          moltype = RNA   length = 82
FEATURE                 Location/Qualifiers
source                  1..82
                        mol_type = transcribed RNA
                        organism = Homo sapiens
SEQUENCE: 226
gtgagtggga ggccagggca cggcaggggg agctgcaggg ctatgggagg ggccccagcg     60
tctgagccct gtcctcccgc ag                                              82

SEQ ID NO: 227          moltype = RNA   length = 82
FEATURE                 Location/Qualifiers
source                  1..82
                        mol_type = transcribed RNA
                        organism = Homo sapiens
SEQUENCE: 227
gtgagtggga ggccagggca cggcaggggg agctgcaggg ctatgggagg ggccccagcg     60
tctgagccct gtcctcccgc ag                                              82

SEQ ID NO: 228          moltype = RNA   length = 65
FEATURE                 Location/Qualifiers
source                  1..65
                        mol_type = transcribed RNA
                        organism = Homo sapiens
SEQUENCE: 228
gagaatgggg ggacagatgg agaggacaca ggctggcact gaggtcccct ccactttcct     60
cctag                                                                 65

SEQ ID NO: 229          moltype = RNA   length = 92
FEATURE                 Location/Qualifiers
source                  1..92
                        mol_type = transcribed RNA
                        organism = Homo sapiens
SEQUENCE: 229
gtcagtgtct gggcggacag ctgcaggaaa gggaagacca aggcttgctg tctgtccagt     60
ctgccaccct accctgtctg ttcttgccac ag                                   92

SEQ ID NO: 230          moltype = RNA   length = 137
FEATURE                 Location/Qualifiers
source                  1..137
                        mol_type = transcribed RNA
                        organism = Homo sapiens
SEQUENCE: 230
agccagacaa gagggtcatg gggagtcact gtcaacccag agcaggcact gccctgcga      60
ccagcctggg gcatcggttg gggtgcaggg gtctgctggt gatgctttcc atctctttgc    120
tttgtcctga ttgtagc                                                   137

SEQ ID NO: 231          moltype = RNA   length = 64
FEATURE                 Location/Qualifiers
source                  1..64
                        mol_type = transcribed RNA
                        organism = Homo sapiens
SEQUENCE: 231
gaaggcgagg ggtagaagag cacaggggtt ctgataaacc cttctgcctg cattctactc     60
ccag                                                                  64

SEQ ID NO: 232          moltype = RNA   length = 67
FEATURE                 Location/Qualifiers
source                  1..67
                        mol_type = transcribed RNA
                        organism = Homo sapiens
SEQUENCE: 232
tacaggccgg ggctttgggt gagggacccc cggagtctgt cacggtctca ccccaactct     60
gccccag                                                               67

SEQ ID NO: 233          moltype = RNA   length = 67
FEATURE                 Location/Qualifiers
source                  1..67
                        mol_type = transcribed RNA
```

```
                        organism = Homo sapiens
SEQUENCE: 233
ccagacccct ggggctgggc aggcggaaag aggtctgaac tgcctctgcc tccttggtct    60
ccggcag                                                              67

SEQ ID NO: 234          moltype = RNA   length = 69
FEATURE                 Location/Qualifiers
source                  1..69
                        mol_type = transcribed RNA
                        organism = Homo sapiens
SEQUENCE: 234
ggccctcggg cctggggttg ggggagctct gtcctgtctc actcattgct cctccctgc     60
ctggcccag                                                            69

SEQ ID NO: 235          moltype = RNA   length = 63
FEATURE                 Location/Qualifiers
source                  1..63
                        mol_type = transcribed RNA
                        organism = Homo sapiens
SEQUENCE: 235
aatgggtggg tgctggtggg agccgtgccc tggccactca ttcggctctc tccctcaccc    60
tag                                                                  63

SEQ ID NO: 236          moltype = RNA   length = 82
FEATURE                 Location/Qualifiers
source                  1..82
                        mol_type = transcribed RNA
                        organism = Homo sapiens
SEQUENCE: 236
tgagctgttg gattcgggc cgtagcactg tctgagaggt ttacatttct cacagtgaac     60
cggtctcttt ttcagctgct tc                                             82

SEQ ID NO: 237          moltype = RNA   length = 68
FEATURE                 Location/Qualifiers
source                  1..68
                        mol_type = transcribed RNA
                        organism = Homo sapiens
SEQUENCE: 237
ctcaggctca gtggtgcatg cttatagtcc cagccactct ggaggctgaa ggaagatggc    60
ttgagcct                                                             68

SEQ ID NO: 238          moltype = RNA   length = 63
FEATURE                 Location/Qualifiers
source                  1..63
                        mol_type = transcribed RNA
                        organism = Homo sapiens
SEQUENCE: 238
cttgcccggg agaaggaggt ggcctggaga gctgctgtct ccagccgccg cctgtctcca    60
cag                                                                  63

SEQ ID NO: 239          moltype = RNA   length = 75
FEATURE                 Location/Qualifiers
source                  1..75
                        mol_type = transcribed RNA
                        organism = Homo sapiens
SEQUENCE: 239
aagcaagact gagggcctc agaccgagct tttggaaaat agaaaagtct cgctctctgc     60
ccctcagcct aactt                                                     75

SEQ ID NO: 240          moltype = RNA   length = 68
FEATURE                 Location/Qualifiers
source                  1..68
                        mol_type = transcribed RNA
                        organism = Homo sapiens
SEQUENCE: 240
cgtggtgagg atatggcagg gaagggagt ttccctctat tccttcccc ccagtaatct      60
tcatcatg                                                             68

SEQ ID NO: 241          moltype = RNA   length = 86
FEATURE                 Location/Qualifiers
source                  1..86
                        mol_type = transcribed RNA
                        organism = Homo sapiens
SEQUENCE: 241
ggggctgggg gtgtgggag agagagtgca cagccagctc aggattaaa gctctttctc      60
tctctctctc tcccacttcc ctgcag                                         86

SEQ ID NO: 242          moltype = RNA   length = 86
FEATURE                 Location/Qualifiers
```

| | |
|---|---|
| source | 1..86<br>mol_type = transcribed RNA<br>organism = Homo sapiens |

SEQUENCE: 242
agggagaagg gtcgggcag ggagggcagg gcaggctctg gggtgggggg tctgtgagtc 60
agccacggct ctgcccacgt ctcccc 86

| | |
|---|---|
| SEQ ID NO: 243 | moltype = RNA length = 73 |
| FEATURE | Location/Qualifiers |
| source | 1..73<br>mol_type = transcribed RNA<br>organism = Homo sapiens |

SEQUENCE: 243
ctggtgtttg aggcgatgtg gggatgtaga dacaacttcc cagtctcatt tcctcatcct 60
gccaggccac cat 73

| | |
|---|---|
| SEQ ID NO: 244 | moltype = RNA length = 98 |
| FEATURE | Location/Qualifiers |
| source | 1..98<br>mol_type = transcribed RNA<br>organism = Homo sapiens |

SEQUENCE: 244
cttggtcaat aggaaagagg tgggacctcc tggcttttcc tctgcagcat ggctcggacc 60
tagtgcaatg tttaagctcc cctctctttc ctgttcag 98

| | |
|---|---|
| SEQ ID NO: 245 | moltype = RNA length = 102 |
| FEATURE | Location/Qualifiers |
| source | 1..102<br>mol_type = transcribed RNA<br>organism = Homo sapiens |

SEQUENCE: 245
tgtgttccct atcctcctta tgtcccaccc ccactcctgt ttgaatattt caccagaaac 60
aggagtgggg ggtgggacgt aaggaggatg gggaaagaa ca 102

| | |
|---|---|
| SEQ ID NO: 246 | moltype = RNA length = 68 |
| FEATURE | Location/Qualifiers |
| source | 1..68<br>mol_type = transcribed RNA<br>organism = Homo sapiens |

SEQUENCE: 246
tgcccaggct ggagcgagtg cagtggtgca gtcagtccta gctcactgca gcctcgaact 60
cctgggct 68

| | |
|---|---|
| SEQ ID NO: 247 | moltype = RNA length = 83 |
| FEATURE | Location/Qualifiers |
| source | 1..83<br>mol_type = transcribed RNA<br>organism = Homo sapiens |

SEQUENCE: 247
aatagagggt gcacaggcac gggagctcag gtgaggcagg gagctgagct cacctgacct 60
cccatgcctg tgcaccctct att 83

| | |
|---|---|
| SEQ ID NO: 248 | moltype = RNA length = 76 |
| FEATURE | Location/Qualifiers |
| source | 1..76<br>mol_type = transcribed RNA<br>organism = Homo sapiens |

SEQUENCE: 248
actgactttg agtctctcct cagggtgctg caggcaaagc tggggaccca gggagagacg 60
taagtgaggg gagatg 76

| | |
|---|---|
| SEQ ID NO: 249 | moltype = RNA length = 63 |
| FEATURE | Location/Qualifiers |
| source | 1..63<br>mol_type = transcribed RNA<br>organism = Homo sapiens |

SEQUENCE: 249
tggtggcggc ggtagttatg ggcttctctt tctcaccagc agccctgggg ccgccgcctc 60
cct 63

| | |
|---|---|
| SEQ ID NO: 250 | moltype = RNA length = 93 |
| FEATURE | Location/Qualifiers |
| source | 1..93<br>mol_type = transcribed RNA<br>organism = Homo sapiens |

SEQUENCE: 250
gcttgttggg gattgggtca ggccagtgtt caagggcccc tcctctagta ctccctgttt 60
gtgttctgcc actgactgag cttctcccca cag 93

```
SEQ ID NO: 251         moltype = RNA   length = 57
FEATURE                Location/Qualifiers
source                 1..57
                       mol_type = transcribed RNA
                       organism = Homo sapiens
SEQUENCE: 251
cattggaggg tgtggaagac atctgggcca actctgatct cttcatctac cccccag      57

SEQ ID NO: 252         moltype = RNA   length = 109
FEATURE                Location/Qualifiers
source                 1..109
                       mol_type = transcribed RNA
                       organism = Homo sapiens
SEQUENCE: 252
ggtcgggctc accatgacac agtgtgagac ctcgggctac aacacaggac ccgggcgctg   60
ctctgacccc tcgtgtcttg tgttgcagcc ggagggacgc aggtccgca              109

SEQ ID NO: 253         moltype = RNA   length = 68
FEATURE                Location/Qualifiers
source                 1..68
                       mol_type = transcribed RNA
                       organism = Homo sapiens
SEQUENCE: 253
gaatggaaga agaaggcggt cggtctgcgg gagccaggcc gcagagccat ccgccttctg   60
tccatgtc                                                            68

SEQ ID NO: 254         moltype = RNA   length = 77
FEATURE                Location/Qualifiers
source                 1..77
                       mol_type = transcribed RNA
                       organism = Homo sapiens
SEQUENCE: 254
gagttgggag gttccctctc caaatgtgtc ttgatccccc accccaagac acatttggag   60
agggaccctc ccaactc                                                  77

SEQ ID NO: 255         moltype = RNA   length = 66
FEATURE                Location/Qualifiers
source                 1..66
                       mol_type = transcribed RNA
                       organism = Homo sapiens
SEQUENCE: 255
gggaggaggg aggagatggg ccaagttccc tctggctgga acgcccttcc ccccttctt    60
cacctg                                                              66

SEQ ID NO: 256         moltype = RNA   length = 98
FEATURE                Location/Qualifiers
source                 1..98
                       mol_type = transcribed RNA
                       organism = Homo sapiens
SEQUENCE: 256
ttgggcaagg tgcggggcta gggctaacag cagtcttact gaaggtttcc tggaaaccac   60
gcacatgctg ttgccactaa cctcaacctt actcggtc                           98

SEQ ID NO: 257         moltype = RNA   length = 67
FEATURE                Location/Qualifiers
source                 1..67
                       mol_type = transcribed RNA
                       organism = Homo sapiens
SEQUENCE: 257
gcgccctccc tctctccccg gtgtgcaaat gtgtgtgtgc ggtgttatgc cggacaagag   60
ggaggtg                                                             67

SEQ ID NO: 258         moltype = RNA   length = 73
FEATURE                Location/Qualifiers
source                 1..73
                       mol_type = transcribed RNA
                       organism = Homo sapiens
SEQUENCE: 258
gtgggcgggg gcaggtgtgt ggtgggtggt ggcctgcggt gagcagggcc ctcacacctg   60
cctcgccccc cag                                                      73

SEQ ID NO: 259         moltype = RNA   length = 82
FEATURE                Location/Qualifiers
source                 1..82
                       mol_type = transcribed RNA
                       organism = Homo sapiens
SEQUENCE: 259
tgtgggcagg gccctgggga gctgaggctc tggggtggc cggggctgac cctgggcctc    60
tgctccccag tgtctgaccg cg                                            82
```

```
SEQ ID NO: 260           moltype = RNA   length = 61
FEATURE                  Location/Qualifiers
source                   1..61
                         mol_type = transcribed RNA
                         organism = Homo sapiens
SEQUENCE: 260
aactgcgggg ccagagcaga gagcccttgc acaccaccag cctctcctcc ctgtgcccca    60
g                                                                   61

SEQ ID NO: 261           moltype = RNA   length = 79
FEATURE                  Location/Qualifiers
source                   1..79
                         mol_type = transcribed RNA
                         organism = Homo sapiens
SEQUENCE: 261
gtgcagatcc ttgggagccc tgttagactc tggattttac acttggagtg aacgggcgcc    60
atcccgaggc tttgcacag                                                 79

SEQ ID NO: 262           moltype = RNA   length = 99
FEATURE                  Location/Qualifiers
source                   1..99
                         mol_type = transcribed RNA
                         organism = Homo sapiens
SEQUENCE: 262
gcaagggaca gggagggtcg tggcgacact cgcgccagct cccgggacgg ctgggctcgg    60
gctggtcgcg gacctccgac cctccactag atgcctggc                          99

SEQ ID NO: 263           moltype = RNA   length = 65
FEATURE                  Location/Qualifiers
source                   1..65
                         mol_type = transcribed RNA
                         organism = Homo sapiens
SEQUENCE: 263
gagggtgggc gagggcggct gagcggctcc atccccggc ctgctcatcc ccctcgccct     60
ctcag                                                               65

SEQ ID NO: 264           moltype = RNA   length = 61
FEATURE                  Location/Qualifiers
source                   1..61
                         mol_type = transcribed RNA
                         organism = Homo sapiens
SEQUENCE: 264
gagggcagcg tgggtgtggc ggaggcaggc gtgaccgttt gccgccctct cgctgctcta    60
g                                                                   61

SEQ ID NO: 265           moltype = RNA   length = 96
FEATURE                  Location/Qualifiers
source                   1..96
                         mol_type = transcribed RNA
                         organism = Homo sapiens
SEQUENCE: 265
ctcgggaggg gcgggagggg ggtccccggt gctcggatct cgagggtgct tattgttcgg    60
tccgagcctg ggtctccctc ttccccccaa cccccc                             96

SEQ ID NO: 266           moltype = RNA   length = 92
FEATURE                  Location/Qualifiers
source                   1..92
                         mol_type = transcribed RNA
                         organism = Homo sapiens
SEQUENCE: 266
cgctgcgctt ctgggcccgc ggcgggcgtg gggctgcccg ggccggtcga ccagcgcgcc    60
gtagctcccg aggcccgagc cgcgacccgc gg                                 92

SEQ ID NO: 267           moltype = RNA   length = 67
FEATURE                  Location/Qualifiers
source                   1..67
                         mol_type = transcribed RNA
                         organism = Homo sapiens
SEQUENCE: 267
gtgggagggg agaggcagca agcacacagg gcctgggact agcatgctga cctccctcct    60
gccccag                                                             67

SEQ ID NO: 268           moltype = RNA   length = 60
FEATURE                  Location/Qualifiers
source                   1..60
                         mol_type = transcribed RNA
                         organism = Homo sapiens
SEQUENCE: 268
```

```
aggcctaggg ggtggcaggc tggccatcag tgtgggctaa ccctgtcctc tccctcccag    60

SEQ ID NO: 269        moltype = RNA    length = 66
FEATURE               Location/Qualifiers
source                1..66
                      mol_type = transcribed RNA
                      organism = Homo sapiens
SEQUENCE: 269
ccgagtgggg cggggcaggt ccctgcaggg actgtgacac tgaaggacct gcaccttcgc    60
ccacag                                                                66

SEQ ID NO: 270        moltype = RNA    length = 74
FEATURE               Location/Qualifiers
source                1..74
                      mol_type = transcribed RNA
                      organism = Homo sapiens
SEQUENCE: 270
cctgcaggag gcagtgggcg agcaggcggg gcagcccaat gccatgggcc tgatctcacc    60
gctgcctcct tccc                                                       74

SEQ ID NO: 271        moltype = RNA    length = 51
FEATURE               Location/Qualifiers
source                1..51
                      mol_type = transcribed RNA
                      organism = Homo sapiens
SEQUENCE: 271
agagatgaag cggggggcg gggtcttgct ctattgccta cgctgatctc a               51

SEQ ID NO: 272        moltype = RNA    length = 68
FEATURE               Location/Qualifiers
source                1..68
                      mol_type = transcribed RNA
                      organism = Homo sapiens
SEQUENCE: 272
gtgcaaagag caggaggaca ggggatttat ctcccaaggg aggtcccctg atcctagtca    60
cggcacca                                                              68

SEQ ID NO: 273        moltype = RNA    length = 73
FEATURE               Location/Qualifiers
source                1..73
                      mol_type = transcribed RNA
                      organism = Homo sapiens
SEQUENCE: 273
ggcgagggga ggcgcaggct cggaaaggcg cgcgaggctc caggctcctt cccgatccac    60
cgctctcctc gct                                                        73

SEQ ID NO: 274        moltype = RNA    length = 96
FEATURE               Location/Qualifiers
source                1..96
                      mol_type = transcribed RNA
                      organism = Homo sapiens
SEQUENCE: 274
gctctgggc gtgccgccgc cgtcgctgcc acctccccta ccgctagtgg aagaagatgg    60
cggaaggcgg agcggcggat ctggacaccc agcggt                              96

SEQ ID NO: 275        moltype = RNA    length = 81
FEATURE               Location/Qualifiers
source                1..81
                      mol_type = transcribed RNA
                      organism = Homo sapiens
SEQUENCE: 275
catcctcctt acgtcccacc ccccactcct gtttctggtg aaatattcaa acaggagtgg    60
gggtgggaca taaggaggat a                                              81

SEQ ID NO: 276        moltype = RNA    length = 65
FEATURE               Location/Qualifiers
source                1..65
                      mol_type = transcribed RNA
                      organism = Homo sapiens
SEQUENCE: 276
gggtgctcgg ggcaggcggc tgggagcggc cctcacattg atggctcctg ccacctcctc    60
cgcag                                                                 65

SEQ ID NO: 277        moltype = RNA    length = 82
FEATURE               Location/Qualifiers
source                1..82
                      mol_type = transcribed RNA
                      organism = Homo sapiens
SEQUENCE: 277
```

```
gctacgggga gcgggagga agtgggcgct gcttctgcgt tatctggaag gagcagccca    60
ctcctgtcct gggctctgtg gt                                            82

SEQ ID NO: 278          moltype = RNA   length = 103
FEATURE                 Location/Qualifiers
source                  1..103
                        mol_type = transcribed RNA
                        organism = Homo sapiens
SEQUENCE: 278
gtgtcggctg tggcgtgact gtccctctgt gtcccccact aggcccactg ctcagtggag    60
cgtggaggac gaggaggagg ccgtccacga gcaatgccag cat                    103

SEQ ID NO: 279          moltype = RNA   length = 62
FEATURE                 Location/Qualifiers
source                  1..62
                        mol_type = transcribed RNA
                        organism = Homo sapiens
SEQUENCE: 279
tggcctaggg ggcggcttgt ggagtgtatg ggctgagcct tgctctgctc ccccgccccc    60
ag                                                                  62

SEQ ID NO: 280          moltype = RNA   length = 72
FEATURE                 Location/Qualifiers
source                  1..72
                        mol_type = transcribed RNA
                        organism = Homo sapiens
SEQUENCE: 280
atgagcgggt gggagcagat cttattgaga gttccttctc ctgctcctga ttgtcttccc    60
ccaccctcac ag                                                       72

SEQ ID NO: 281          moltype = RNA   length = 80
FEATURE                 Location/Qualifiers
source                  1..80
                        mol_type = transcribed RNA
                        organism = Homo sapiens
SEQUENCE: 281
acctctacct cccggcagag gaggctgcag aggctggctt tccaaaactc tgcccctcc     60
gctgctgcca agtggctggt                                               80

SEQ ID NO: 282          moltype = RNA   length = 64
FEATURE                 Location/Qualifiers
source                  1..64
                        mol_type = transcribed RNA
                        organism = Homo sapiens
SEQUENCE: 282
tctgggcgag gggtgggctc tcagaggggc tggcagtact gctctgaggc ctgcctctcc    60
ccag                                                                64

SEQ ID NO: 283          moltype = RNA   length = 98
FEATURE                 Location/Qualifiers
source                  1..98
                        mol_type = transcribed RNA
                        organism = Homo sapiens
SEQUENCE: 283
ttctcacccc cgcctgacac gggcgacagc tgcggcccgc tgtgttcact cgggccgagt    60
gcgtctcctg tcaggcaagg gagagcagag ccccctg                            98

SEQ ID NO: 284          moltype = RNA   length = 97
FEATURE                 Location/Qualifiers
source                  1..97
                        mol_type = transcribed RNA
                        organism = Homo sapiens
SEQUENCE: 284
cccgggacct tggtccaggc gctggtctgc gtggtgctcg ggtggataag tctgatctga    60
gcaccacaca ggccgggcgc cgggaccaag ggggctc                            97

SEQ ID NO: 285          moltype = RNA   length = 69
FEATURE                 Location/Qualifiers
source                  1..69
                        mol_type = transcribed RNA
                        organism = Homo sapiens
SEQUENCE: 285
ccgggcaggc aggtgtaggg tggagcccac tgtggctcct gactcagccc tgctgccttc    60
acctgccag                                                           69

SEQ ID NO: 286          moltype = RNA   length = 64
FEATURE                 Location/Qualifiers
source                  1..64
                        mol_type = transcribed RNA
```

```
                            organism = Homo sapiens
SEQUENCE: 286
gaggcactgg gtaggtgggg ctccagggct cctgacacct ggacctctcc tccccaggcc    60
caca                                                                 64

SEQ ID NO: 287              moltype = RNA    length = 66
FEATURE                     Location/Qualifiers
source                      1..66
                            mol_type = transcribed RNA
                            organism = Homo sapiens
SEQUENCE: 287
agcagccctc ggcggcccgg ggggcgggcg gcggtgcccg tcccggggct gcgcgaggca    60
caggcg                                                               66

SEQ ID NO: 288              moltype = RNA    length = 65
FEATURE                     Location/Qualifiers
source                      1..65
                            mol_type = transcribed RNA
                            organism = Homo sapiens
SEQUENCE: 288
agccctgggg gtggtctcta gccaaggctc tggggtctca cccttggctg gtctctgctc    60
cgcag                                                                65

SEQ ID NO: 289              moltype = RNA    length = 55
FEATURE                     Location/Qualifiers
source                      1..55
                            mol_type = transcribed RNA
                            organism = Homo sapiens
SEQUENCE: 289
ccggatccga gtcacggcac caaatttcat gcgtgtccgt gtgaagagac cacca         55

SEQ ID NO: 290              moltype = RNA    length = 115
FEATURE                     Location/Qualifiers
source                      1..115
                            mol_type = transcribed RNA
                            organism = Homo sapiens
SEQUENCE: 290
gagcaaaaac cagagaacaa catgggagcg ttcctaaccc ctaaggcaac tggatgggag    60
acctgaccca tccagttctc tgaggggct cttgtgtgtt ctacaaggtt gttca         115

SEQ ID NO: 291              moltype = RNA    length = 115
FEATURE                     Location/Qualifiers
source                      1..115
                            mol_type = transcribed RNA
                            organism = Homo sapiens
SEQUENCE: 291
ggtgccgagg gccgtccggc atcctaggcg ggtcgctgcg gtacctcct cctgtctgtg     60
gcggtgggat cccgtggccg tgttttcctg gtgcccggc cgtgcctgag gtttc         115

SEQ ID NO: 292              moltype = RNA    length = 87
FEATURE                     Location/Qualifiers
source                      1..87
                            mol_type = transcribed RNA
                            organism = Homo sapiens
SEQUENCE: 292
gtgaggcggg gccaggaggg tgtgtggcgt gggtgctgcg gggccgtcag ggtgcctgcg    60
ggacgctcac ctggctggcc cgcccag                                        87

SEQ ID NO: 293              moltype = RNA    length = 86
FEATURE                     Location/Qualifiers
source                      1..86
                            mol_type = transcribed RNA
                            organism = Homo sapiens
SEQUENCE: 293
attctaggtg gggagactga cggctggagg cccataagct gtctaaaact tcggccccca    60
gatttctggt ctccccactt cagaac                                         86

SEQ ID NO: 294              moltype = RNA    length = 90
FEATURE                     Location/Qualifiers
source                      1..90
                            mol_type = transcribed RNA
                            organism = Homo sapiens
SEQUENCE: 294
tctaagaaac gcagtggtct ctgaagcctg caggggcagg ccagccctgc actgaacgcc    60
tgttcttgcc aggtggcaga aggttgctgc                                     90

SEQ ID NO: 295              moltype = RNA    length = 81
FEATURE                     Location/Qualifiers
source                      1..81
```

```
                        mol_type = transcribed RNA
                        organism = Homo sapiens
SEQUENCE: 295
ctccctggga gggcgtggat gatggtggga gaggagcccc actgtggaag tctgaccccc    60
acatcgcccc accttcccca g                                              81

SEQ ID NO: 296          moltype = RNA   length = 66
FEATURE                 Location/Qualifiers
source                  1..66
                        mol_type = transcribed RNA
                        organism = Homo sapiens
SEQUENCE: 296
tcaagacggg gagtcaggca gtggtggaga tggagagccc tgagcctcca ctctcctggc    60
ccccag                                                               66

SEQ ID NO: 297          moltype = RNA   length = 94
FEATURE                 Location/Qualifiers
source                  1..94
                        mol_type = transcribed RNA
                        organism = Homo sapiens
SEQUENCE: 297
gtgaggtgtg ggcccggccc caggagcggg gcctgggcag ccccgtgtgt tgaggaagga    60
aggcagggcc cccgctcccc gggcctgacc ccac                                94

SEQ ID NO: 298          moltype = RNA   length = 90
FEATURE                 Location/Qualifiers
source                  1..90
                        mol_type = transcribed RNA
                        organism = Homo sapiens
SEQUENCE: 298
cgggcgggc gggtccggcc gcctccgagc ccggccggca gccccggcc ttaaagcgcg      60
ggctgtccgg aggggtcggc tttcccaccg                                     90

SEQ ID NO: 299          moltype = RNA   length = 60
FEATURE                 Location/Qualifiers
source                  1..60
                        mol_type = transcribed RNA
                        organism = Homo sapiens
SEQUENCE: 299
caaggtgggg gagatggggg ttgaacttca tttctcatgc tcatcccat ctcctttcag     60

SEQ ID NO: 300          moltype = RNA   length = 109
FEATURE                 Location/Qualifiers
source                  1..109
                        mol_type = transcribed RNA
                        organism = Homo sapiens
SEQUENCE: 300
tcccgcattc cctctgcttt ggtcaggtgg tgccctcctt ccatgggtag agccagagat    60
ggtgggttct ggctggtcag atgggagtgg acagagaccc ggggtcctc               109

SEQ ID NO: 301          moltype = RNA   length = 84
FEATURE                 Location/Qualifiers
source                  1..84
                        mol_type = transcribed RNA
                        organism = Homo sapiens
SEQUENCE: 301
ctccccatgg ccctgtctcc caacccttgt accagtgctg ggctcagacc ctggtacagg    60
cctggggac agggacctgg ggac                                            84

SEQ ID NO: 302          moltype = RNA   length = 80
FEATURE                 Location/Qualifiers
source                  1..80
                        mol_type = transcribed RNA
                        organism = Homo sapiens
SEQUENCE: 302
ggttccggag ccccggcgcg ggcgggttct ggggtgtaga cgctgctggc cagcccgccc    60
cagccgaggt tctcggcacc                                                80

SEQ ID NO: 303          moltype = RNA   length = 80
FEATURE                 Location/Qualifiers
source                  1..80
                        mol_type = transcribed RNA
                        organism = Homo sapiens
SEQUENCE: 303
tgagaggccg caccttgcct tgctgcccgg gccgtgcacc cgtgggcccc agggcgacgc    60
ggcggggcg gccctagcga                                                 80

SEQ ID NO: 304          moltype = RNA   length = 106
FEATURE                 Location/Qualifiers
```

```
source                  1..106
                        mol_type = transcribed RNA
                        organism = Homo sapiens
SEQUENCE: 304
agaagaatgc ccaaccagcc ctcagttgct acagttccct gttgtttcag ctcgacaaca    60
acaggcggct gtagcaatgg ggggctggat gggcatctca atgtgc                  106

SEQ ID NO: 305          moltype = RNA   length = 86
FEATURE                 Location/Qualifiers
source                  1..86
                        mol_type = transcribed RNA
                        organism = Homo sapiens
SEQUENCE: 305
agcactgccc ccggtgagtc agggtggggc tggcccctg cttcgtgccc atccgcgctc     60
tgactctctg cccacctgca ggagct                                         86

SEQ ID NO: 306          moltype = RNA   length = 53
FEATURE                 Location/Qualifiers
source                  1..53
                        mol_type = transcribed RNA
                        organism = Homo sapiens
SEQUENCE: 306
ggtgggggtt ggaggcgtgg gttttagaac ctatcccttt ctagccctga gca            53

SEQ ID NO: 307          moltype = RNA   length = 80
FEATURE                 Location/Qualifiers
source                  1..80
                        mol_type = transcribed RNA
                        organism = Homo sapiens
SEQUENCE: 307
cgtgtgagcc cgccctgtgc ccggcccact tctgcttcct cttagcgcag gaggggtccc    60
gcactgggag gggccctcac                                                80

SEQ ID NO: 308          moltype = RNA   length = 79
FEATURE                 Location/Qualifiers
source                  1..79
                        mol_type = transcribed RNA
                        organism = Homo sapiens
SEQUENCE: 308
gtgaggtggg ggccagcagg gagtgggctg ggctgggctg gccaaggta caaggcctca     60
ccctgcatcc cgcacccag                                                 79

SEQ ID NO: 309          moltype = RNA   length = 50
FEATURE                 Location/Qualifiers
source                  1..50
                        mol_type = transcribed RNA
                        organism = Homo sapiens
SEQUENCE: 309
acccgggcgt ggtggtgggg gtgggtgcct gtaattccag ctagttggga               50

SEQ ID NO: 310          moltype = RNA   length = 88
FEATURE                 Location/Qualifiers
source                  1..88
                        mol_type = transcribed RNA
                        organism = Homo sapiens
SEQUENCE: 310
gtggggccag gcggtggtgg gcactgctgg ggtgggcaca gcagccatgc agagcgggca    60
tttgaccccg tgccaccctt ttccccag                                       88

SEQ ID NO: 311          moltype = RNA   length = 62
FEATURE                 Location/Qualifiers
source                  1..62
                        mol_type = transcribed RNA
                        organism = Homo sapiens
SEQUENCE: 311
gagggtggtg gaggaagagg gcagctccca tgactgcctg accgccttct ctcctcccc     60
ag                                                                   62

SEQ ID NO: 312          moltype = RNA   length = 73
FEATURE                 Location/Qualifiers
source                  1..73
                        mol_type = transcribed RNA
                        organism = Homo sapiens
SEQUENCE: 312
gaaaacaacc aggtgggctt cccggagggc ggaacaccca gccccagcat ccagggctca    60
cctaccacgt ttg                                                       73

SEQ ID NO: 313          moltype = RNA   length = 65
FEATURE                 Location/Qualifiers
```

```
source                  1..65
                        mol_type = transcribed RNA
                        organism = Homo sapiens
SEQUENCE: 313
gagggctagg tgggggcttt gaagccccga gatgcctcac gtcttcaccc ctctcaccta    60
agcag                                                                65

SEQ ID NO: 314          moltype = RNA  length = 73
FEATURE                 Location/Qualifiers
source                  1..73
                        mol_type = transcribed RNA
                        organism = Homo sapiens
SEQUENCE: 314
aggccaggtg ggtatggagg agccctcata tggcagttgg cgagggccca gtgagcccct    60
ctctgctctc cag                                                       73

SEQ ID NO: 315          moltype = RNA  length = 93
FEATURE                 Location/Qualifiers
source                  1..93
                        mol_type = transcribed RNA
                        organism = Homo sapiens
SEQUENCE: 315
ccttccggcg tcccaggcgg ggcgccgcgg gaccgccctc gtgtctgtgg cggtgggatc    60
ccgcggccgt gttttcctgg tggcccggcc atg                                 93

SEQ ID NO: 316          moltype = RNA  length = 87
FEATURE                 Location/Qualifiers
source                  1..87
                        mol_type = transcribed RNA
                        organism = Homo sapiens
SEQUENCE: 316
ccctcatctc tgggcagggg cttattgtag gagtctctga agagagctgt ggactgacct    60
gctttaaccc ttccccaggt tcccatt                                        87

SEQ ID NO: 317          moltype = RNA  length = 51
FEATURE                 Location/Qualifiers
source                  1..51
                        mol_type = transcribed RNA
                        organism = Homo sapiens
SEQUENCE: 317
acagaccccg gggagcccgg cggtgaagct cctggtatcc tgggtgtctg a              51

SEQ ID NO: 318          moltype = RNA  length = 49
FEATURE                 Location/Qualifiers
source                  1..49
                        mol_type = transcribed RNA
                        organism = Homo sapiens
SEQUENCE: 318
ttcccagcca acgcaccaaa aatgatatgg gtctgttgtc tggagaaac                 49

SEQ ID NO: 319          moltype = RNA  length = 96
FEATURE                 Location/Qualifiers
source                  1..96
                        mol_type = transcribed RNA
                        organism = Homo sapiens
SEQUENCE: 319
cgggccccgg gcgggcggga gggacgggac gcggtgcagt gttgtttttt ccccgccaa    60
tattgcactc gtcccggcct ccggcccccc cggccc                              96

SEQ ID NO: 320          moltype = RNA  length = 67
FEATURE                 Location/Qualifiers
source                  1..67
                        mol_type = transcribed RNA
                        organism = Homo sapiens
SEQUENCE: 320
gtggcactca aactgtgggg gcactttctg ctctctggtg aaagtgccgc catcttttga    60
gtgttac                                                              67

SEQ ID NO: 321          moltype = RNA  length = 89
FEATURE                 Location/Qualifiers
source                  1..89
                        mol_type = transcribed RNA
                        organism = Homo sapiens
SEQUENCE: 321
agcctgtggg aaagagaaga gcagggcagg gtgaaggccc ggcggagaca ctctgcccac    60
cccacaccct gcctatgggc cacacagct                                      89

SEQ ID NO: 322          moltype = RNA  length = 70
FEATURE                 Location/Qualifiers
```

```
source                      1..70
                            mol_type = transcribed RNA
                            organism = Homo sapiens
SEQUENCE: 322
ctcgggcccg accgcgccgg cccgcacctc ccggcccgga gctgcgggct gcggtcaggg    60
cgatcccggg                                                          70

SEQ ID NO: 323              moltype = RNA  length = 79
FEATURE                     Location/Qualifiers
source                      1..79
                            mol_type = transcribed RNA
                            organism = Homo sapiens
SEQUENCE: 323
ctcgaggtgc tggggacgc gtgagcgcga gccgcttcct cacggctcgg ccgcggcgcg     60
tagcccccgc cacatcggg                                                79

SEQ ID NO: 324              moltype = RNA  length = 94
FEATURE                     Location/Qualifiers
source                      1..94
                            mol_type = transcribed RNA
                            organism = Homo sapiens
SEQUENCE: 324
ataaaggaag ttaggctgag gggcagagag cgagactttt ctattttcca aaagctcggt    60
ctgaggcccc tcagtcttgc ttcctaaccc gcgc                                94

SEQ ID NO: 325              moltype = RNA  length = 47
FEATURE                     Location/Qualifiers
source                      1..47
                            mol_type = transcribed RNA
                            organism = Homo sapiens
SEQUENCE: 325
ctcggcgcgg ggcgcgggct ccgggttggg gcgagccaac gccgggg                  47

SEQ ID NO: 326              moltype = RNA  length = 77
FEATURE                     Location/Qualifiers
source                      1..77
                            mol_type = transcribed RNA
                            organism = Homo sapiens
SEQUENCE: 326
catgagaaat cctgctggtc aaccatagcc ctggtcagac tctccggggc tgtgattgac    60
cagcaggact tctcatg                                                  77

SEQ ID NO: 327              moltype = RNA  length = 80
FEATURE                     Location/Qualifiers
source                      1..80
                            mol_type = transcribed RNA
                            organism = Homo sapiens
SEQUENCE: 327
gagaggccaa gaccttggga atgggggtaa gggccttctg agcccaggtc cgaactctcc    60
attcctctgc agagcgctct                                               80

SEQ ID NO: 328              moltype = RNA  length = 70
FEATURE                     Location/Qualifiers
source                      1..70
                            mol_type = transcribed RNA
                            organism = Homo sapiens
SEQUENCE: 328
ggccgcggcg cgcaagatgg cggcgggccc gggcaccgcc ccttccgccc gccgggcgt    60
cgcacgaggc                                                          70

SEQ ID NO: 329              moltype = RNA  length = 62
FEATURE                     Location/Qualifiers
source                      1..62
                            mol_type = transcribed RNA
                            organism = Homo sapiens
SEQUENCE: 329
gctggggtc ccccgacagt gtggagctgg ggccgggtcc cggggagggg ggttctgggc    60
ag                                                                  62

SEQ ID NO: 330              moltype = RNA  length = 62
FEATURE                     Location/Qualifiers
source                      1..62
                            mol_type = transcribed RNA
                            organism = Homo sapiens
SEQUENCE: 330
ccttctgcgg cagagctggg gtcaccagcc ctcatgtact tgtgacttct ccctgccac    60
ag                                                                  62

SEQ ID NO: 331              moltype = RNA  length = 68
```

| FEATURE | Location/Qualifiers |
|---|---|
| source | 1..68 |
| | mol_type = transcribed RNA |
| | organism = Homo sapiens |

SEQUENCE: 331
agggttgggg ggacaggatg agaggctgtc ttcattccct cttgaccacc cctcgtttct  60
tccccag                                                             68

| SEQ ID NO: 332 | moltype = RNA   length = 64 |
|---|---|
| FEATURE | Location/Qualifiers |
| source | 1..64 |
| | mol_type = transcribed RNA |
| | organism = Homo sapiens |

SEQUENCE: 332
gagctctggg aggggctggg tttggcagga cagtttccaa gccctgtctc ctcccatctt  60
ccag                                                                64

| SEQ ID NO: 333 | moltype = RNA   length = 65 |
|---|---|
| FEATURE | Location/Qualifiers |
| source | 1..65 |
| | mol_type = transcribed RNA |
| | organism = Homo sapiens |

SEQUENCE: 333
gtctcctggg gggaggagac cctgctctcc ctggcagcaa gcctctcctg cccttccaga  60
ttagc                                                               65

| SEQ ID NO: 334 | moltype = RNA   length = 67 |
|---|---|
| FEATURE | Location/Qualifiers |
| source | 1..67 |
| | mol_type = transcribed RNA |
| | organism = Homo sapiens |

SEQUENCE: 334
ggcagccagg gggatgggcg agcttgggcc cattcctttc cttaccctac ccccatccc   60
cctgtag                                                             67

| SEQ ID NO: 335 | moltype = RNA   length = 72 |
|---|---|
| FEATURE | Location/Qualifiers |
| source | 1..72 |
| | mol_type = transcribed RNA |
| | organism = Homo sapiens |

SEQUENCE: 335
tgtgggactg caaatgggag ctcagcacct gcctgccacc cacgcagacc agccctgct   60
ctgttcccac ag                                                       72

| SEQ ID NO: 336 | moltype = RNA   length = 81 |
|---|---|
| FEATURE | Location/Qualifiers |
| source | 1..81 |
| | mol_type = transcribed RNA |
| | organism = Homo sapiens |

SEQUENCE: 336
tacaggtgca ggggaactgt agatgaaaag gcttggcact tgagggaaag cctcagttca  60
ttctcattt gctcacctgt t                                              81

| SEQ ID NO: 337 | moltype = RNA   length = 109 |
|---|---|
| FEATURE | Location/Qualifiers |
| source | 1..109 |
| | mol_type = transcribed RNA |
| | organism = Homo sapiens |

SEQUENCE: 337
tgctattgtc ttactgctac agcagggctg gggattgcag tatccgctgt tgctgctgct  60
cccagtcctg cccctgctgc tacctagtcc agcctcaccg catcccaga              109

| SEQ ID NO: 338 | moltype = RNA   length = 80 |
|---|---|
| FEATURE | Location/Qualifiers |
| source | 1..80 |
| | mol_type = transcribed RNA |
| | organism = Homo sapiens |

SEQUENCE: 338
ctgcagcgtg cttctccagg ccccgcgcgc ggacagacac acggacaagt cccgccaggg  60
gctgggcgcg cgccagccgg                                               80

| SEQ ID NO: 339 | moltype = RNA   length = 80 |
|---|---|
| FEATURE | Location/Qualifiers |
| source | 1..80 |
| | mol_type = transcribed RNA |
| | organism = Homo sapiens |

SEQUENCE: 339
tgccgtcggc ctggggagga ggaagggcaa gtccaaaggt atacagttgg tctgttcatt  60
ctctcttttt ggcctacaag                                               80

```
SEQ ID NO: 340          moltype = RNA   length = 84
FEATURE                 Location/Qualifiers
source                  1..84
                        mol_type = transcribed RNA
                        organism = Homo sapiens
SEQUENCE: 340
ccgcagccgc cgcgccgggc ccgggttggc cgctgacccc cgcggggccc ccggcggccg   60
gggcgggggc gggggctgcc ccgg                                          84

SEQ ID NO: 341          moltype = RNA   length = 153
FEATURE                 Location/Qualifiers
source                  1..153
                        mol_type = transcribed RNA
                        organism = Homo sapiens
SEQUENCE: 341
gctccgcccc acgtcgcatg cgccccggga acgcgtgggg cggagcttcc ggaggccccg   60
ctctgctgcc gaccctgtgg agcggagggt gaagcctccg gatgccagtc cctcatcgct  120
ggcctggtcg cgctgtggcg aaggggcgg agc                                153

SEQ ID NO: 342          moltype = RNA   length = 153
FEATURE                 Location/Qualifiers
source                  1..153
                        mol_type = transcribed RNA
                        organism = Homo sapiens
SEQUENCE: 342
gctccgcccc acgtcgcatg cgccccggga acgcgtgggg cggagcttcc ggaggccccg   60
ccctgctgcc gaccctgtgg agcggagggt gaagcctccg gatgccagtc cctcatcgct  120
ggcccggtcg cgctgtggcg aaggggcgg agc                                153

SEQ ID NO: 343          moltype = RNA   length = 80
FEATURE                 Location/Qualifiers
source                  1..80
                        mol_type = transcribed RNA
                        organism = Homo sapiens
SEQUENCE: 343
aggacccttc cagagggccc ccctcaatc ctgttgtgcc taattcagag ggttgggtgg    60
aggctctcct gaagggctct                                               80

SEQ ID NO: 344          moltype = RNA   length = 94
FEATURE                 Location/Qualifiers
source                  1..94
                        mol_type = transcribed RNA
                        organism = Homo sapiens
SEQUENCE: 344
cgggcagcgg gtgccaggca cggtgtcagc aggcaacatg gccagagagc cggggcctcc   60
gggcggcgcc gtgtccgcga ccgcgtaccc tgac                               94

SEQ ID NO: 345          moltype = RNA   length = 52
FEATURE                 Location/Qualifiers
source                  1..52
                        mol_type = transcribed RNA
                        organism = Homo sapiens
SEQUENCE: 345
tagccgggcg tggtggtggg ggcctgtggt cccagctact ttggaggctg ag           52

SEQ ID NO: 346          moltype = RNA   length = 70
FEATURE                 Location/Qualifiers
source                  1..70
                        mol_type = transcribed RNA
                        organism = Homo sapiens
SEQUENCE: 346
gtccctgggg gctgggatgg gccatggtgt gctctgatcc ccctgtggtc tcttggcccc   60
caggaactcc                                                          70

SEQ ID NO: 347          moltype = RNA   length = 83
FEATURE                 Location/Qualifiers
source                  1..83
                        mol_type = transcribed RNA
                        organism = Homo sapiens
SEQUENCE: 347
ggcccggctc cgggtctcgg cccgtacagt ccggccggcc atgctggcgg ggctggggcc   60
ggggccgagc ccgcggcggg gcc                                           83

SEQ ID NO: 348          moltype = RNA   length = 90
FEATURE                 Location/Qualifiers
source                  1..90
                        mol_type = transcribed RNA
                        organism = Homo sapiens
```

```
SEQUENCE: 348
ggcgcctctg cagctccggc tccccctggc ctctcgggaa ctacaagtcc caggggggcct    60
ggcggtgggc ggcgggcgga agaggcgggg                                      90

SEQ ID NO: 349          moltype = RNA   length = 85
FEATURE                 Location/Qualifiers
source                  1..85
                        mol_type = transcribed RNA
                        organism = Homo sapiens
SEQUENCE: 349
tcctccccgg agccaggatg cagctcaagc cacagcaggg tgtttagcgc tcttcagtgg    60
ctccagattg tggcgctggt gcagg                                           85

SEQ ID NO: 350          moltype = RNA   length = 89
FEATURE                 Location/Qualifiers
source                  1..89
                        mol_type = transcribed RNA
                        organism = Homo sapiens
SEQUENCE: 350
tctccgttta tcccaccact gccaccatta ttgctactgt tcagcaggtg ctgctggtgg    60
tgatggtgat agtctggtgg gggcggtgg                                       89

SEQ ID NO: 351          moltype = RNA   length = 70
FEATURE                 Location/Qualifiers
source                  1..70
                        mol_type = transcribed RNA
                        organism = Homo sapiens
SEQUENCE: 351
aaaagcctgt ccctaagtcc ctcccagcct tccagagttg gtgccaggaa ggatttaggg    60
acaggctttg                                                            70

SEQ ID NO: 352          moltype = RNA   length = 66
FEATURE                 Location/Qualifiers
source                  1..66
                        mol_type = transcribed RNA
                        organism = Homo sapiens
SEQUENCE: 352
cctggagggg ggcactgcgc aagcaaagcc agggaccctg agaggctttg cttcctgctc    60
ccctag                                                                66

SEQ ID NO: 353          moltype = RNA   length = 62
FEATURE                 Location/Qualifiers
source                  1..62
                        mol_type = transcribed RNA
                        organism = Homo sapiens
SEQUENCE: 353
cttcctggtg ggtggggagg agaagtgccg tcctcatgag cccctctctg tcccacccat    60
ag                                                                    62

SEQ ID NO: 354          moltype = RNA   length = 97
FEATURE                 Location/Qualifiers
source                  1..97
                        mol_type = transcribed RNA
                        organism = Homo sapiens
SEQUENCE: 354
ctcaggtgct ctggctgctt gggttcctgg catgctgatt tgtgacttaa gattaaaatc    60
acattgccag ggattaccac gcaaccacga ccttggc                              97

SEQ ID NO: 355          moltype = RNA   length = 85
FEATURE                 Location/Qualifiers
source                  1..85
                        mol_type = transcribed RNA
                        organism = Homo sapiens
SEQUENCE: 355
gtgagctgct ggggacgcgg gtcgggggtct gcagggcggt gcggcagccg ccacctgacg    60
ccgcgccttt gtctgtgtcc cacag                                           85

SEQ ID NO: 356          moltype = RNA   length = 83
FEATURE                 Location/Qualifiers
source                  1..83
                        mol_type = transcribed RNA
                        organism = Homo sapiens
SEQUENCE: 356
gtctactccc agggtgccaa gctgtttcgt gttccctccc tagggatcc caggtagggg    60
cagcagagga cctgggcctg gac                                             83

SEQ ID NO: 357          moltype = RNA   length = 93
FEATURE                 Location/Qualifiers
source                  1..93
```

SEQUENCE: 357
tacttatggc accccactcc tggtaccata gtcataagtt aggagatgtt agagctgtga    60
gtaccatgac ttaagtgtgg tggcttaaac atg                                93

SEQ ID NO: 358          moltype = RNA   length = 90
FEATURE                 Location/Qualifiers
source                  1..90
                        mol_type = transcribed RNA
                        organism = Homo sapiens
SEQUENCE: 358
ctgtgggctg ggccagggag cagctggtgg gtgggaagta agatctgacc tggactccat    60
cccacccacc ccctgtttcc tggcccacag                                    90

SEQ ID NO: 359          moltype = RNA   length = 74
FEATURE                 Location/Qualifiers
source                  1..74
                        mol_type = transcribed RNA
                        organism = Homo sapiens
SEQUENCE: 359
gggaggaaga agggaggagg agcggagggg cccttgtctt cccagagcct ctcccttcct    60
ccctcccc tccc                                                       74

SEQ ID NO: 360          moltype = RNA   length = 73
FEATURE                 Location/Qualifiers
source                  1..73
                        mol_type = transcribed RNA
                        organism = Homo sapiens
SEQUENCE: 360
acctttccag ctcatcccac ctctgccacc aaaacactca tcgcggggtc agagggagtg    60
ccaaaaaagg taa                                                      73

SEQ ID NO: 361          moltype = RNA   length = 70
FEATURE                 Location/Qualifiers
source                  1..70
                        mol_type = transcribed RNA
                        organism = Homo sapiens
SEQUENCE: 361
cacagtctga ctcagtgact catgtgctgg cagtggccac gtaaatagag ctactgtgtc    60
tgaaagcaat                                                          70

SEQ ID NO: 362          moltype = RNA   length = 65
FEATURE                 Location/Qualifiers
source                  1..65
                        mol_type = transcribed RNA
                        organism = Homo sapiens
SEQUENCE: 362
gcttctggga ggaggggatc ttgggagtga tcccaacagc tgagctccct gaatccctgt    60
cccag                                                               65

SEQ ID NO: 363          moltype = RNA   length = 84
FEATURE                 Location/Qualifiers
source                  1..84
                        mol_type = transcribed RNA
                        organism = Homo sapiens
SEQUENCE: 363
tgtgcagtgg aagggggggc cgatacactg tacgagagtg agtagcaggt ctcacagtga    60
accggtctct ttccctactg tgtc                                          84

SEQ ID NO: 364          moltype = RNA   length = 86
FEATURE                 Location/Qualifiers
source                  1..86
                        mol_type = transcribed RNA
                        organism = Homo sapiens
SEQUENCE: 364
tgccagtctc taggtccctg agacccttta acctgtgagg acatccaggg tcacaggtga    60
ggttcttggg agcctggcgt ctggcc                                        86

SEQ ID NO: 365          moltype = RNA   length = 75
FEATURE                 Location/Qualifiers
source                  1..75
                        mol_type = transcribed RNA
                        organism = Homo sapiens
SEQUENCE: 365
tcatccctgg gtggggattt gttgcattac ttgtgttcta tataaagtat tgcacttgtc    60
ccggcctgtg gaaga                                                    75

SEQ ID NO: 366          moltype = RNA   length = 68

```
FEATURE                 Location/Qualifiers
source                  1..68
                        mol_type = transcribed RNA
                        organism = Homo sapiens
SEQUENCE: 366
gcatcctgta ctgagctgcc ccgaggccct tcatgctgcc cagctcgggg cagctcagta    60
caggatac                                                             68

SEQ ID NO: 367          moltype = RNA   length = 64
FEATURE                 Location/Qualifiers
source                  1..64
                        mol_type = transcribed RNA
                        organism = Homo sapiens
SEQUENCE: 367
tcctgtactg agctgccccg agctgggcag catgaagggc ctcggggcag ctcagtacag    60
gatg                                                                 64

SEQ ID NO: 368          moltype = RNA   length = 64
FEATURE                 Location/Qualifiers
source                  1..64
                        mol_type = transcribed RNA
                        organism = Homo sapiens
SEQUENCE: 368
gggtggggc ggggcggcag gggcctcccc cagtgccagg ccccattctg cttctctccc    60
agct                                                                 64

SEQ ID NO: 369          moltype = RNA   length = 110
FEATURE                 Location/Qualifiers
source                  1..110
                        mol_type = transcribed RNA
                        organism = Homo sapiens
SEQUENCE: 369
tcacctggcc atgtgacttg tgggcttccc tttgtcatcc ttcgcctagg gctctgagca    60
gggcagggac agcaaagggg tgctcagttg tcacttccca cagcacggag               110

SEQ ID NO: 370          moltype = RNA   length = 67
FEATURE                 Location/Qualifiers
source                  1..67
                        mol_type = transcribed RNA
                        organism = Homo sapiens
SEQUENCE: 370
aaatctctct ccatatcttt cctgcagccc ccaggtgggg gggaagaaaa ggtggggaat    60
tagattc                                                              67

SEQ ID NO: 371          moltype = RNA   length = 67
FEATURE                 Location/Qualifiers
source                  1..67
                        mol_type = transcribed RNA
                        organism = Homo sapiens
SEQUENCE: 371
cagggaggag gtggtactag gggccagcaa cctgattacc cctctttggc cctttgtacc    60
cctccag                                                              67

SEQ ID NO: 372          moltype = RNA   length = 89
FEATURE                 Location/Qualifiers
source                  1..89
                        mol_type = transcribed RNA
                        organism = Homo sapiens
SEQUENCE: 372
gccggcgccc gagctctggc tccgtgtctt cactcccgtg cttgtccgag gagggaggga    60
gggacggggg ctgtgctggg gcagctgga                                      89

SEQ ID NO: 373          moltype = RNA   length = 66
FEATURE                 Location/Qualifiers
source                  1..66
                        mol_type = transcribed RNA
                        organism = Homo sapiens
SEQUENCE: 373
tgactgggga gcagaaggag aacccaagaa aagctgactt ggaggtccct ccttctgtcc    60
ccacag                                                               66

SEQ ID NO: 374          moltype = RNA   length = 90
FEATURE                 Location/Qualifiers
source                  1..90
                        mol_type = transcribed RNA
                        organism = Homo sapiens
SEQUENCE: 374
aggcctcgct gttctctatg gcttttatt cctatgtgat tctactgctc actcatatag    60
ggattggagc cgtggcgcac ggcggggaca                                     90
```

```
SEQ ID NO: 375          moltype = RNA   length = 63
FEATURE                 Location/Qualifiers
source                  1..63
                        mol_type = transcribed RNA
                        organism = Homo sapiens
SEQUENCE: 375
gcatgctggg cgaggctggc atctagcaca ggcggtagat gcttgctctt gccattgcaa    60
tga                                                                  63

SEQ ID NO: 376          moltype = RNA   length = 78
FEATURE                 Location/Qualifiers
source                  1..78
                        mol_type = transcribed RNA
                        organism = Homo sapiens
SEQUENCE: 376
gggcccagaa gggggcgcag tcactgacgt gaagggacca catcccgctt catgtcagtg    60
actcctgccc cttggtct                                                  78

SEQ ID NO: 377          moltype = RNA   length = 90
FEATURE                 Location/Qualifiers
source                  1..90
                        mol_type = transcribed RNA
                        organism = Homo sapiens
SEQUENCE: 377
gtgtctctct ggagaccctg cagccttccc acccaccagg gagctttcca tgggctgtgg    60
ggaaggcgtc agtgtcgggt gagggaacac                                     90

SEQ ID NO: 378          moltype = RNA   length = 54
FEATURE                 Location/Qualifiers
source                  1..54
                        mol_type = transcribed RNA
                        organism = Homo sapiens
SEQUENCE: 378
agcagcaggg gagagagagg agtcctctag acaccgactc tgtctcctgc agat          54

SEQ ID NO: 379          moltype = RNA   length = 100
FEATURE                 Location/Qualifiers
source                  1..100
                        mol_type = transcribed RNA
                        organism = Homo sapiens
SEQUENCE: 379
agctcagggc ggctgcgcag agggctggac tcagcggcgg agctggctgc tggcctcagt    60
tctgcctctg tccaggtcct tgtgacccgc ccgctctcct                          100

SEQ ID NO: 380          moltype = RNA   length = 59
FEATURE                 Location/Qualifiers
source                  1..59
                        mol_type = transcribed RNA
                        organism = Homo sapiens
SEQUENCE: 380
gtccaggcag gagccggact ggacctcagg gaagaggctg acccggcccc tcttgcggc     59

SEQ ID NO: 381          moltype = RNA   length = 54
FEATURE                 Location/Qualifiers
source                  1..54
                        mol_type = transcribed RNA
                        organism = Homo sapiens
SEQUENCE: 381
acgcgggtgc gggccggcgg ggtagaagcc acccggcccg gcccggcccg gcga          54

SEQ ID NO: 382          moltype = RNA   length = 73
FEATURE                 Location/Qualifiers
source                  1..73
                        mol_type = transcribed RNA
                        organism = Homo sapiens
SEQUENCE: 382
ggccggctgg ggttcctggg gatgggattt gcttcctgtc acaaatcaca ttgccaggga    60
tttccaaccg acc                                                       73

SEQ ID NO: 383          moltype = RNA   length = 69
FEATURE                 Location/Qualifiers
source                  1..69
                        mol_type = transcribed RNA
                        organism = Homo sapiens
SEQUENCE: 383
ctttcggcca gcgggacggc atccgaggtg ggctaggctc gggcccgtgg cgggtgcggg    60
ggtgggagg                                                            69
```

SEQ ID NO: 384            moltype = RNA   length = 69
FEATURE                   Location/Qualifiers
source                    1..69
                          mol_type = transcribed RNA
                          organism = Homo sapiens
SEQUENCE: 384
tggggtaggg gtgggggaat tcagggtgt cgaactcatg gctgccacct ttgtgtcccc    60
atcctgcag                                                          69

SEQ ID NO: 385            moltype = RNA   length = 70
FEATURE                   Location/Qualifiers
source                    1..70
                          mol_type = transcribed RNA
                          organism = Homo sapiens
SEQUENCE: 385
ggtttctcct tgaggagaca tggtgggggc cggtcaggca gcccatgcca tgtgtcctca    60
tggagaggcc                                                          70

SEQ ID NO: 386            moltype = RNA   length = 72
FEATURE                   Location/Qualifiers
source                    1..72
                          mol_type = transcribed RNA
                          organism = Homo sapiens
SEQUENCE: 386
cttgggaatg gcaaggaaac cgttaccatt actgagttta gtaatggtaa tggttctctt    60
gctatacccca ga                                                      72

SEQ ID NO: 387            moltype = RNA   length = 67
FEATURE                   Location/Qualifiers
source                    1..67
                          mol_type = transcribed RNA
                          organism = Homo sapiens
SEQUENCE: 387
ctggtccatt tccctgccat tcccttggct tcaatttact cccagggctg gcagtgacat    60
gggtcaa                                                             67

SEQ ID NO: 388            moltype = RNA   length = 94
FEATURE                   Location/Qualifiers
source                    1..94
                          mol_type = transcribed RNA
                          organism = Homo sapiens
SEQUENCE: 388
cagtgcgacg ggcggagctt ccagacgctc cgccccacgt cgcatgcgcc ccgggaaagc    60
gtggggcgga gcttccggag gccccgccct gctg                               94

SEQ ID NO: 389            moltype = RNA   length = 88
FEATURE                   Location/Qualifiers
source                    1..88
                          mol_type = transcribed RNA
                          organism = Homo sapiens
SEQUENCE: 389
gcgacgggcg gagcttccag acgctccgcc ccacgtcgca tgcgccccgg gaaagcgtgg    60
ggcggagctt ccggaggccc cgccctgc                                      88

SEQ ID NO: 390            moltype = RNA   length = 94
FEATURE                   Location/Qualifiers
source                    1..94
                          mol_type = transcribed RNA
                          organism = Homo sapiens
SEQUENCE: 390
cagtgcgacg ggcggagctt ccagacgctc cgccccacgt cgcatgcgcc ccgggaaagc    60
gtggggcgga gcttccggag gccccgccct gctg                               94

SEQ ID NO: 391            moltype = RNA   length = 94
FEATURE                   Location/Qualifiers
source                    1..94
                          mol_type = transcribed RNA
                          organism = Homo sapiens
SEQUENCE: 391
cagtgcgacg ggcggagctt ccagacgctc cgccccacgt cgcatgcgcc ccgggaaagc    60
gtggggcgga gcttccggag gccccgccct gctg                               94

SEQ ID NO: 392            moltype = RNA   length = 59
FEATURE                   Location/Qualifiers
source                    1..59
                          mol_type = transcribed RNA
                          organism = Homo sapiens
SEQUENCE: 392
ctgtgtcggg gagtctgggg tccggaattc tccagagcct ctgtgcccct acttcccag     59

```
SEQ ID NO: 393            moltype = RNA   length = 84
FEATURE                   Location/Qualifiers
source                    1..84
                          mol_type = transcribed RNA
                          organism = Homo sapiens
SEQUENCE: 393
gaggctgggc ggggcgcggc cggatcggtc gagagcgtcc tggctgatga cggtctcccg    60
tgcccacgcc ccaaacgcag tctc                                          84

SEQ ID NO: 394            moltype = RNA   length = 78
FEATURE                   Location/Qualifiers
source                    1..78
                          mol_type = transcribed RNA
                          organism = Homo sapiens
SEQUENCE: 394
ggcctcaggc aggcgcaccc gaccacatgc atggctggtg gcggcgtgca ggggtcgggt    60
gggccaggct gtggggcg                                                 78

SEQ ID NO: 395            moltype = RNA   length = 89
FEATURE                   Location/Qualifiers
source                    1..89
                          mol_type = transcribed RNA
                          organism = Homo sapiens
SEQUENCE: 395
accatgctgt agtgtgtgta aacatcctac actctcagct gtgagctcaa ggtggctggg    60
agaggggttgt ttactccttc tgccatgga                                    89

SEQ ID NO: 396            moltype = RNA   length = 52
FEATURE                   Location/Qualifiers
source                    1..52
                          mol_type = transcribed RNA
                          organism = Homo sapiens
SEQUENCE: 396
tctgggctga gccgagctgg gttaagccga gctgggttgg gctgggctgg gt            52

SEQ ID NO: 397            moltype = RNA   length = 61
FEATURE                   Location/Qualifiers
source                    1..61
                          mol_type = transcribed RNA
                          organism = Homo sapiens
SEQUENCE: 397
tcacccggtg agggcgggtg gaggaggagg gtccccacca tcagccttca ctgggacggg    60
a                                                                   61

SEQ ID NO: 398            moltype = RNA   length = 119
FEATURE                   Location/Qualifiers
source                    1..119
                          mol_type = transcribed RNA
                          organism = Homo sapiens
SEQUENCE: 398
agcctgcgcc ggagccgggg cctgagcccg ggccgcgcag gccgtgaact cgtcgagctg    60
cgcgtgcggc cggtgctcaa cctgccgggt cctggccccg cgctcccgcg cgccctgga    119

SEQ ID NO: 399            moltype = RNA   length = 23
FEATURE                   Location/Qualifiers
source                    1..23
                          mol_type = transcribed RNA
                          organism = Homo sapiens
SEQUENCE: 399
ctcctggggc ccgcactctc gct                                           23

SEQ ID NO: 400            moltype = RNA   length = 18
FEATURE                   Location/Qualifiers
source                    1..18
                          mol_type = transcribed RNA
                          organism = Homo sapiens
SEQUENCE: 400
ctcctggggc ccgcactc                                                 18

SEQ ID NO: 401            moltype = RNA   length = 22
FEATURE                   Location/Qualifiers
source                    1..22
                          mol_type = transcribed RNA
                          organism = Homo sapiens
SEQUENCE: 401
ccgggaacgt cgagactgga gc                                            22

SEQ ID NO: 402            moltype = RNA   length = 15
```

```
FEATURE                 Location/Qualifiers
source                  1..15
                        mol_type = transcribed RNA
                        organism = Homo sapiens
SEQUENCE: 402
cgggaacgtc gagac                                                        15

SEQ ID NO: 403          moltype = RNA   length = 22
FEATURE                 Location/Qualifiers
source                  1..22
                        mol_type = transcribed RNA
                        organism = Homo sapiens
SEQUENCE: 403
cgcggcgggg acggcgattg gt                                                22

SEQ ID NO: 404          moltype = RNA   length = 17
FEATURE                 Location/Qualifiers
source                  1..17
                        mol_type = transcribed RNA
                        organism = Homo sapiens
SEQUENCE: 404
cggcggggac ggcgatt                                                      17

SEQ ID NO: 405          moltype = RNA   length = 24
FEATURE                 Location/Qualifiers
source                  1..24
                        mol_type = transcribed RNA
                        organism = Homo sapiens
SEQUENCE: 405
gaggctggga aggcaaaggg acgt                                              24

SEQ ID NO: 406          moltype = RNA   length = 15
FEATURE                 Location/Qualifiers
source                  1..15
                        mol_type = transcribed RNA
                        organism = Homo sapiens
SEQUENCE: 406
gaaggaggct gggaa                                                        15

SEQ ID NO: 407          moltype = RNA   length = 23
FEATURE                 Location/Qualifiers
source                  1..23
                        mol_type = transcribed RNA
                        organism = Homo sapiens
SEQUENCE: 407
ggtgggtgag gtcgggcccc aag                                               23

SEQ ID NO: 408          moltype = RNA   length = 20
FEATURE                 Location/Qualifiers
source                  1..20
                        mol_type = transcribed RNA
                        organism = Homo sapiens
SEQUENCE: 408
cggggtgggt gaggtcgggc                                                   20

SEQ ID NO: 409          moltype = RNA   length = 17
FEATURE                 Location/Qualifiers
source                  1..17
                        mol_type = transcribed RNA
                        organism = Homo sapiens
SEQUENCE: 409
ggtgagcgct cgctggc                                                      17

SEQ ID NO: 410          moltype = RNA   length = 15
FEATURE                 Location/Qualifiers
source                  1..15
                        mol_type = transcribed RNA
                        organism = Homo sapiens
SEQUENCE: 410
cggtgagcgc tcgct                                                        15

SEQ ID NO: 411          moltype = RNA   length = 26
FEATURE                 Location/Qualifiers
source                  1..26
                        mol_type = transcribed RNA
                        organism = Homo sapiens
SEQUENCE: 411
ccttctggag aggctttgtg cggata                                            26
```

| | | |
|---|---|---|
| SEQ ID NO: 412<br>FEATURE<br>source<br><br>SEQUENCE: 412<br>ccttctggag aggct | moltype = RNA   length = 15<br>Location/Qualifiers<br>1..15<br>mol_type = transcribed RNA<br>organism = Homo sapiens | <br><br><br><br><br>15 |
| SEQ ID NO: 413<br>FEATURE<br>source<br><br>SEQUENCE: 413<br>tcgaggactg gtggaagggc cttt | moltype = RNA   length = 24<br>Location/Qualifiers<br>1..24<br>mol_type = transcribed RNA<br>organism = Homo sapiens | <br><br><br><br><br>24 |
| SEQ ID NO: 414<br>FEATURE<br>source<br><br>SEQUENCE: 414<br>tcgaggactg gtggaa | moltype = RNA   length = 16<br>Location/Qualifiers<br>1..16<br>mol_type = transcribed RNA<br>organism = Homo sapiens | <br><br><br><br><br>16 |
| SEQ ID NO: 415<br>FEATURE<br>source<br><br>SEQUENCE: 415<br>agtgggaggc cagggcacg | moltype = RNA   length = 19<br>Location/Qualifiers<br>1..19<br>mol_type = transcribed RNA<br>organism = Homo sapiens | <br><br><br><br><br>19 |
| SEQ ID NO: 416<br>FEATURE<br>source<br><br>SEQUENCE: 416<br>aggggggagct gcagg | moltype = RNA   length = 15<br>Location/Qualifiers<br>1..15<br>mol_type = transcribed RNA<br>organism = Homo sapiens | <br><br><br><br><br>15 |
| SEQ ID NO: 417<br>FEATURE<br>source<br><br>SEQUENCE: 417<br>tgctggtgat gctttc | moltype = RNA   length = 16<br>Location/Qualifiers<br>1..16<br>mol_type = transcribed RNA<br>organism = Homo sapiens | <br><br><br><br><br>16 |
| SEQ ID NO: 418<br>FEATURE<br>source<br><br>SEQUENCE: 418<br>tgctggtgat gctttc | moltype = RNA   length = 16<br>Location/Qualifiers<br>1..16<br>mol_type = transcribed RNA<br>organism = Homo sapiens | <br><br><br><br><br>16 |
| SEQ ID NO: 419<br>FEATURE<br>source<br><br>SEQUENCE: 419<br>cggggccgta gcactgtctg aga | moltype = RNA   length = 23<br>Location/Qualifiers<br>1..23<br>mol_type = transcribed RNA<br>organism = Homo sapiens | <br><br><br><br><br>23 |
| SEQ ID NO: 420<br>FEATURE<br>source<br><br>SEQUENCE: 420<br>cggggccgta gcactgtctg | moltype = RNA   length = 20<br>Location/Qualifiers<br>1..20<br>mol_type = transcribed RNA<br>organism = Homo sapiens | <br><br><br><br><br>20 |
| SEQ ID NO: 421<br>FEATURE<br>source<br><br>SEQUENCE: 421<br>gaggctgaag gaagatgg | moltype = RNA   length = 18<br>Location/Qualifiers<br>1..18<br>mol_type = transcribed RNA<br>organism = Homo sapiens | <br><br><br><br><br>18 |

```
SEQ ID NO: 422          moltype = RNA   length = 15
FEATURE                 Location/Qualifiers
source                  1..15
                        mol_type = transcribed RNA
                        organism = Homo sapiens
SEQUENCE: 422
gaggctgaag gaaga                                                         15

SEQ ID NO: 423          moltype = RNA   length = 23
FEATURE                 Location/Qualifiers
source                  1..23
                        mol_type = transcribed RNA
                        organism = Homo sapiens
SEQUENCE: 423
tgaggatatg gcagggaagg gga                                                23

SEQ ID NO: 424          moltype = RNA   length = 19
FEATURE                 Location/Qualifiers
source                  1..19
                        mol_type = transcribed RNA
                        organism = Homo sapiens
SEQUENCE: 424
tgaggatatg gcagggaag                                                     19

SEQ ID NO: 425          moltype = RNA   length = 23
FEATURE                 Location/Qualifiers
source                  1..23
                        mol_type = transcribed RNA
                        organism = Homo sapiens
SEQUENCE: 425
agggtcgggg cagggagggc agg                                                23

SEQ ID NO: 426          moltype = RNA   length = 15
FEATURE                 Location/Qualifiers
source                  1..15
                        mol_type = transcribed RNA
                        organism = Homo sapiens
SEQUENCE: 426
gggagaaggg tcggg                                                         15

SEQ ID NO: 427          moltype = RNA   length = 21
FEATURE                 Location/Qualifiers
source                  1..21
                        mol_type = transcribed RNA
                        organism = Homo sapiens
SEQUENCE: 427
gaggcgatgt ggggatgtag a                                                  21

SEQ ID NO: 428          moltype = RNA   length = 20
FEATURE                 Location/Qualifiers
source                  1..20
                        mol_type = transcribed RNA
                        organism = Homo sapiens
SEQUENCE: 428
cccagtctca tttcctcatc                                                    20

SEQ ID NO: 429          moltype = RNA   length = 21
FEATURE                 Location/Qualifiers
source                  1..21
                        mol_type = transcribed RNA
                        organism = Homo sapiens
SEQUENCE: 429
cttcccccca gtaatcttca t                                                  21

SEQ ID NO: 430          moltype = RNA   length = 21
FEATURE                 Location/Qualifiers
source                  1..21
                        mol_type = transcribed RNA
                        organism = Homo sapiens
SEQUENCE: 430
cttcccccca gtaatcttca t                                                  21

SEQ ID NO: 431          moltype = RNA   length = 21
FEATURE                 Location/Qualifiers
source                  1..21
                        mol_type = transcribed RNA
                        organism = Homo sapiens
SEQUENCE: 431
```
cccaggctgg agcgagtgca g                                               21

SEQ ID NO: 432          moltype = RNA   length = 15
FEATURE                 Location/Qualifiers
source                  1..15
                        mol_type = transcribed RNA
                        organism = Homo sapiens
SEQUENCE: 432
agctcactgc agcct                                                      15

SEQ ID NO: 433          moltype = RNA   length = 22
FEATURE                 Location/Qualifiers
source                  1..22
                        mol_type = transcribed RNA
                        organism = Homo sapiens
SEQUENCE: 433
caggcacggg agctcaggtg ag                                              22

SEQ ID NO: 434          moltype = RNA   length = 17
FEATURE                 Location/Qualifiers
source                  1..17
                        mol_type = transcribed RNA
                        organism = Homo sapiens
SEQUENCE: 434
caggcacggg agctcag                                                    17

SEQ ID NO: 435          moltype = RNA   length = 16
FEATURE                 Location/Qualifiers
source                  1..16
                        mol_type = transcribed RNA
                        organism = Homo sapiens
SEQUENCE: 435
ggacccaggg agagac                                                     16

SEQ ID NO: 436          moltype = RNA   length = 16
FEATURE                 Location/Qualifiers
source                  1..16
                        mol_type = transcribed RNA
                        organism = Homo sapiens
SEQUENCE: 436
ggacccaggg agagac                                                     16

SEQ ID NO: 437          moltype = RNA   length = 25
FEATURE                 Location/Qualifiers
source                  1..25
                        mol_type = transcribed RNA
                        organism = Homo sapiens
SEQUENCE: 437
tggcggcggt agttatgggc ttctc                                           25

SEQ ID NO: 438          moltype = RNA   length = 25
FEATURE                 Location/Qualifiers
source                  1..25
                        mol_type = transcribed RNA
                        organism = Homo sapiens
SEQUENCE: 438
tggcggcggt agttatgggc ttctc                                           25

SEQ ID NO: 439          moltype = RNA   length = 21
FEATURE                 Location/Qualifiers
source                  1..21
                        mol_type = transcribed RNA
                        organism = Homo sapiens
SEQUENCE: 439
caactctgat ctcttcatct a                                               21

SEQ ID NO: 440          moltype = RNA   length = 20
FEATURE                 Location/Qualifiers
source                  1..20
                        mol_type = transcribed RNA
                        organism = Homo sapiens
SEQUENCE: 440
tctcttcatc tacccccag                                                  20

SEQ ID NO: 441          moltype = RNA   length = 23
FEATURE                 Location/Qualifiers
source                  1..23
                        mol_type = transcribed RNA
                        organism = Homo sapiens

```
SEQUENCE: 441
ggctacaaca caggacccgg gcg                                              23

SEQ ID NO: 442          moltype = RNA   length = 21
FEATURE                 Location/Qualifiers
source                  1..21
                        mol_type = transcribed RNA
                        organism = Homo sapiens
SEQUENCE: 442
ggctacaaca caggacccgg g                                                21

SEQ ID NO: 443          moltype = RNA   length = 23
FEATURE                 Location/Qualifiers
source                  1..23
                        mol_type = transcribed RNA
                        organism = Homo sapiens
SEQUENCE: 443
agaagaaggc ggtcggtctg cgg                                              23

SEQ ID NO: 444          moltype = RNA   length = 21
FEATURE                 Location/Qualifiers
source                  1..21
                        mol_type = transcribed RNA
                        organism = Homo sapiens
SEQUENCE: 444
aagaaggcgg tcggtctgcg g                                                21

SEQ ID NO: 445          moltype = RNA   length = 20
FEATURE                 Location/Qualifiers
source                  1..20
                        mol_type = transcribed RNA
                        organism = Homo sapiens
SEQUENCE: 445
aagacacatt tggagaggga                                                  20

SEQ ID NO: 446          moltype = RNA   length = 16
FEATURE                 Location/Qualifiers
source                  1..16
                        mol_type = transcribed RNA
                        organism = Homo sapiens
SEQUENCE: 446
agacacattt ggagag                                                      16

SEQ ID NO: 447          moltype = RNA   length = 26
FEATURE                 Location/Qualifiers
source                  1..26
                        mol_type = transcribed RNA
                        organism = Homo sapiens
SEQUENCE: 447
aggagggagg agatgggcca agttcc                                           26

SEQ ID NO: 448          moltype = RNA   length = 15
FEATURE                 Location/Qualifiers
source                  1..15
                        mol_type = transcribed RNA
                        organism = Homo sapiens
SEQUENCE: 448
gggaggaggg aggag                                                       15

SEQ ID NO: 449          moltype = RNA   length = 25
FEATURE                 Location/Qualifiers
source                  1..25
                        mol_type = transcribed RNA
                        organism = Homo sapiens
SEQUENCE: 449
tgcggggcta gggctaacag cagtc                                            25

SEQ ID NO: 450          moltype = RNA   length = 15
FEATURE                 Location/Qualifiers
source                  1..15
                        mol_type = transcribed RNA
                        organism = Homo sapiens
SEQUENCE: 450
tgcggggcta gggct                                                       15

SEQ ID NO: 451          moltype = RNA   length = 20
FEATURE                 Location/Qualifiers
source                  1..20
                        mol_type = transcribed RNA
``` organism = Homo sapiens
SEQUENCE: 451
ctccccggtg tgcaaatgtg                                                    20

SEQ ID NO: 452         moltype = RNA   length = 15
FEATURE                Location/Qualifiers
source                 1..15
                       mol_type = transcribed RNA
                       organism = Homo sapiens
SEQUENCE: 452
gtgtgcggtg ttatg                                                         15

SEQ ID NO: 453         moltype = RNA   length = 22
FEATURE                Location/Qualifiers
source                 1..22
                       mol_type = transcribed RNA
                       organism = Homo sapiens
SEQUENCE: 453
cctcacacct gcctcgcccc cc                                                 22

SEQ ID NO: 454         moltype = RNA   length = 15
FEATURE                Location/Qualifiers
source                 1..15
                       mol_type = transcribed RNA
                       organism = Homo sapiens
SEQUENCE: 454
tcacacctgc ctcgc                                                         15

SEQ ID NO: 455         moltype = RNA   length = 24
FEATURE                Location/Qualifiers
source                 1..24
                       mol_type = transcribed RNA
                       organism = Homo sapiens
SEQUENCE: 455
tggggagctg aggctctggg ggtg                                               24

SEQ ID NO: 456         moltype = RNA   length = 15
FEATURE                Location/Qualifiers
source                 1..15
                       mol_type = transcribed RNA
                       organism = Homo sapiens
SEQUENCE: 456
ggccctgggg agctg                                                         15

SEQ ID NO: 457         moltype = RNA   length = 27
FEATURE                Location/Qualifiers
source                 1..27
                       mol_type = transcribed RNA
                       organism = Homo sapiens
SEQUENCE: 457
gtgaacgggc gccatcccga ggctttg                                            27

SEQ ID NO: 458         moltype = RNA   length = 16
FEATURE                Location/Qualifiers
source                 1..16
                       mol_type = transcribed RNA
                       organism = Homo sapiens
SEQUENCE: 458
gtgaacgggc gccatc                                                        16

SEQ ID NO: 459         moltype = RNA   length = 21
FEATURE                Location/Qualifiers
source                 1..21
                       mol_type = transcribed RNA
                       organism = Homo sapiens
SEQUENCE: 459
gagggcagcg tgggtgtggc g                                                  21

SEQ ID NO: 460         moltype = RNA   length = 21
FEATURE                Location/Qualifiers
source                 1..21
                       mol_type = transcribed RNA
                       organism = Homo sapiens
SEQUENCE: 460
gagggcagcg tgggtgtggc g                                                  21

SEQ ID NO: 461         moltype = RNA   length = 23
FEATURE                Location/Qualifiers
source                 1..23

```
                              mol_type = transcribed RNA
                              organism = Homo sapiens
SEQUENCE: 461
gggggtcccc ggtgctcgga tct                                              23

SEQ ID NO: 462                moltype = RNA   length = 16
FEATURE                       Location/Qualifiers
source                        1..16
                              mol_type = transcribed RNA
                              organism = Homo sapiens
SEQUENCE: 462
tcgggagggg cgggag                                                      16

SEQ ID NO: 463                moltype = RNA   length = 25
FEATURE                       Location/Qualifiers
source                        1..25
                              mol_type = transcribed RNA
                              organism = Homo sapiens
SEQUENCE: 463
ttctgggccc gcggcgggcg tgggg                                            25

SEQ ID NO: 464                moltype = RNA   length = 15
FEATURE                       Location/Qualifiers
source                        1..15
                              mol_type = transcribed RNA
                              organism = Homo sapiens
SEQUENCE: 464
cgcggcgggc gtggg                                                       15

SEQ ID NO: 465                moltype = RNA   length = 22
FEATURE                       Location/Qualifiers
source                        1..22
                              mol_type = transcribed RNA
                              organism = Homo sapiens
SEQUENCE: 465
tgggagggga gaggcagcaa gc                                               22

SEQ ID NO: 466                moltype = RNA   length = 22
FEATURE                       Location/Qualifiers
source                        1..22
                              mol_type = transcribed RNA
                              organism = Homo sapiens
SEQUENCE: 466
tgggagggga gaggcagcaa gc                                               22

SEQ ID NO: 467                moltype = RNA   length = 21
FEATURE                       Location/Qualifiers
source                        1..21
                              mol_type = transcribed RNA
                              organism = Homo sapiens
SEQUENCE: 467
aggaggcagt gggcgagcag g                                                21

SEQ ID NO: 468                moltype = RNA   length = 21
FEATURE                       Location/Qualifiers
source                        1..21
                              mol_type = transcribed RNA
                              organism = Homo sapiens
SEQUENCE: 468
aggaggcagt gggcgagcag g                                                21

SEQ ID NO: 469                moltype = RNA   length = 15
FEATURE                       Location/Qualifiers
source                        1..15
                              mol_type = transcribed RNA
                              organism = Homo sapiens
SEQUENCE: 469
tgaagcgggg gggcg                                                       15

SEQ ID NO: 470                moltype = RNA   length = 15
FEATURE                       Location/Qualifiers
source                        1..15
                              mol_type = transcribed RNA
                              organism = Homo sapiens
SEQUENCE: 470
tgaagcgggg gggcg                                                       15

SEQ ID NO: 471                moltype = RNA   length = 17
FEATURE                       Location/Qualifiers
```

```
source                  1..17
                        mol_type = transcribed RNA
                        organism = Homo sapiens
SEQUENCE: 471
tcctagtcac ggcacca                                                      17

SEQ ID NO: 472          moltype = RNA  length = 17
FEATURE                 Location/Qualifiers
source                  1..17
                        mol_type = transcribed RNA
                        organism = Homo sapiens
SEQUENCE: 472
tcctagtcac ggcacca                                                      17

SEQ ID NO: 473          moltype = RNA  length = 23
FEATURE                 Location/Qualifiers
source                  1..23
                        mol_type = transcribed RNA
                        organism = Homo sapiens
SEQUENCE: 473
ggaggcgcag gctcggaaag gcg                                               23

SEQ ID NO: 474          moltype = RNA  length = 15
FEATURE                 Location/Qualifiers
source                  1..15
                        mol_type = transcribed RNA
                        organism = Homo sapiens
SEQUENCE: 474
gcaggctcgg aaagg                                                        15

SEQ ID NO: 475          moltype = RNA  length = 23
FEATURE                 Location/Qualifiers
source                  1..23
                        mol_type = transcribed RNA
                        organism = Homo sapiens
SEQUENCE: 475
ctagtggaag aagatggcgg aag                                               23

SEQ ID NO: 476          moltype = RNA  length = 15
FEATURE                 Location/Qualifiers
source                  1..15
                        mol_type = transcribed RNA
                        organism = Homo sapiens
SEQUENCE: 476
tagtggaaga agatg                                                        15

SEQ ID NO: 477          moltype = RNA  length = 23
FEATURE                 Location/Qualifiers
source                  1..23
                        mol_type = transcribed RNA
                        organism = Homo sapiens
SEQUENCE: 477
acaggagtgg gggtgggaca taa                                               23

SEQ ID NO: 478          moltype = RNA  length = 20
FEATURE                 Location/Qualifiers
source                  1..20
                        mol_type = transcribed RNA
                        organism = Homo sapiens
SEQUENCE: 478
acaggagtgg gggtgggaca                                                   20

SEQ ID NO: 479          moltype = RNA  length = 25
FEATURE                 Location/Qualifiers
source                  1..25
                        mol_type = transcribed RNA
                        organism = Homo sapiens
SEQUENCE: 479
agcggggagg aagtgggcgc tgctt                                             25

SEQ ID NO: 480          moltype = RNA  length = 21
FEATURE                 Location/Qualifiers
source                  1..21
                        mol_type = transcribed RNA
                        organism = Homo sapiens
SEQUENCE: 480
agcggggagg aagtgggcgc t                                                 21

SEQ ID NO: 481          moltype = RNA  length = 22
```

```
FEATURE                 Location/Qualifiers
source                  1..22
                        mol_type = transcribed RNA
                        organism = Homo sapiens
SEQUENCE: 481
ccggcagagg aggctgcaga gg                                            22

SEQ ID NO: 482          moltype = RNA   length = 19
FEATURE                 Location/Qualifiers
source                  1..19
                        mol_type = transcribed RNA
                        organism = Homo sapiens
SEQUENCE: 482
ccggcagagg aggctgcag                                                19

SEQ ID NO: 483          moltype = RNA   length = 15
FEATURE                 Location/Qualifiers
source                  1..15
                        mol_type = transcribed RNA
                        organism = Homo sapiens
SEQUENCE: 483
tctgggcgag gggtg                                                    15

SEQ ID NO: 484          moltype = RNA   length = 15
FEATURE                 Location/Qualifiers
source                  1..15
                        mol_type = transcribed RNA
                        organism = Homo sapiens
SEQUENCE: 484
tctgggcgag gggtg                                                    15

SEQ ID NO: 485          moltype = RNA   length = 26
FEATURE                 Location/Qualifiers
source                  1..26
                        mol_type = transcribed RNA
                        organism = Homo sapiens
SEQUENCE: 485
gtcccggggc tgcgcgaggc acaggc                                        26

SEQ ID NO: 486          moltype = RNA   length = 15
FEATURE                 Location/Qualifiers
source                  1..15
                        mol_type = transcribed RNA
                        organism = Homo sapiens
SEQUENCE: 486
ggcccggggg gcggg                                                    15

SEQ ID NO: 487          moltype = RNA   length = 21
FEATURE                 Location/Qualifiers
source                  1..21
                        mol_type = transcribed RNA
                        organism = Homo sapiens
SEQUENCE: 487
cggatccgag tcacggcacc a                                             21

SEQ ID NO: 488          moltype = RNA   length = 15
FEATURE                 Location/Qualifiers
source                  1..15
                        mol_type = transcribed RNA
                        organism = Homo sapiens
SEQUENCE: 488
ggatccgagt cacgg                                                    15

SEQ ID NO: 489          moltype = RNA   length = 21
FEATURE                 Location/Qualifiers
source                  1..21
                        mol_type = transcribed RNA
                        organism = Homo sapiens
SEQUENCE: 489
atccagttct ctgagggggc t                                             21

SEQ ID NO: 490          moltype = RNA   length = 21
FEATURE                 Location/Qualifiers
source                  1..21
                        mol_type = transcribed RNA
                        organism = Homo sapiens
SEQUENCE: 490
atccagttct ctgagggggc t                                             21
```

| | | |
|---|---|---|
| SEQ ID NO: 491<br>FEATURE<br>source | moltype = RNA length = 23<br>Location/Qualifiers<br>1..23<br>mol_type = transcribed RNA<br>organism = Homo sapiens | |
| SEQUENCE: 491<br>ggcccggccg tgcctgaggt ttc | | 23 |
| SEQ ID NO: 492<br>FEATURE<br>source | moltype = RNA length = 15<br>Location/Qualifiers<br>1..15<br>mol_type = transcribed RNA<br>organism = Homo sapiens | |
| SEQUENCE: 492<br>ggcggtggga tcccg | | 15 |
| SEQ ID NO: 493<br>FEATURE<br>source | moltype = RNA length = 18<br>Location/Qualifiers<br>1..18<br>mol_type = transcribed RNA<br>organism = Homo sapiens | |
| SEQUENCE: 493<br>tctaggtggg gagactga | | 18 |
| SEQ ID NO: 494<br>FEATURE<br>source | moltype = RNA length = 16<br>Location/Qualifiers<br>1..16<br>mol_type = transcribed RNA<br>organism = Homo sapiens | |
| SEQUENCE: 494<br>gtggggagac tgacgg | | 16 |
| SEQ ID NO: 495<br>FEATURE<br>source | moltype = RNA length = 17<br>Location/Qualifiers<br>1..17<br>mol_type = transcribed RNA<br>organism = Homo sapiens | |
| SEQUENCE: 495<br>tgcaggggca ggccagc | | 17 |
| SEQ ID NO: 496<br>FEATURE<br>source | moltype = RNA length = 17<br>Location/Qualifiers<br>1..17<br>mol_type = transcribed RNA<br>organism = Homo sapiens | |
| SEQUENCE: 496<br>tgcaggggca ggccagc | | 17 |
| SEQ ID NO: 497<br>FEATURE<br>source | moltype = RNA length = 25<br>Location/Qualifiers<br>1..25<br>mol_type = transcribed RNA<br>organism = Homo sapiens | |
| SEQUENCE: 497<br>aaggcagggc ccccgctccc cgggc | | 25 |
| SEQ ID NO: 498<br>FEATURE<br>source | moltype = RNA length = 15<br>Location/Qualifiers<br>1..15<br>mol_type = transcribed RNA<br>organism = Homo sapiens | |
| SEQUENCE: 498<br>gtgtgttgag gaagg | | 15 |
| SEQ ID NO: 499<br>FEATURE<br>source | moltype = RNA length = 26<br>Location/Qualifiers<br>1..26<br>mol_type = transcribed RNA<br>organism = Homo sapiens | |
| SEQUENCE: 499<br>gcgggctgtc cggaggggtc ggcttt | | 26 |
| SEQ ID NO: 500<br>FEATURE<br>source | moltype = RNA length = 16<br>Location/Qualifiers<br>1..16<br>mol_type = transcribed RNA<br>organism = Homo sapiens | |
| SEQUENCE: 500<br>gctgtccgga ggggtc | | 16 |

| | | |
|---|---|---|
| SEQ ID NO: 501<br>FEATURE<br>source | moltype = RNA   length = 20<br>Location/Qualifiers<br>1..20<br>mol_type = transcribed RNA<br>organism = Homo sapiens | |
| SEQUENCE: 501<br>ggctggtcag atgggagtgg | | 20 |
| SEQ ID NO: 502<br>FEATURE<br>source | moltype = RNA   length = 20<br>Location/Qualifiers<br>1..20<br>mol_type = transcribed RNA<br>organism = Homo sapiens | |
| SEQUENCE: 502<br>ggctggtcag atgggagtgg | | 20 |
| SEQ ID NO: 503<br>FEATURE<br>source | moltype = RNA   length = 24<br>Location/Qualifiers<br>1..24<br>mol_type = transcribed RNA<br>organism = Homo sapiens | |
| SEQUENCE: 503<br>ctggtacagg cctgggggac aggg | | 24 |
| SEQ ID NO: 504<br>FEATURE<br>source | moltype = RNA   length = 18<br>Location/Qualifiers<br>1..18<br>mol_type = transcribed RNA<br>organism = Homo sapiens | |
| SEQUENCE: 504<br>ctggtacagg cctggggg | | 18 |
| SEQ ID NO: 505<br>FEATURE<br>source | moltype = RNA   length = 23<br>Location/Qualifiers<br>1..23<br>mol_type = transcribed RNA<br>organism = Homo sapiens | |
| SEQUENCE: 505<br>gccccggcgc gggcgggttc tgg | | 23 |
| SEQ ID NO: 506<br>FEATURE<br>source | moltype = RNA   length = 16<br>Location/Qualifiers<br>1..16<br>mol_type = transcribed RNA<br>organism = Homo sapiens | |
| SEQUENCE: 506<br>ggagccccgg cgcggg | | 16 |
| SEQ ID NO: 507<br>FEATURE<br>source | moltype = RNA   length = 20<br>Location/Qualifiers<br>1..20<br>mol_type = transcribed RNA<br>organism = Homo sapiens | |
| SEQUENCE: 507<br>ccccagggcg acgcggcggg | | 20 |
| SEQ ID NO: 508<br>FEATURE<br>source | moltype = RNA   length = 15<br>Location/Qualifiers<br>1..15<br>mol_type = transcribed RNA<br>organism = Homo sapiens | |
| SEQUENCE: 508<br>cgcggcgggg gcggc | | 15 |
| SEQ ID NO: 509<br>FEATURE<br>source | moltype = RNA   length = 21<br>Location/Qualifiers<br>1..21<br>mol_type = transcribed RNA<br>organism = Homo sapiens | |
| SEQUENCE: 509<br>gtgagtcagg gtggggctgg c | | 21 |
| SEQ ID NO: 510<br>FEATURE<br>source | moltype = RNA   length = 21<br>Location/Qualifiers<br>1..21<br>mol_type = transcribed RNA<br>organism = Homo sapiens | |
| SEQUENCE: 510 | | |

```
gtgagtcagg gtggggctgg c                                          21

SEQ ID NO: 511           moltype = RNA  length = 21
FEATURE                  Location/Qualifiers
source                   1..21
                         mol_type = transcribed RNA
                         organism = Homo sapiens
SEQUENCE: 511
gttggaggcg tgggttttag a                                          21

SEQ ID NO: 512           moltype = RNA  length = 15
FEATURE                  Location/Qualifiers
source                   1..15
                         mol_type = transcribed RNA
                         organism = Homo sapiens
SEQUENCE: 512
gttggaggcg tgggt                                                 15

SEQ ID NO: 513           moltype = RNA  length = 23
FEATURE                  Location/Qualifiers
source                   1..23
                         mol_type = transcribed RNA
                         organism = Homo sapiens
SEQUENCE: 513
aggaggggtc ccgcactggg agg                                        23

SEQ ID NO: 514           moltype = RNA  length = 15
FEATURE                  Location/Qualifiers
source                   1..15
                         mol_type = transcribed RNA
                         organism = Homo sapiens
SEQUENCE: 514
tgggaggggc cctca                                                 15

SEQ ID NO: 515           moltype = RNA  length = 23
FEATURE                  Location/Qualifiers
source                   1..23
                         mol_type = transcribed RNA
                         organism = Homo sapiens
SEQUENCE: 515
gtgggctggg ctgggctggg cca                                        23

SEQ ID NO: 516           moltype = RNA  length = 15
FEATURE                  Location/Qualifiers
source                   1..15
                         mol_type = transcribed RNA
                         organism = Homo sapiens
SEQUENCE: 516
gggctgggct gggct                                                 15

SEQ ID NO: 517           moltype = RNA  length = 24
FEATURE                  Location/Qualifiers
source                   1..24
                         mol_type = transcribed RNA
                         organism = Homo sapiens
SEQUENCE: 517
cgggcgtggt ggtggggtg ggtg                                        24

SEQ ID NO: 518           moltype = RNA  length = 15
FEATURE                  Location/Qualifiers
source                   1..15
                         mol_type = transcribed RNA
                         organism = Homo sapiens
SEQUENCE: 518
cgggcgtggt ggtgg                                                 15

SEQ ID NO: 519           moltype = RNA  length = 18
FEATURE                  Location/Qualifiers
source                   1..18
                         mol_type = transcribed RNA
                         organism = Homo sapiens
SEQUENCE: 519
ggtgggcttc ccggaggg                                              18

SEQ ID NO: 520           moltype = RNA  length = 15
FEATURE                  Location/Qualifiers
source                   1..15
                         mol_type = transcribed RNA
                         organism = Homo sapiens
```

```
SEQUENCE: 520
ggtgggcttc ccgga                                                            15

SEQ ID NO: 521          moltype = RNA   length = 26
FEATURE                 Location/Qualifiers
source                  1..26
                        mol_type = transcribed RNA
                        organism = Homo sapiens
SEQUENCE: 521
cggtgggatc ccgcggccgt gttttc                                                26

SEQ ID NO: 522          moltype = RNA   length = 15
FEATURE                 Location/Qualifiers
source                  1..15
                        mol_type = transcribed RNA
                        organism = Homo sapiens
SEQUENCE: 522
ggggcgccgc gggac                                                            15

SEQ ID NO: 523          moltype = RNA   length = 25
FEATURE                 Location/Qualifiers
source                  1..25
                        mol_type = transcribed RNA
                        organism = Homo sapiens
SEQUENCE: 523
tgggcagggg cttattgtag gagtc                                                 25

SEQ ID NO: 524          moltype = RNA   length = 19
FEATURE                 Location/Qualifiers
source                  1..19
                        mol_type = transcribed RNA
                        organism = Homo sapiens
SEQUENCE: 524
tgggcagggg cttattgta                                                        19

SEQ ID NO: 525          moltype = RNA   length = 20
FEATURE                 Location/Qualifiers
source                  1..20
                        mol_type = transcribed RNA
                        organism = Homo sapiens
SEQUENCE: 525
ccccggggag cccggcggtg                                                       20

SEQ ID NO: 526          moltype = RNA   length = 15
FEATURE                 Location/Qualifiers
source                  1..15
                        mol_type = transcribed RNA
                        organism = Homo sapiens
SEQUENCE: 526
accccgggga gcccg                                                            15

SEQ ID NO: 527          moltype = RNA   length = 26
FEATURE                 Location/Qualifiers
source                  1..26
                        mol_type = transcribed RNA
                        organism = Homo sapiens
SEQUENCE: 527
agggacggga cgcggtgcag tgttgt                                                26

SEQ ID NO: 528          moltype = RNA   length = 15
FEATURE                 Location/Qualifiers
source                  1..15
                        mol_type = transcribed RNA
                        organism = Homo sapiens
SEQUENCE: 528
ggcgggcggg aggga                                                            15

SEQ ID NO: 529          moltype = RNA   length = 22
FEATURE                 Location/Qualifiers
source                  1..22
                        mol_type = transcribed RNA
                        organism = Homo sapiens
SEQUENCE: 529
actcaaactg tgggggcact tt                                                    22

SEQ ID NO: 530          moltype = RNA   length = 19
FEATURE                 Location/Qualifiers
source                  1..19
                        mol_type = transcribed RNA
```

```
                                organism = Homo sapiens
SEQUENCE: 530
actcaaactg tggggcac                                                           19

SEQ ID NO: 531          moltype = RNA   length = 16
FEATURE                 Location/Qualifiers
source                  1..16
                        mol_type = transcribed RNA
                        organism = Homo sapiens
SEQUENCE: 531
gtgaaggccc ggcgga                                                             16

SEQ ID NO: 532          moltype = RNA   length = 15
FEATURE                 Location/Qualifiers
source                  1..15
                        mol_type = transcribed RNA
                        organism = Homo sapiens
SEQUENCE: 532
gtgaaggccc ggcgg                                                              15

SEQ ID NO: 533          moltype = RNA   length = 24
FEATURE                 Location/Qualifiers
source                  1..24
                        mol_type = transcribed RNA
                        organism = Homo sapiens
SEQUENCE: 533
gctgcgggct gcggtcaggg cgat                                                    24

SEQ ID NO: 534          moltype = RNA   length = 20
FEATURE                 Location/Qualifiers
source                  1..20
                        mol_type = transcribed RNA
                        organism = Homo sapiens
SEQUENCE: 534
gctgcgggct gcggtcaggg                                                         20

SEQ ID NO: 535          moltype = RNA   length = 30
FEATURE                 Location/Qualifiers
source                  1..30
                        mol_type = transcribed RNA
                        organism = Homo sapiens
SEQUENCE: 535
tgaggggcag agagcgagac ttttctattt                                              30

SEQ ID NO: 536          moltype = RNA   length = 15
FEATURE                 Location/Qualifiers
source                  1..15
                        mol_type = transcribed RNA
                        organism = Homo sapiens
SEQUENCE: 536
tgaggggcag agagc                                                              15

SEQ ID NO: 537          moltype = RNA   length = 23
FEATURE                 Location/Qualifiers
source                  1..23
                        mol_type = transcribed RNA
                        organism = Homo sapiens
SEQUENCE: 537
caccttgcct tgctgcccgg gcc                                                     23

SEQ ID NO: 538          moltype = RNA   length = 22
FEATURE                 Location/Qualifiers
source                  1..22
                        mol_type = transcribed RNA
                        organism = Homo sapiens
SEQUENCE: 538
caccttgcct tgctgcccgg gc                                                      22

SEQ ID NO: 539          moltype = RNA   length = 21
FEATURE                 Location/Qualifiers
source                  1..21
                        mol_type = transcribed RNA
                        organism = Homo sapiens
SEQUENCE: 539
tgggaatggg ggtaagggcc t                                                       21

SEQ ID NO: 540          moltype = RNA   length = 15
FEATURE                 Location/Qualifiers
source                  1..15
```

```
                        mol_type = transcribed RNA
                        organism = Homo sapiens
SEQUENCE: 540
cttctgagcc caggt                                                          15

SEQ ID NO: 541          moltype = RNA  length = 15
FEATURE                 Location/Qualifiers
source                  1..15
                        mol_type = transcribed RNA
                        organism = Homo sapiens
SEQUENCE: 541
ggcggcgggc ccggg                                                          15

SEQ ID NO: 542          moltype = RNA  length = 15
FEATURE                 Location/Qualifiers
source                  1..15
                        mol_type = transcribed RNA
                        organism = Homo sapiens
SEQUENCE: 542
ggcggcgggc ccggg                                                          15

SEQ ID NO: 543          moltype = RNA  length = 16
FEATURE                 Location/Qualifiers
source                  1..16
                        mol_type = transcribed RNA
                        organism = Homo sapiens
SEQUENCE: 543
ctggggtcc cccgac                                                          16

SEQ ID NO: 544          moltype = RNA  length = 15
FEATURE                 Location/Qualifiers
source                  1..15
                        mol_type = transcribed RNA
                        organism = Homo sapiens
SEQUENCE: 544
gtgtggagct ggggc                                                          15

SEQ ID NO: 545          moltype = RNA  length = 22
FEATURE                 Location/Qualifiers
source                  1..22
                        mol_type = transcribed RNA
                        organism = Homo sapiens
SEQUENCE: 545
tgtgggactg caaatgggag ct                                                  22

SEQ ID NO: 546          moltype = RNA  length = 22
FEATURE                 Location/Qualifiers
source                  1..22
                        mol_type = transcribed RNA
                        organism = Homo sapiens
SEQUENCE: 546
tgtgggactg caaatgggag ct                                                  22

SEQ ID NO: 547          moltype = RNA  length = 23
FEATURE                 Location/Qualifiers
source                  1..23
                        mol_type = transcribed RNA
                        organism = Homo sapiens
SEQUENCE: 547
acagcagggc tggggattgc agt                                                 23

SEQ ID NO: 548          moltype = RNA  length = 19
FEATURE                 Location/Qualifiers
source                  1..19
                        mol_type = transcribed RNA
                        organism = Homo sapiens
SEQUENCE: 548
tgctgctccc agtcctgcc                                                      19

SEQ ID NO: 549          moltype = RNA  length = 17
FEATURE                 Location/Qualifiers
source                  1..17
                        mol_type = transcribed RNA
                        organism = Homo sapiens
SEQUENCE: 549
aggggctggg cgcgcgc                                                        17

SEQ ID NO: 550          moltype = RNA  length = 15
FEATURE                 Location/Qualifiers
```

```
source                  1..15
                        mol_type = transcribed RNA
                        organism = Homo sapiens
SEQUENCE: 550
cagggctgg gcgcg                                                            15

SEQ ID NO: 551          moltype = RNA   length = 17
FEATURE                 Location/Qualifiers
source                  1..17
                        mol_type = transcribed RNA
                        organism = Homo sapiens
SEQUENCE: 551
ggggcggggg cggggc                                                          17

SEQ ID NO: 552          moltype = RNA   length = 15
FEATURE                 Location/Qualifiers
source                  1..15
                        mol_type = transcribed RNA
                        organism = Homo sapiens
SEQUENCE: 552
cgcgccgggc ccggg                                                           15

SEQ ID NO: 553          moltype = RNA   length = 23
FEATURE                 Location/Qualifiers
source                  1..23
                        mol_type = transcribed RNA
                        organism = Homo sapiens
SEQUENCE: 553
tggggcggag cttccggagg ccc                                                  23

SEQ ID NO: 554          moltype = RNA   length = 16
FEATURE                 Location/Qualifiers
source                  1..16
                        mol_type = transcribed RNA
                        organism = Homo sapiens
SEQUENCE: 554
atcgctggcc tggtcg                                                          16

SEQ ID NO: 555          moltype = RNA   length = 22
FEATURE                 Location/Qualifiers
source                  1..22
                        mol_type = transcribed RNA
                        organism = Homo sapiens
SEQUENCE: 555
gagggttggg tggaggctct cc                                                   22

SEQ ID NO: 556          moltype = RNA   length = 15
FEATURE                 Location/Qualifiers
source                  1..15
                        mol_type = transcribed RNA
                        organism = Homo sapiens
SEQUENCE: 556
gagggttggg tggag                                                           15

SEQ ID NO: 557          moltype = RNA   length = 18
FEATURE                 Location/Qualifiers
source                  1..18
                        mol_type = transcribed RNA
                        organism = Homo sapiens
SEQUENCE: 557
ctccgggcgg cgccgtgt                                                        18

SEQ ID NO: 558          moltype = RNA   length = 18
FEATURE                 Location/Qualifiers
source                  1..18
                        mol_type = transcribed RNA
                        organism = Homo sapiens
SEQUENCE: 558
ctccgggcgg cgccgtgt                                                        18

SEQ ID NO: 559          moltype = RNA   length = 21
FEATURE                 Location/Qualifiers
source                  1..21
                        mol_type = transcribed RNA
                        organism = Homo sapiens
SEQUENCE: 559
gccgggcgtg gtggtgggggg c                                                   21

SEQ ID NO: 560          moltype = RNA   length = 15
```

```
FEATURE                 Location/Qualifiers
source                  1..15
                        mol_type = transcribed RNA
                        organism = Homo sapiens
SEQUENCE: 560
tagccgggcg tggtg                                                        15

SEQ ID NO: 561          moltype = RNA   length = 16
FEATURE                 Location/Qualifiers
source                  1..16
                        mol_type = transcribed RNA
                        organism = Homo sapiens
SEQUENCE: 561
ggcggtgggc ggcggg                                                       16

SEQ ID NO: 562          moltype = RNA   length = 15
FEATURE                 Location/Qualifiers
source                  1..15
                        mol_type = transcribed RNA
                        organism = Homo sapiens
SEQUENCE: 562
ggcctctcgg gaact                                                        15

SEQ ID NO: 563          moltype = RNA   length = 20
FEATURE                 Location/Qualifiers
source                  1..20
                        mol_type = transcribed RNA
                        organism = Homo sapiens
SEQUENCE: 563
atcccaccac tgccaccatt                                                   20

SEQ ID NO: 564          moltype = RNA   length = 15
FEATURE                 Location/Qualifiers
source                  1..15
                        mol_type = transcribed RNA
                        organism = Homo sapiens
SEQUENCE: 564
atcccaccac tgcca                                                        15

SEQ ID NO: 565          moltype = RNA   length = 25
FEATURE                 Location/Qualifiers
source                  1..25
                        mol_type = transcribed RNA
                        organism = Homo sapiens
SEQUENCE: 565
caggaaggat ttagggacag gcttt                                             25

SEQ ID NO: 566          moltype = RNA   length = 19
FEATURE                 Location/Qualifiers
source                  1..19
                        mol_type = transcribed RNA
                        organism = Homo sapiens
SEQUENCE: 566
caggaaggat ttagggaca                                                    19

SEQ ID NO: 567          moltype = RNA   length = 26
FEATURE                 Location/Qualifiers
source                  1..26
                        mol_type = transcribed RNA
                        organism = Homo sapiens
SEQUENCE: 567
aaaatcacat tgccagggat taccac                                            26

SEQ ID NO: 568          moltype = RNA   length = 15
FEATURE                 Location/Qualifiers
source                  1..15
                        mol_type = transcribed RNA
                        organism = Homo sapiens
SEQUENCE: 568
aatcacattg ccagg                                                        15

SEQ ID NO: 569          moltype = RNA   length = 23
FEATURE                 Location/Qualifiers
source                  1..23
                        mol_type = transcribed RNA
                        organism = Homo sapiens
SEQUENCE: 569
tagggggcagc agaggacctg ggc                                              23
```

| | | |
|---|---|---|
| SEQ ID NO: 570<br>FEATURE<br>source | moltype = RNA   length = 20<br>Location/Qualifiers<br>1..20<br>mol_type = transcribed RNA<br>organism = Homo sapiens | |
| SEQUENCE: 570<br>tagggggcagc agaggacctg | | 20 |
| SEQ ID NO: 571<br>FEATURE<br>source | moltype = RNA   length = 22<br>Location/Qualifiers<br>1..22<br>mol_type = transcribed RNA<br>organism = Homo sapiens | |
| SEQUENCE: 571<br>accccactcc tggtaccata gt | | 22 |
| SEQ ID NO: 572<br>FEATURE<br>source | moltype = RNA   length = 15<br>Location/Qualifiers<br>1..15<br>mol_type = transcribed RNA<br>organism = Homo sapiens | |
| SEQUENCE: 572<br>accccactcc tggta | | 15 |
| SEQ ID NO: 573<br>FEATURE<br>source | moltype = RNA   length = 25<br>Location/Qualifiers<br>1..25<br>mol_type = transcribed RNA<br>organism = Homo sapiens | |
| SEQUENCE: 573<br>ctgggccagg gagcagctgg tgggt | | 25 |
| SEQ ID NO: 574<br>FEATURE<br>source | moltype = RNA   length = 20<br>Location/Qualifiers<br>1..20<br>mol_type = transcribed RNA<br>organism = Homo sapiens | |
| SEQUENCE: 574<br>tgggccaggg agcagctggt | | 20 |
| SEQ ID NO: 575<br>FEATURE<br>source | moltype = RNA   length = 23<br>Location/Qualifiers<br>1..23<br>mol_type = transcribed RNA<br>organism = Homo sapiens | |
| SEQUENCE: 575<br>aagggaggag gagcggaggg gcc | | 23 |
| SEQ ID NO: 576<br>FEATURE<br>source | moltype = RNA   length = 15<br>Location/Qualifiers<br>1..15<br>mol_type = transcribed RNA<br>organism = Homo sapiens | |
| SEQUENCE: 576<br>gggaggagga gcgga | | 15 |
| SEQ ID NO: 577<br>FEATURE<br>source | moltype = RNA   length = 20<br>Location/Qualifiers<br>1..20<br>mol_type = transcribed RNA<br>organism = Homo sapiens | |
| SEQUENCE: 577<br>atcccacctc tgccaccaaa | | 20 |
| SEQ ID NO: 578<br>FEATURE<br>source | moltype = RNA   length = 15<br>Location/Qualifiers<br>1..15<br>mol_type = transcribed RNA<br>organism = Homo sapiens | |
| SEQUENCE: 578<br>atcccacctc tgcca | | 15 |
| SEQ ID NO: 579<br>FEATURE<br>source | moltype = RNA   length = 23<br>Location/Qualifiers<br>1..23<br>mol_type = transcribed RNA<br>organism = Homo sapiens | |
| SEQUENCE: 579<br>gggggccgat acactgtacg aga | | 23 |

```
SEQ ID NO: 580            moltype = RNA  length = 20
FEATURE                   Location/Qualifiers
source                    1..20
                          mol_type = transcribed RNA
                          organism = Homo sapiens
SEQUENCE: 580
gggggccgat acactgtacg                                                       20

SEQ ID NO: 581            moltype = RNA  length = 23
FEATURE                   Location/Qualifiers
source                    1..23
                          mol_type = transcribed RNA
                          organism = Homo sapiens
SEQUENCE: 581
cacaggtgag gttcttggga gcc                                                   23

SEQ ID NO: 582            moltype = RNA  length = 15
FEATURE                   Location/Qualifiers
source                    1..15
                          mol_type = transcribed RNA
                          organism = Homo sapiens
SEQUENCE: 582
acaggtgagg ttctt                                                            15

SEQ ID NO: 583            moltype = RNA  length = 25
FEATURE                   Location/Qualifiers
source                    1..25
                          mol_type = transcribed RNA
                          organism = Homo sapiens
SEQUENCE: 583
gggtggggat tgttgcatt acttg                                                  25

SEQ ID NO: 584            moltype = RNA  length = 20
FEATURE                   Location/Qualifiers
source                    1..20
                          mol_type = transcribed RNA
                          organism = Homo sapiens
SEQUENCE: 584
gggtggggat ttgttgcatt                                                       20

SEQ ID NO: 585            moltype = RNA  length = 23
FEATURE                   Location/Qualifiers
source                    1..23
                          mol_type = transcribed RNA
                          organism = Homo sapiens
SEQUENCE: 585
cggggcagct cagtacagga tac                                                   23

SEQ ID NO: 586            moltype = RNA  length = 15
FEATURE                   Location/Qualifiers
source                    1..15
                          mol_type = transcribed RNA
                          organism = Homo sapiens
SEQUENCE: 586
agctcagtac aggat                                                            15

SEQ ID NO: 587            moltype = RNA  length = 17
FEATURE                   Location/Qualifiers
source                    1..17
                          mol_type = transcribed RNA
                          organism = Homo sapiens
SEQUENCE: 587
gcggggcggc aggggcc                                                          17

SEQ ID NO: 588            moltype = RNA  length = 15
FEATURE                   Location/Qualifiers
source                    1..15
                          mol_type = transcribed RNA
                          organism = Homo sapiens
SEQUENCE: 588
gggggcgggg cggca                                                            15

SEQ ID NO: 589            moltype = RNA  length = 22
FEATURE                   Location/Qualifiers
source                    1..22
                          mol_type = transcribed RNA
                          organism = Homo sapiens
SEQUENCE: 589
```

```
ggcagggaca gcaaagggt gc                                                          22

SEQ ID NO: 590          moltype = RNA   length = 18
FEATURE                 Location/Qualifiers
source                  1..18
                        mol_type = transcribed RNA
                        organism = Homo sapiens
SEQUENCE: 590
gcagggacag caaaggg                                                               18

SEQ ID NO: 591          moltype = RNA   length = 16
FEATURE                 Location/Qualifiers
source                  1..16
                        mol_type = transcribed RNA
                        organism = Homo sapiens
SEQUENCE: 591
tgggggggaa gaaaag                                                                16

SEQ ID NO: 592          moltype = RNA   length = 16
FEATURE                 Location/Qualifiers
source                  1..16
                        mol_type = transcribed RNA
                        organism = Homo sapiens
SEQUENCE: 592
tgggggggaa gaaaag                                                                16

SEQ ID NO: 593          moltype = RNA   length = 23
FEATURE                 Location/Qualifiers
source                  1..23
                        mol_type = transcribed RNA
                        organism = Homo sapiens
SEQUENCE: 593
gagggaggga cggggctgt gct                                                         23

SEQ ID NO: 594          moltype = RNA   length = 15
FEATURE                 Location/Qualifiers
source                  1..15
                        mol_type = transcribed RNA
                        organism = Homo sapiens
SEQUENCE: 594
gaggagggag ggagg                                                                 15

SEQ ID NO: 595          moltype = RNA   length = 24
FEATURE                 Location/Qualifiers
source                  1..24
                        mol_type = transcribed RNA
                        organism = Homo sapiens
SEQUENCE: 595
tgactgggga gcagaaggag aacc                                                       24

SEQ ID NO: 596          moltype = RNA   length = 15
FEATURE                 Location/Qualifiers
source                  1..15
                        mol_type = transcribed RNA
                        organism = Homo sapiens
SEQUENCE: 596
gactggggag cagaa                                                                 15

SEQ ID NO: 597          moltype = RNA   length = 22
FEATURE                 Location/Qualifiers
source                  1..22
                        mol_type = transcribed RNA
                        organism = Homo sapiens
SEQUENCE: 597
atatagggat tggagccgtg gc                                                         22

SEQ ID NO: 598          moltype = RNA   length = 20
FEATURE                 Location/Qualifiers
source                  1..20
                        mol_type = transcribed RNA
                        organism = Homo sapiens
SEQUENCE: 598
atatagggat tggagccgtg                                                            20

SEQ ID NO: 599          moltype = RNA   length = 19
FEATURE                 Location/Qualifiers
source                  1..19
                        mol_type = transcribed RNA
                        organism = Homo sapiens
```

-continued

```
SEQUENCE: 599
gctgggcgag gctggcatc                                                    19

SEQ ID NO: 600          moltype = RNA   length = 17
FEATURE                 Location/Qualifiers
source                  1..17
                        mol_type = transcribed RNA
                        organism = Homo sapiens
SEQUENCE: 600
gctgggcgag gctggca                                                      17

SEQ ID NO: 601          moltype = RNA   length = 23
FEATURE                 Location/Qualifiers
source                  1..23
                        mol_type = transcribed RNA
                        organism = Homo sapiens
SEQUENCE: 601
tggggaaggc gtcagtgtcg ggt                                               23

SEQ ID NO: 602          moltype = RNA   length = 16
FEATURE                 Location/Qualifiers
source                  1..16
                        mol_type = transcribed RNA
                        organism = Homo sapiens
SEQUENCE: 602
tggggaaggc gtcagt                                                       16

SEQ ID NO: 603          moltype = RNA   length = 21
FEATURE                 Location/Qualifiers
source                  1..21
                        mol_type = transcribed RNA
                        organism = Homo sapiens
SEQUENCE: 603
cagcagggga gagagaggag t                                                 21

SEQ ID NO: 604          moltype = RNA   length = 20
FEATURE                 Location/Qualifiers
source                  1..20
                        mol_type = transcribed RNA
                        organism = Homo sapiens
SEQUENCE: 604
cagcagggga gagagaggag                                                   20

SEQ ID NO: 605          moltype = RNA   length = 26
FEATURE                 Location/Qualifiers
source                  1..26
                        mol_type = transcribed RNA
                        organism = Homo sapiens
SEQUENCE: 605
agggctggac tcagcggcgg agctgg                                            26

SEQ ID NO: 606          moltype = RNA   length = 17
FEATURE                 Location/Qualifiers
source                  1..17
                        mol_type = transcribed RNA
                        organism = Homo sapiens
SEQUENCE: 606
gcggcggagc tggctgc                                                      17

SEQ ID NO: 607          moltype = RNA   length = 24
FEATURE                 Location/Qualifiers
source                  1..24
                        mol_type = transcribed RNA
                        organism = Homo sapiens
SEQUENCE: 607
caggcaggag ccggactgga cctc                                              24

SEQ ID NO: 608          moltype = RNA   length = 21
FEATURE                 Location/Qualifiers
source                  1..21
                        mol_type = transcribed RNA
                        organism = Homo sapiens
SEQUENCE: 608
tccaggcagg agccggactg g                                                 21

SEQ ID NO: 609          moltype = RNA   length = 19
FEATURE                 Location/Qualifiers
source                  1..19
                        mol_type = transcribed RNA
```

```
                              organism = Homo sapiens
SEQUENCE: 609
gggtgcgggc cggcggggt                                                    19

SEQ ID NO: 610           moltype = RNA  length = 15
FEATURE                  Location/Qualifiers
source                   1..15
                         mol_type = transcribed RNA
                         organism = Homo sapiens
SEQUENCE: 610
tgcgggccgg cgggg                                                        15

SEQ ID NO: 611           moltype = RNA  length = 27
FEATURE                  Location/Qualifiers
source                   1..27
                         mol_type = transcribed RNA
                         organism = Homo sapiens
SEQUENCE: 611
atcacattgc cagggatttc caaccga                                           27

SEQ ID NO: 612           moltype = RNA  length = 15
FEATURE                  Location/Qualifiers
source                   1..15
                         mol_type = transcribed RNA
                         organism = Homo sapiens
SEQUENCE: 612
aatcacattg ccagg                                                        15

SEQ ID NO: 613           moltype = RNA  length = 19
FEATURE                  Location/Qualifiers
source                   1..19
                         mol_type = transcribed RNA
                         organism = Homo sapiens
SEQUENCE: 613
tggcgggtgc ggggtggg                                                     19

SEQ ID NO: 614           moltype = RNA  length = 15
FEATURE                  Location/Qualifiers
source                   1..15
                         mol_type = transcribed RNA
                         organism = Homo sapiens
SEQUENCE: 614
tggcgggtgc ggggg                                                        15

SEQ ID NO: 615           moltype = RNA  length = 21
FEATURE                  Location/Qualifiers
source                   1..21
                         mol_type = transcribed RNA
                         organism = Homo sapiens
SEQUENCE: 615
ttgaggagac atggtggggg c                                                 21

SEQ ID NO: 616           moltype = RNA  length = 15
FEATURE                  Location/Qualifiers
source                   1..15
                         mol_type = transcribed RNA
                         organism = Homo sapiens
SEQUENCE: 616
ttgaggagac atggt                                                        15

SEQ ID NO: 617           moltype = RNA  length = 27
FEATURE                  Location/Qualifiers
source                   1..27
                         mol_type = transcribed RNA
                         organism = Homo sapiens
SEQUENCE: 617
aaaccgttac cattactgag tttagta                                           27

SEQ ID NO: 618           moltype = RNA  length = 15
FEATURE                  Location/Qualifiers
source                   1..15
                         mol_type = transcribed RNA
                         organism = Homo sapiens
SEQUENCE: 618
gaaaccgtta ccatt                                                        15

SEQ ID NO: 619           moltype = RNA  length = 23
FEATURE                  Location/Qualifiers
source                   1..23
```

```
                        mol_type = transcribed RNA
                        organism = Homo sapiens
SEQUENCE: 619
ccagggctgg cagtgacatg ggt                                               23

SEQ ID NO: 620          moltype = RNA  length = 19
FEATURE                 Location/Qualifiers
source                  1..19
                        mol_type = transcribed RNA
                        organism = Homo sapiens
SEQUENCE: 620
cagggctggc agtgacatg                                                    19

SEQ ID NO: 621          moltype = RNA  length = 23
FEATURE                 Location/Qualifiers
source                  1..23
                        mol_type = transcribed RNA
                        organism = Homo sapiens
SEQUENCE: 621
tggggcggag cttccggagg ccc                                               23

SEQ ID NO: 622          moltype = RNA  length = 15
FEATURE                 Location/Qualifiers
source                  1..15
                        mol_type = transcribed RNA
                        organism = Homo sapiens
SEQUENCE: 622
gccccgggaa agcgt                                                        15

SEQ ID NO: 623          moltype = RNA  length = 24
FEATURE                 Location/Qualifiers
source                  1..24
                        mol_type = transcribed RNA
                        organism = Homo sapiens
SEQUENCE: 623
agacacattt ggagagggaa cctc                                              24

SEQ ID NO: 624          moltype = RNA  length = 16
FEATURE                 Location/Qualifiers
source                  1..16
                        mol_type = transcribed RNA
                        organism = Homo sapiens
SEQUENCE: 624
agacacattt ggagag                                                       16

SEQ ID NO: 625          moltype = RNA  length = 24
FEATURE                 Location/Qualifiers
source                  1..24
                        mol_type = transcribed RNA
                        organism = Homo sapiens
SEQUENCE: 625
gatcggtcga gagcgtcctg gctg                                              24

SEQ ID NO: 626          moltype = RNA  length = 15
FEATURE                 Location/Qualifiers
source                  1..15
                        mol_type = transcribed RNA
                        organism = Homo sapiens
SEQUENCE: 626
gctgggcggg gcgcg                                                        15

SEQ ID NO: 627          moltype = RNA  length = 23
FEATURE                 Location/Qualifiers
source                  1..23
                        mol_type = transcribed RNA
                        organism = Homo sapiens
SEQUENCE: 627
ctggggacg cgtgagcgcg agc                                                23

SEQ ID NO: 628          moltype = RNA  length = 21
FEATURE                 Location/Qualifiers
source                  1..21
                        mol_type = transcribed RNA
                        organism = Homo sapiens
SEQUENCE: 628
ctggggacg cgtgagcgcg a                                                  21

SEQ ID NO: 629          moltype = RNA  length = 27
FEATURE                 Location/Qualifiers
```

```
source                  1..27
                        mol_type = transcribed RNA
                        organism = Homo sapiens
SEQUENCE: 629
caaggtggct gggagagggt tgtttac                                            27

SEQ ID NO: 630          moltype = RNA   length = 15
FEATURE                 Location/Qualifiers
source                  1..15
                        mol_type = transcribed RNA
                        organism = Homo sapiens
SEQUENCE: 630
gtgagctcaa ggtgg                                                         15

SEQ ID NO: 631          moltype = RNA   length = 29
FEATURE                 Location/Qualifiers
source                  1..29
                        mol_type = transcribed RNA
                        organism = Homo sapiens
SEQUENCE: 631
gctgggttaa gccgagctgg gttgggctg                                          29

SEQ ID NO: 632          moltype = RNA   length = 19
FEATURE                 Location/Qualifiers
source                  1..19
                        mol_type = transcribed RNA
                        organism = Homo sapiens
SEQUENCE: 632
ctgggttggg ctgggctgg                                                     19

SEQ ID NO: 633          moltype = RNA   length = 19
FEATURE                 Location/Qualifiers
source                  1..19
                        mol_type = transcribed RNA
                        organism = Homo sapiens
SEQUENCE: 633
gagggcgggt ggaggagga                                                     19

SEQ ID NO: 634          moltype = RNA   length = 15
FEATURE                 Location/Qualifiers
source                  1..15
                        mol_type = transcribed RNA
                        organism = Homo sapiens
SEQUENCE: 634
gcgggtggag gagga                                                         15

SEQ ID NO: 635          moltype = RNA   length = 20
FEATURE                 Location/Qualifiers
source                  1..20
                        mol_type = transcribed RNA
                        organism = Homo sapiens
SEQUENCE: 635
caggggggact gggggtgagc                                                   20

SEQ ID NO: 636          moltype = RNA   length = 25
FEATURE                 Location/Qualifiers
source                  1..25
                        mol_type = transcribed RNA
                        organism = Homo sapiens
SEQUENCE: 636
acttgggcag gagggaccct gtatg                                              25

SEQ ID NO: 637          moltype = RNA   length = 22
FEATURE                 Location/Qualifiers
source                  1..22
                        mol_type = transcribed RNA
                        organism = Homo sapiens
SEQUENCE: 637
agcccgcccc agccgaggtt ct                                                 22

SEQ ID NO: 638          moltype = RNA   length = 17
FEATURE                 Location/Qualifiers
source                  1..17
                        mol_type = transcribed RNA
                        organism = Homo sapiens
SEQUENCE: 638
ggatggagga ggggtct                                                       17

SEQ ID NO: 639          moltype = RNA   length = 17
```

```
FEATURE                 Location/Qualifiers
source                  1..17
                        mol_type = transcribed RNA
                        organism = Homo sapiens
SEQUENCE: 639
gggagtctac agcaggg                                                          17

SEQ ID NO: 640          moltype = RNA  length = 22
FEATURE                 Location/Qualifiers
source                  1..22
                        mol_type = transcribed RNA
                        organism = Homo sapiens
SEQUENCE: 640
gtgcggaacg ctggccgggg cg                                                    22

SEQ ID NO: 641          moltype = RNA  length = 24
FEATURE                 Location/Qualifiers
source                  1..24
                        mol_type = transcribed RNA
                        organism = Homo sapiens
SEQUENCE: 641
ggaggccggg gtgggcggg gcgg                                                   24

SEQ ID NO: 642          moltype = RNA  length = 23
FEATURE                 Location/Qualifiers
source                  1..23
                        mol_type = transcribed RNA
                        organism = Homo sapiens
SEQUENCE: 642
aggaagccct ggaggggctg gag                                                   23

SEQ ID NO: 643          moltype = RNA  length = 68
FEATURE                 Location/Qualifiers
source                  1..68
                        mol_type = transcribed RNA
                        organism = Homo sapiens
SEQUENCE: 643
gggcgcaggg ggactggggg tgagcaggcc cagaacccag ctcgtgctca ctctcagtcc           60
ctccctag                                                                    68

SEQ ID NO: 644          moltype = RNA  length = 70
FEATURE                 Location/Qualifiers
source                  1..70
                        mol_type = transcribed RNA
                        organism = Homo sapiens
SEQUENCE: 644
tgtgcacttg ggcaggaggg accctgtatg tctccccgca gcaccgtcat cgtgtccctc           60
ttgtccacag                                                                  70

SEQ ID NO: 645          moltype = RNA  length = 80
FEATURE                 Location/Qualifiers
source                  1..80
                        mol_type = transcribed RNA
                        organism = Homo sapiens
SEQUENCE: 645
ggttccggag ccccggcgcg ggcgggttct ggggtgtaga cgctgctggc cagcccgccc           60
cagccgaggt tctcggcacc                                                       80

SEQ ID NO: 646          moltype = RNA  length = 60
FEATURE                 Location/Qualifiers
source                  1..60
                        mol_type = transcribed RNA
                        organism = Homo sapiens
SEQUENCE: 646
tgtgaatgac cccttccag agccaaaatc accaggatg gaggagggt cttgggtact              60

SEQ ID NO: 647          moltype = RNA  length = 76
FEATURE                 Location/Qualifiers
source                  1..76
                        mol_type = transcribed RNA
                        organism = Homo sapiens
SEQUENCE: 647
ccgatgcctc gggagtctac agcagggcca tgtctgtgag ggcccaaggg tgcatgtgtc           60
tcccaggttt cggtgc                                                           76

SEQ ID NO: 648          moltype = RNA  length = 61
FEATURE                 Location/Qualifiers
source                  1..61
                        mol_type = transcribed RNA
```

```
                        organism = Homo sapiens
SEQUENCE: 648
gtgcggaacg ctggccgggg cgggagggga agggacgccc ggccggaacg ccgcactcac    60
g                                                                   61

SEQ ID NO: 649          moltype = RNA   length = 64
FEATURE                 Location/Qualifiers
source                  1..64
                        mol_type = transcribed RNA
                        organism = Homo sapiens
SEQUENCE: 649
ccccgggccc ggcgttccct ccccttccgt gcgccagtgg aggccggggt ggggcgggggc   60
gggg                                                                64

SEQ ID NO: 650          moltype = RNA   length = 64
FEATURE                 Location/Qualifiers
source                  1..64
                        mol_type = transcribed RNA
                        organism = Homo sapiens
SEQUENCE: 650
ccccgggccc ggcgttccct ccccttccgt gcgccagtgg aggccggggt ggggcgggggc   60
gggg                                                                64

SEQ ID NO: 651          moltype = RNA   length = 118
FEATURE                 Location/Qualifiers
source                  1..118
                        mol_type = transcribed RNA
                        organism = Homo sapiens
SEQUENCE: 651
gcaggtgaac tggcaggcca ggaagaggag gaagccctgg aggggctgga ggtgatggat    60
gttttcctcc ggttctcagg gctccacctc tttcgggccg tagagccagg gctggtgc    118

SEQ ID NO: 652          moltype = RNA   length = 23
FEATURE                 Location/Qualifiers
source                  1..23
                        mol_type = transcribed RNA
                        organism = Homo sapiens
SEQUENCE: 652
cagcccgccc cagccgaggt tct                                           23

SEQ ID NO: 653          moltype = RNA   length = 17
FEATURE                 Location/Qualifiers
source                  1..17
                        mol_type = transcribed RNA
                        organism = Homo sapiens
SEQUENCE: 653
agcccgcccc agccgag                                                  17

SEQ ID NO: 654          moltype = RNA   length = 16
FEATURE                 Location/Qualifiers
source                  1..16
                        mol_type = transcribed RNA
                        organism = Homo sapiens
SEQUENCE: 654
cgggcccggc gttccc                                                   16

SEQ ID NO: 655          moltype = RNA   length = 15
FEATURE                 Location/Qualifiers
source                  1..15
                        mol_type = transcribed RNA
                        organism = Homo sapiens
SEQUENCE: 655
ccgggcccgg cgttc                                                    15

SEQ ID NO: 656          moltype = RNA   length = 25
FEATURE                 Location/Qualifiers
source                  1..25
                        mol_type = transcribed RNA
                        organism = Homo sapiens
SEQUENCE: 656
aggaagccct ggaggggctg gaggt                                         25
```

```
SEQ ID NO: 657         moltype = RNA  length = 15
FEATURE                Location/Qualifiers
source                 1..15
                       mol_type = transcribed RNA
                       organism = Homo sapiens
SEQUENCE: 657
aggaagagga ggaag                                                    15
```